United States Patent
Park et al.

(10) Patent No.: US 12,421,219 B2
(45) Date of Patent: Sep. 23, 2025

(54) COMPOUND FOR ORGANIC ELECTRONIC ELEMENT, ORGANIC ELECTRONIC ELEMENT USING SAME, AND ELECTRONIC DEVICE COMPRISING SAME

(71) Applicant: DUK SAN NEOLUX CO., LTD., Cheonan-si (KR)

(72) Inventors: Hyoung Keun Park, Chuncheon-si (KR); Sun Hee Lee, Hwaseong-si (KR); Yun Suk Lee, Seongnam-si (KR); Ki Ho So, Cheonan-si (KR); Jong Gwang Park, Ulsan (KR); Yeon Seok Jeong, Gangwon-do (KR); Soung Yun Mun, Cheonan-si (KR); Jung Wook Lee, Gunsan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 87 days.

(21) Appl. No.: 15/779,160

(22) PCT Filed: Nov. 9, 2016

(86) PCT No.: PCT/KR2016/012861
§ 371 (c)(1),
(2) Date: May 25, 2018

(87) PCT Pub. No.: WO2017/090918
PCT Pub. Date: Jun. 1, 2017

(65) Prior Publication Data
US 2019/0047992 A1 Feb. 14, 2019

(30) Foreign Application Priority Data
Nov. 26, 2015 (KR) .......... 10-2015-0166381

(51) Int. Cl.
*C07D 405/04* (2006.01)
*C07D 405/10* (2006.01)
(Continued)

(52) U.S. Cl.
CPC ......... *C07D 409/04* (2013.01); *C07D 405/04* (2013.01); *C07D 405/10* (2013.01);
(Continued)

(58) Field of Classification Search
CPC .. C07D 409/04; C07D 405/04; C07D 209/56; C07D 307/91; C07D 307/92;
(Continued)

(56) References Cited

U.S. PATENT DOCUMENTS 9,145,363 B2 * 9/2015 Yabunouchi ......... C07D 405/14
2005/0236970 A1 * 10/2005 Matsudate .......... H01L 27/3246
313/500
(Continued)

FOREIGN PATENT DOCUMENTS

CN 103804279 A 5/2014
EP 2166584 A1 * 3/2010 ......... H01L 51/0074
(Continued)

OTHER PUBLICATIONS

KR-101389527-B1—translation (Year: 2014).*
(Continued)

*Primary Examiner* — Jennifer A Boyd
*Assistant Examiner* — Rachel Simbana
(74) *Attorney, Agent, or Firm* — Vorys, Sater, Seymour and Pease LLP; Mih Suhn Koh

(57) ABSTRACT

The present invention provides a novel compound capable of improving the luminous efficiency, stability and life of an element, an organic electronic element using the same, and an electronic device comprising same.

12 Claims, 2 Drawing Sheets

(51) Int. Cl.

| | |
|---|---|
| *C07D 405/14* | (2006.01) |
| *C07D 409/04* | (2006.01) |
| *C07D 409/10* | (2006.01) |
| *C07D 409/14* | (2006.01) |
| *C07D 513/04* | (2006.01) |
| *C09K 11/06* | (2006.01) |
| *H05B 33/14* | (2006.01) |
| *H05B 33/20* | (2006.01) |
| *H10K 50/11* | (2023.01) |
| *H10K 50/125* | (2023.01) |
| *H10K 50/15* | (2023.01) |
| *H10K 50/18* | (2023.01) |
| *H10K 50/81* | (2023.01) |
| *H10K 50/82* | (2023.01) |
| *H10K 85/30* | (2023.01) |
| *H10K 85/60* | (2023.01) |
| *H10K 101/40* | (2023.01) |

(52) U.S. Cl.
CPC ......... *C07D 405/14* (2013.01); *C07D 409/10* (2013.01); *C07D 409/14* (2013.01); *C07D 513/04* (2013.01); *C09K 11/06* (2013.01); *H05B 33/14* (2013.01); *H05B 33/20* (2013.01); *H10K 50/11* (2023.02); *H10K 50/125* (2023.02); *H10K 50/18* (2023.02); *H10K 50/81* (2023.02); *H10K 50/82* (2023.02); *H10K 85/633* (2023.02); *H10K 85/636* (2023.02); *H10K 85/654* (2023.02); *H10K 85/6572* (2023.02); *H10K 85/6574* (2023.02); *H10K 85/6576* (2023.02); *H10K 50/15* (2023.02); *H10K 85/324* (2023.02); *H10K 85/342* (2023.02); *H10K 2101/40* (2023.02)

(58) Field of Classification Search
CPC .. C07D 333/50; C07D 333/74; C07D 333/76; H01L 51/0058; H01L 51/0073; H01L 51/0074; H10K 85/636
See application file for complete search history.

(56) References Cited

U.S. PATENT DOCUMENTS

| | | | | |
|---|---|---|---|---|
| 2011/0297924 A1* | 12/2011 | Yabunouchi | .......... | H01L 51/006 257/40 |
| 2012/0319091 A1* | 12/2012 | Kato | .................. | H01L 51/0051 257/40 |
| 2014/0306190 A1* | 10/2014 | Lee | ......................... | C07C 13/66 585/27 |
| 2015/0137094 A1* | 5/2015 | Itoi | .................... | H01L 51/0072 257/40 |
| 2015/0155524 A1* | 6/2015 | Liu | .................... | H01L 51/5262 257/40 |
| 2016/0028020 A1* | 1/2016 | Lee | ................... | H10K 85/6576 257/40 |
| 2016/0322578 A1* | 11/2016 | Hwang | ................ | H10K 85/633 |
| 2017/0062736 A1* | 3/2017 | Parham | ................ | A61N 5/0616 |

FOREIGN PATENT DOCUMENTS

| | | | | | |
|---|---|---|---|---|---|
| KR | 10-2013-0096334 | A | | 8/2013 | |
| KR | 2013096334 | A | * | 8/2013 | .......... C07D 209/82 |
| KR | 20130096334 | A | * | 8/2013 | |
| KR | 10-2014-0018789 | A | | 2/2014 | |
| KR | 101389527 | B1 | * | 4/2014 | ........ H01L 51/0074 |
| KR | 10-2015-0001101 | A | | 1/2015 | |
| KR | 10-2015-0004099 | A | | 1/2015 | |
| KR | 2015001101 | A | * | 1/2015 | ............. C09K 11/06 |
| KR | 10-2015-0031892 | A | | 3/2015 | |
| KR | 10-1614738 | B1 | | 4/2016 | |
| WO | WO-2006128800 | A1 | * | 12/2006 | ........ H01L 51/0061 |
| WO | 2013/168534 | A1 | | 11/2013 | |
| WO | WO-2014104545 | A1 | * | 7/2014 | ............. C07D 471/04 |
| WO | WO-2017105078 | A1 | * | 6/2017 | ............. C07C 13/72 |

OTHER PUBLICATIONS

WO-2014104545-A1—translation (Year: 2014).*
KR-2015001101-A—translation (Year: 2015).*
KR-20130096334-A—translation (Year: 2013).*
WO-2017105078-A1—translation (Year: 2017).*
KR-2013096334-A—translation (Year: 2013).*

* cited by examiner

COMPOUND FOR ORGANIC ELECTRONIC ELEMENT, ORGANIC ELECTRONIC ELEMENT USING SAME, AND ELECTRONIC DEVICE COMPRISING SAME

BACKGROUND

Technical Field

The present invention relates to compound for organic electric element, organic electric element using the same, and an electronic device thereof.

Background Art

In general, organic light emitting phenomenon refers to a phenomenon that converts electric energy into light energy by using an organic material. An organic electric element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electric element may be classified into a light emitting material and a charge transport material, such as a hole injection material, a hole transport material, an electron transport material, an electron injection material and the like depending on its function.

In the organic electroluminescent device, the most problematic is the lifetime and the efficiency. As the display becomes large, the efficiency and the lifetime problem must be solved.

Efficiency, life span, driving voltage and the like are related to each other. As the efficiency is increased, the driving voltage is relatively decreased, and as the driving voltage drops, the crystallization of the organic material due to joule heating generated during driving is reduced, and as a result, the life span tends to increase.

However, simply improving the organic material layer cannot maximize the efficiency. This is because, when the optimal combination of the energy level and T1 value between each organic material layer and the intrinsic properties (mobility, interface characteristics, etc.) of the material are achieved, long life and high efficiency can be achieved at the same time.

Further, recently, in organic electroluminescent devices, in order to solve the emission problem in the a hole transport layer, an electron blocking layer must be present between the hole transport layer and an emitting layer, and it is necessary to develop an electron blocking layer commonly used for each of the emitting layers (R, G, B)

In general, electrons are transferred from the electron transport layer to the emitting layer, and holes are transferred from the hole transport layer to the emitting layer to generate excitons by recombination.

However, the material used for the hole transport layer has a low HOMO value and therefore has mostly low T1 value. As a result, the exciton generated in the emitting layer is transferred to the hole transport layer, resulting in charge unbalance in the emitting layer, and light is emitted at the interface of the hole transport layer.

When light is emitted from the interface of the hole transport layer, color purity and efficiency of the organic electronic device are lowered and the lifetime is shortened. Therefore, it is urgently required to develop an emitting auxiliary layer having a high T1 value and having a HOMO level between the HOMO energy level of the hole transport layer and the HOMO energy level of the emitting layer.

In addition, it is necessary to develop a hole injection layer material that retards penetration/diffusion of metal oxides from an anode electrode (ITO) into an organic material layer, which is one cause for the shortened life span of an organic electric element, and has stability against Joule heating generated during the operation of an organic electric element, that is, a high glass transition temperature. Also, it has been reported that a low glass transition temperature of a hole transport layer material has a great effect on the life span of an organic electric element because the uniformity of a thin film surface collapses during the operation of the element. In general, deposition is a main method of forming an OLED, and thus it is necessary to develop a material that is durable to such a deposition method, that is, a highly heat-resistant material.

That is, in order to sufficiently exhibit the excellent characteristics of the organic electric element, a material for forming an organic material layer in an element such as a hole injection material, a hole transport material, a light emitting material, an electron transport material, an electron injection material, an electron blocking layer material should be supported by stable and efficient materials. However, such a stable and efficient organic material layer material for an organic electric element has not been sufficiently developed yet. Therefore, development of new materials is continuously required, and development of materials for the electron blocking layer and the hole transport layer is urgently required.

Prior art reference: KR10-2013-000 76842A.

DETAILED DESCRIPTION OF THE INVENTION

Summary

In order to solve the problems of the background art described above, an embodiment of the present invention has revealed a compound having a novel structure, and it has also been found that when the compound is applied to an organic electronic device, the luminous efficiency, stability and lifetime of the device can be greatly improved.

An object of the present invention is to provide a compound, an organic electric element using the same and an electronic device thereof.

Technical Solution

In order to solve the problems of the background art described above, an embodiment of the present invention has revealed a compound having a novel structure, and it has also been found that when the compound is applied to an organic electronic device, the luminous efficiency, stability and lifetime of the device can be greatly improved.

An object of the present invention is to provide a compound, an organic electric element using the same and an electronic device thereof.

Effects of the Invention

By using the compound according to the present invention, it is possible to achieve a high luminous efficiency, a low driving voltage, and a high heat resistance of the element, and can greatly improve the color purity and lifetime of the element.

| | |
|---|---|
| 100: organic electric element, | 110: substrate |
| 120: the first electrode(anode), | 130: the hole injection layer |
| 140: the hole transport layer, | 141: a buffer layer |
| 150: the emitting layer, | 151: the emitting auxiliary layer |
| 160: the electron transport layer, | 170: the electron injection layer |
| 180: the second electrode(cathode) | |

Figure 1:
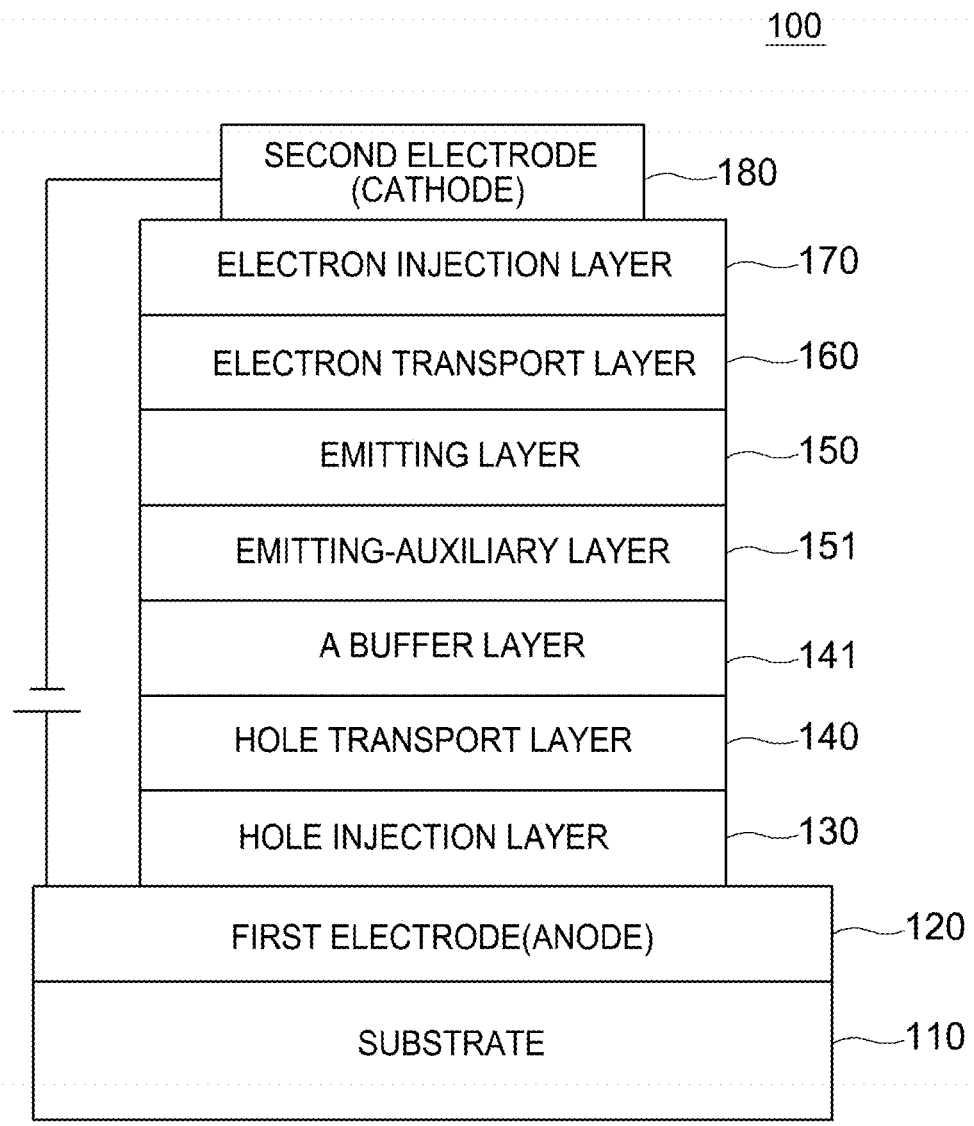
FIG. 1 is an illustration of an organic electric element according to the present invention.
Figure 2:
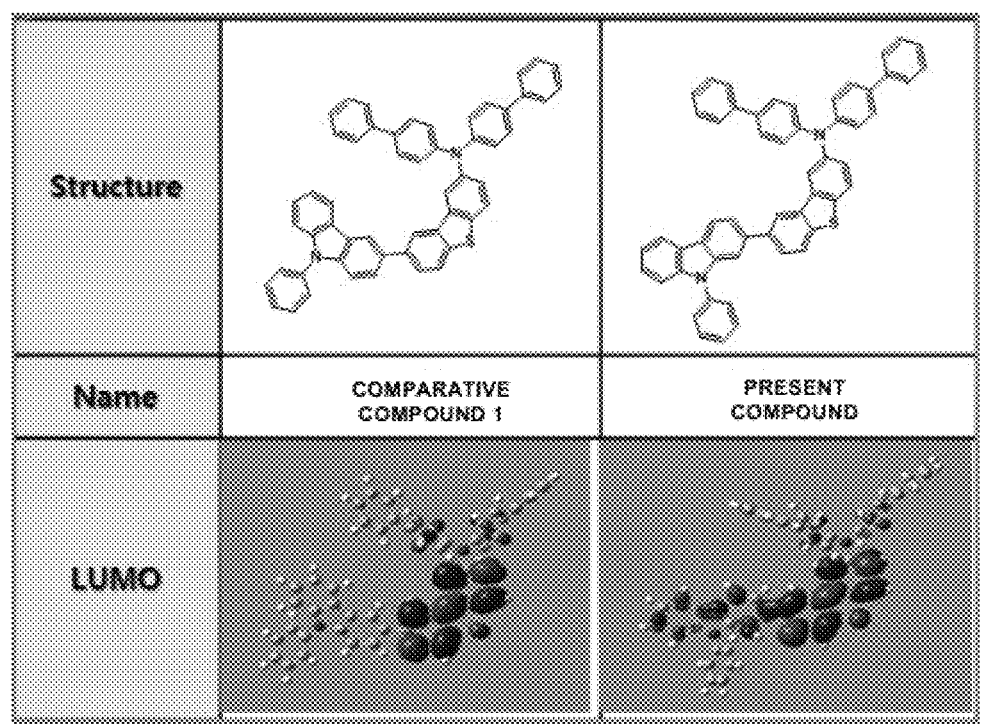

FIG. 2 is an illustration of electronic cloud degree of LUMO of Comparative compound and present compound.

DETAILED DESCRIPTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected", "coupled" or "connected" between each component.

As used in the specification and the accompanying claims, unless otherwise stated, the following is the meaning of the term as follows.

Unless otherwise stated, the term "halo" or "halogen", as used herein, comprises fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), an cycloalkyl group substituted with a alkyl or an alkyl group substituted with a cycloalkyl.

Unless otherwise stated, the term "haloalkyl" or "halogen alkyl", as used herein, means an alkyl group substituted with a halogen.

Unless otherwise stated, the term "heteroalkyl", as used herein, means alkyl substituted one or more of carbon atoms consisting of an alkyl with hetero atom.

Unless otherwise stated, the term "alkenyl" or "alkynyl", as used herein, has double or triple bonds of 2 to 60 carbon atoms, but is not limited thereto, and comprises a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "alkenoxyl group", "alkenoxy group", "alkenyloxy group" or "alkenyloxy group", as used herein, means an oxygen radical attached to an alkenyl group, but is not limited thereto, and has 2 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

Unless otherwise stated, the term "aryl group" or "arylene group", as used herein, has 6 to 60 carbon atoms, but is not limited thereto. Herein, the aryl group or arylene group means a monocyclic and polycyclic aromatic group, and includes an aromatic ring formed by neighboring substituents participating in a bond or a reaction. Examples of "aryl group" may comprise a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heteroalkyl", as used herein, means alkyl containing one or more of hetero atoms. Unless otherwise stated, the term "heteroaryl group" or "heteroarylene group", as used herein, means a C2 to C60 aryl containing one or more of hetero atoms or arylene group, but is not limited thereto, and comprises at least one of monocyclic and polycyclic rings, and may also be formed in conjunction with an adjacent group.

Unless otherwise stated, the term "heterocyclic group", as used herein, contains one or more heteroatoms, but is not limited thereto, has 2 to 60 carbon atoms, comprises any one of monocyclic and polycyclic rings, and may comprise heteroaliphadic ring and/or heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may comprise a ring containing $SO_2$ instead of carbon consisting of cycle. For example, "heterocyclic group" comprises compound below.

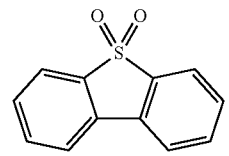 [SMILES: O=S1(=O)c2ccccc2-c2ccccc21]

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and comprises a saturated or unsaturated ring.

Other hetero compounds or hetero radicals other than the above-mentioned hetero compounds contain, but are not limited thereto, one or more heteroatoms.

Unless otherwise stated, the term "carbonyl", as used herein, is represented by —COR', wherein R' may be hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "ether", as used herein, is represented by —R—O—R', wherein R or R' may be independently hydrogen, an alkyl having 1 to 20 carbon atoms, an aryl having 6 to 30 carbon atoms, a cycloalkyl having 3 to 30 carbon atoms, an alkenyl having 2 to 20 carbon atoms, an alkynyl having 2 to 20 carbon atoms, or the combination of these.

Unless otherwise stated, the term "substituted or unsubstituted", as used herein, means that substitution is substituted by at least one substituent selected from the group consisting of, but is not limited thereto, deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group.

Unless otherwise expressly stated, the Formula used in the present invention, as used herein, is applied in the same manner as the substituent definition according to the definition of the exponent of the following Formula.

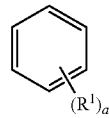

wherein, when a is an integer of zero, the substituent $R^1$ is absent, when a is an integer of 1, the sole substituent $R^1$ is linked to any one of the carbon constituting the benzene ring, when a is an integer of 2 or 3, each substituent $R^1$s may be the same and different, when a is an integer of 4 to 6, and is linked to the benzene ring in a similar manner, whereas the indication of hydrogen bound to the carbon forming the benzene ring is omitted.

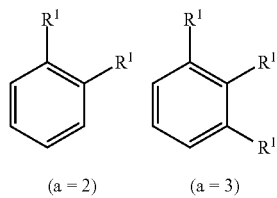

Hereinafter, a compound according to an aspect of the present invention and an organic electric element comprising the same will be described.

The present invention provides a compound represented Formula (1) below.

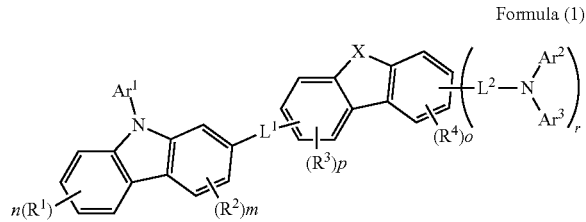

Formula (1)

{In Formula (1),
1) $Ar^1$ is selected from the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring;
2) $Ar^2$ and $Ar^3$ are each independently from the group consisting of a $C_6$-$C_{60}$ aryl group; a $C_2$-$C_{60}$ heterocyclic group including at least one hetero atom of O, N, S, Si or P;
3) X is O or S,
4) $L^1$ and $L^2$ are independently selected from the group consisting of a single bond, a $C_6$-$C_{60}$ arylene group, and a fluorenylene group; a fused ring group of a $C_3$-$C_{60}$ aliphatic ring and a $C_6$-$C_{60}$ aromatic ring; and a $C_2$-$C_{60}$ heterocyclic group including at least one hetero atom of O, N, S, Si or P;
5) n is an integer of 0 to 4, and m, p and o are an integer of 0 to 3,
when m, n, o or p are 1 or more, $R^1$, $R^2$, $R^3$, and $R^4$ are each independently selected from a deuterium; a halogen; the group consisting of a $C_6$-$C_{60}$ aryl group; a fluorenyl group; a $C_2$-$C_{60}$ heterocyclic group including at least one hetero atom of O, N, S, Si and P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$); (wherein, L' is selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic, and $R_a$ and $R_b$ are be independently selected from the group consisting of a $C_6$-$C_{60}$ aryl group; a fluorenylene group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, or P), or an adjacent plurality of $R^1$ or a plurality of $R^2$ or a plurality of $R^3$ or a plurality of $R^4$ may be bonded to each other to form an aromatic or a heteroaromatic ring.
6) r is an integer of 1 or 2, and when r is 2, two $L^2$s may be the same or different, and two $Ar^2$s may be the same or different, and two $Ar^3$s may be the same or different,
wherein, the aryl group, fluorenyl group, arylene group, heterocyclic group, fused ring group, alkyl group, alkenyl group, alkoxy group and aryloxy group may be substituted with one or more substituents selected from the group consisting of deuterium; halogen; a silane group substituted or unsubstituted with $C_1$-$C_{20}$ alkyl group or $C_6$-$C_{20}$ aryl group; siloxane group; boron group; germanium group; cyano group; nitro group; -L'-N($R_a$)($R_b$); a $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group and $C_8$-$C_{20}$ arylalkenyl group, and also, these substituents may combine each other and form a saturated or unsaturated ring, wherein the term 'ring' means $C_3$-$C_{60}$ aliphatic ring or $C_6$-$C_{60}$ aromatic ring or a $C_2$-$C_{60}$ heterocyclic ring or a fused ring formed by the combination of thereof and comprises a saturated or unsaturated ring.}

A specific example of the present invention provides a compound wherein the compound represented by the Formula (1) is represented by the following Formula (2) or (3).

Formula (2)

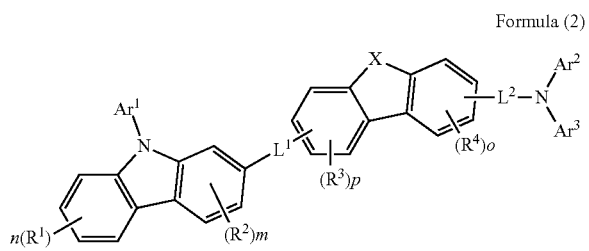

Formula (3)

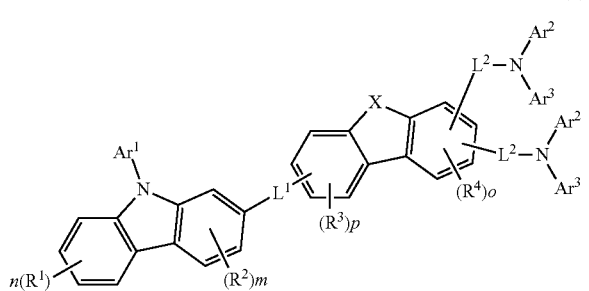

More specific examples of the present invention provide a compound wherein the compound represented by Formula (1) is any one represented by the following Formulas (4) to (7).

Formula (4)

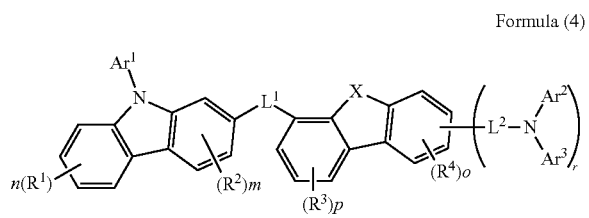

Formula (5)

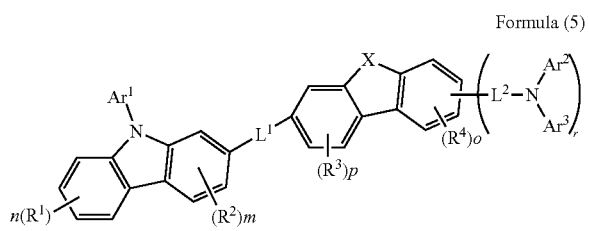

Formula (6)

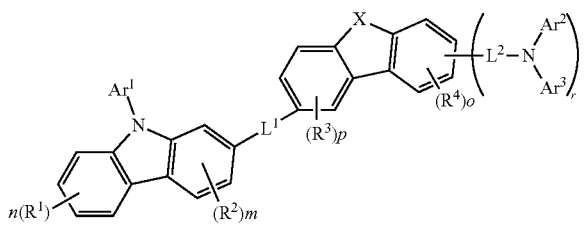

Formula (7)

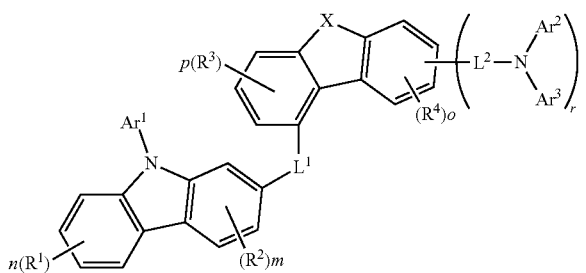

The present invention also provides a compound wherein the compound represented by the Formula (1) is included in any one of the following Formulas (8) to (11).

Formula (8)

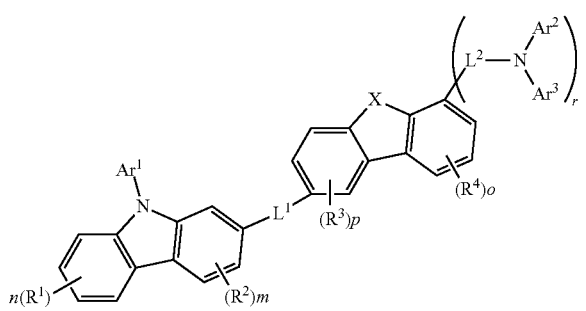

Formula (9)

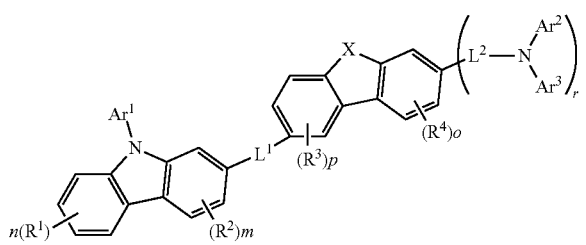

Formula (10)

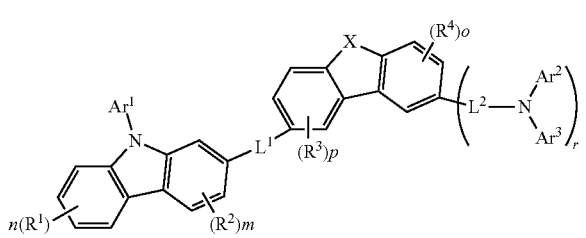

Formula (11)
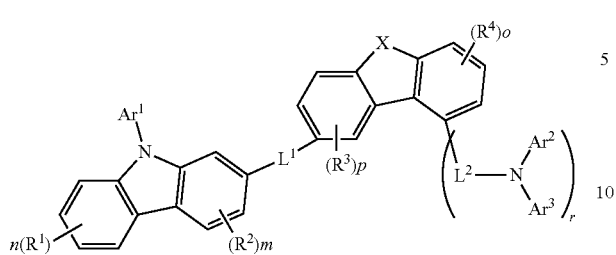
In another specific example of the present invention, the linking position of the ring containing X in Formula (1) provides a compound represented by any one of the following structures [A-1] to [A-20].
[A-1]
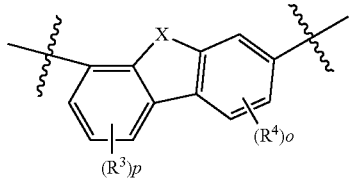
[A-2]
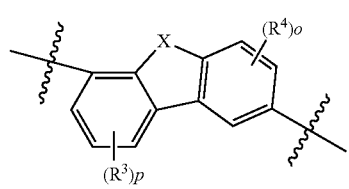
[A-3]
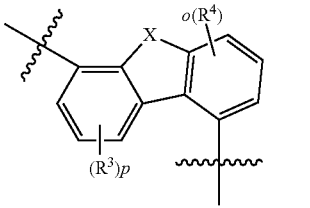
[A-4]
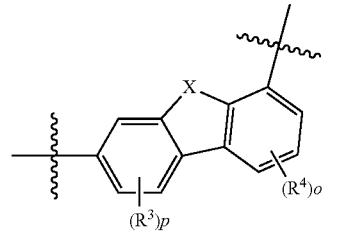
[A-5]
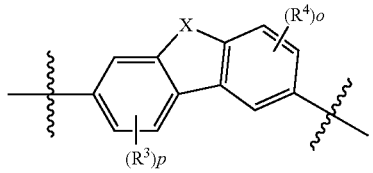
[A-6]
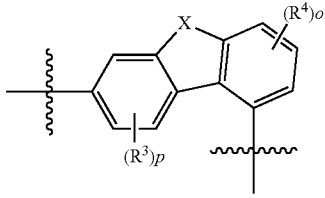
[A-7]
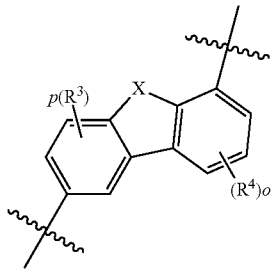
[A-8]
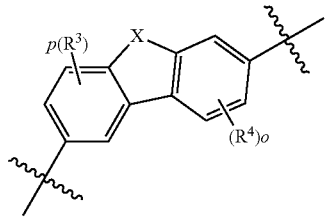
[A-9]
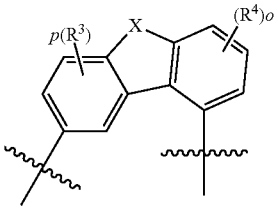
[A-10]
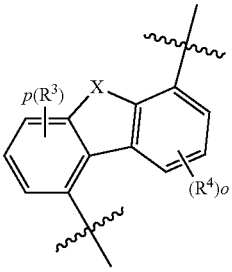
[A-11]
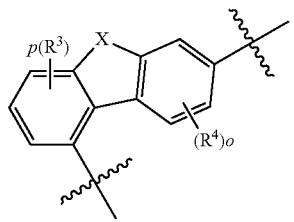

[A-12]
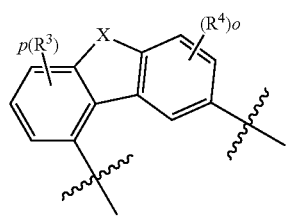
[A-13]
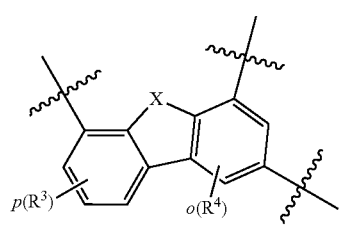
[A-14]
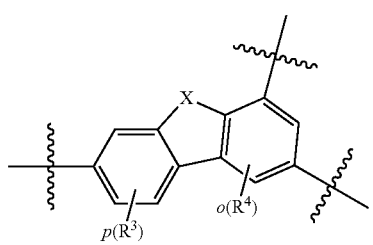
[A-15]
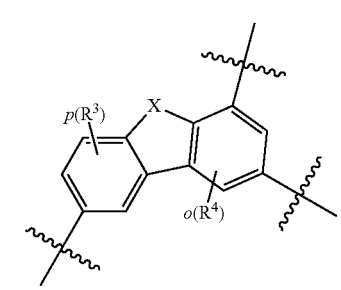
[A-16]
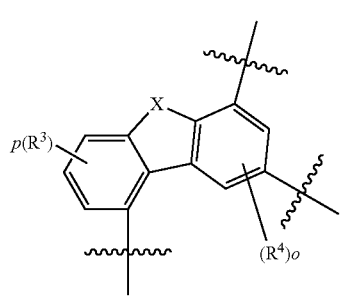
[A-17]
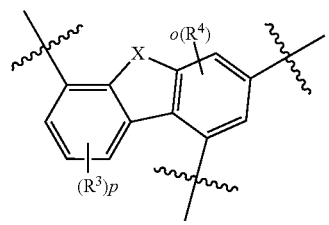
[A-18]
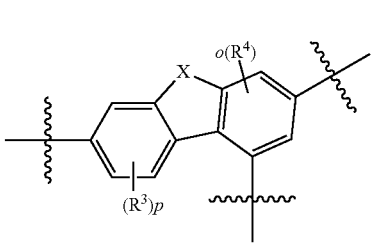
[A-19]
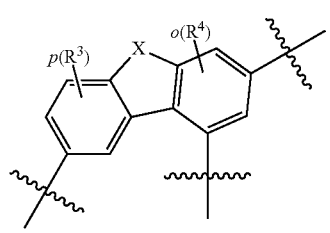
[A-20]
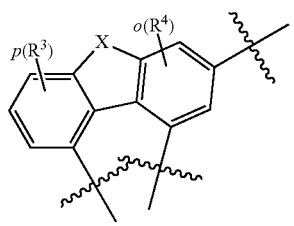
For example, in the present invention, Formula (1) comprises a compound represented by any one of the following compounds 1-1 to 4-20.

1-1
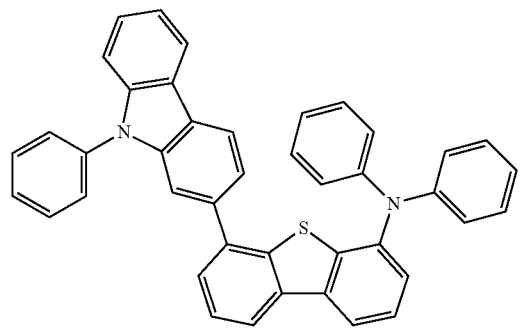
1-2
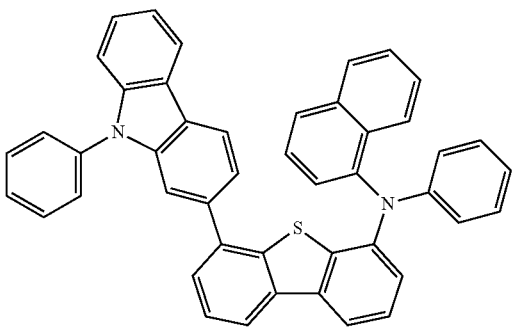
1-3
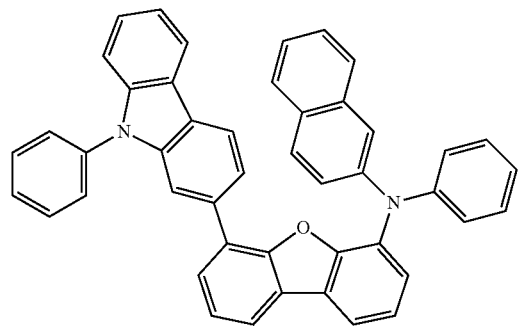
1-4
1-5
1-6
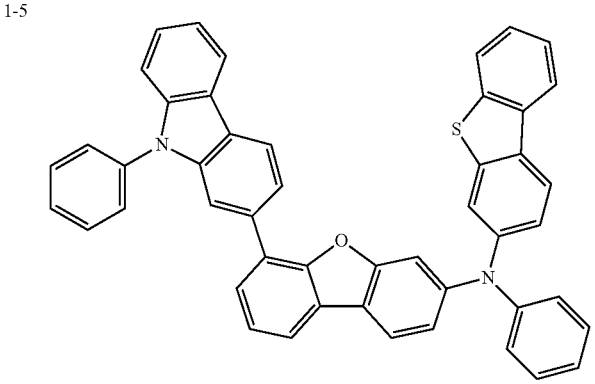
1-7
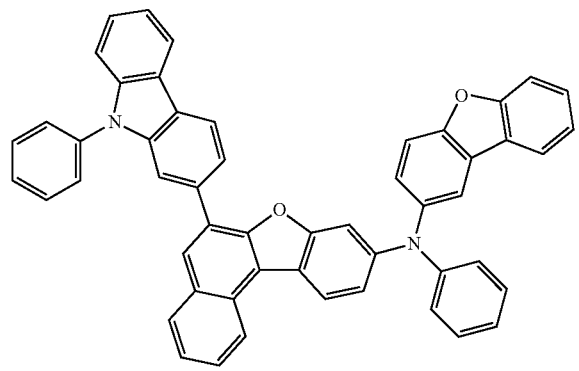
1-8
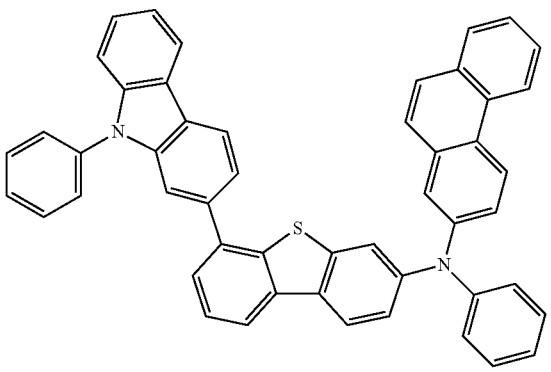

1-9
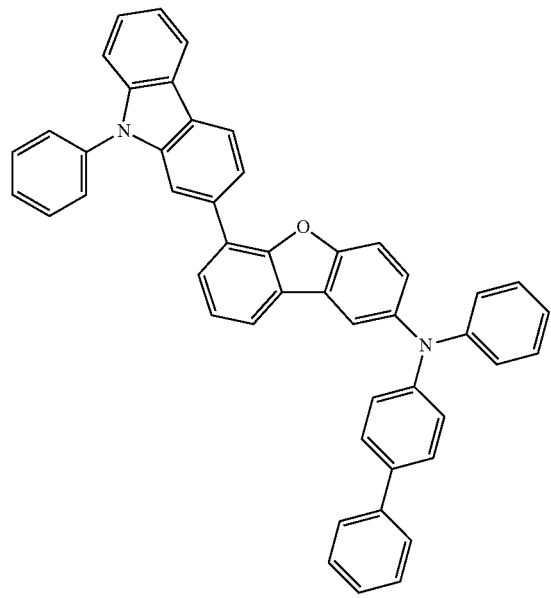
1-10
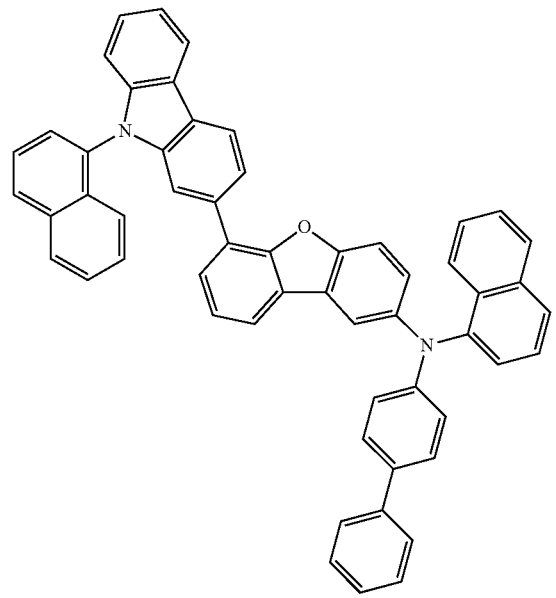
1-11
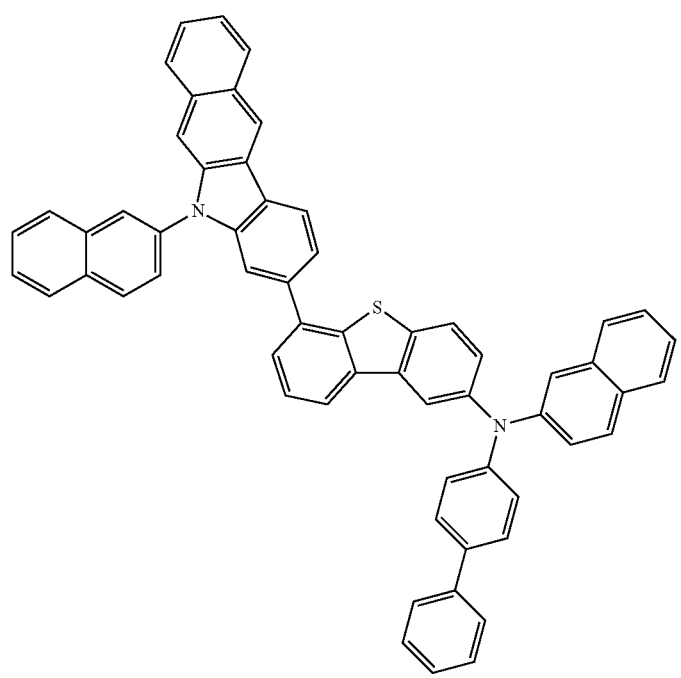

1-12
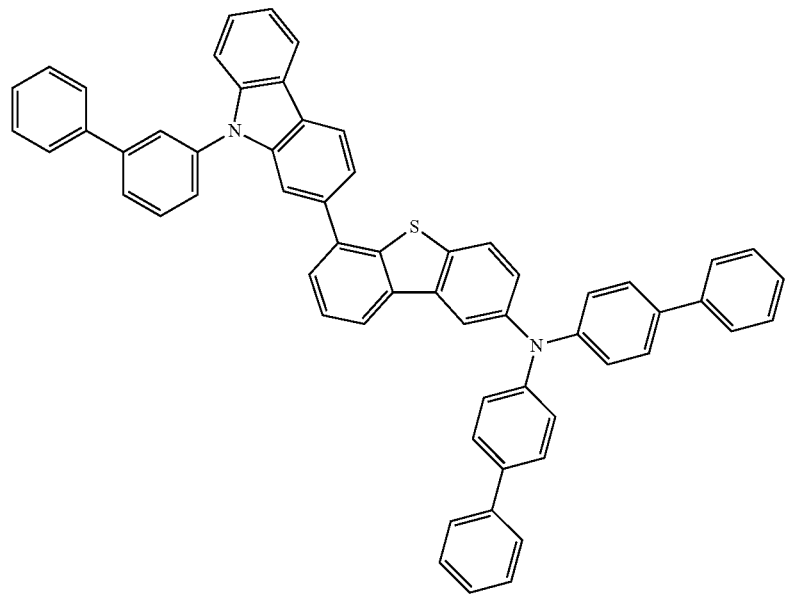
1-13
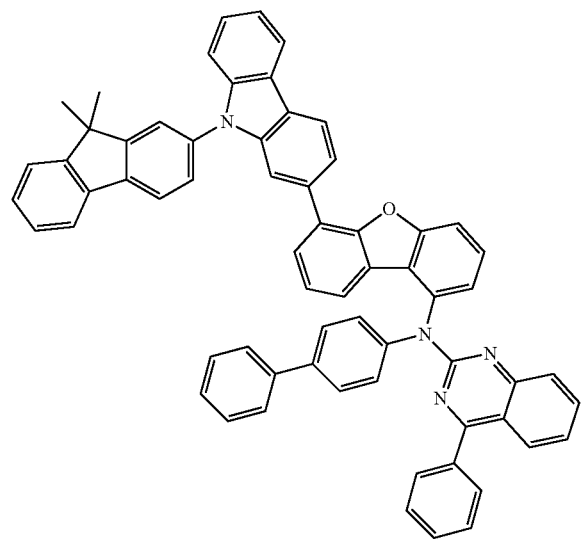
1-14
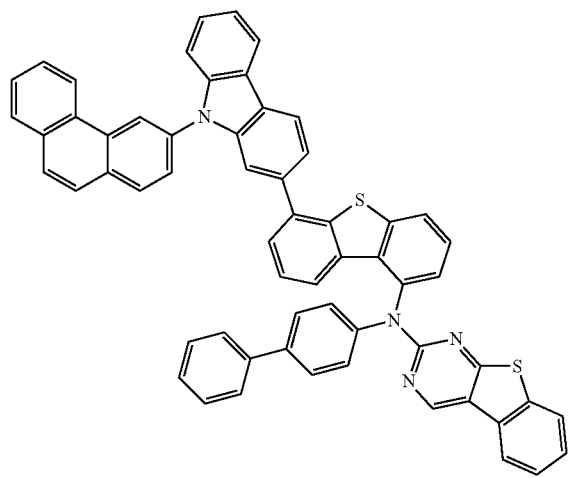

-continued
1-15
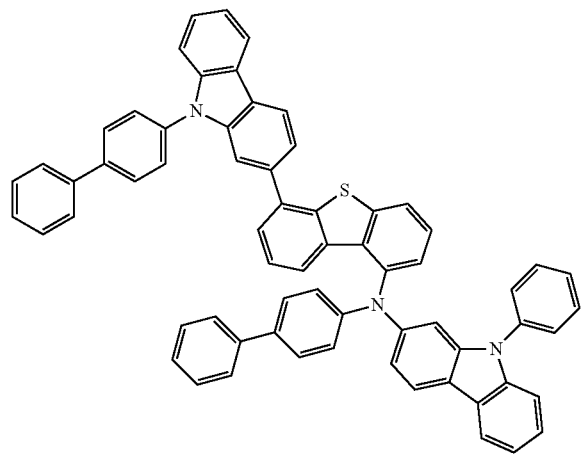
1-16
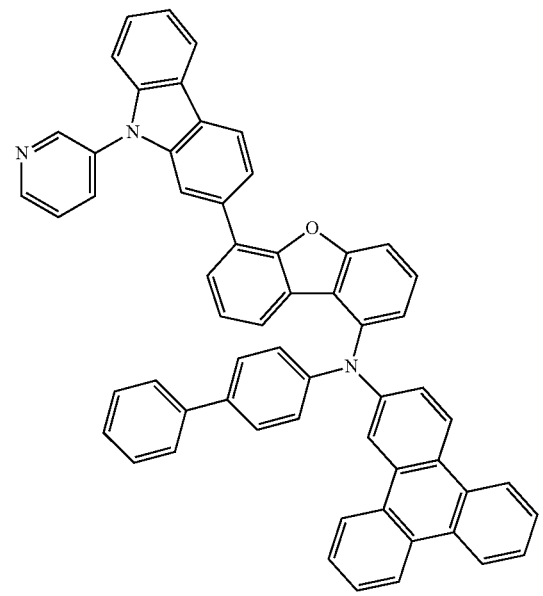
1-17
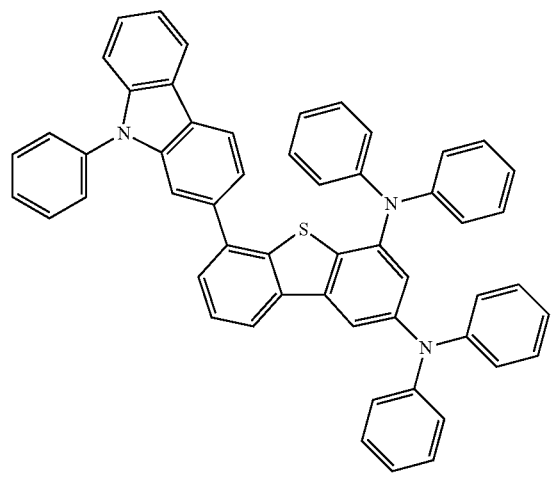
1-18
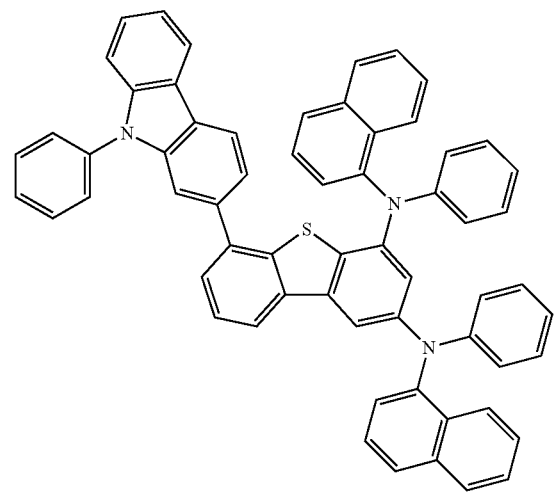
1-19
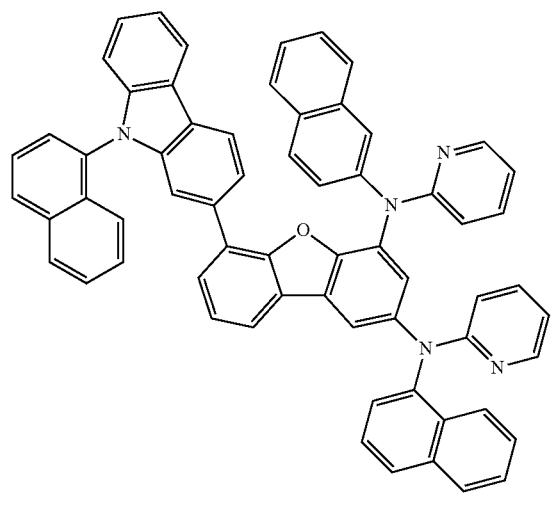
1-20
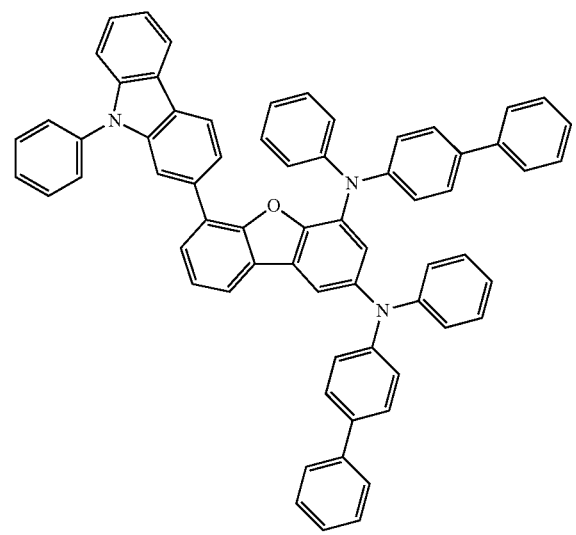

-continued
1-21
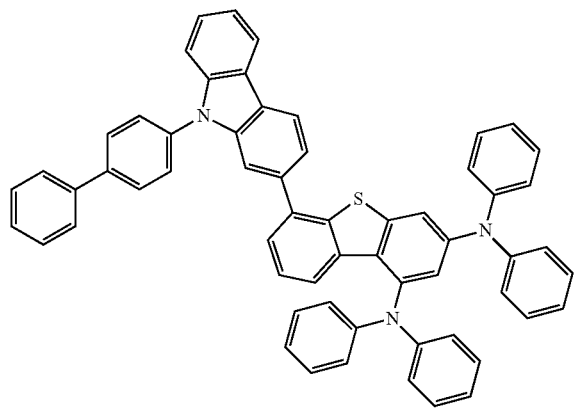
1-22
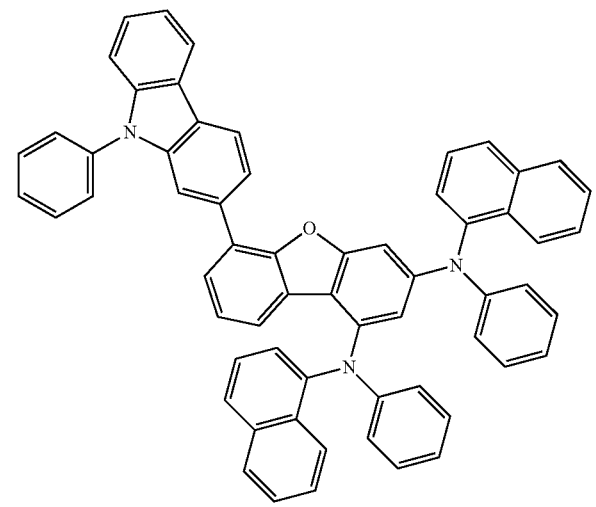
1-23
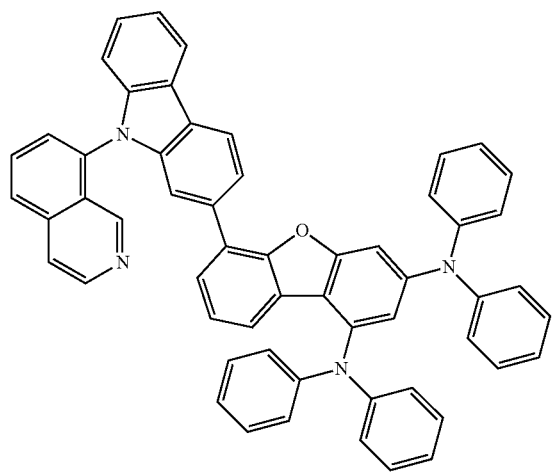
1-24
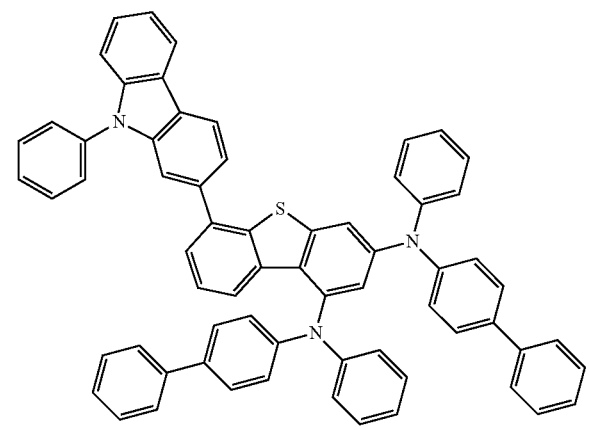
1-25
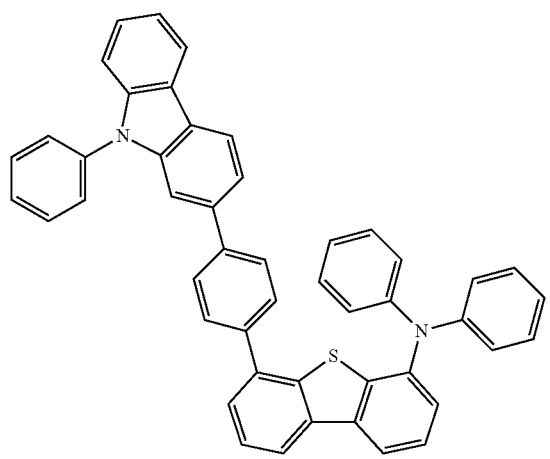
1-26
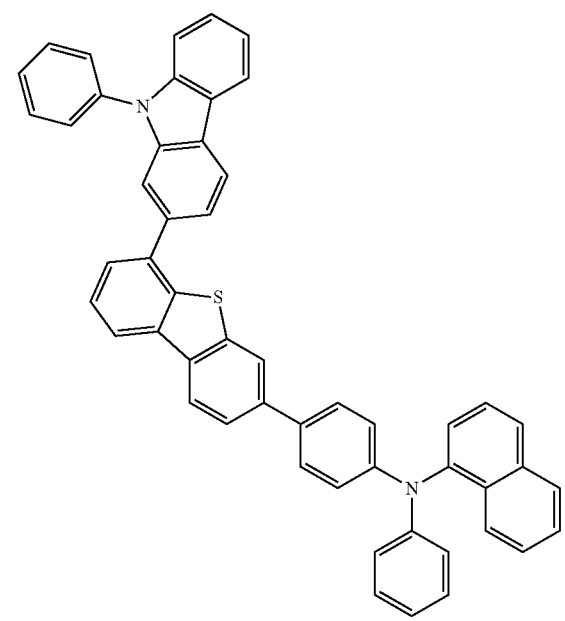

-continued
1-27
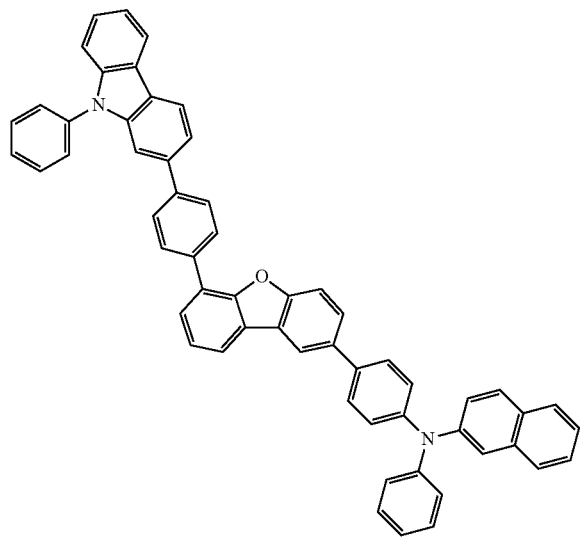
1-28
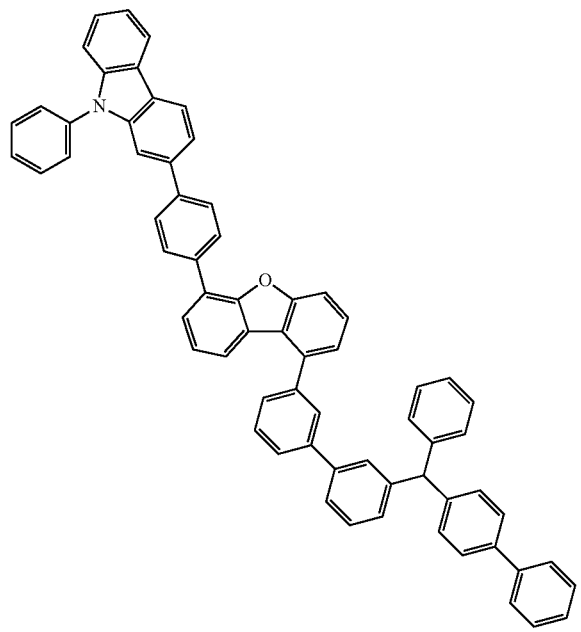
2-1
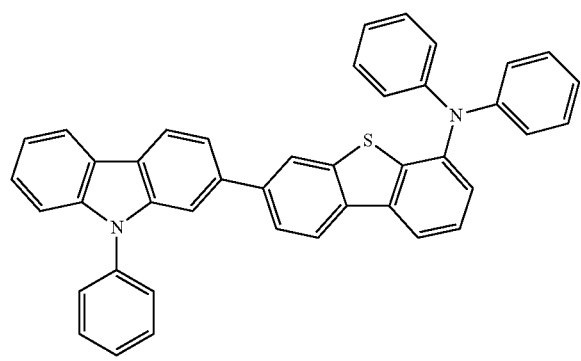
2-2
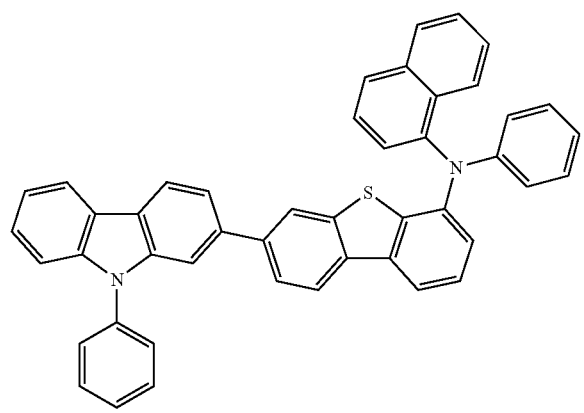
2-3
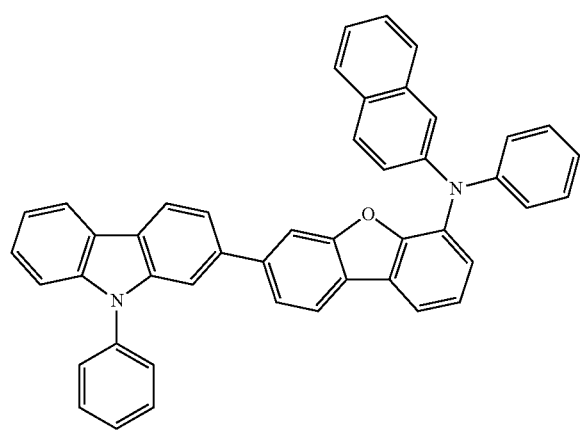
2-4
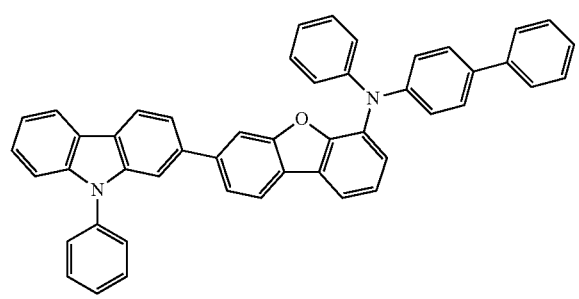

-continued
2-5
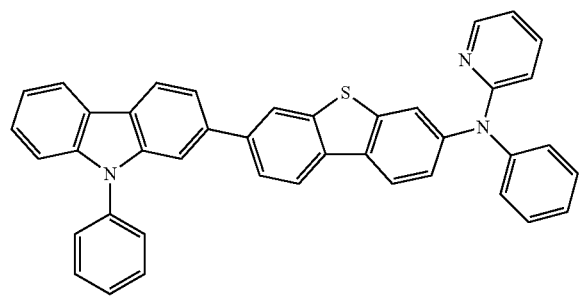
2-6
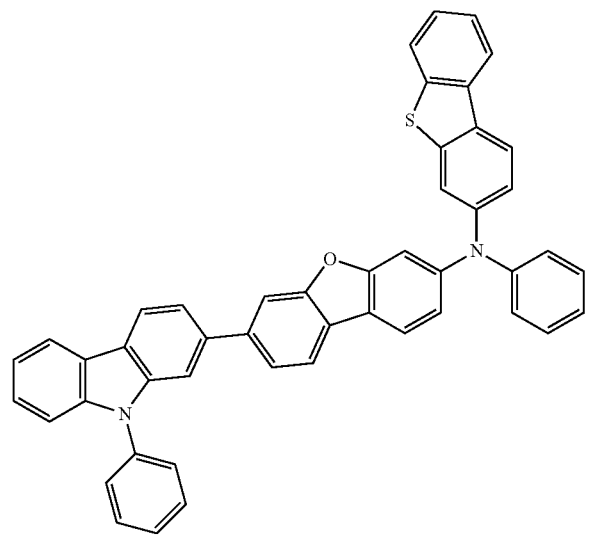
2-7
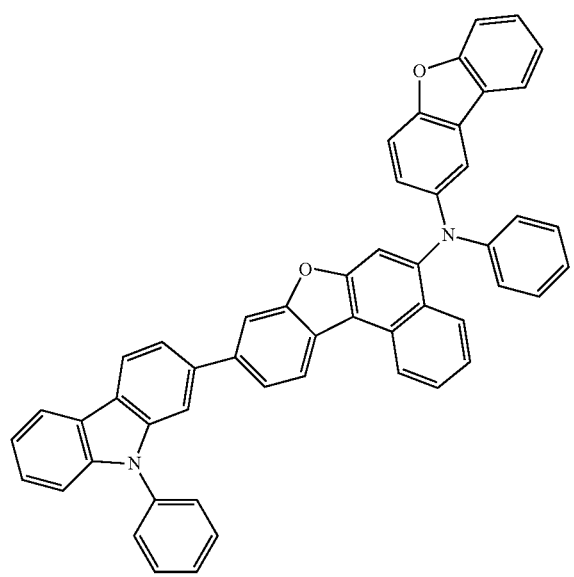
2-8
2-9
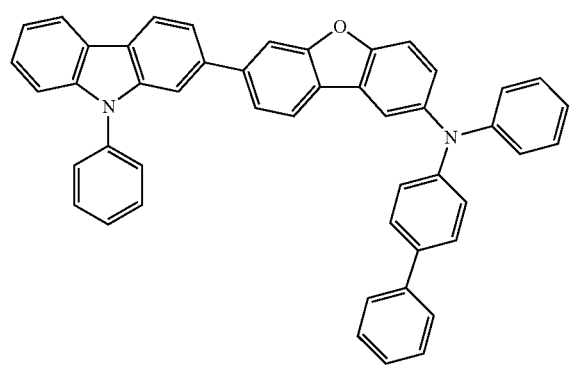
2-10
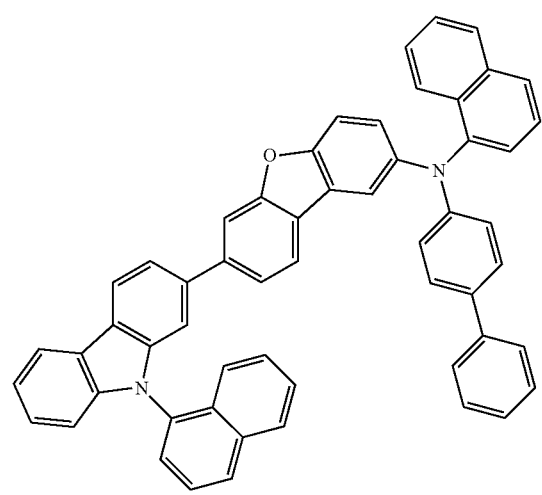

-continued
2-11
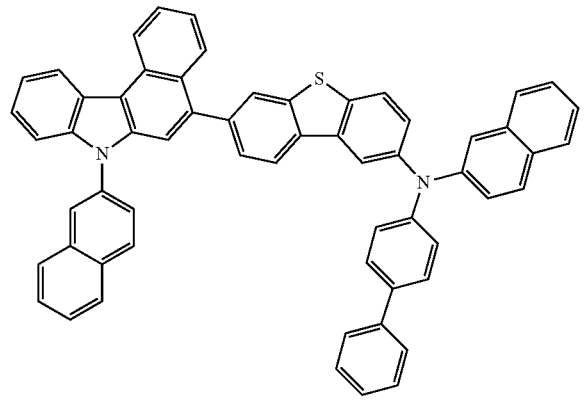
2-12
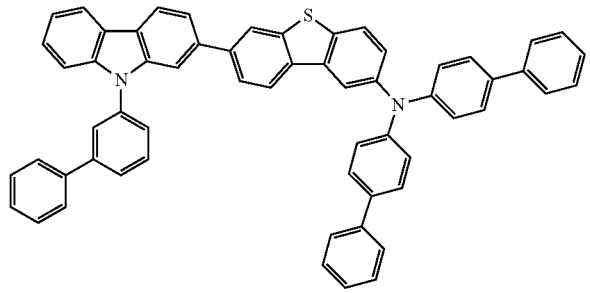
2-13
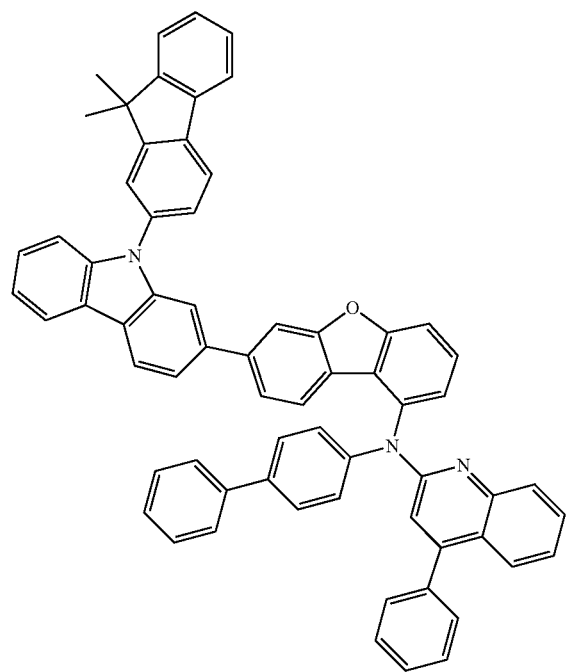
2-14
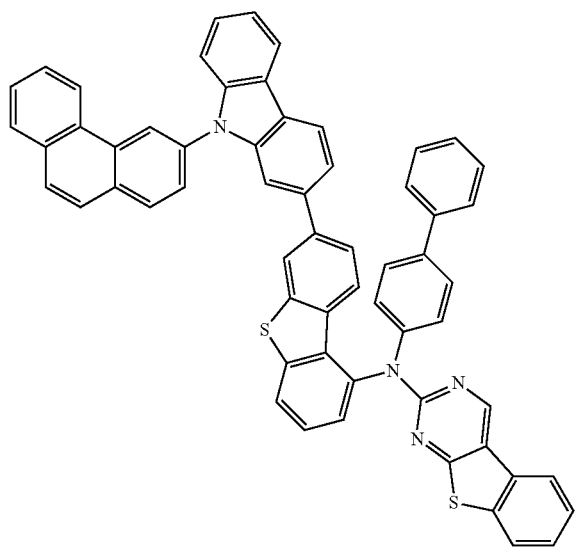

-continued
2-15
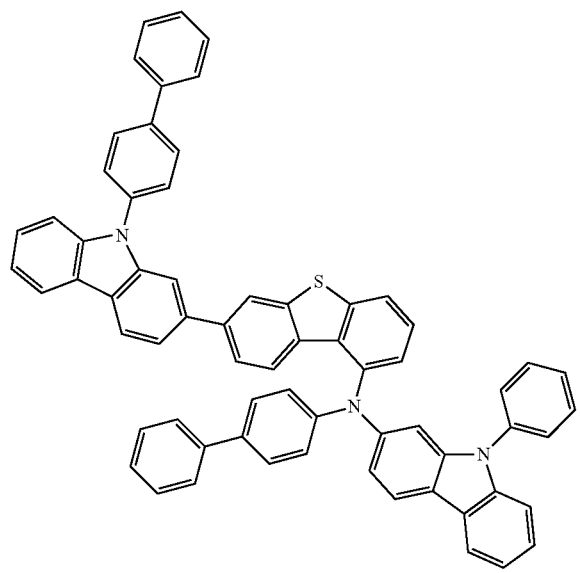
2-16
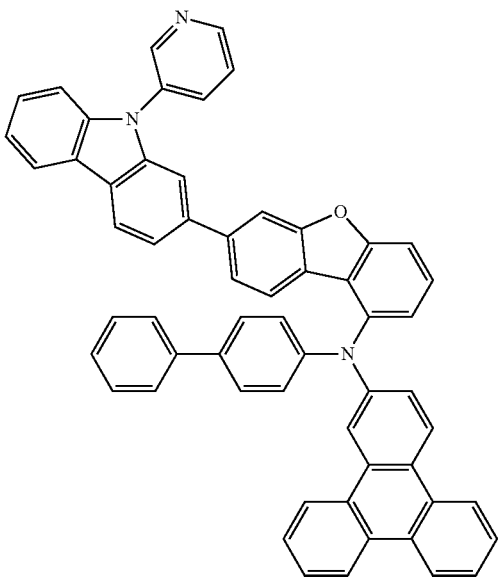
2-17
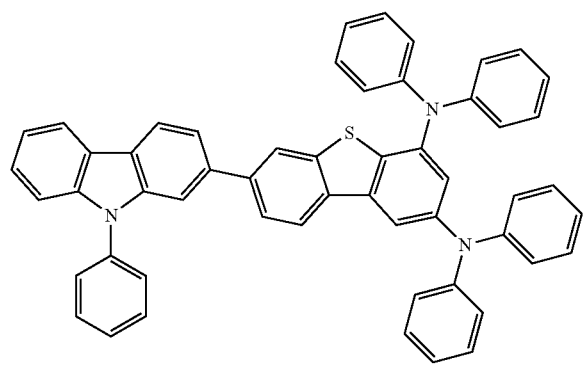
2-18
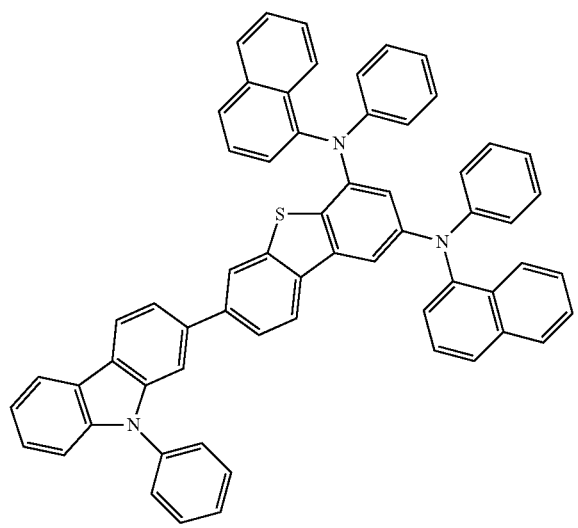

-continued
2-19
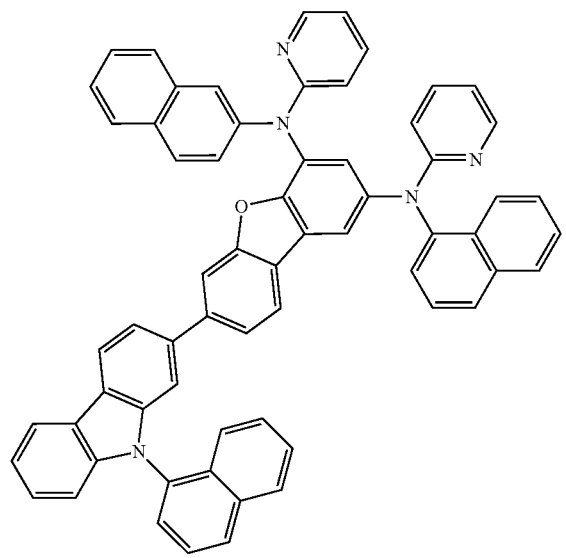
2-20
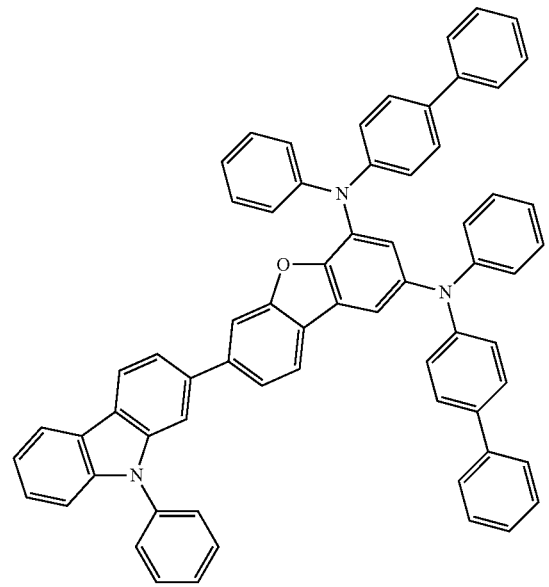
2-21
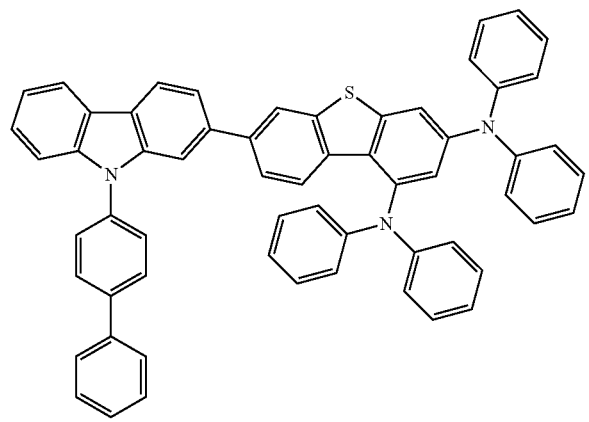
2-22
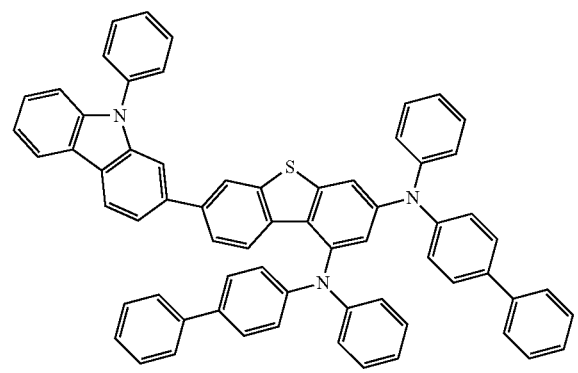
2-23
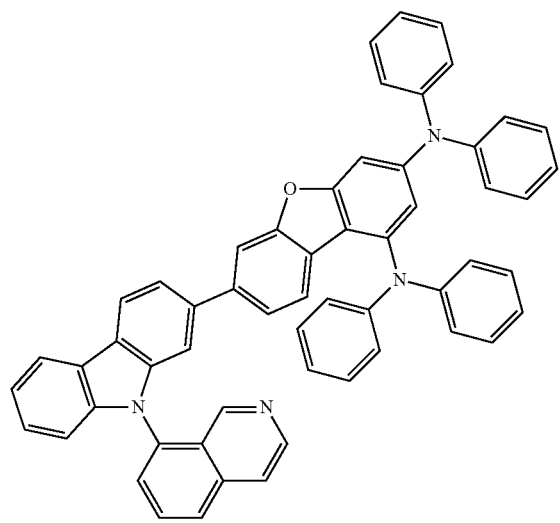
2-24

-continued
2-25
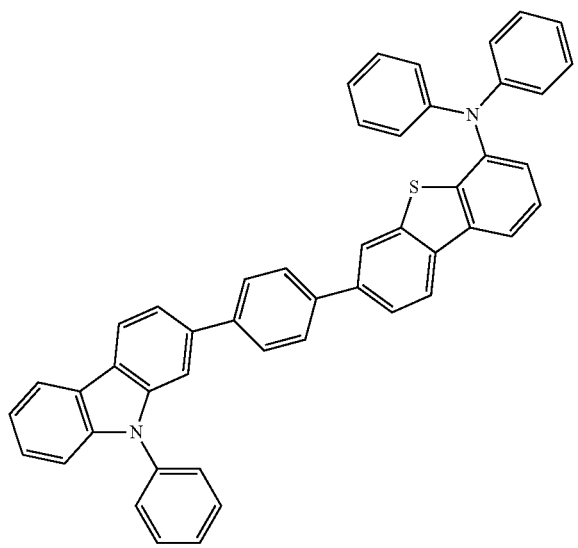
2-26
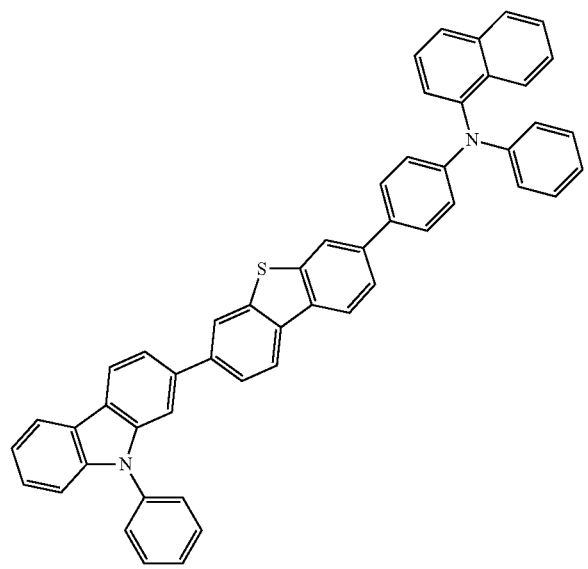
2-27
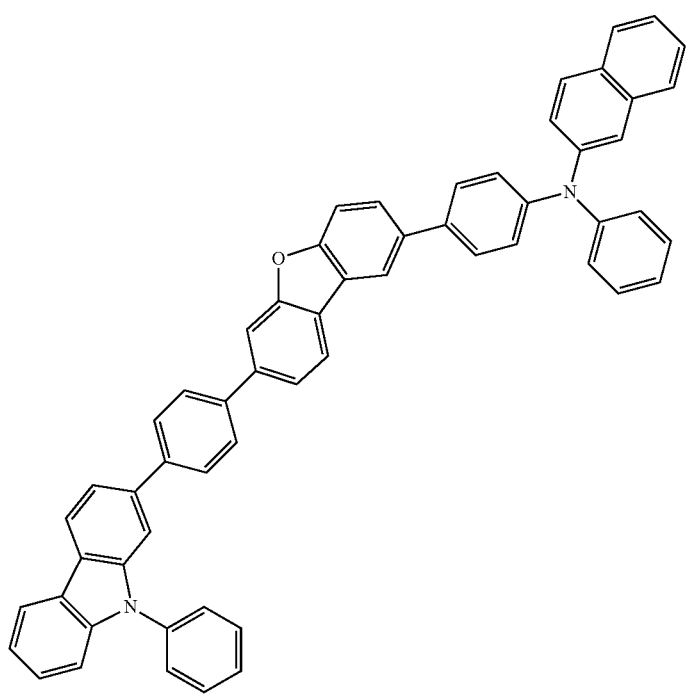

2-28
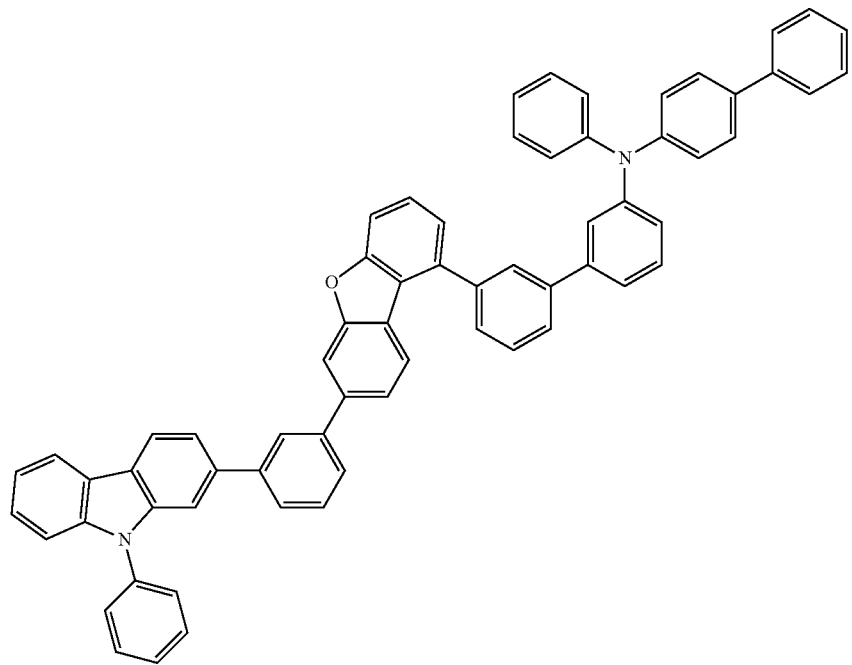
3-1
3-2
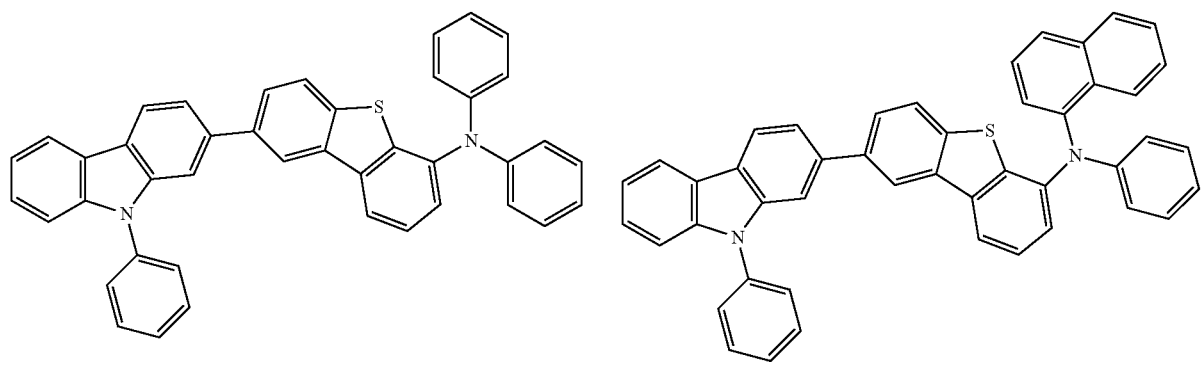
3-3
3-4
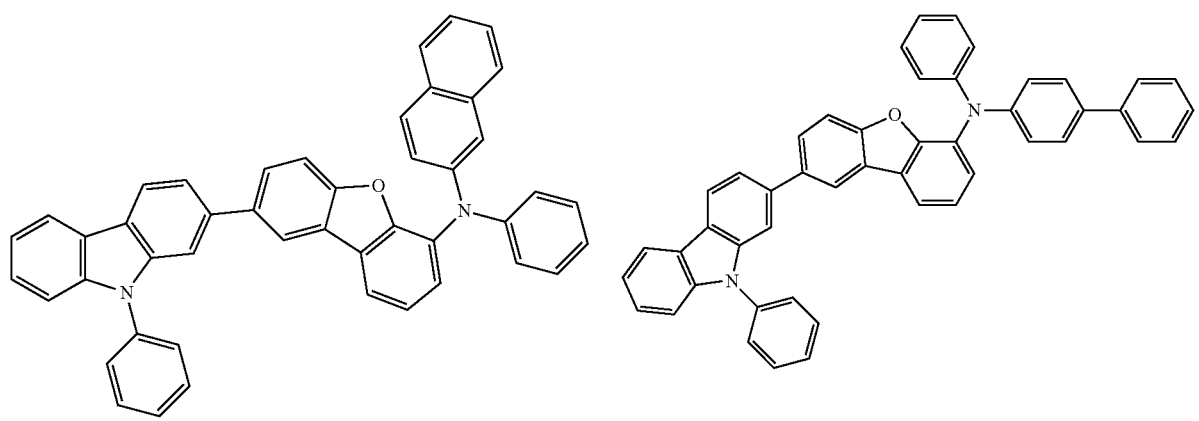

-continued
3-5
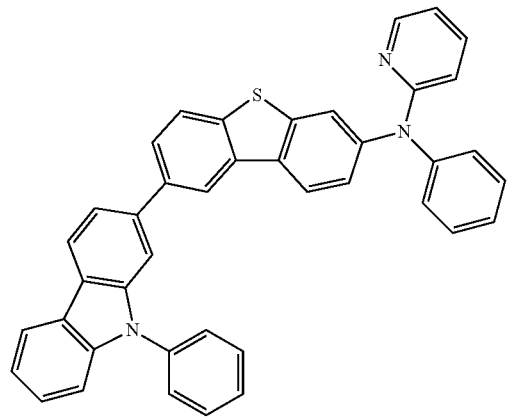
3-6
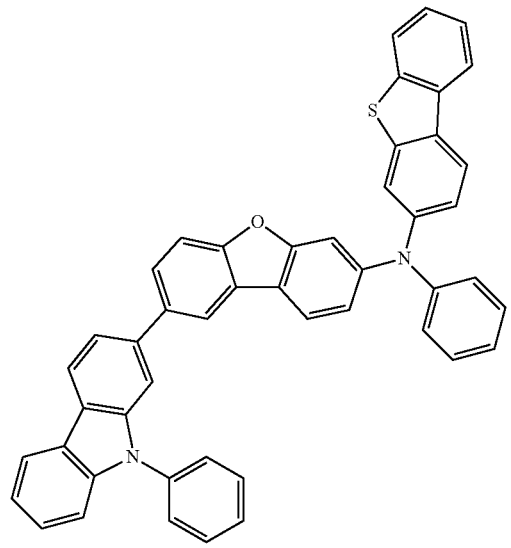
3-7
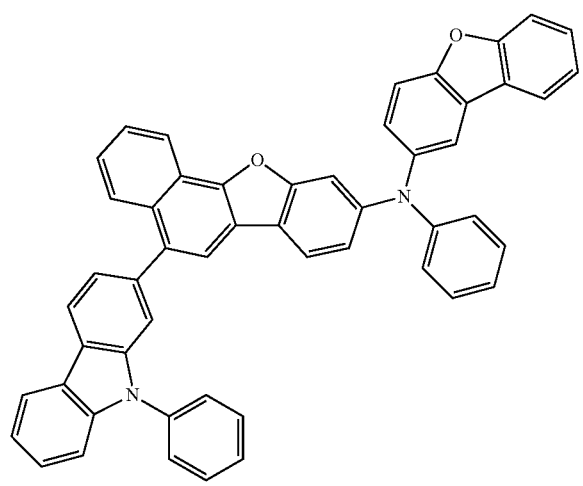
3-8
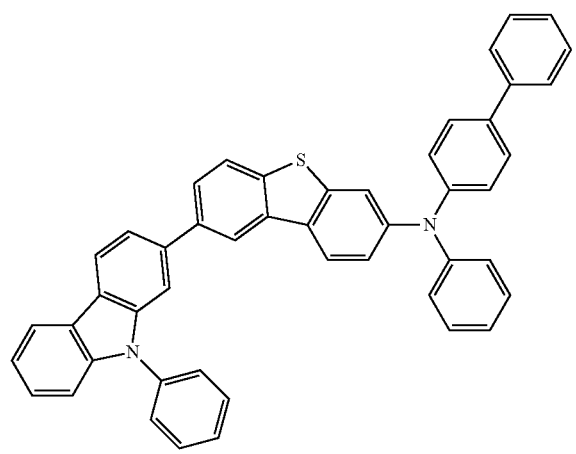
3-9
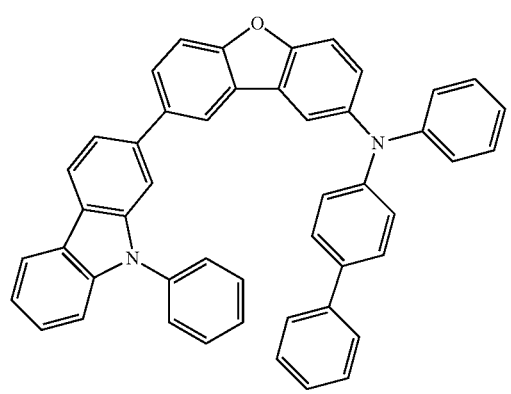
3-10
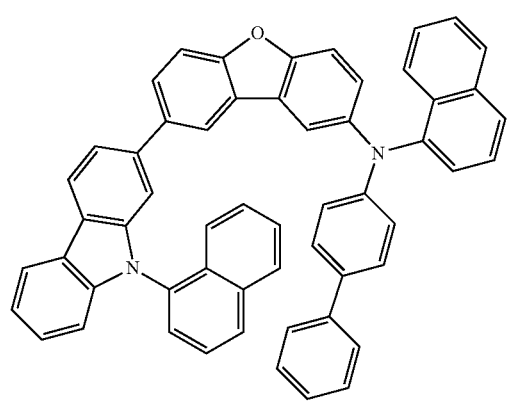

-continued
3-11
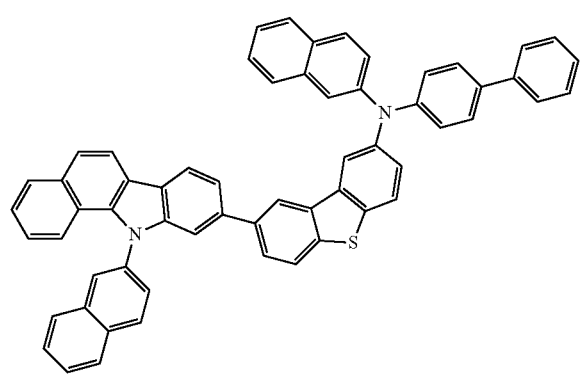
3-12
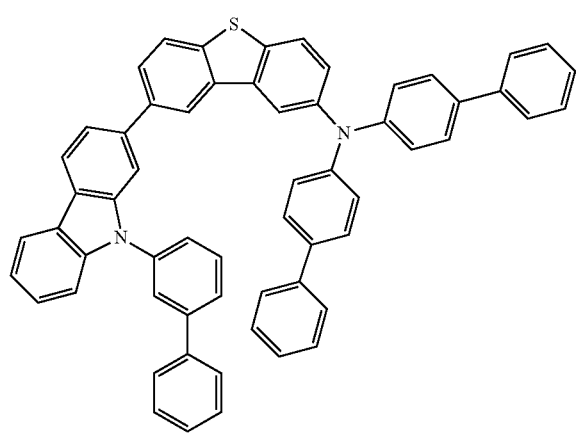
3-13
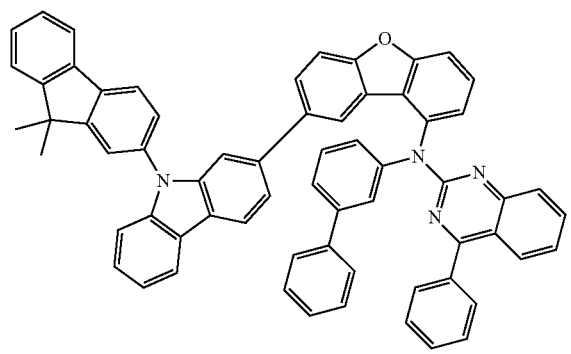
3-14
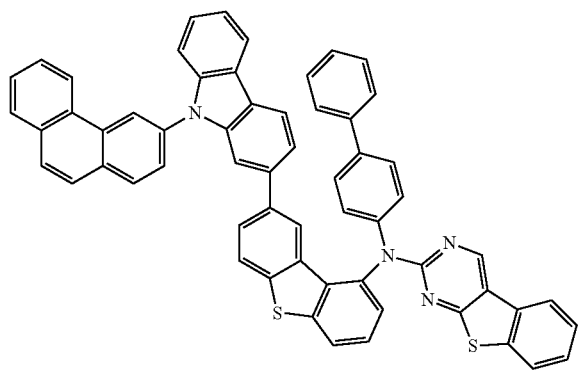
3-15
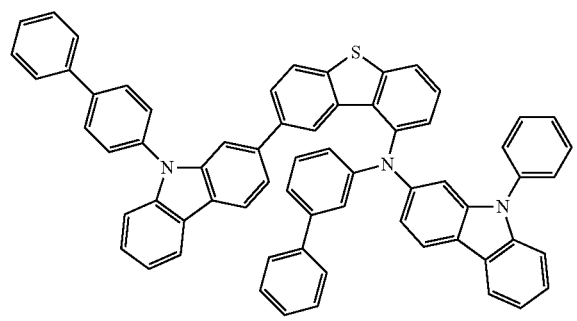
3-16
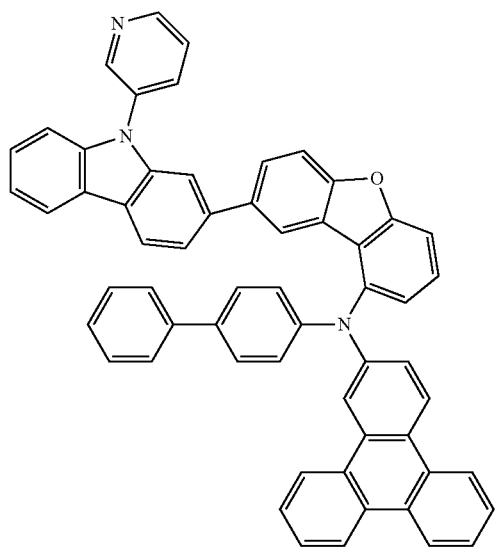

-continued
3-17
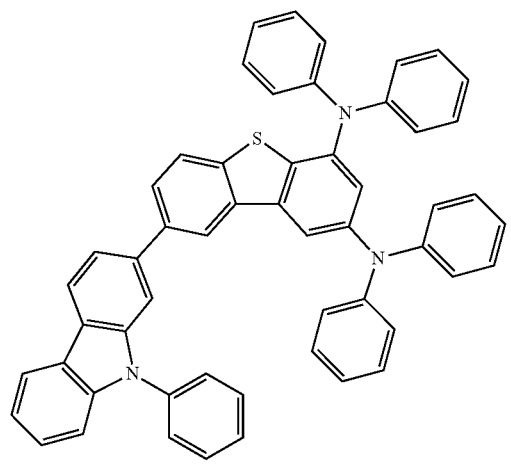
3-18
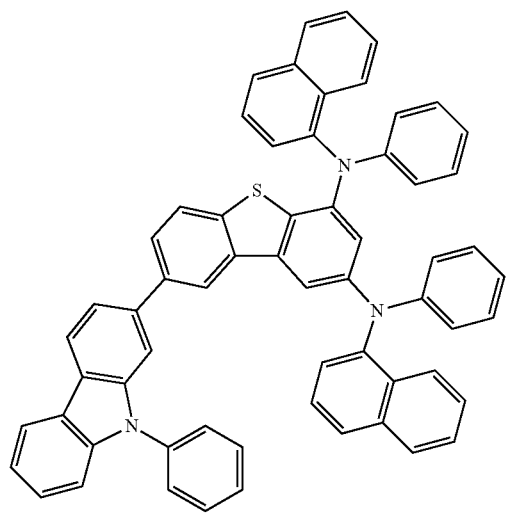
3-19
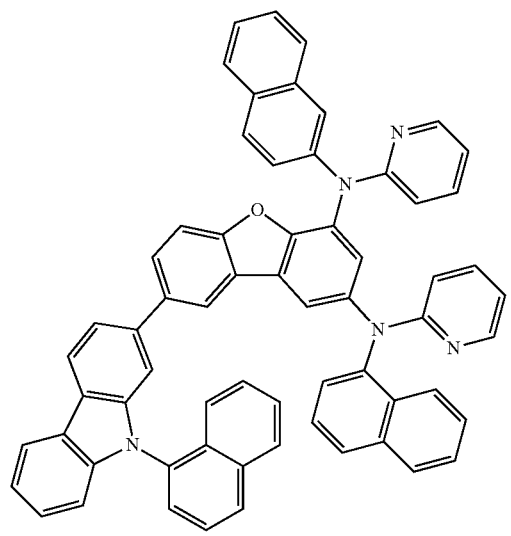
3-20
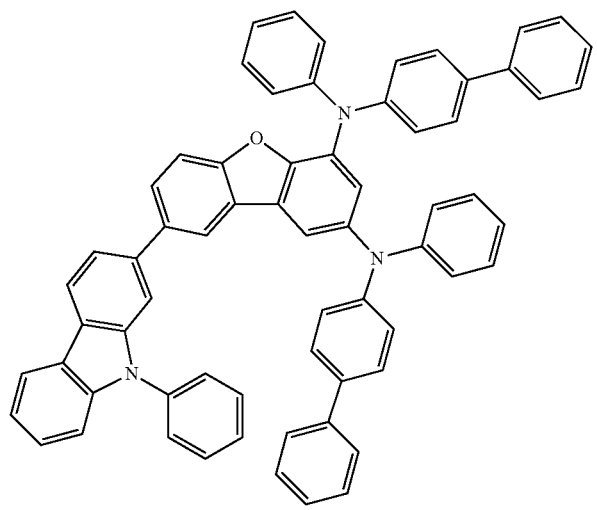
3-21
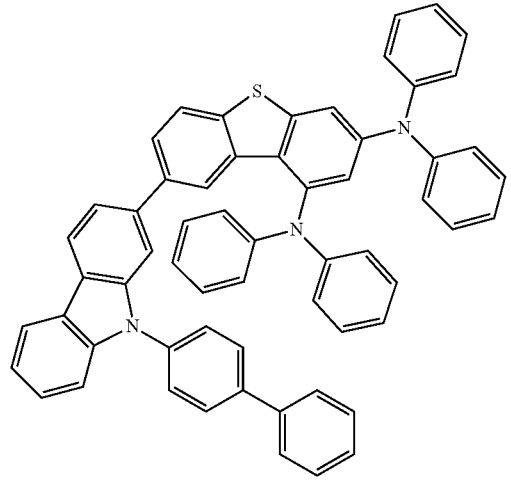
3-22
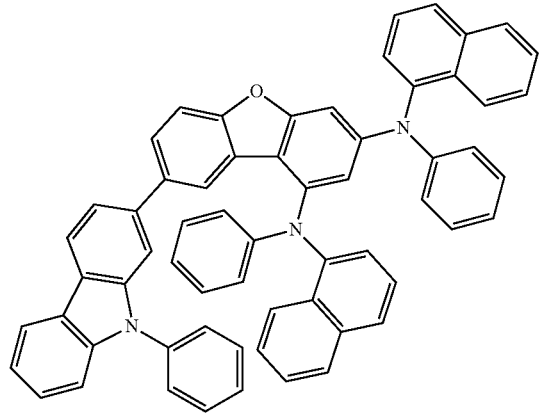

-continued
3-23
3-24
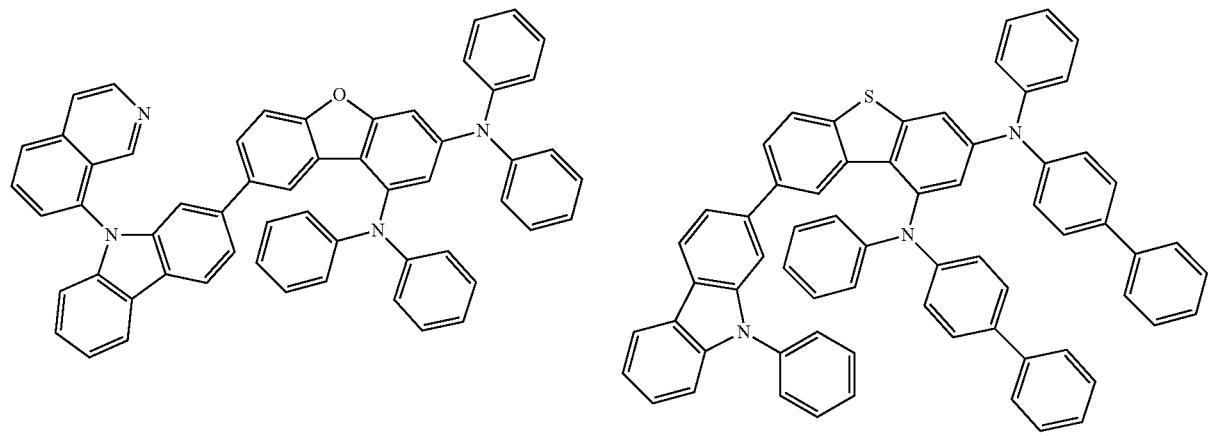
3-25
3-26
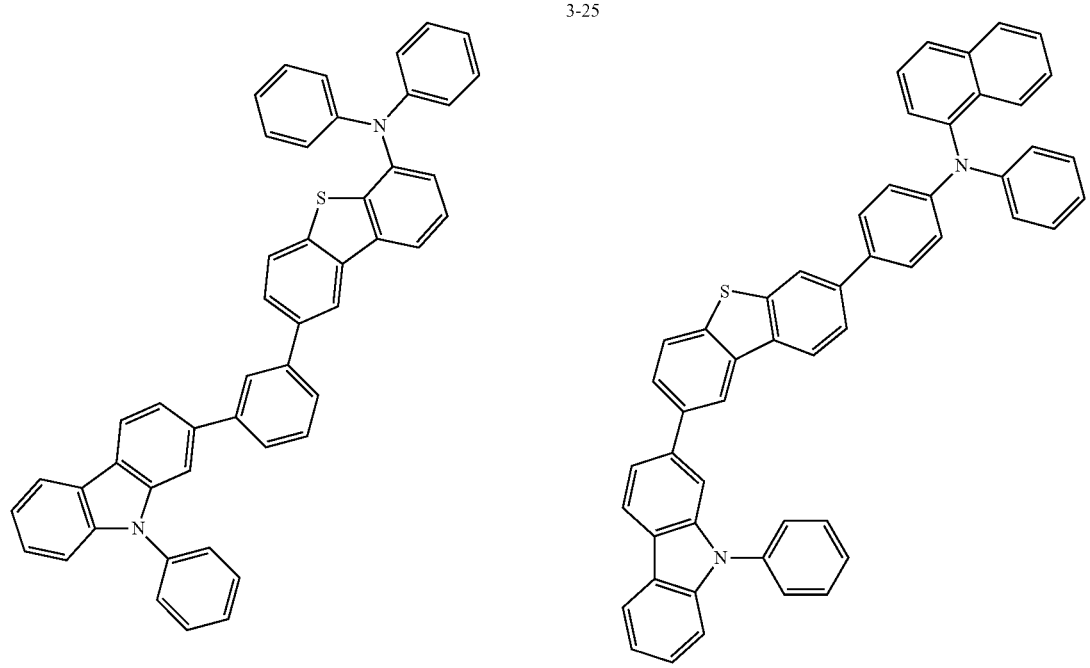

-continued
3-27
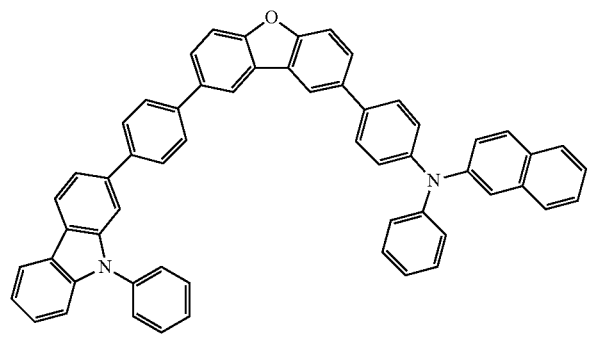
3-28
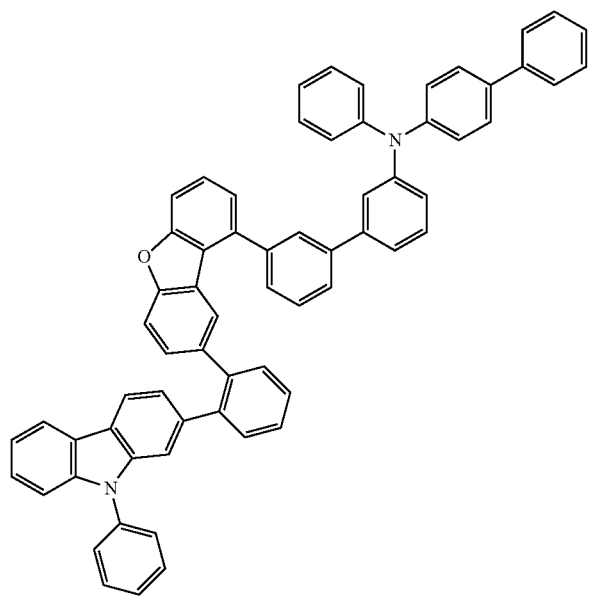
4-1
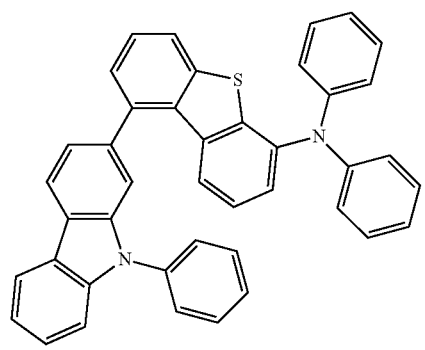
4-2
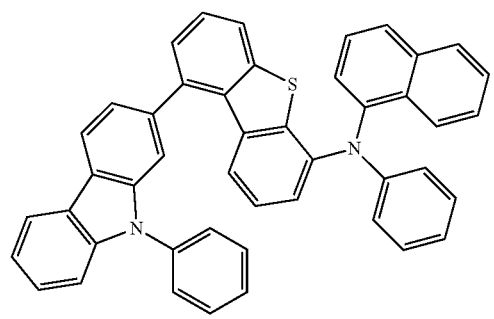
4-3
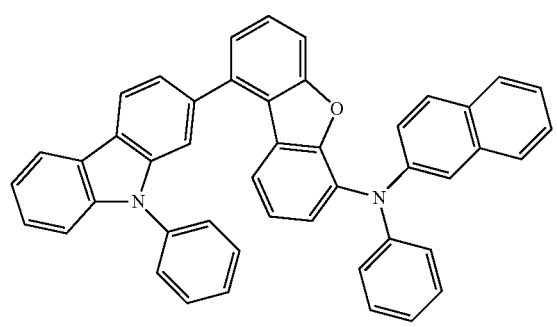
4-4
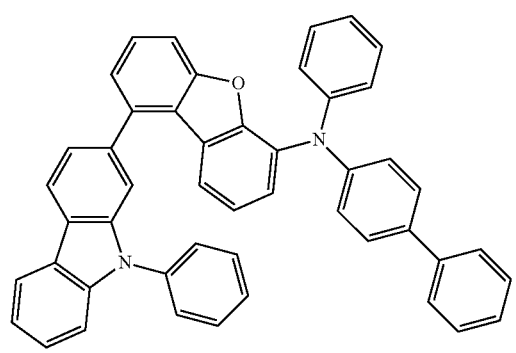

4-5
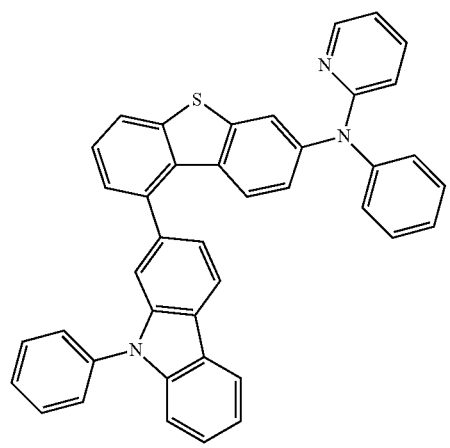
4-6
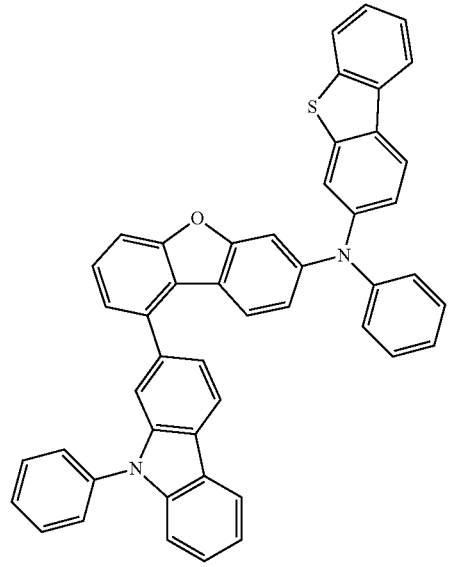
4-7
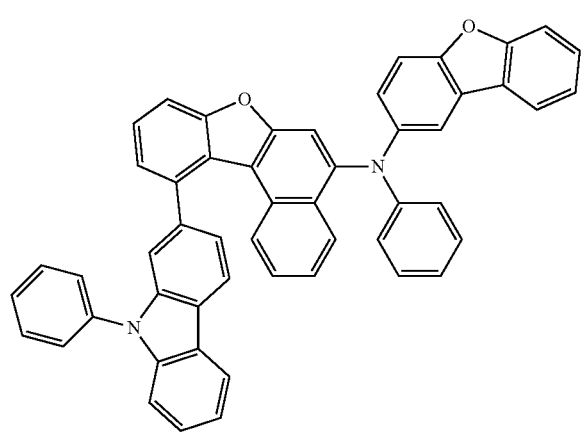
4-8
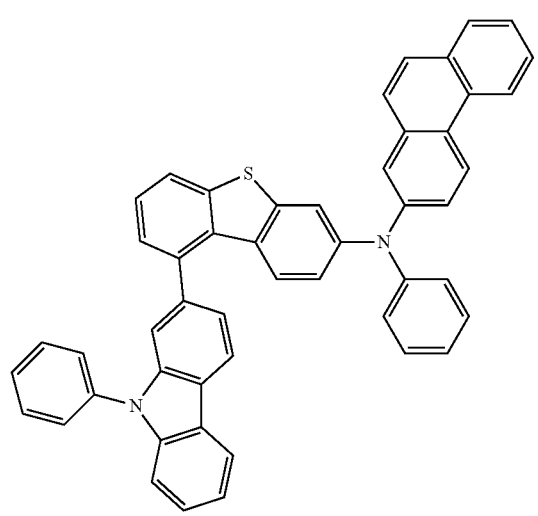
4-9
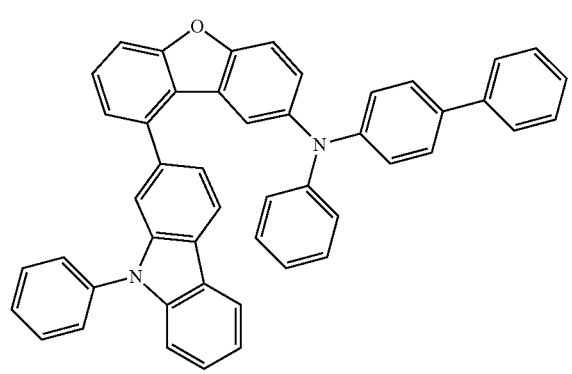
4-10
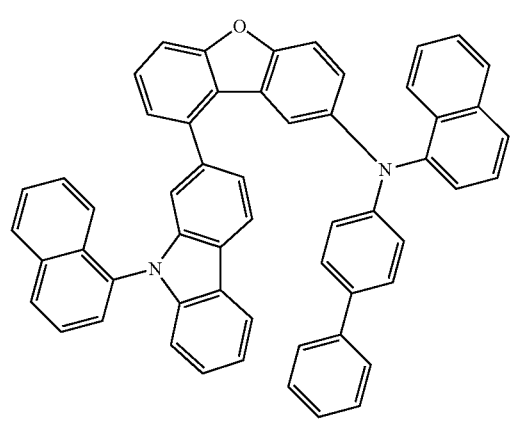

-continued
4-11
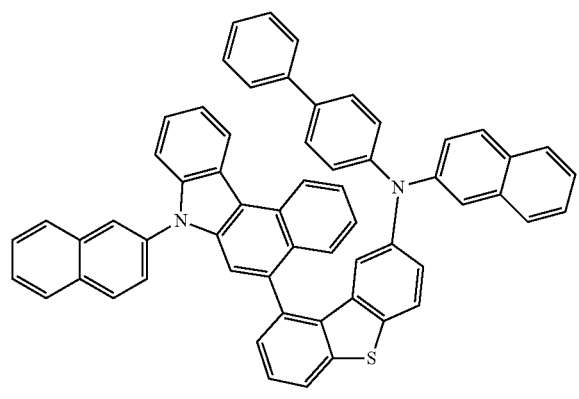
4-12
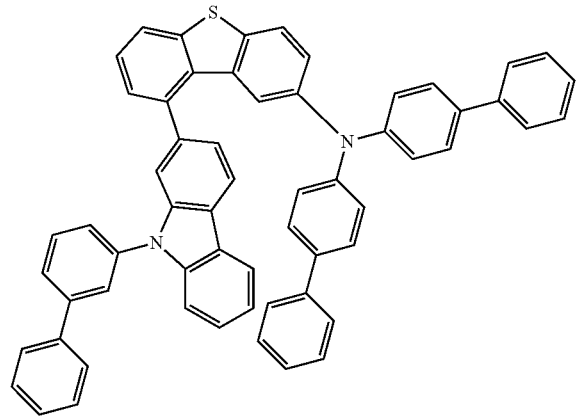
4-13
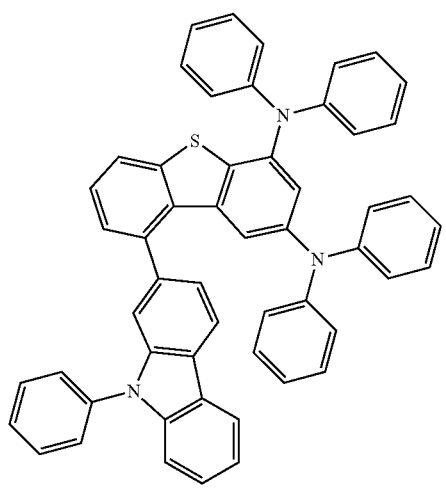
4-14
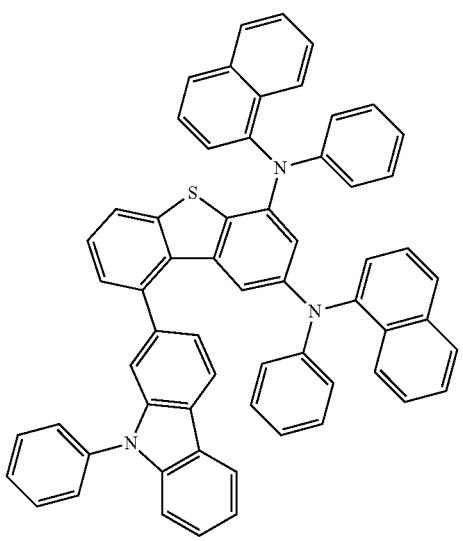
4-15
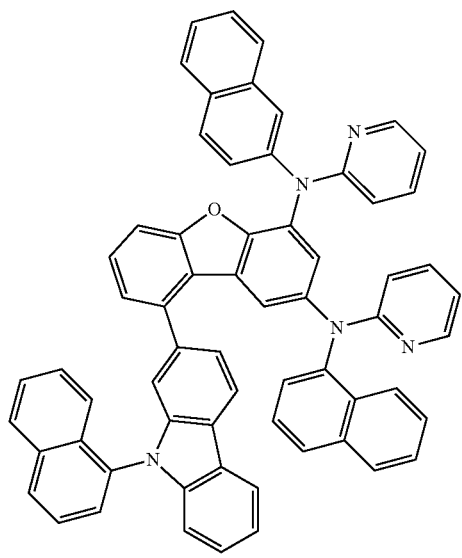
4-16
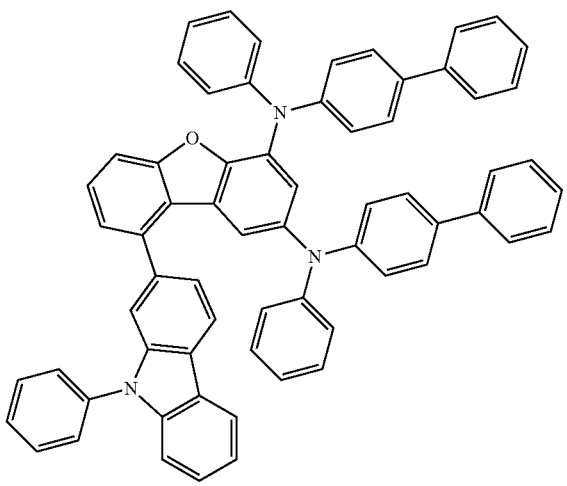

-continued 4-17
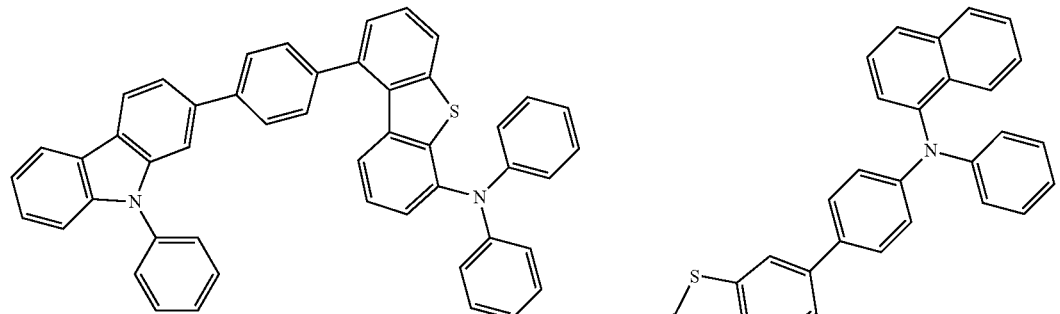

4-18
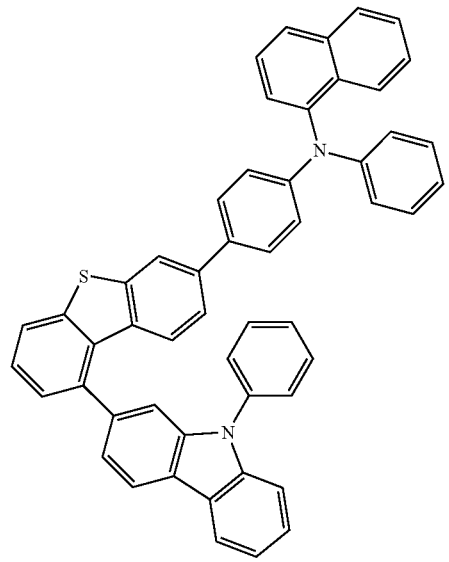

4-19
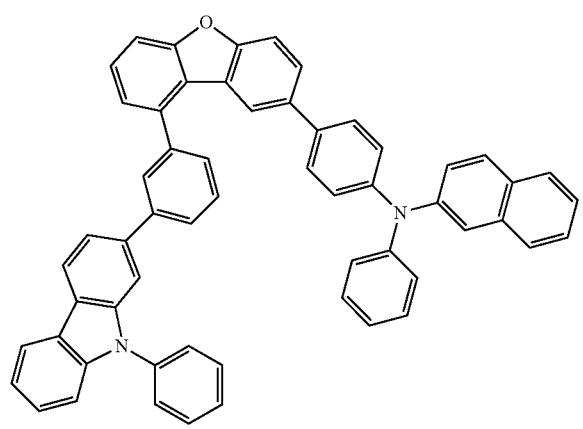

4-20
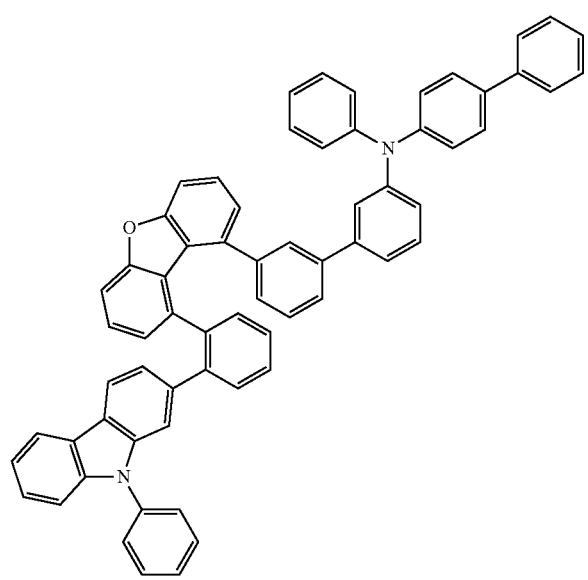

Also, the present invention provides an organic electric element comprising a first electrode, a second electrode and an organic material layer formed between the first electrode and the second electrode, wherein the organic electric element comprises an hole transport layer formed between the first electrode and the emitting layer, and an emitting auxiliary layer formed between the hole transport layer and the emitting layer, wherein the emitting auxiliary layer includes a compound represented by Formula (1), and wherein the hole transport layer includes a compound represented by Formula (13).

Formula (1)
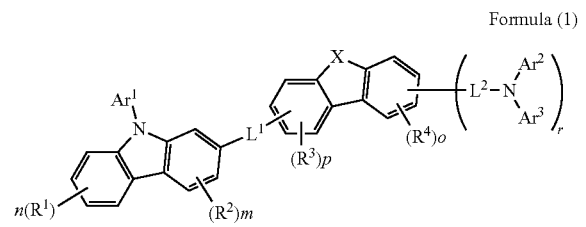

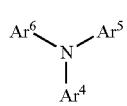

Formula (13)

{In Formula (1) or Formula (13),
$R^1$, $R^2$, $R^3$, $R^4$, m, n, o, p, $L^1$, $L^2$, $Ar^1$, $Ar^2$, and $Ar^3$ are the same as defined above, 1) $Ar^4$ and $Ar^5$ are each independently selected from the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$); or $Ar^4$ and $Ar^5$ may be bonded to each other to form a ring, 2) $Ar^6$ is at least any one of the following Formulas (2-a), (2-b) and (2-c),

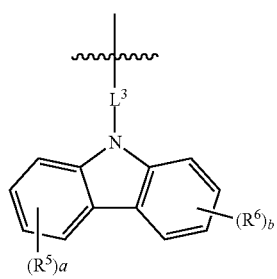

Formula (2-a)

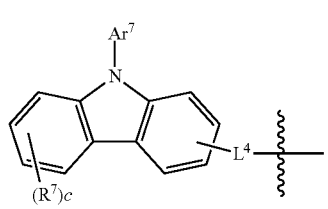

Formula (2-b)

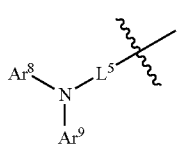

Formula (2-c)

3) a, b, and c are integers of 0 to 4, and $R^5$, $R^6$ and $R^7$ are the same or different and are each independently selected from a deuterium; a halogen; the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$); or in case a, b and c are 2 or more, and $R^5$, $R^6$ and $R^7$ are each in plural and are the same or different, or a plurality of $R^5$ or a plurality of $R^6$ or a plurality of $R^7$ may be bonded to each other to form a ring, 4) $L^3$ and $L^5$ are each independently selected from the group consisting of a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic group including at least one hetero atom of O, N, S, Si or P;

5) $L^4$ is selected from a single bond of $C_6$-$C_{60}$; an arylene group; a fluorenylene group; a fused ring group of a $C_3$-$C_{60}$ aliphatic ring and a $C_6$-$C_{60}$ aromatic ring; and a $C_2$-$C_{60}$ heterocyclic group including at least one hetero atom of O, N, S, Si or P;

6) where, L' may be selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic, and the $R_a$ and $R_b$ may be independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, or P;

7) $Ar^7$, $Ar^8$ and $Ar^9$ are each independently selected from the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring;

Here, the aryl group, the fluorenyl group, the arylene group, the heterocyclic group, the fused ring group, the alkyl group, the alkenyl group, the alkoxy group and the aryloxy group may be each substituted with one or more substituents selected from a group consisting of a deuterium; halogen; a silane group substituted or unsubstituted with a $C_1$-$C_{20}$ alkyl group or a $C_6$-$C_{60}$ aryl group; a siloxane group; a boron group; a germanium group; a cyano; a nitro group; -L'-N($R_a$)($R_b$); a $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group and $C_8$-$C_{20}$ arylalkenyl group, and also, these substituents may be bonded to each other to form a ring, wherein the term 'ring' means $C_3$-$C_{60}$ aliphatic ring or $C_6$-$C_{60}$ aromatic ring or a $C_2$-$C_{60}$ heterocyclic ring or a fused ring formed by the combination of them, and includes a saturated or unsaturated ring.}

As another example of the present invention, the compound represented by Formula (13) comprises any one of compounds represented by the following Formulas (13-1) to (13-71).

55      56
13-1
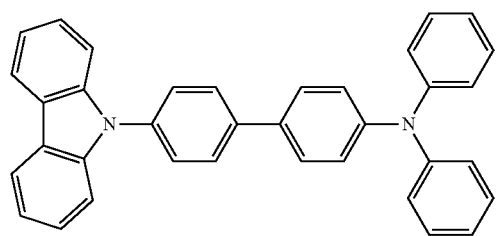
13-2
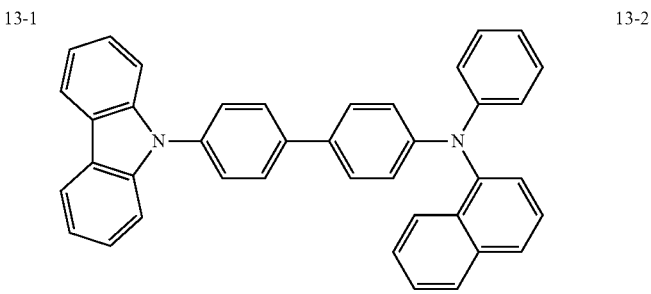
13-3
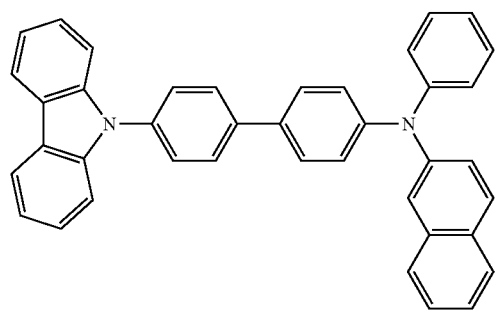
13-4
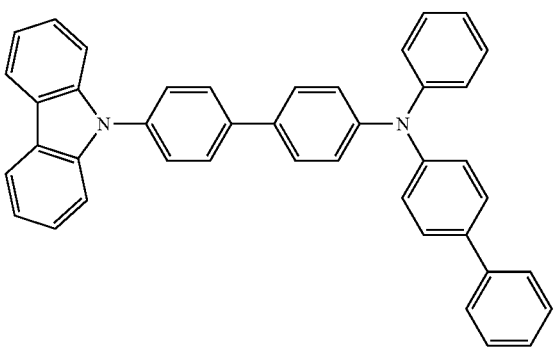
13-5
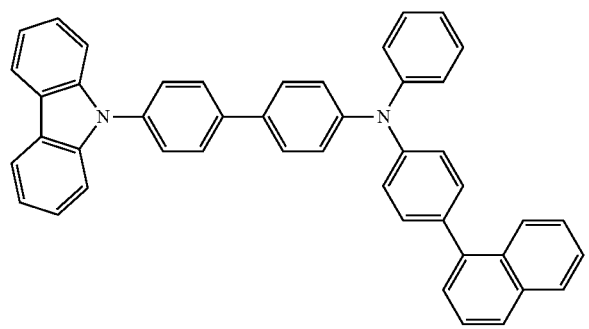
13-6
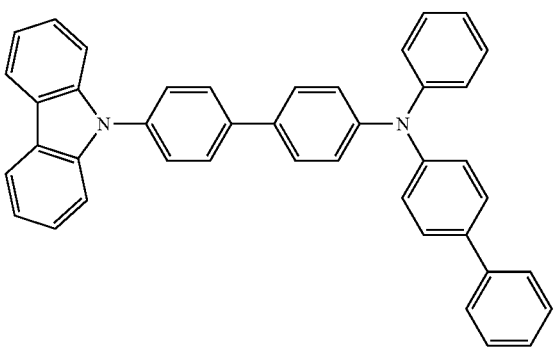
13-7
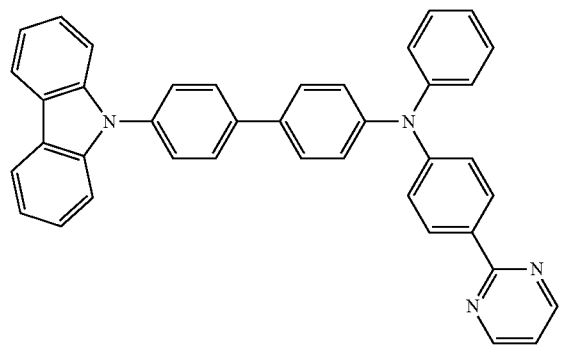
13-8
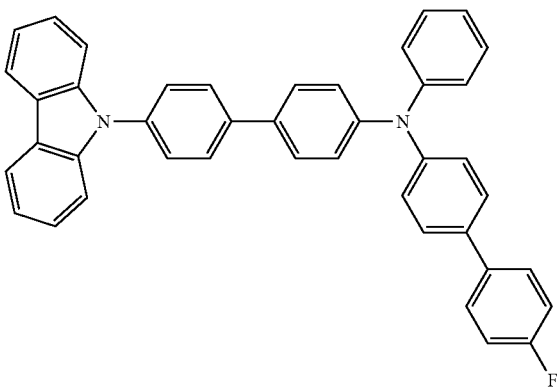

-continued
13-9
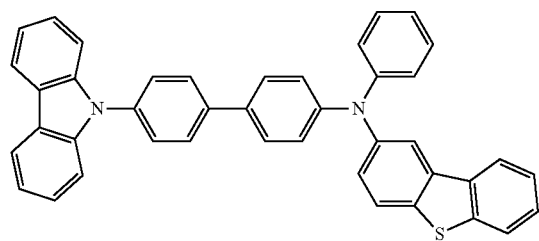
13-10
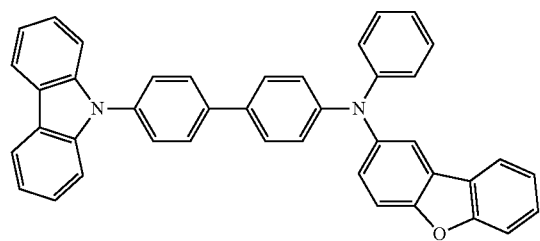
13-11
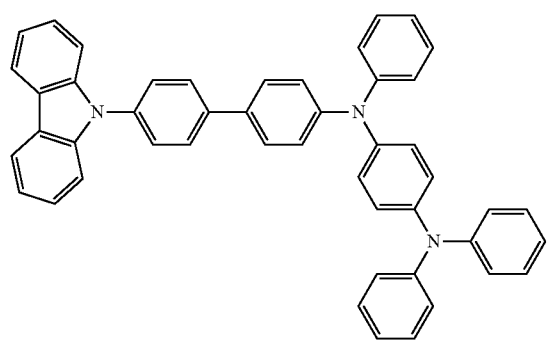
13-12
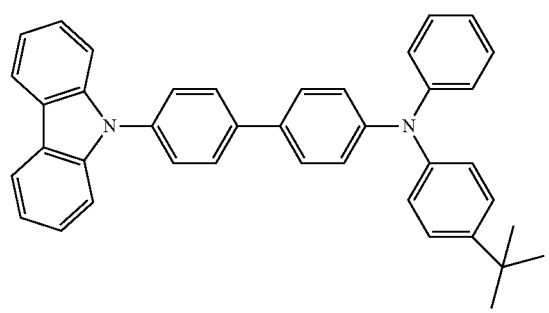
13-13
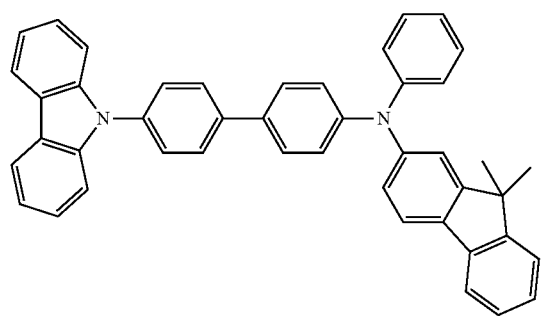
13-14
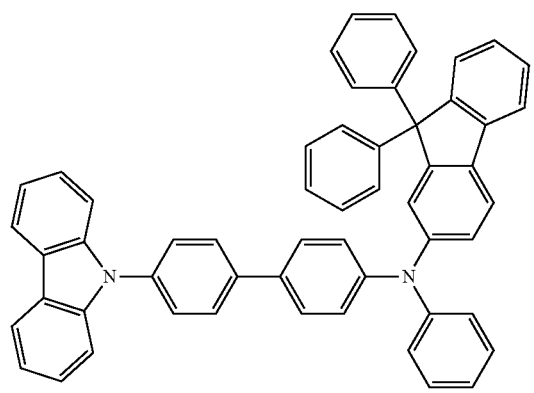
13-15
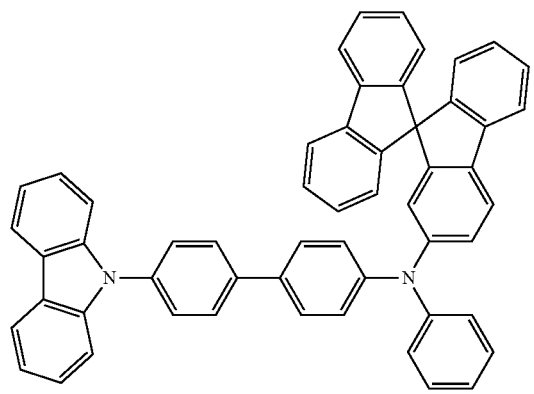
13-16
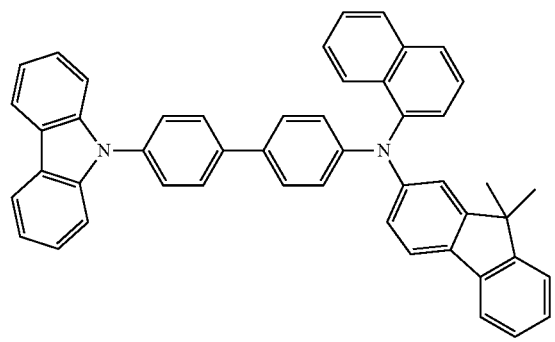

-continued
13-17
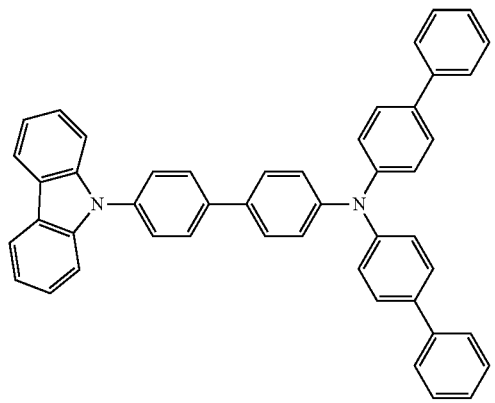
13-18
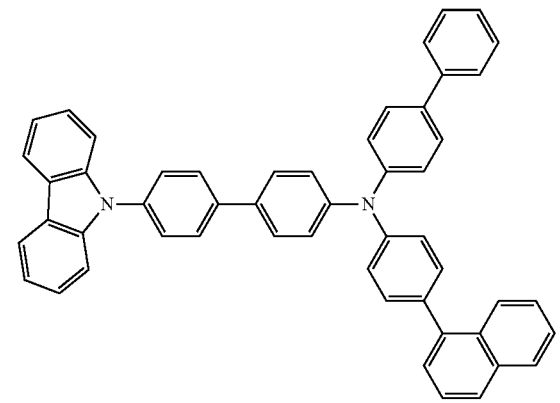
13-19
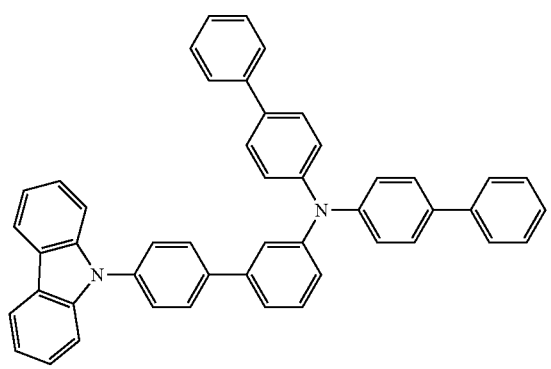
13-20
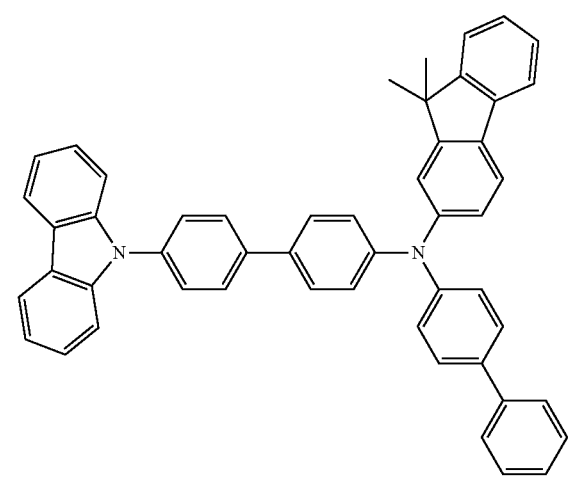
13-21
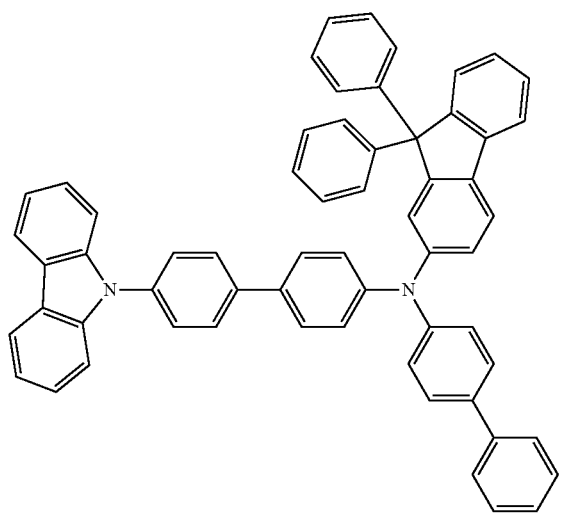
13-22
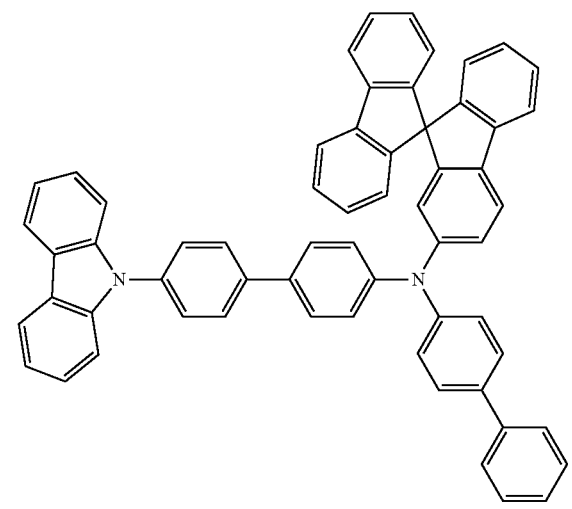

-continued
13-23
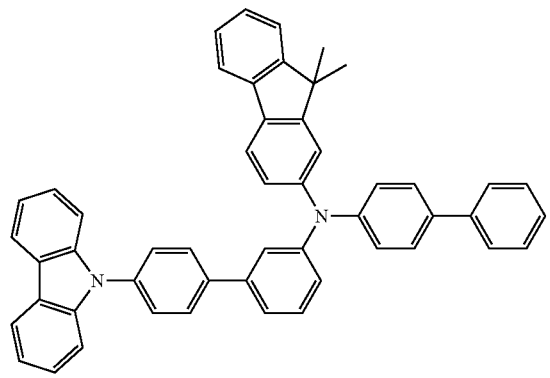
13-24
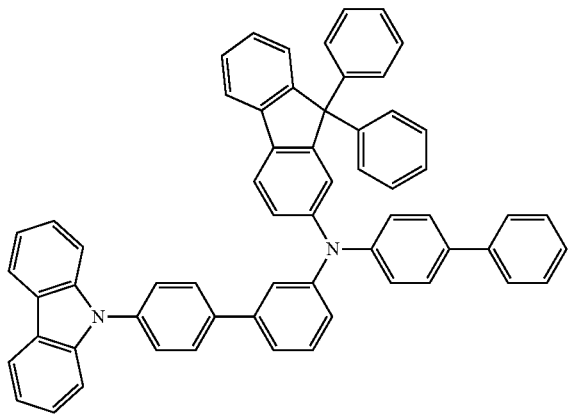
13-25
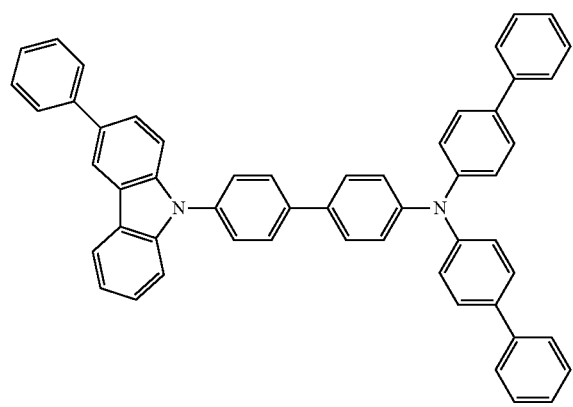
13-26
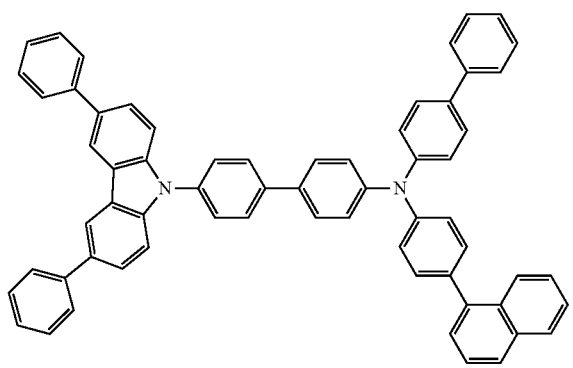
13-27
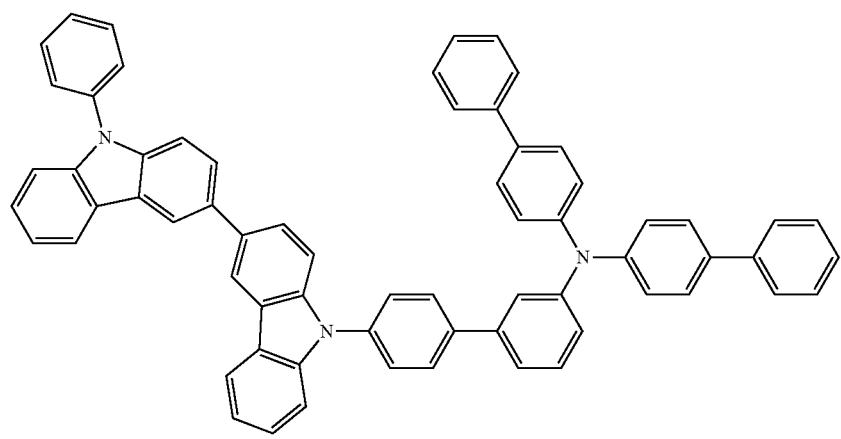

13-28
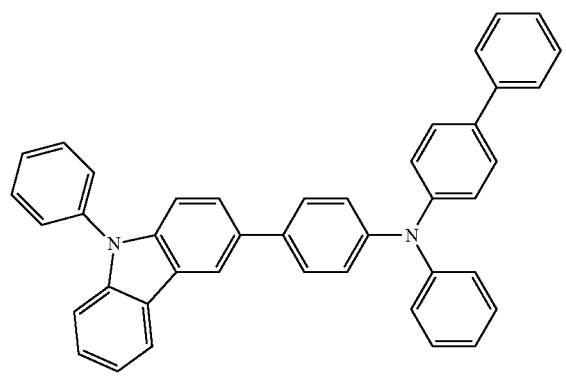
13-29
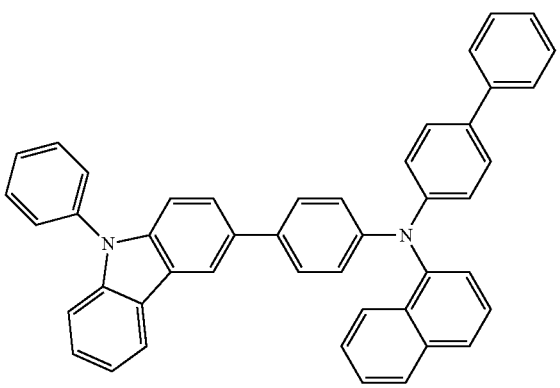
13-30
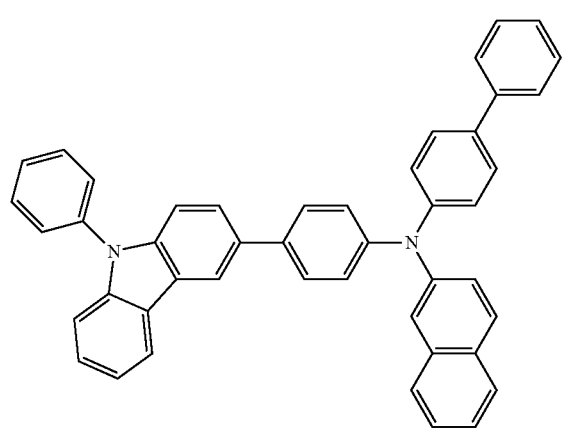
13-31
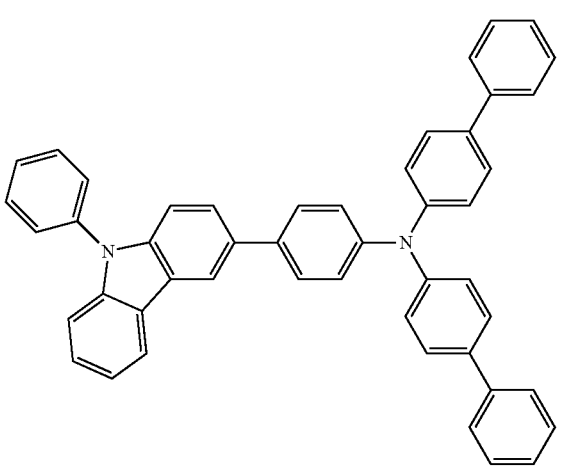
13-32
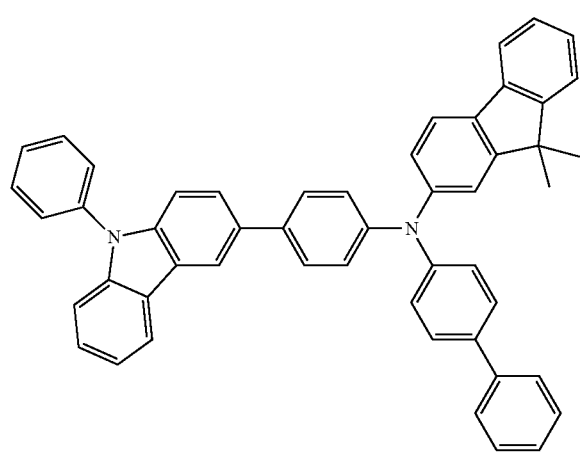
13-33
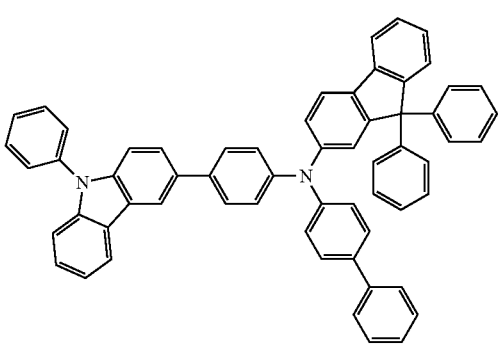

-continued
13-34
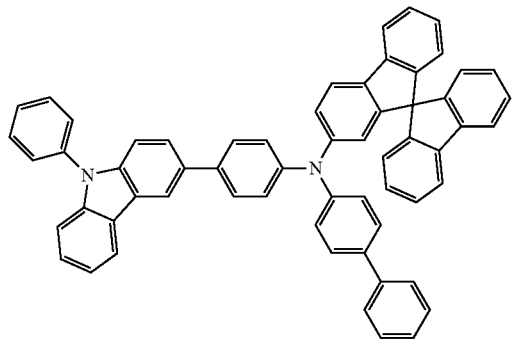
13-35
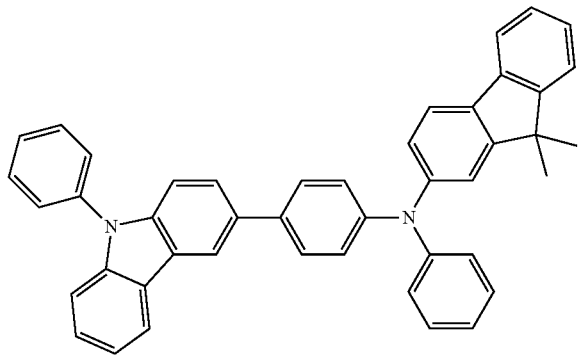
13-36
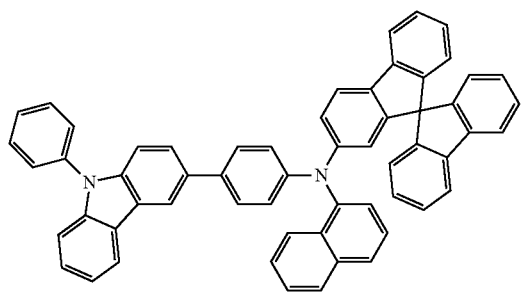
13-37
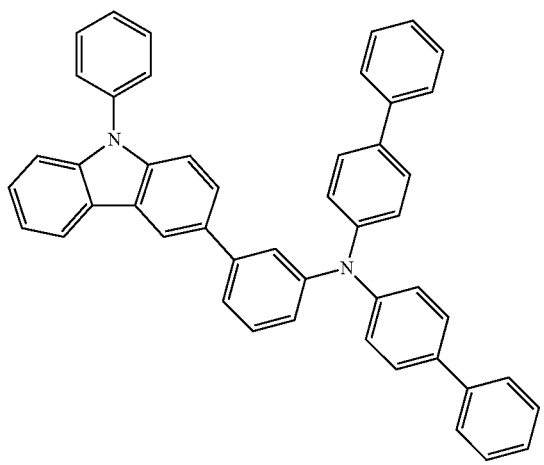
13-38
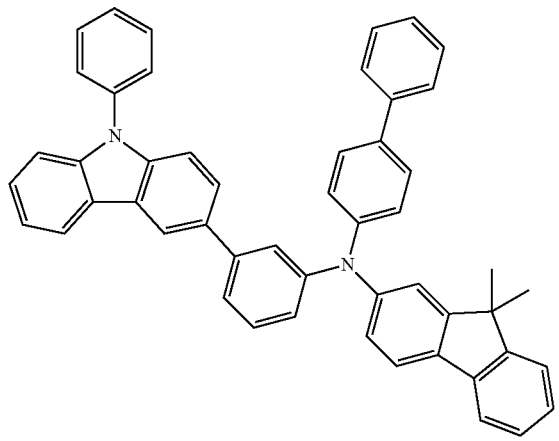
13-39
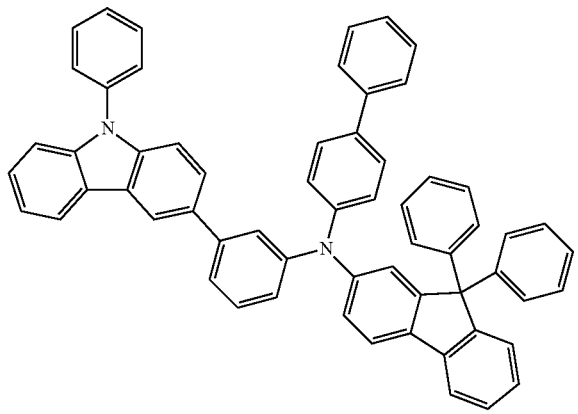
13-40
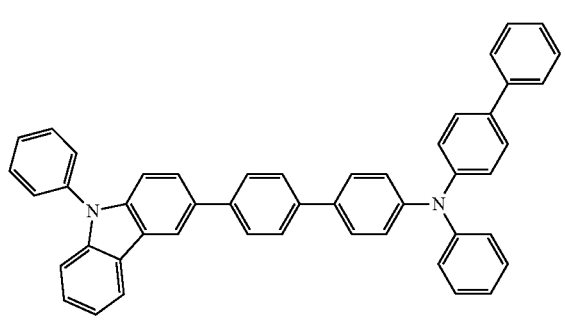
13-41
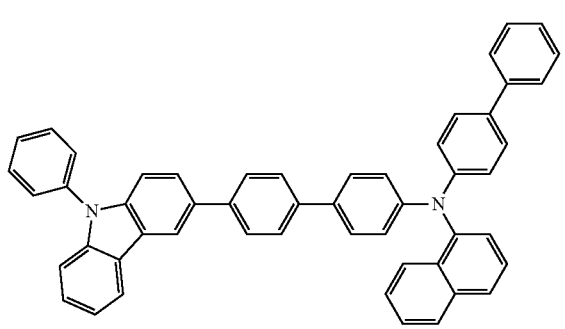

-continued
13-42
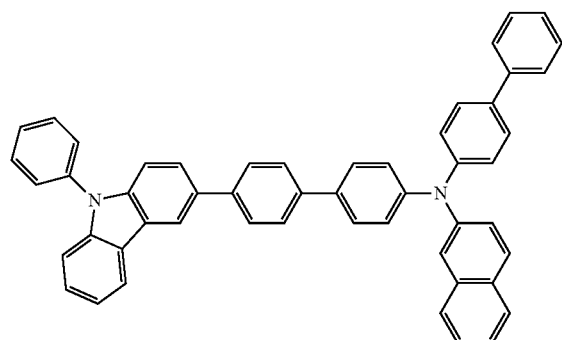
13-43
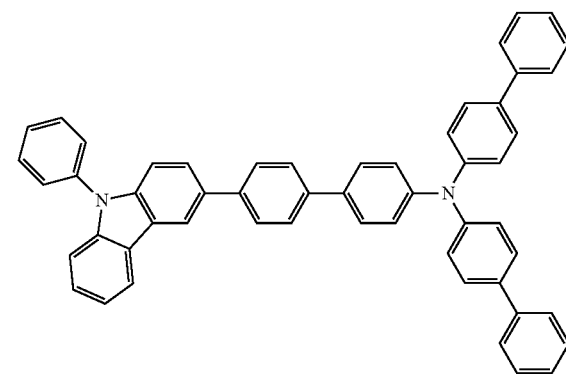
13-44
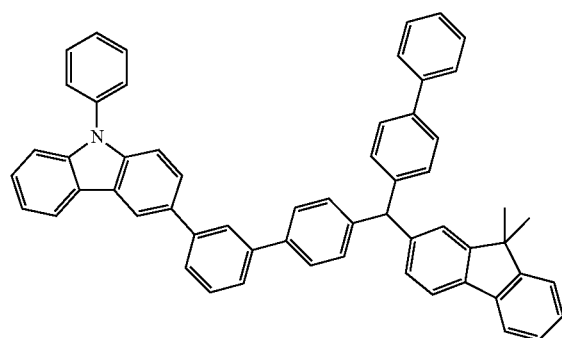
13-45
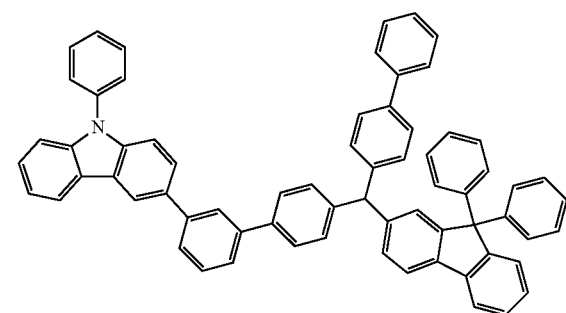
13-46
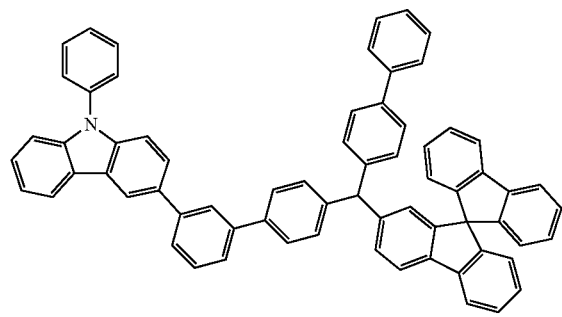
13-47
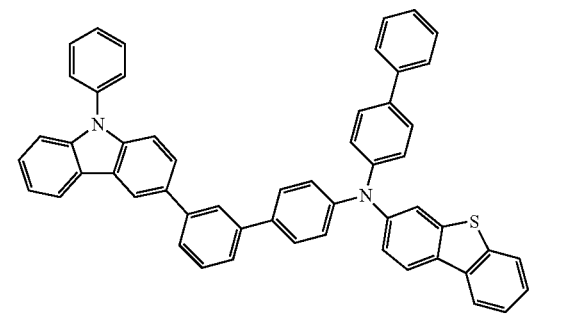
13-48
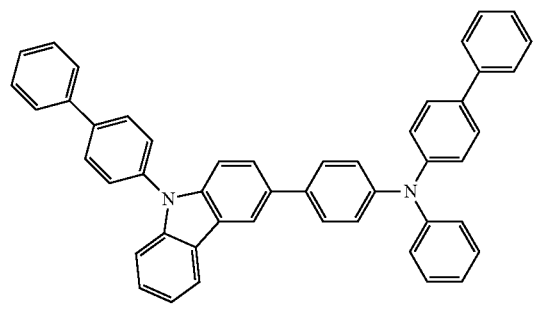
13-49
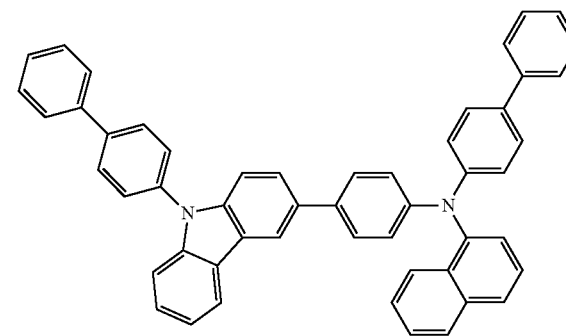

13-50
13-51
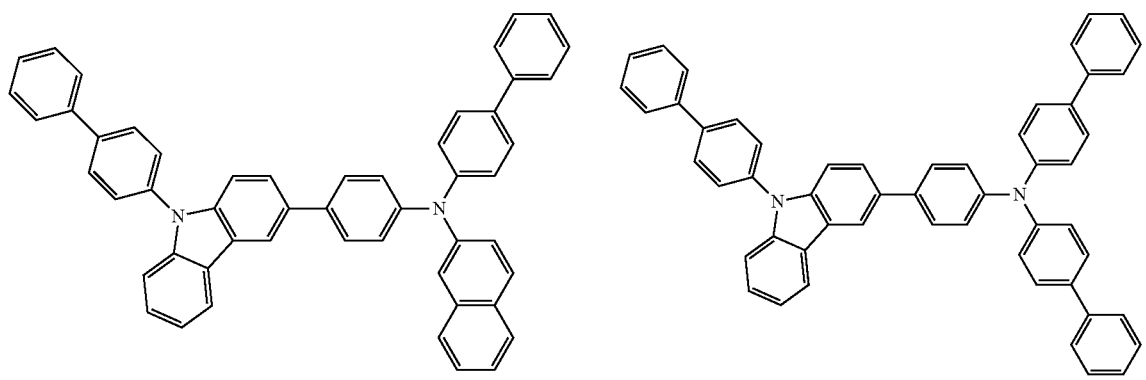
13-52
13-53
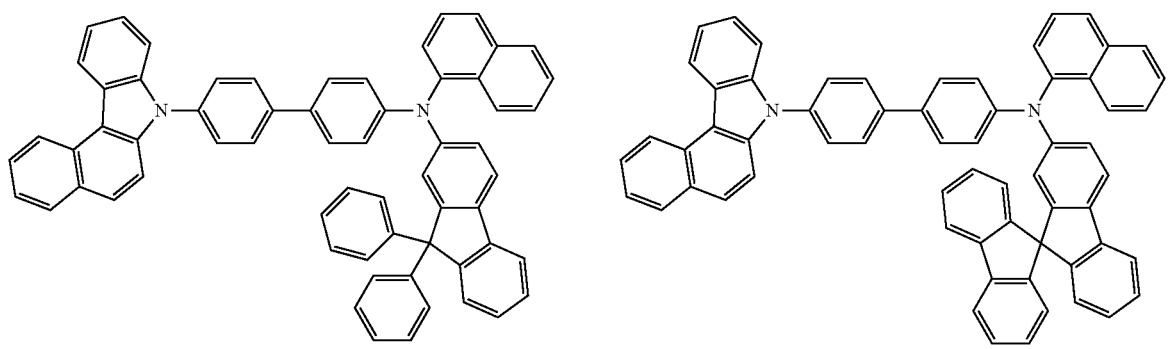
13-54
13-55
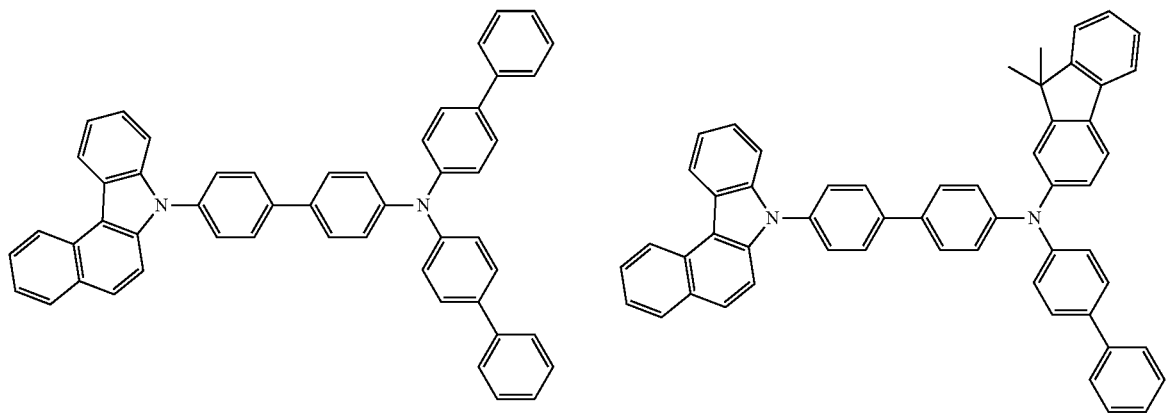
13-56
13-57
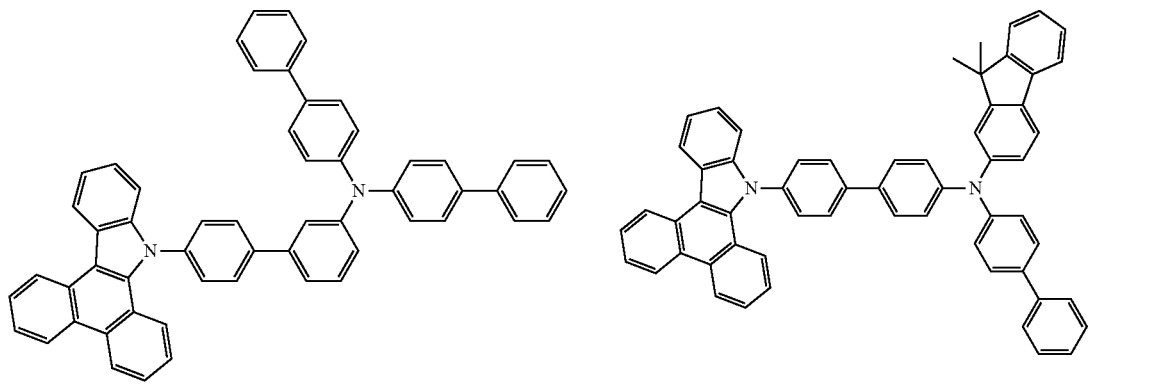

-continued
13-58
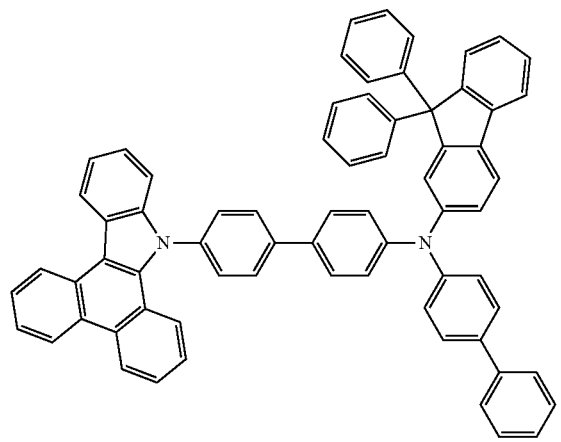
13-59
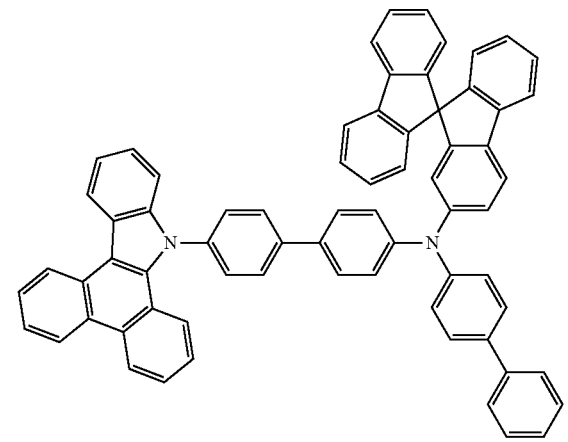
13-60
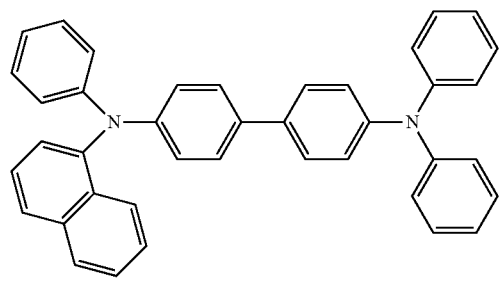
13-61
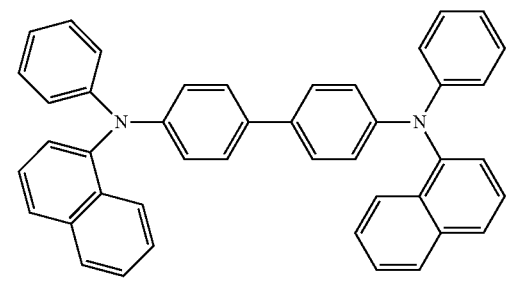
13-62
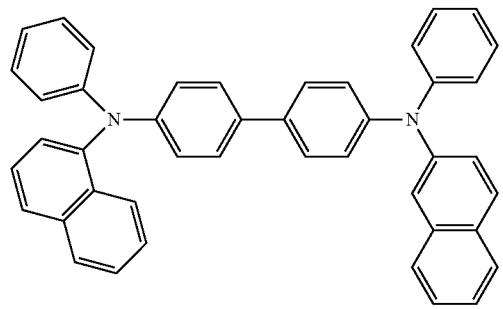
13-63
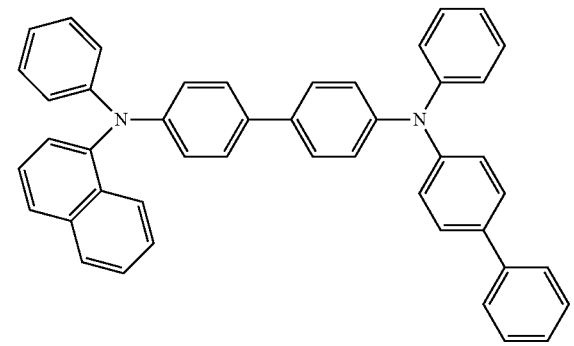
13-64
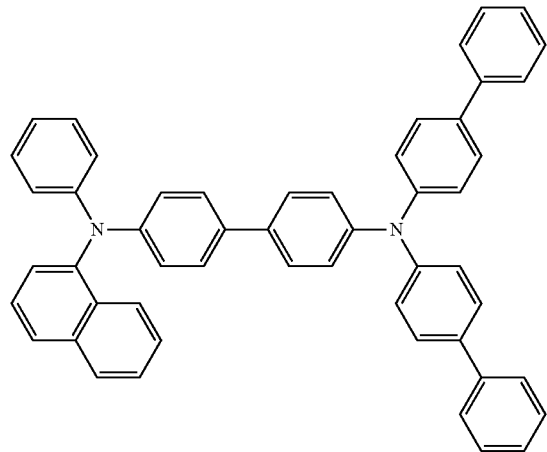
13-65
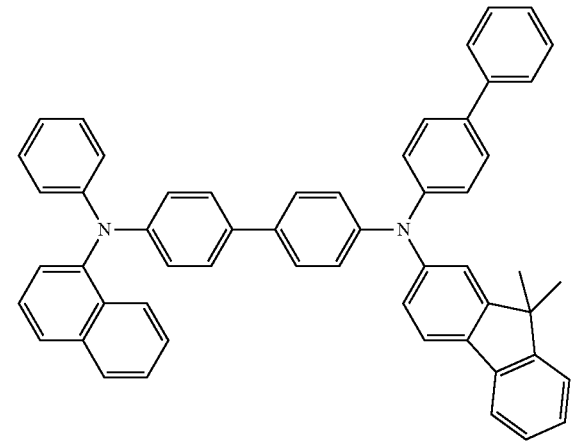

-continued 13-66
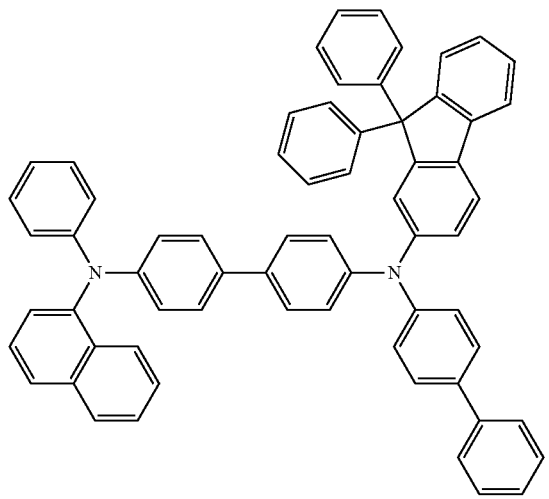

13-67
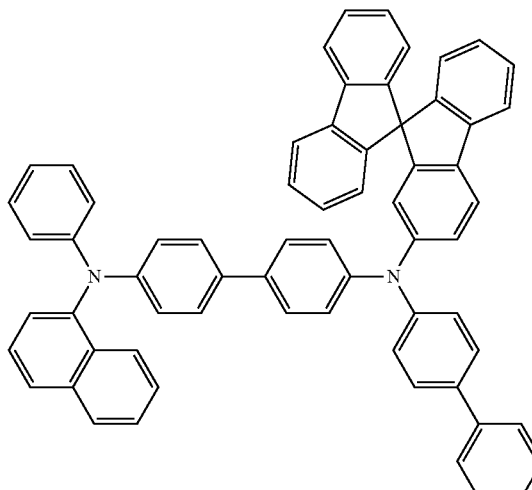

13-68
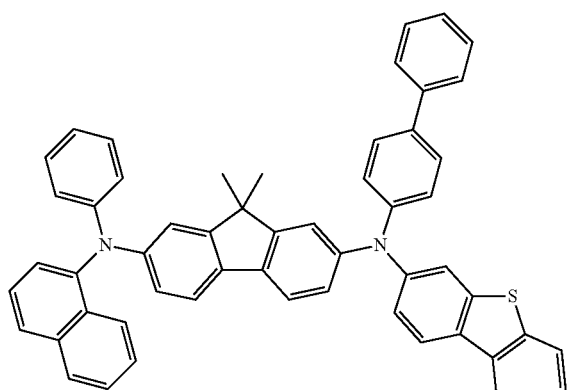

13-69
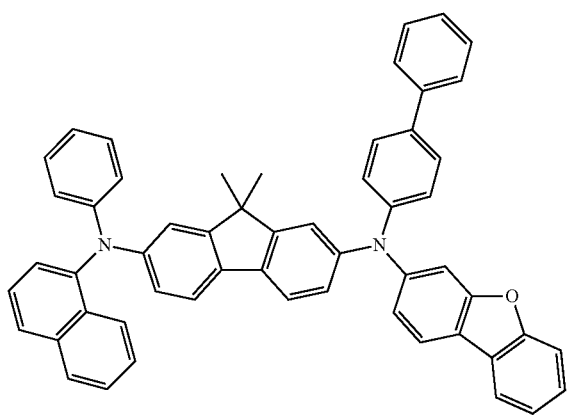

13-70
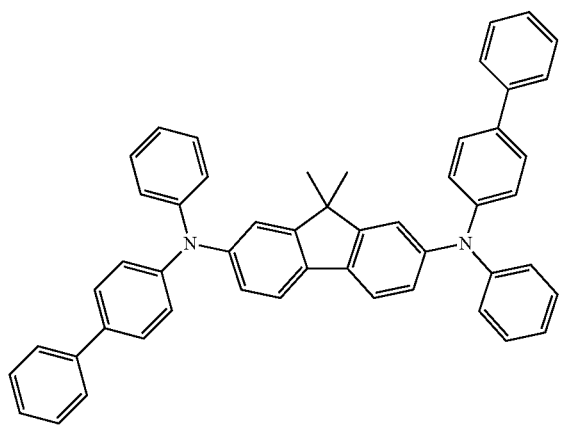

13-71
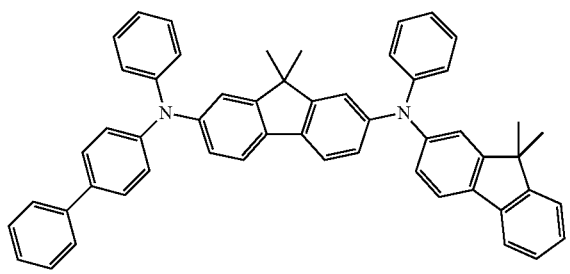

Referring to the Figure, the organic electric element (100) according to the present invention comprises a first electrode (120) formed on a substrate (110), a second electrode (180), and an organic material layer including the compound represented by Formula (1) between the first electrode (120) and the second electrode (180). Here, the first electrode (120) may be an anode (positive electrode), and the second electrode (180) may be a cathode (negative electrode). In the case of an inverted organic electric element, the first electrode may be a cathode, and the second electrode may be an anode.

The organic material layer may comprise a hole injection layer (130), a hole transport layer (140), an emitting layer (150), an emitting auxiliary layer (151), an electron transport layer (160), and an electron injection layer (170) formed in sequence on the first electrode (120).

Although not shown, the organic electric element according to the present invention may further comprise a protective layer formed on at least one surface of the first electrode and the second electrode opposite to the organic material layer.

Otherwise, even if the same core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and unique properties of materials (mobility, interfacial characteristics, etc.) of each organic material layer is achieved, a long life span and high efficiency can be achieved at the same time.

The organic electroluminescent device according to an embodiment of the present invention may be manufactured using a PVD (physical vapor deposition) method. For example, a metal or a metal oxide having conductivity or an alloy thereof is deposited on a substrate to form a cathode, and the organic material layer including the hole injection layer (130), the hole transport layer (140), the emitting layer (150), the electron transport layer (160), and the electron injection layer (170) is formed thereon, and then depositing a material usable as a cathode thereon can manufacture an organic electroluminescent device according to an embodiment of the present invention.

Accordingly, the present invention provides an organic electric element comprising a first electrode; a second electrode; and an organic material layer between the first electrode and the second electrode, wherein the organic material layer comprises a hole injection layer, a hole transport layer, an emitting auxiliary layer and an emitting layer, and the organic material layer comprises a compound included in Formula (1).

In addition, the present invention provides a compound, wherein at least one of the hole injection layer, the hole transport layer, the emitting-auxiliary layer, and the emitting layer includes a compound according to Formula (1), wherein the compound comprises a single compound or at least 2 or more compounds.

The present invention also provides an organic electric element wherein the emitting auxiliary layer contains a single compound or at least 2 or more compounds of the above compounds.

The present invention provides a compound further comprising a light efficiency enhancing layer formed on at least one of the opposite side to the organic material layer among one side of the first electrode, or one of the opposite side to the organic material layer among one side of the second electrode.

Also, the present invention provides the organic electric element wherein the organic material layer is formed by one of a spin coating process, a nozzle printing process, an inkjet printing process, a slot coating process, a dip coating process or a roll-to-roll process, and since the organic material layer according to the present invention can be formed by various methods, the scope of the present invention is not limited by the method of forming the organic material layer.

As another specific example, the present invention provides an organic electric element characterized in that the organic layer is mixed with the same or different compound of the compound represented by Formula (1).

The present invention also provides an organic electric element wherein a hole transport layer and an emitting-auxiliary layer contain a compound represented by Formula (1), and wherein a hole transport layer or an emitting-auxiliary layer contains a compound represented by Formula (1) in another aspect.

The present invention also provides an electronic device comprising a display device including the organic electric element; and a control unit for driving the display device.

According to another aspect, the present invention provides an electronic device characterized in that the organic electric element is at least one of an OLED, an organic solar cell, an organic photo conductor, an organic transistor and an element for monochromic or white illumination. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, synthesis examples of the compound represented by Formula (1) according to the present invention and preparation examples of the organic electric element will be described in detail by way of example, but are not limited to the following examples of the invention.

Synthesis Example 1

The final products 1 represented by Formula (1) of the present invention can be synthesized by reaction between Sub 1 and Sub 2 as illustrated in the following Reaction Scheme 1.

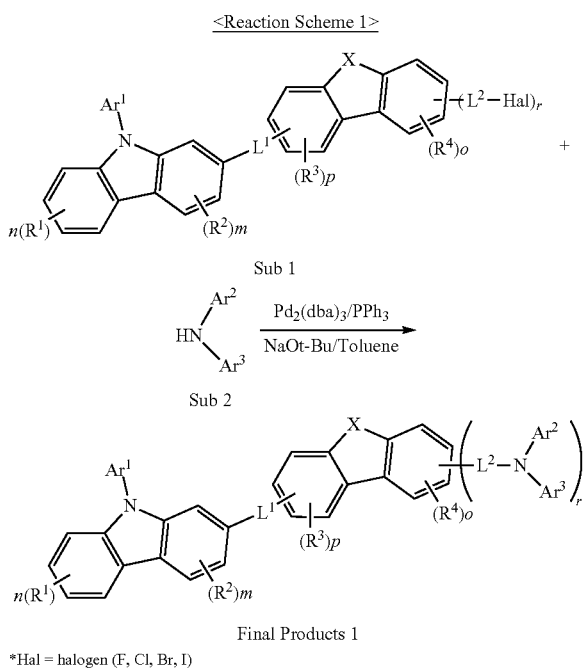

Synthesis Examples of Sub 1

Sub 1 of Reaction Scheme 1 can be synthesized by the reaction path of the following Reaction Scheme 2, but is not limited thereto.

<Reaction Scheme 2>

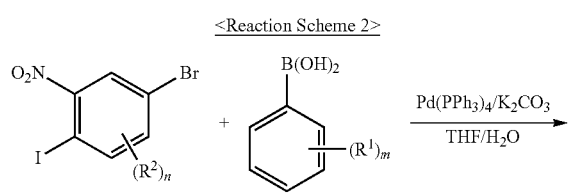

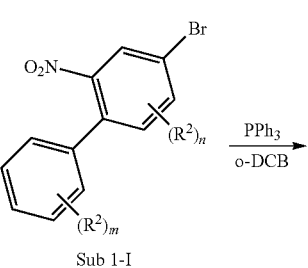

Sub 1-I

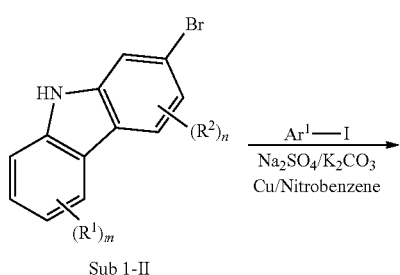

Sub 1-II

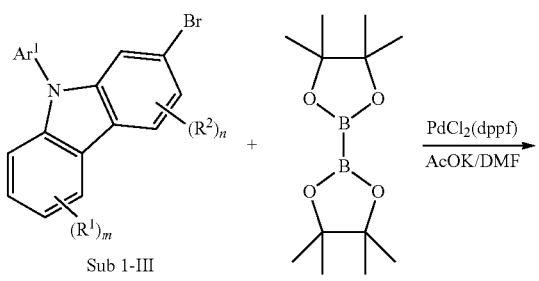

Sub 1-III

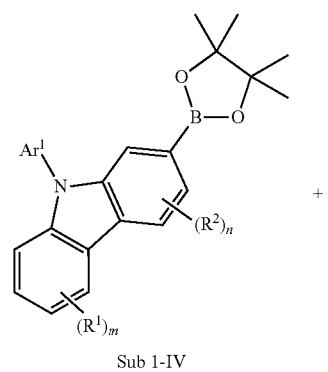

Sub 1-IV

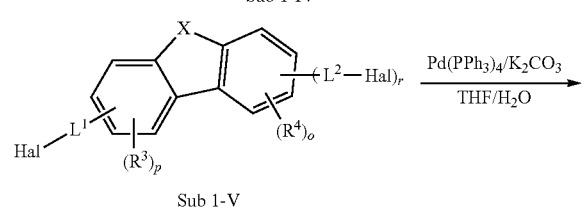

Sub 1-V

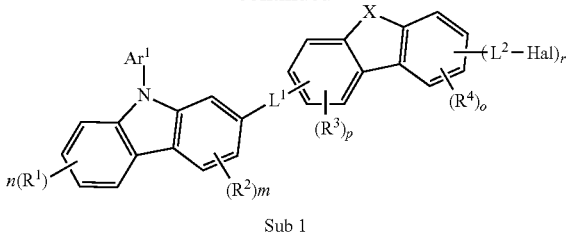

Sub 1

Synthesis Examples of Sub 1-I

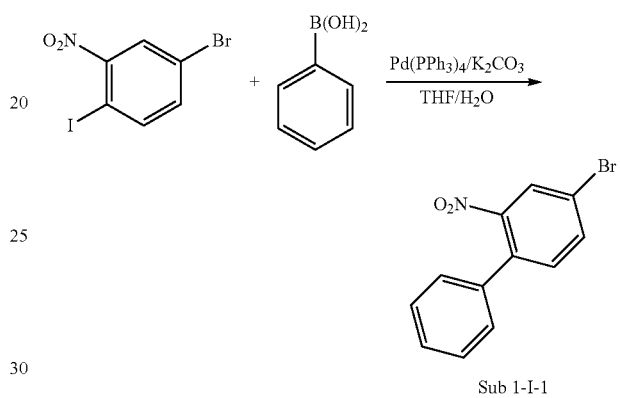

Sub 1-I-1

The starting material, phenylboronic acid (76.84 g, 630.2 mmol) was dissolved in THF (2780 mL) in a round bottom flask, and 4-bromo-1-iodo-2-nitrobenzene (309.96 g, 945.3 mmol), Pd(PPh$_3$)$_4$ (36.41 g, 31.5 mmol), K$_2$CO$_3$ (261.3 g, 1890.6 mmol), and water (1390 mL) were added and stirred at 80° C. When the reaction was completed, the reaction mixture was extracted with CH$_2$Cl$_2$ and water. The organic layer was dried over MgSO$_4$ and concentrated. The resulting compound was separated by silicagel column chromatography and recrystallized to obtain 122.68 g (yield: 70%) of the product.

Synthesis Examples of Sub 1-II

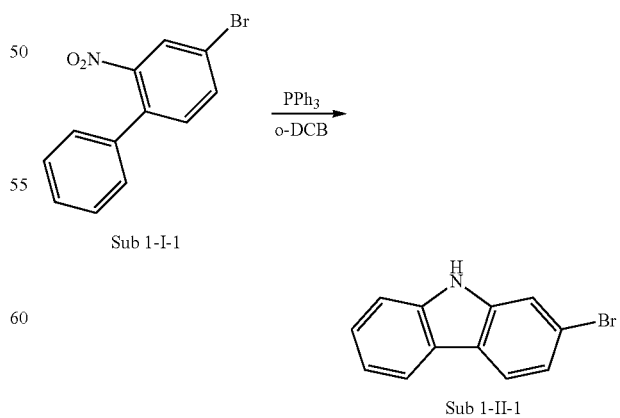

Sub 1-I-1

Sub 1-II-1

Sub 1-I-1 (122.68 g, 441.1 mmol) obtained in the above synthesis was dissolved in 1810 mL of o-dichlorobenzene in a round bottom flask, and triphenylphosphine (289.26 g, 1102.8 mmol) was added and stirred at 200° C. After the reaction was completed, o-dichlorobenzene was removed by distillation and extracted with CH$_2$Cl$_2$ and water. The organic layer was dried over MgSO$_4$ and concentrated. The resulting compound was separated by silicagel column chromatography and recrystallized to obtain 80.34 g (yield: 74%) of the product.

Synthesis Examples of Sub 1-III 1)

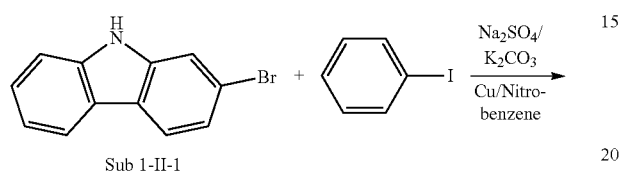

Sub 1-II-1

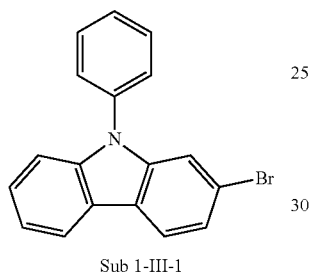

Sub 1-III-1

Sub 1-II-1 (80.34 g, 326.5 mmol) was dissolved in 653 mL of nitrobenzene in a round bottom flask, and iodobenzene (99.9 g, 489.7 mmol), Na$_2$SO$_4$ (46.37 g, 326.5 mmol), K$_2$CO$_3$ (45.12 g, 326.5 mmol), Cu (6.22 g, 97.9 mmol) were added and stirred at 200° C. After the reaction was completed, o-dichlorobenzene was removed by distillation and extracted with CH$_2$Cl$_2$ and water. The organic layer was dried over MgSO$_4$ and concentrated. The resulting compound was separated by silicagel column chromatography and recrystallized to obtain 76.78 g (yield: 73%) of the product.

Synthesis Examples of Sub 1-III 2)

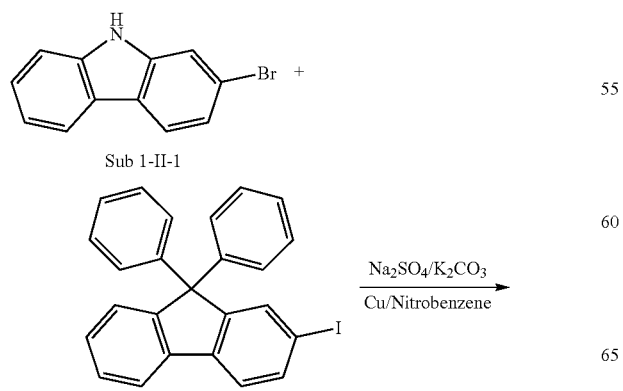

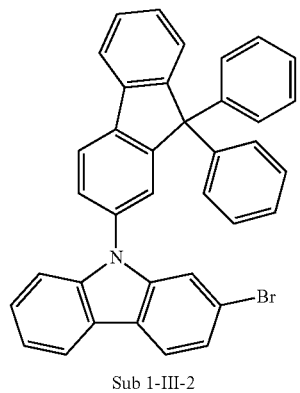

Sub 1-III-2

Sub 1-II-1 (70 g, 284.4 mmol) was dissolved in 570 mL of nitrobenzene, and 2-iodo-9,9-diphenyl-9H-fluorene (189.6 g, 426.7 mmol), Na$_2$SO$_4$ (40.4 g, 284.4 mmol), K$_2$CO$_3$ (39.3 g, 284.4 mmol), and Cu (5.42 g, 85.3 mmol) were reacted using the synthesis method of Sub 1-III-1 described above to give 108.8 g of the product. (yield: 68%).

Synthesis Examples of Sub 1-IV

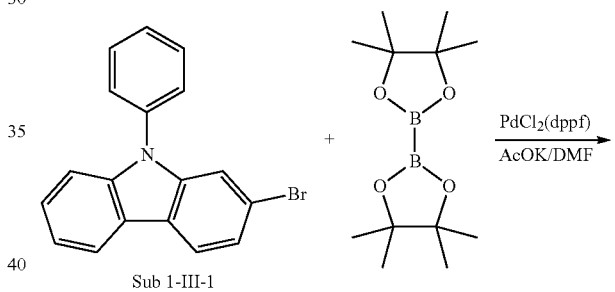

Sub 1-III-1

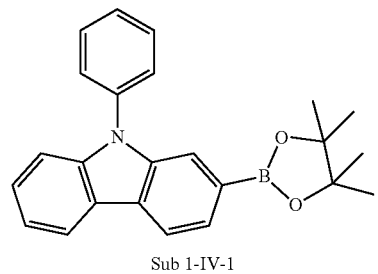

Sub 1-IV-1

Sub 1-III-1 (76.78 g, 238.3 mmol) was dissolved in DMF in a round bottom flask, and Bis(pinacolato)diboron (66.57 g, 262.1 mmol), Pd(dppf)Cl$_2$ (5.84 g, 7.1 mmol), KOAc (70.16 g, 714.9 mmol) were added and stirred at 200° C. When the reaction was completed, the DMF is removed by distillation and extracted with CH$_2$Cl$_2$ and water. The organic layer was dried over MgSO$_4$ and concentrated. The resulting compound was separated by silicagel column chromatography and recrystallized to obtain 73.92 g (yield: 84%) of the product.

Synthesis Examples of Sub 1 1)

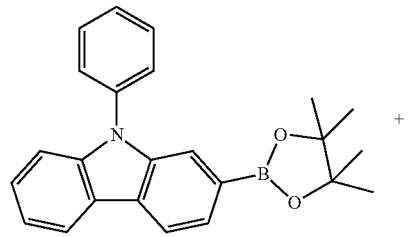
Sub 1-IV-1

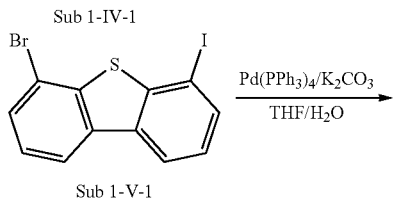
Sub 1-V-1

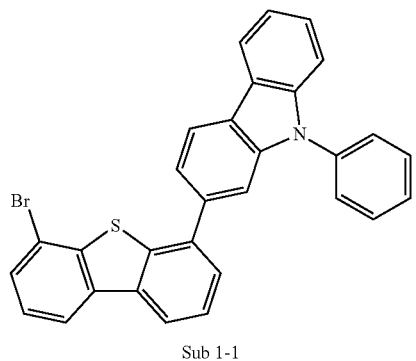
Sub 1-1

Sub 1-IV-1 (73.92 g, 200.2 mmol) was dissolved in 880 ml of THF in a round bottom flask, and Sub 1-V-1 (116.8 g, 300.3 mmol), Pd(PPh$_3$)$_4$ (11.6 g, 10 mmol), K$_2$CO$_3$ (83 g, 600.6 mmol), and water (440 mL) were added and stirred at 80° C. When the reaction was completed, the reaction mixture was extracted with CH$_2$Cl$_2$ and water. The organic layer was dried over MgSO$_4$ and concentrated. The resulting compound was separated by silicagel column chromatography and recrystallized to obtain 75.7 g (yield: 75%) of the product.

Synthesis Examples of Sub 1 2)

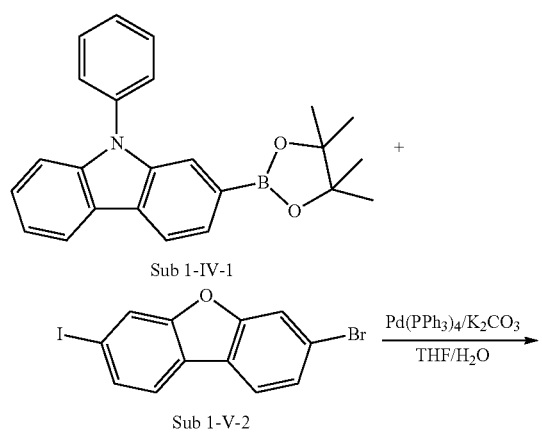
Sub 1-IV-1

Sub 1-V-2

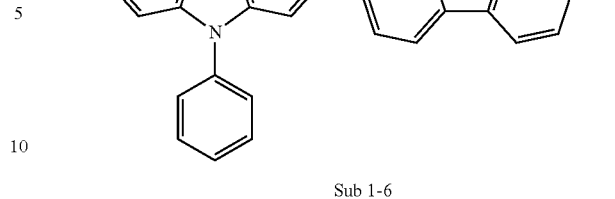
Sub 1-6

Sub 1-IV-1 (73.92 g, 200.2 mmol) and Sub 1-V-2 (112.0 g, 300.3 mmol) were reacted using the synthesis method of Sub 1-1 to give 74.3 g of the product. (yield: 76%).

Synthesis Examples of Sub 1 3)

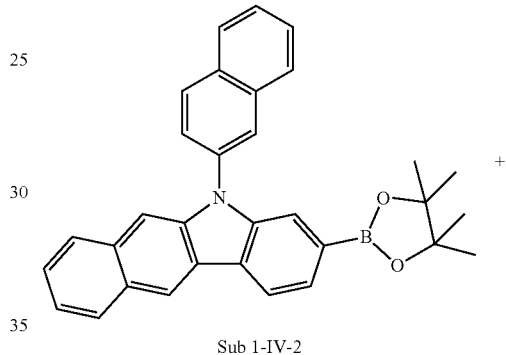
Sub 1-IV-2

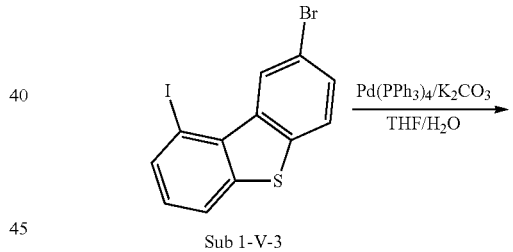
Sub 1-V-3

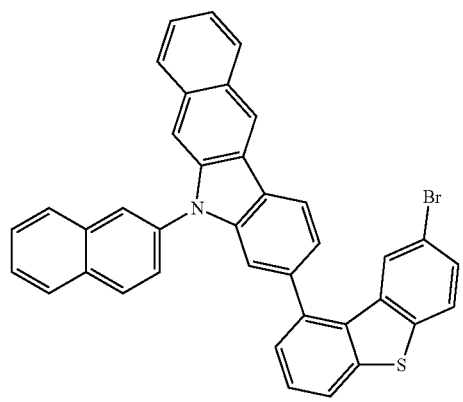
Sub 1-11

Sub 1-IV-2 (93.9 g, 200.2 mmol) and Sub 1-V-3 (116.8 g, 300.3 mmol) were reacted using the synthesis method of Sub 1-1 to give 85.9 g of the product. (yield: 71%).

Synthesis Examples of Sub 1 4)
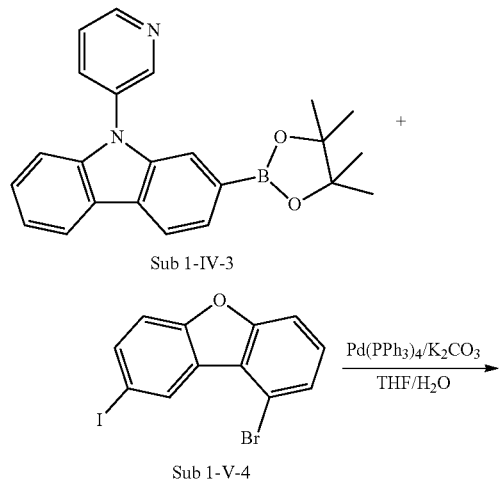
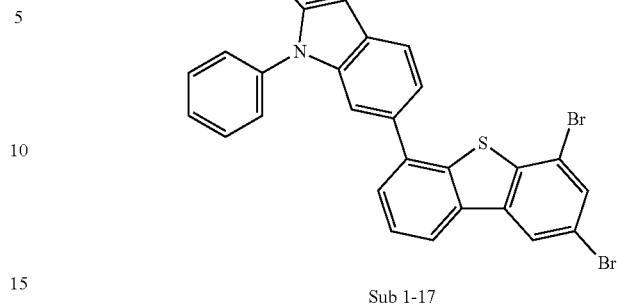
Sub 1-IV-1 (73.92 g, 200.2 mmol)과 Sub 1-V-5 (140.5 g, 300.3 mmol) were reacted using the synthesis method of Sub 1-1 to give 84.1 g of the product. (yield: 72%).
Synthesis Examples of Sub 1 6)
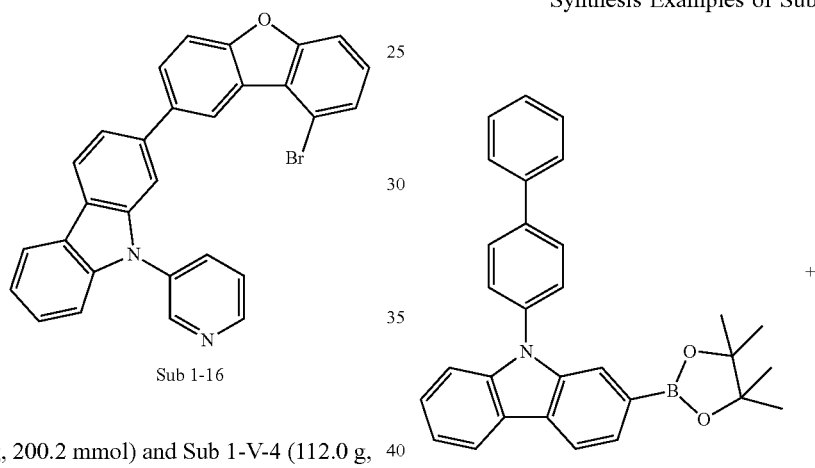
Sub 1-IV-3 (74.1 g, 200.2 mmol) and Sub 1-V-4 (112.0 g, 300.3 mmol) were reacted using the synthesis method of Sub 1-1 to give 68.6 g of the product. (yield: 70%).
Synthesis Examples of Sub 1 5)
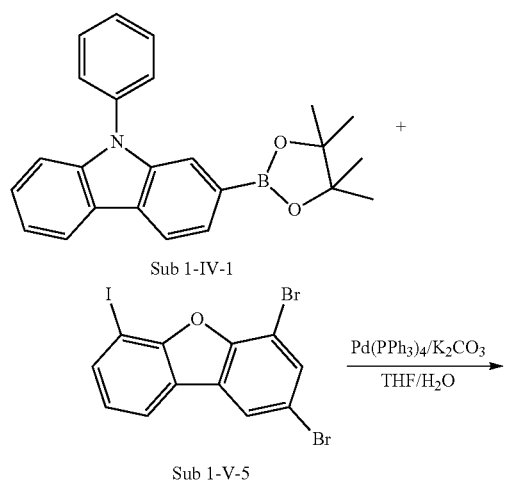
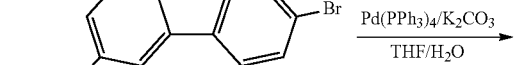
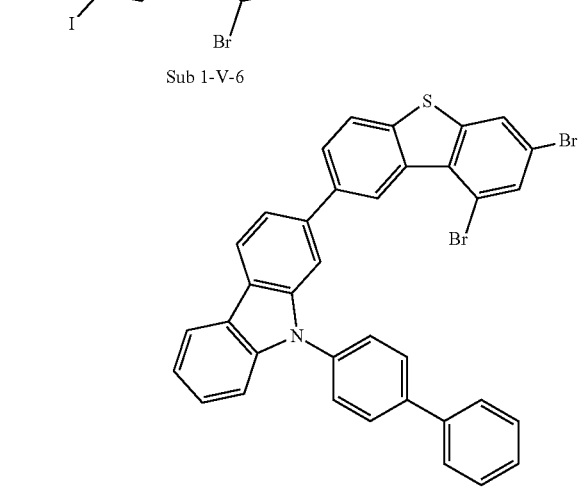

Sub 1-IV-4 (89.2 g, 200.2 mmol) and Sub 1-V-6 (140.5 g, 300.3 mmol) were reacted using the synthesis method of Sub 1-1 to give 92.4 g of the product. (yield: 70%).
Examples of Sub 1 include, but are not limited to, the following.
Sub 1-1
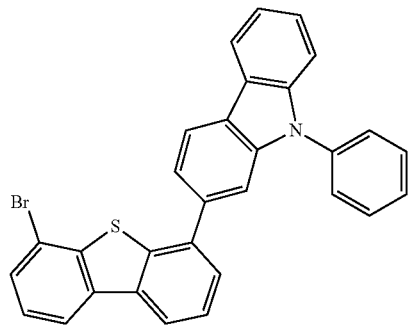
Sub 1-2
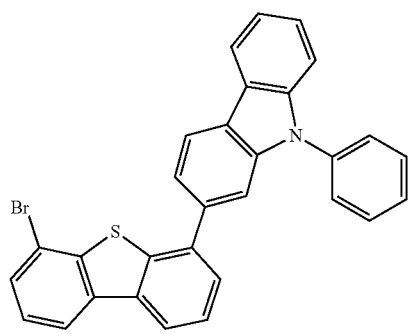
Sub 1-3
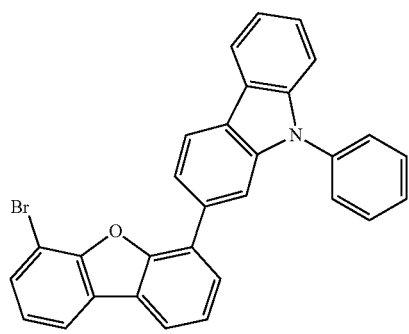
Sub 1-4
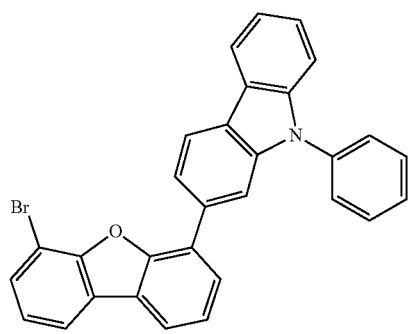
Sub 1-5
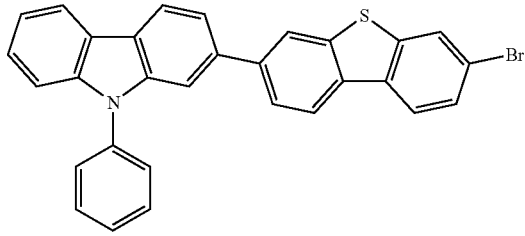
Sub 1-6
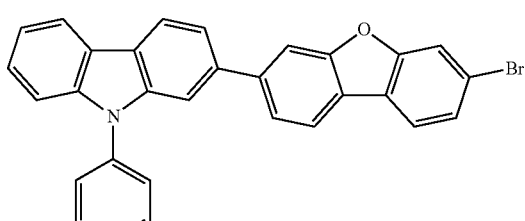
Sub 1-7
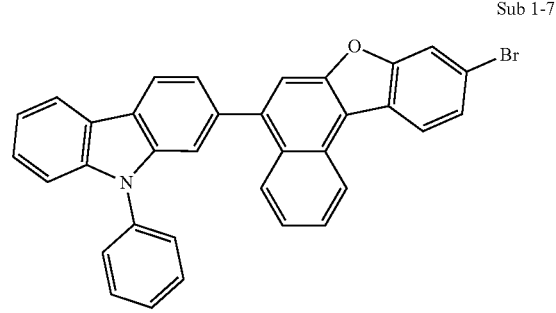
Sub 1-8
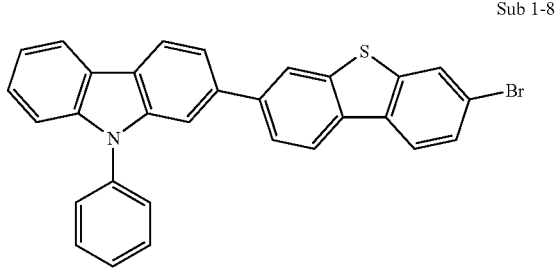
Sub 1-9
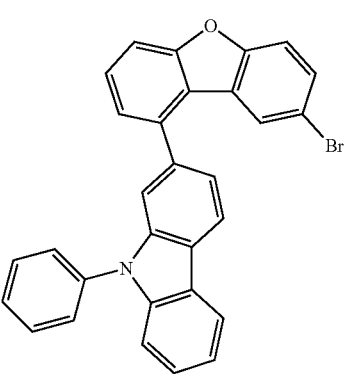

87
-continued
Sub 1-10
Sub 1-11
Sub 1-12
Sub 1-13
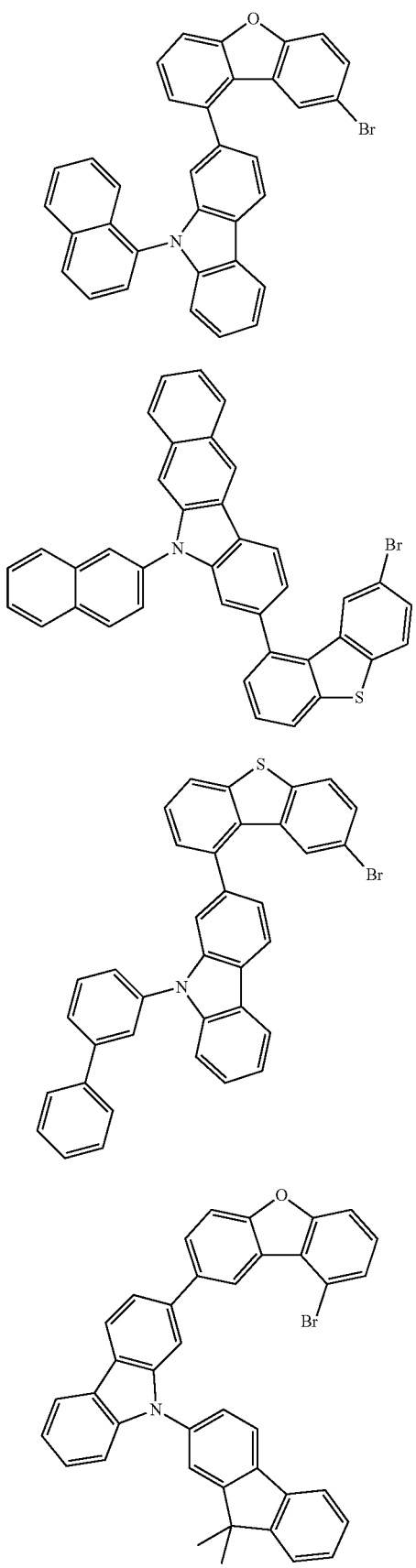
88
-continued
Sub 1-14
Sub 1-15
Sub 1-16
Sub 1-17
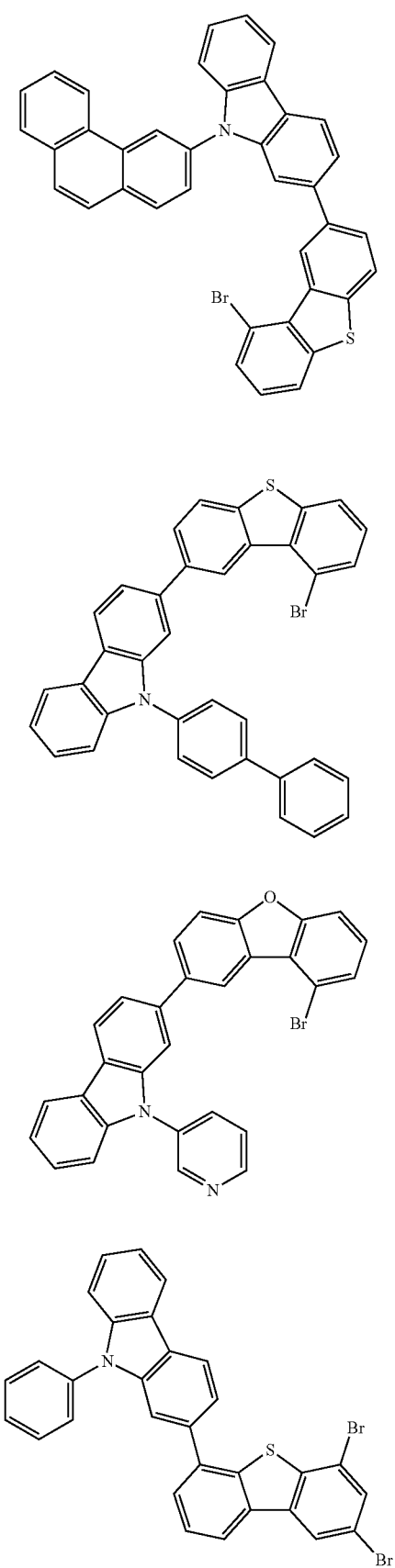

-continued
Sub 1-18
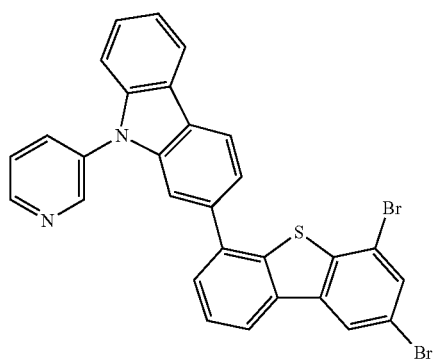
Sub 1-19
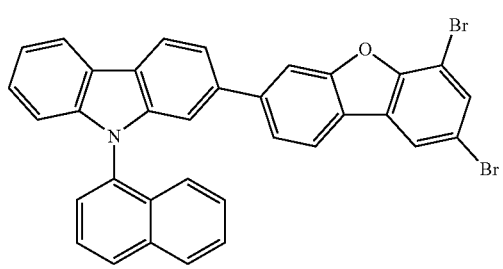
Sub 1-20
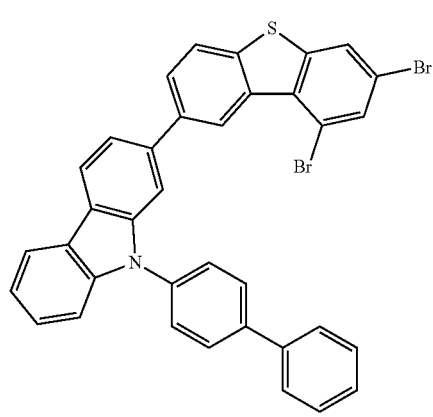
Sub 1-21
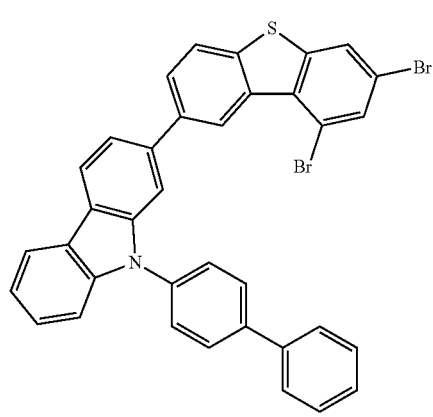
-continued
Sub 1-22
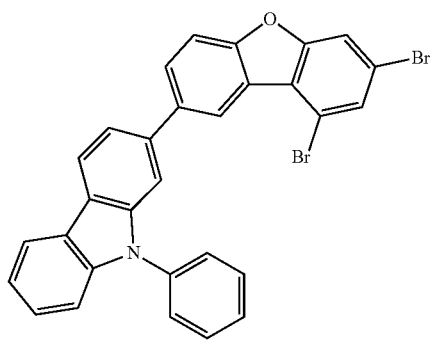
Sub 1-23
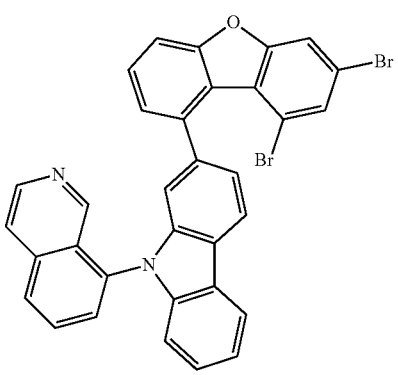
Sub 1-24
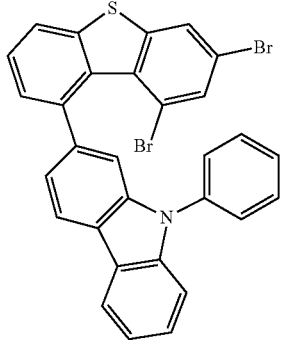
Sub 1-25
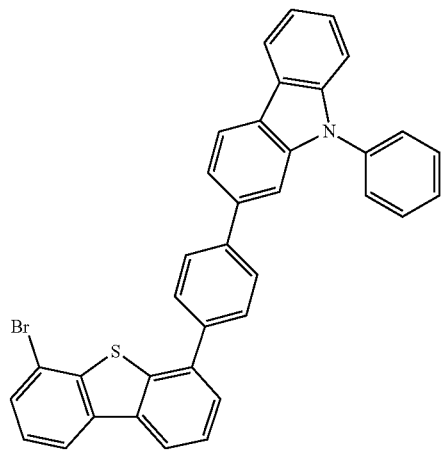

Sub 1-26

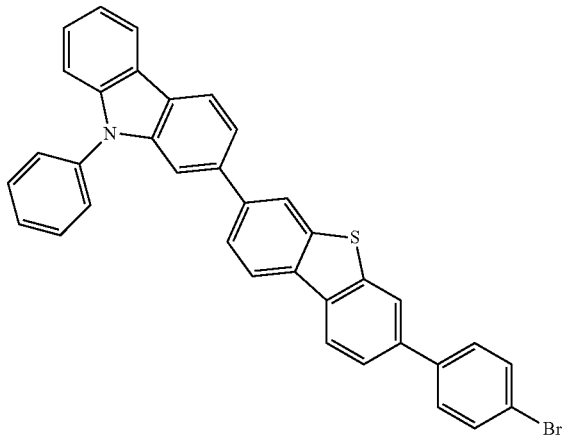

Sub-1-27

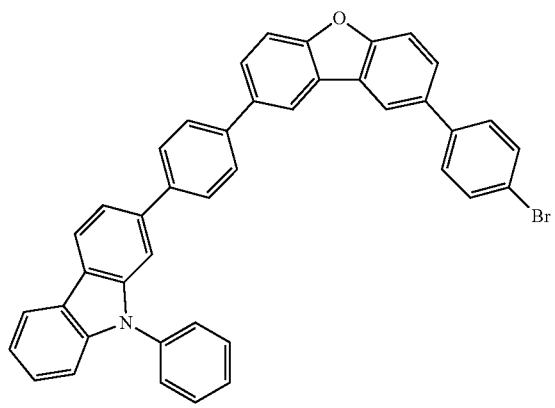

Sub 1-28

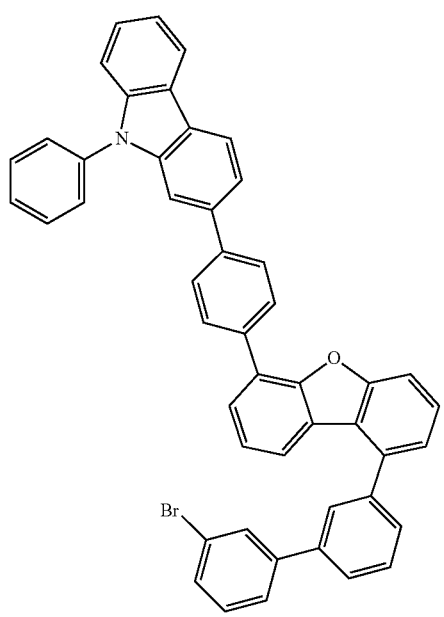

TABLE 1

| compound | FD-MS |
|---|---|
| Sub 1-1 | m/z = 503.03($C_{30}H_{18}BrNS$ = 504.44) |
| Sub 1-2 | m/z = 503.03($C_{30}H_{18}BrNS$ = 504.44) |
| Sub 1-3 | m/z = 487.06($C_{30}H_{18}BrNO$ = 488.37) |
| Sub 1-4 | m/z = 487.06($C_{30}H_{18}BrNO$ = 488.37) |
| Sub 1-5 | m/z = 503.03($C_{30}H_{18}BrNS$ = 504.44) |
| Sub 1-6 | m/z = 487.06($C_{30}H_{18}BrNO$ = 488.37) |
| Sub 1-7 | m/z = 537.07($C_{34}H_{20}BrNO$ = 538.43) |
| Sub 1-8 | m/z = 503.03($C_{30}H_{18}BrNS$ = 504.44) |
| Sub 1-9 | m/z = 487.06($C_{30}H_{18}BrNO$ = 488.37) |
| Sub 1-10 | m/z = 537.07($C_{34}H_{20}BrNO$ = 538.43) |
| Sub 1-11 | m/z = 603.07($C_{38}H_{22}BrNS$ = 604.56) |
| Sub 1-12 | m/z = 579.07($C_{36}H_{22}BrNS$ = 580.54) |
| Sub 1-13 | m/z = 603.12($C_{39}H_{26}BrNO$ = 604.53) |
| Sub 1-14 | m/z = 603.07($C_{38}H_{22}BrNS$ = 604.56) |
| Sub 1-15 | m/z = 579.07($C_{36}H_{22}BrNS$ = 580.54) |
| Sub 1-16 | m/z = 488.05($C_{29}H_{17}BrN_2O$ = 489.36) |
| Sub 1-17 | m/z = 580.94($C_{30}H_{17}Br_2NS$ = 583.3) |
| Sub 1-18 | m/z = 581.94($C_{29}H_{16}Br_2N_2S$ = 584.32) |
| Sub 1-19 | m/z = 614.98($C_{34}H_{19}Br_2NO$ = 617.3) |
| Sub 1-20 | m/z = 564.97($C_{30}H_{17}Br_2NO$ = 567.27) |
| Sub 1-21 | m/z = 656.98($C_{36}H_{21}Br_2NS$ = 658.4) |
| Sub 1-22 | m/z = 564.97($C_{30}H_{17}Br_2NO$ = 567.27) |
| Sub 1-23 | m/z = 616.0($C_{33}H_{18}Br_2N_2O$ = 618.3) |
| Sub 1-24 | m/z = 580.94($C_{30}H_{17}Br_2NS$ = 583.3) |
| Sub 1-25 | m/z = 579.07($C_{36}H_{22}BrNS$ = 580.54) |
| Sub 1-26 | m/z = 579.07($C_{36}H_{22}BrNS$ = 580.54) |
| Sub 1-27 | m/z = 639.12($C_{42}H_{26}BrNO$ = 640.57) |
| Sub 1-28 | m/z = 715.15($C_{48}H_{30}BrNO$ = 716.66) |

Synthesis Examples of Sub 2

Sub 2 of Reaction Scheme 1 can be synthesized by the reaction path of the following Reaction Scheme 3, but is not limited thereto.

<Reaction Scheme 3>

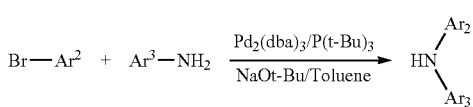

Sub 2

Synthesis Examples of Sub 2-1

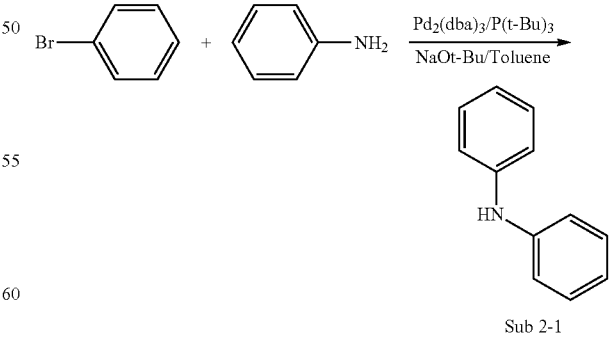

Sub 2-1 bromobenzene (37.1 g, 236.2 mmol) was added to a round bottom flask and dissolved in toluene (2200 mL), and aniline (20 g, 214.8 mmol), $Pd_2(dba)_3$ (9.83 g, 10.7 mmol), P(t-Bu)$_3$ (4.34 g, 21.5 mmol), NaOt-Bu (62 g, 644.3 mmol) were added in order and stirred at 100° C. After the reaction was completed, the reaction mixture was extracted with ether and water. The organic layer was dried over MgSO₄ and concentrated. The resulting compound was separated by silica-gel column chromatography and recrystallized to obtain 28 g of the product. (yield: 77%)

Synthesis Examples of Sub 2-13

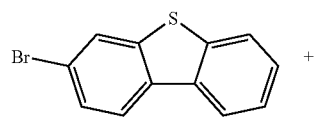
+
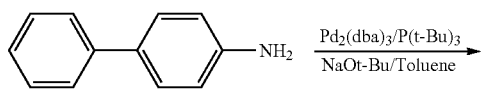
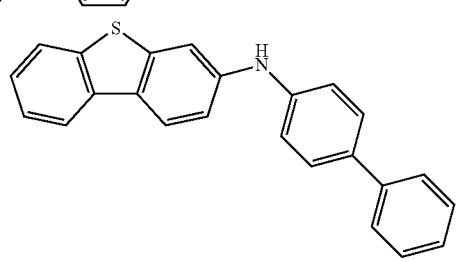

Sub 2-13

3-bromodibenzo[b,d]thiophene (42.8 g, 162.5 mmol), toluene (1550 mL), [1,1'-biphenyl]-4-amine (25 g, 147.7 mmol), Pd₂(dba)₃ (6.76 g, 162.5 mmol), P(t-Bu)₃ (3 g, 14.8 mmol), NaOt-Bu (42.6 g, 443.2 mmol) were reacted using the synthesis method of Sub 2-1 to give 37.9 g of the product. (yield: 73%).

Examples of Sub 2 include, but are not limited to, the following.

Sub 2-1
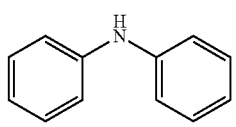

Sub 2-2
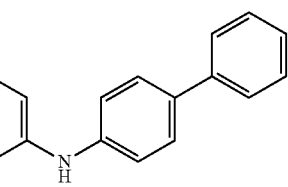

Sub 2-3
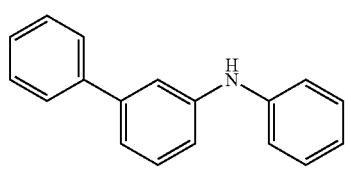

Sub 2-4
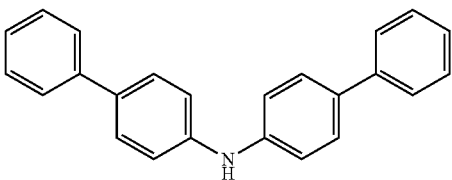

Sub 2-5
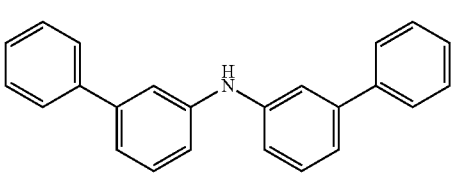

Sub 2-6
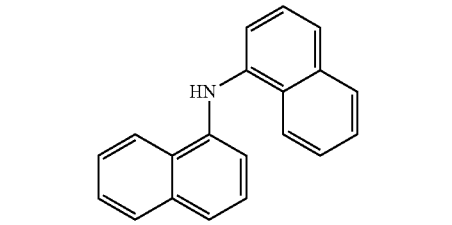

Sub 2-7
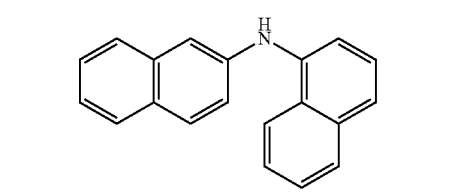

Sub 2-8
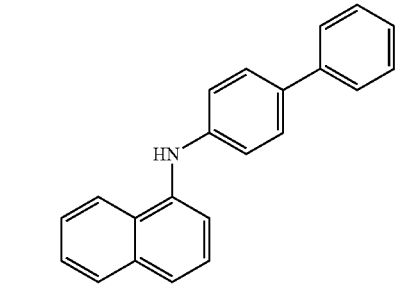

Sub 2-9
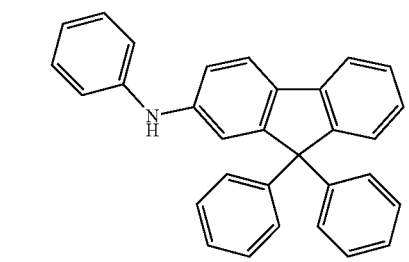

Sub 2-10
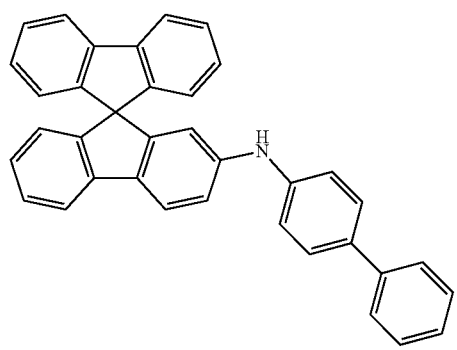
Sub 2-11
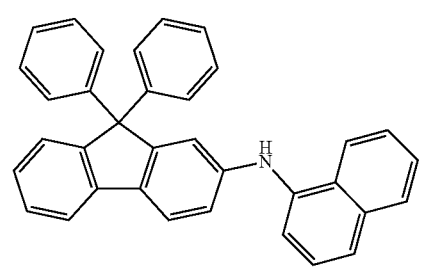
Sub 2-12
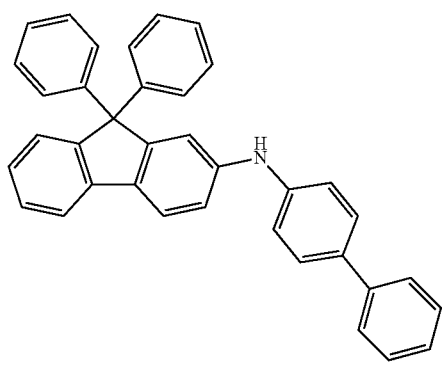
Sub 2-13
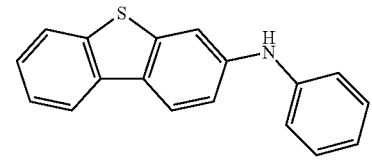
Sub 2-14
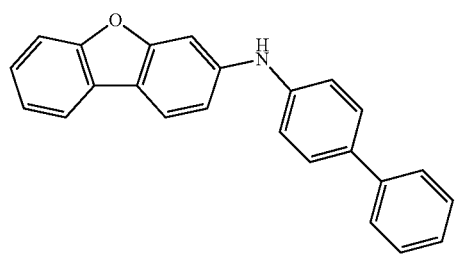
Sub 2-15
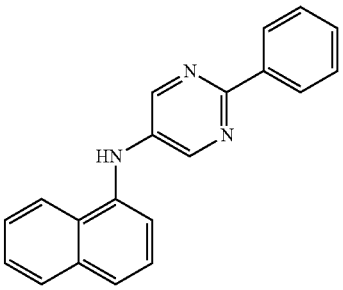
Sub 2-16
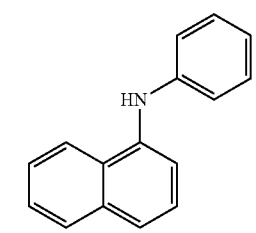
Sub 2-17
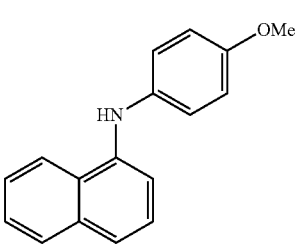
Sub 2-18
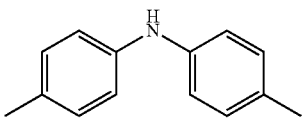
Sub 2-19
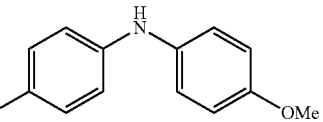
Sub 2-20
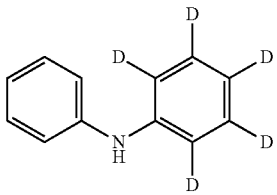
Sub 2-21
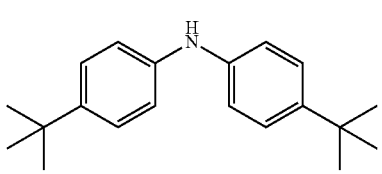

Sub 2-22
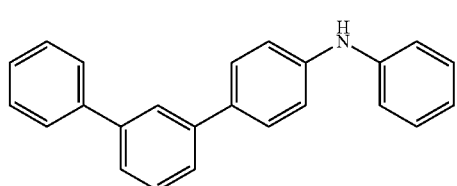
Sub 2-23
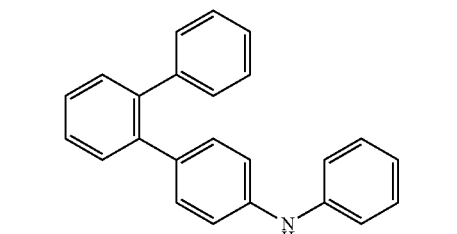
Sub 2-28
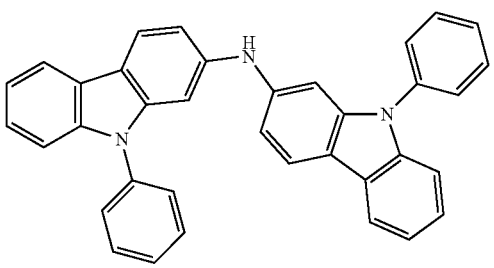
Sub 2-29
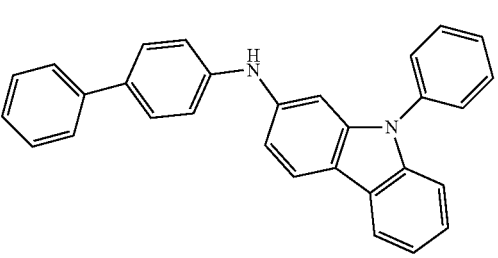
Sub 2-24
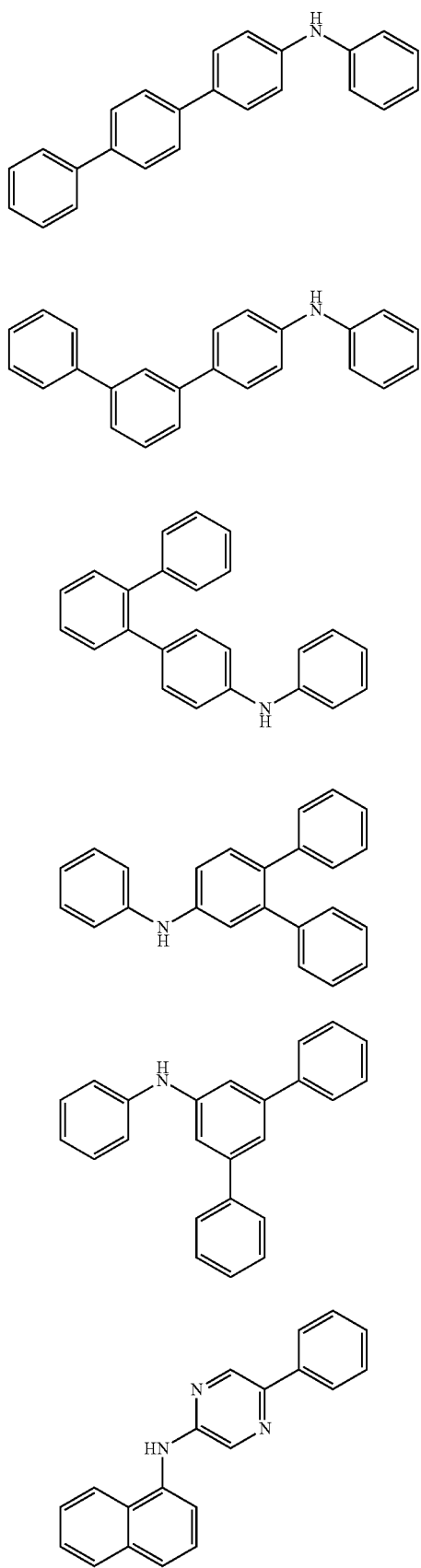
Sub 2-30
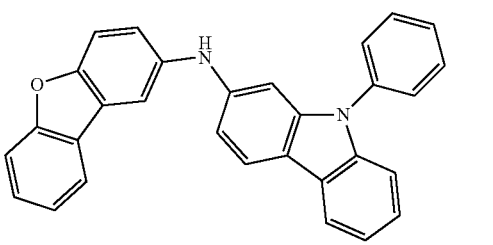
Sub 2-25
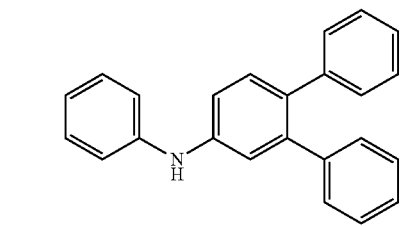
Sub 2-31
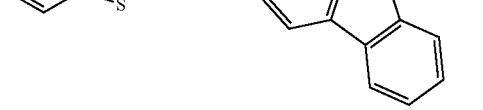
Sub 2-26
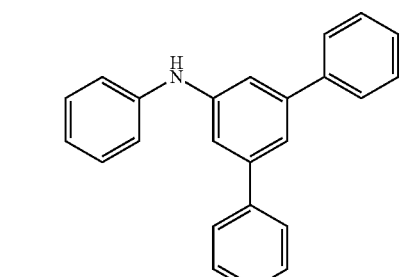
Sub 2-32
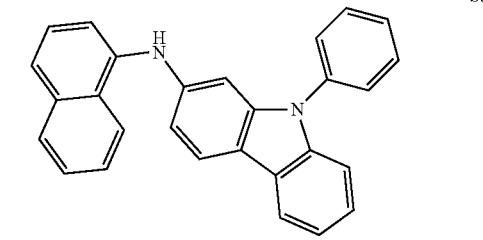
Sub 2-27
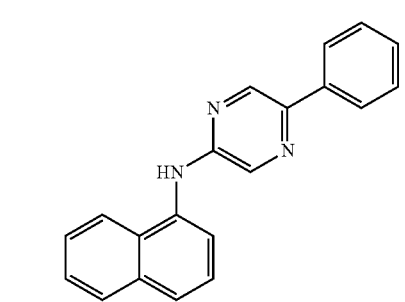
Sub 2-33
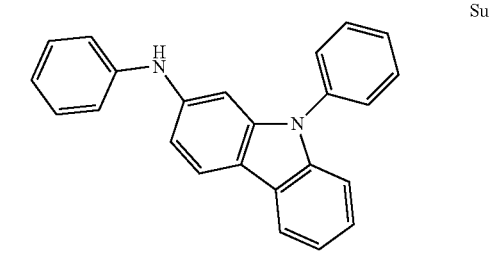

Sub 2-34
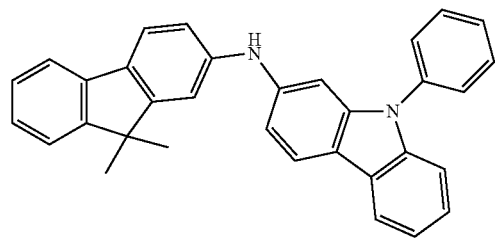
Sub 2-35
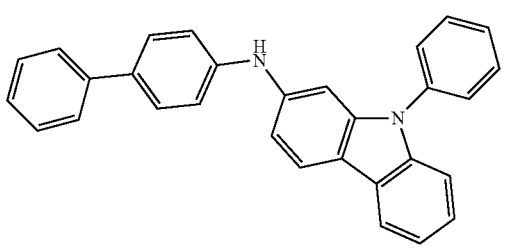
Sub 2-36
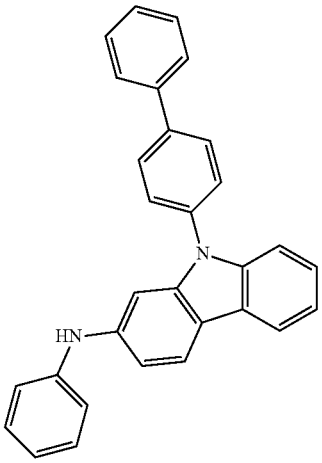
Sub 2-37
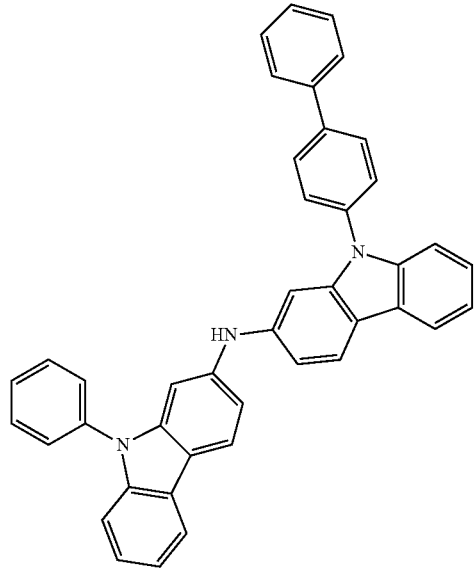
Sub 2-38
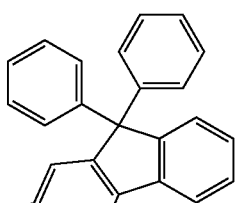
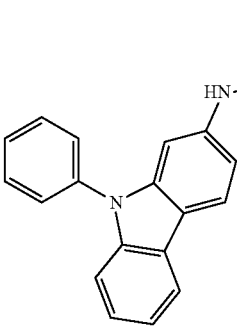
Sub 2-39
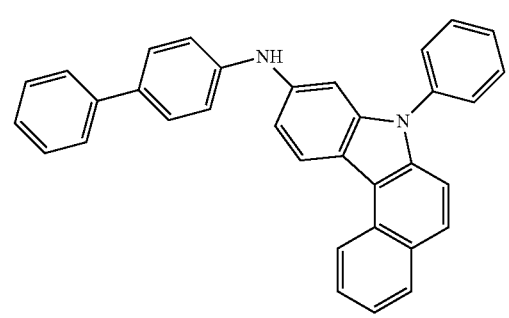
Sub 2-40
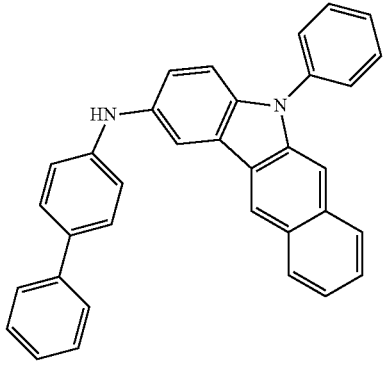
Sub 2-41
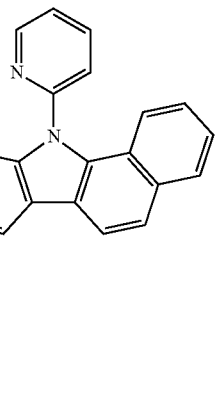

Sub 2-42

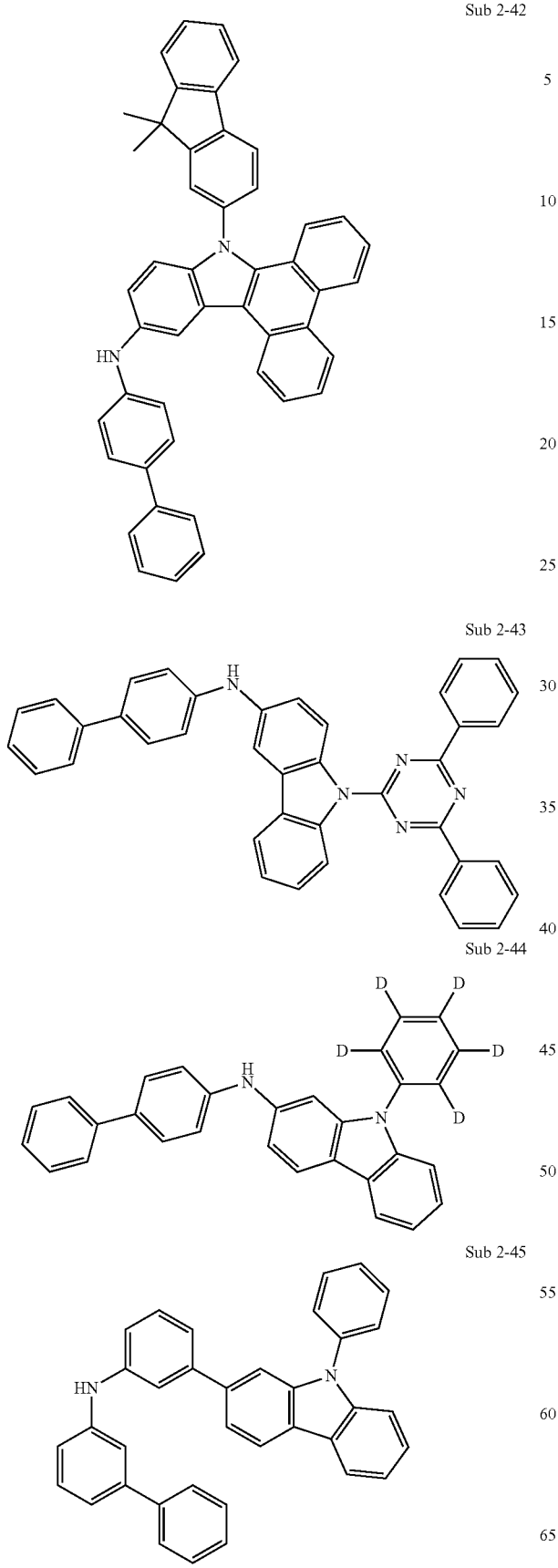

Sub 2-43

Sub 2-44

Sub 2-45

Sub 2-46

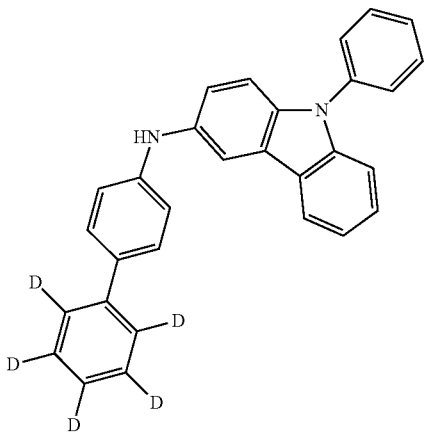

TABLE 2

| compound | FD-MS |
| --- | --- |
| Sub 2-1 | m/z = 169.09($C_{12}H_{11}N$ = 169.22) |
| Sub 2-2 | m/z = 245.12($C_{18}H_{15}N$ = 245.32) |
| Sub 2-3 | m/z = 245.12($C_{18}H_{15}N$ = 245.32) |
| Sub 2-4 | m/z = 321.15($C_{24}H_{19}N$ = 321.41) |
| Sub 2-5 | m/z = 321.15($C_{24}H_{19}N$ = 321.41) |
| Sub 2-6 | m/z = 269.12($C_{20}H_{15}N$ = 269.34) |
| Sub 2-7 | m/z = 269.12($C_{20}H_{15}N$ = 269.34) |
| Sub 2-8 | m/z = 295.14($C_{22}H_{17}N$ = 295.38) |
| Sub 2-9 | m/z = 409.18($C_{31}H_{23}N$ = 409.52) |
| Sub 2-10 | m/z = 483.20($C_{37}H_{25}N$ = 483.60) |
| Sub 2-11 | m/z = 459.20($C_{35}H_{25}N$ = 459.58) |
| Sub 2-12 | m/z = 485.21($C_{37}H_{27}N$ = 485.62) |
| Sub 2-13 | m/z = 275.08($C_{18}H_{13}NS$ = 275.37) |
| Sub 2-14 | m/z = 335.13($C_{24}H_{17}NO$ = 335.40) |
| Sub 2-15 | m/z = 297.13($C_{20}H_{15}N_3$ = 297.35) |
| Sub 2-16 | m/z = 219.10($C_{16}H_{13}N$ = 219.28) |
| Sub 2-17 | m/z = 249.12($C_{17}H_{15}NO$ = 249.31) |
| Sub 2-18 | m/z = 197.12($C_{14}H_{15}N$ = 197.28) |
| Sub 2-19 | m/z = 229.11($C_{14}H_{15}NO_2$ = 229.27) |
| Sub 2-20 | m/z = 174.12($C_{12}H_6D_5N$ = 174.25) |
| Sub 2-21 | m/z = 281.21($C_{20}H_{27}N$ = 281.44) |
| Sub 2-22 | m/z = 321.15($C_{24}H_{19}N$ = 321.41) |
| Sub 2-23 | m/z = 321.15($C_{24}H_{19}N$ = 321.41) |
| Sub 2-24 | m/z = 321.15($C_{24}H_{19}N$ = 321.41) |
| Sub 2-25 | m/z = 321.15($C_{24}H_{19}N$ = 321.41) |
| Sub 2-26 | m/z = 321.15($C_{24}H_{19}N$ = 321.41) |
| Sub 2-27 | m/z = 297.13($C_{20}H_{15}N_3$ = 297.35) |
| Sub 2-28 | m/z = 499.20($C_{36}H_{25}N_3$ = 499.60) |
| Sub 2-29 | m/z = 499.20($C_{36}H_{22}N_2$ = 410.51) |
| Sub 2-30 | m/z = 424.16($C_{30}H_{20}N_2O$ = 424.49) |
| Sub 2-31 | m/z = 440.13($C_{30}H_{20}N_2S$ = 440.56) |
| Sub 2-32 | m/z = 384.16($C_{28}H_{20}N_2$ = 384.47) |
| Sub 2-33 | m/z = 334.15($C_{24}H_{18}N_2$ = 334.41) |
| Sub 2-34 | m/z = 450.21($C_{33}H_{26}N_2$ = 450.57) |
| Sub 2-35 | m/z = 410.18($C_{30}H_{22}N_2$ = 410.51) |
| Sub 2-36 | m/z = 410.18($C_{30}H_{22}N_2$ = 410.51) |
| Sub 2-37 | m/z = 575.24($C_{42}H_{29}N_3$ = 575.70) |
| Sub 2-38 | m/z = 574.24($C_{43}H_{30}N_2$ = 574.71) |
| Sub 2-39 | m/z = 460.19($C_{34}H_{24}N_2$ = 460.57) |
| Sub 2-40 | m/z = 460.19($C_{34}H_{24}N_2$ = 460.57) |
| Sub 2-41 | m/z = 461.19($C_{33}H_{23}N_3$ = 461.56) |
| Sub 2-42 | m/z = 626.27($C_{47}H_{34}N_2$ = 626.79) |
| Sub 2-43 | m/z = 565.23($C_{39}H_{27}N_5$ = 565.67) |
| Sub 2-44 | m/z = 415.21($C_{30}H_{17}D_5N_2$ = 415.54) |
| Sub 2-45 | m/z = 486.21($C_{36}H_{26}N_2$ = 486.61) |
| Sub 2-46 | m/z = 415.21($C_{30}H_{17}D_5N_2$ = 415.54) |

Synthesis Example of Final Products 1

Synthesis Example of 1-1

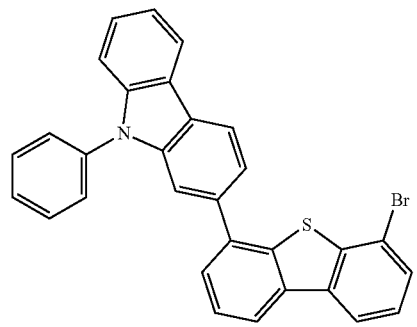

Sub 1-1

+

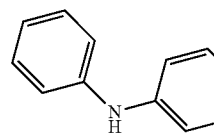

Sub 2-1

Pd$_2$(dba)$_3$/PPh$_3$
—————————→
NaOt-Bu/Toluene

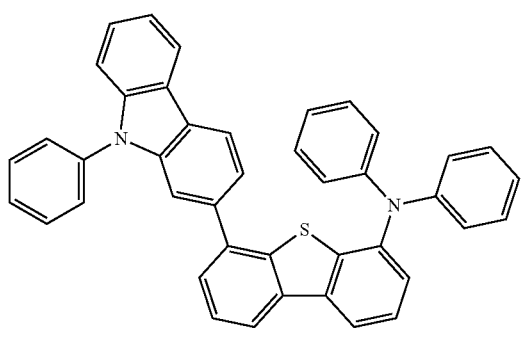

1-1

Sub 2-1 (8.0 g, 47.3 mmol) was added to a round bottom flask and dissolved in toluene (500 mL), and Sub 1-1 (26.2 g, 52.0 mmol), Pd$_2$(dba)$_3$ (2.2 g, 2.4 mmol), P(t-Bu)$_3$ (1 g, 4.73 mmol), NaOt-Bu (13.6 g, 141.8 mmol) were added and stirred at 100° C. After the reaction was completed, the reaction mixture was extracted with CH$_2$Cl$_2$ and water. The organic layer was dried over MgSO$_4$ and concentrated. The resulting compound was separated by silicagel column chromatography and recrystallized to obtain 23.1 g of the product. (yield: 75%)

Synthesis Example of 1-6

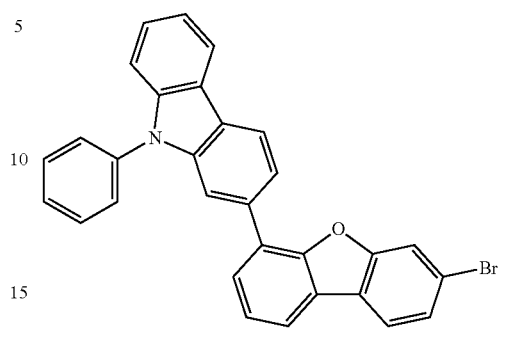

Sub 1-29

+

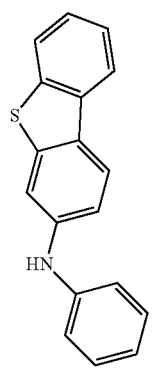

Sub 2-13

Pd$_2$(dba)$_3$/PPh$_3$
—————————→
NaOt-Bu/Toluene

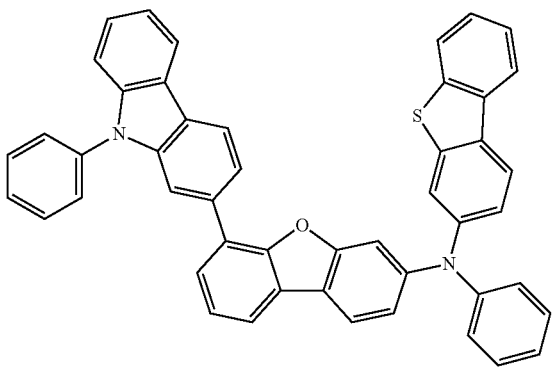

1-6

Sub 2-13 (13.0 g, 47.3 mmol) and Sub 1-29 (25.4 g, 52.0 mmol) were reacted using the synthesis method of 1-1 to give 27 g of the product (yield: 76%).

Synthesis Example of 2-11
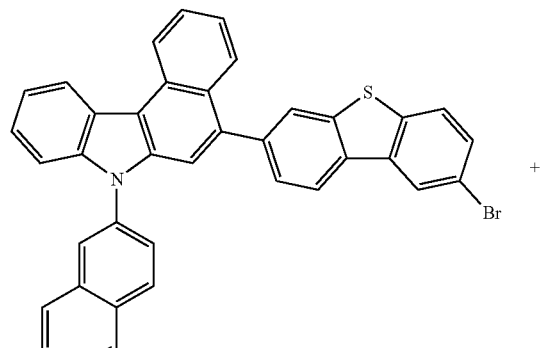
Sub 1-30
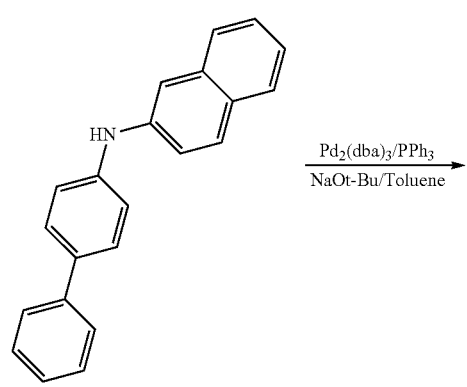
Sub 2-47
2-11
Sub 2-47 (14.0 g, 47.3 mmol) and Sub 1-30 (31.4 g, 52.0 mmol) were reacted using the synthesis method of 1-1 to give 31.5 g of the product (yield: 74%).
Synthesis Example of 2-16
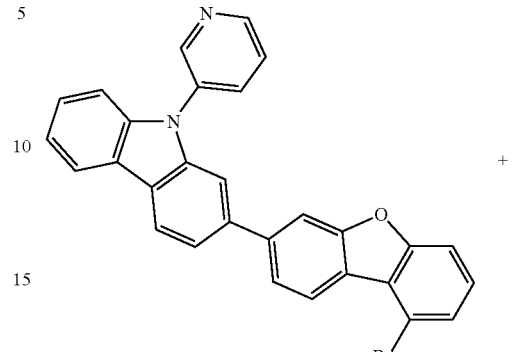
Sub 1-31
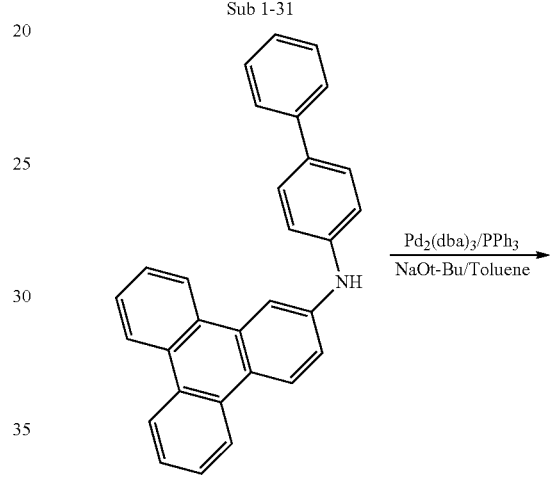
Sub 2-48
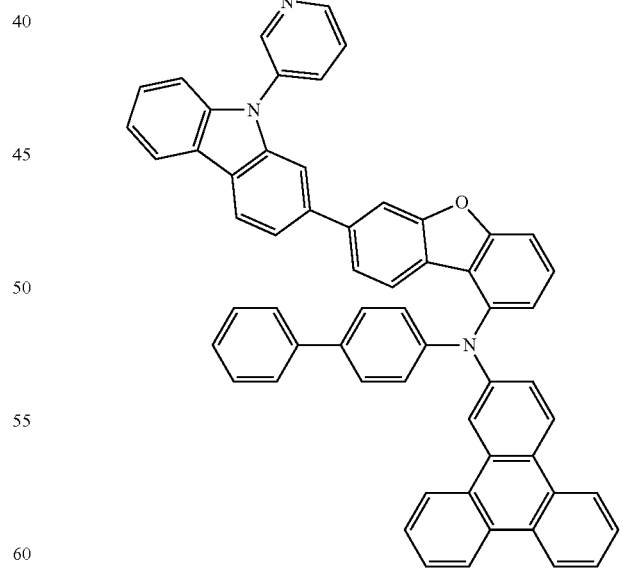
2-16
Sub 2-48 (18.7 g, 47.3 mmol) and Sub 1-31 (25.4 g, 52.0 mmol) were reacted using the synthesis method of 1-1 to give 28.4 g of the product (yield: 68%).
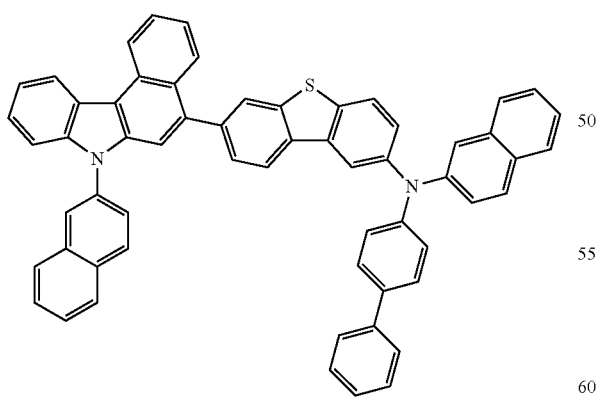

Synthesis Example of 3-8
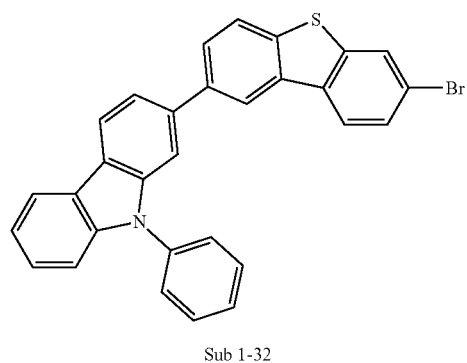
Sub 1-32
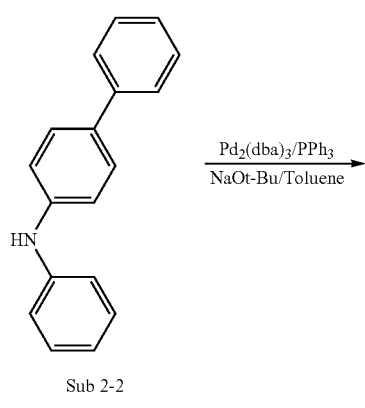
Sub 2-2
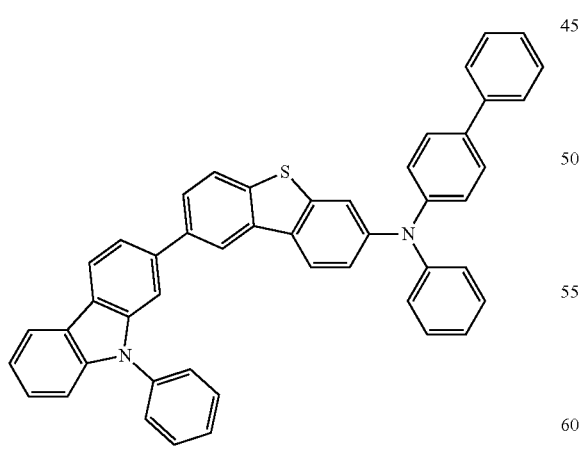
3-8
Synthesis Example of 3-17
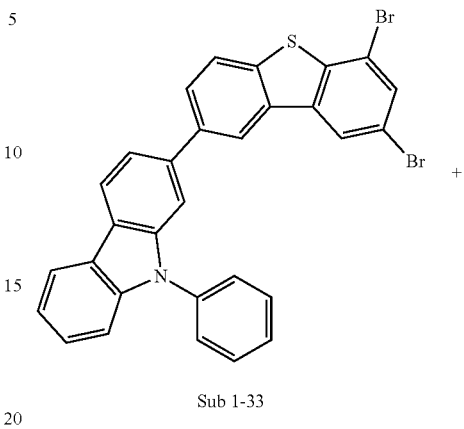
Sub 1-33
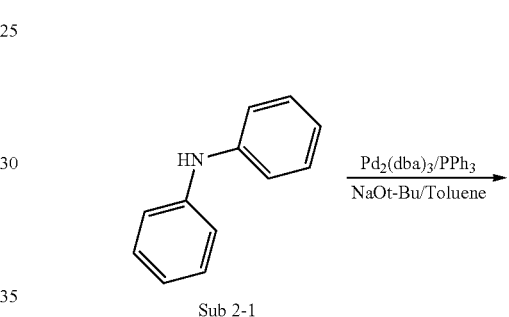
Sub 2-1
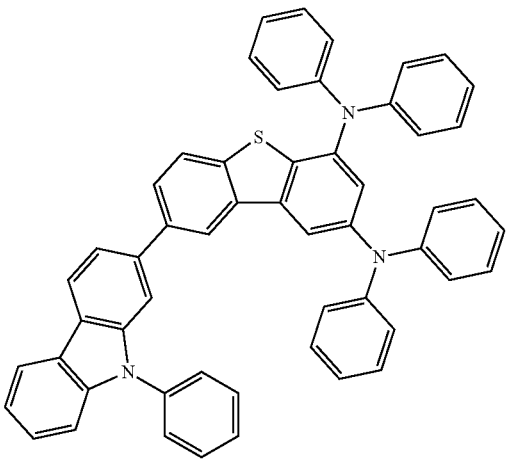
3-17
Sub 2-2 (11.6 g, 47.3 mmol) and Sub 1-32 (26.2 g, 52.0 mmol) were reacted using the synthesis method of 1-1 to give 26.8 g of the product (yield: 77%).
Sub 2-1 (16.0 g, 94.6 mmol) and Sub 1-33 (30.3 g, 52.0 mmol) were reacted using the synthesis method of 1-1 to give 28.4 g of the product (yield: 72%).

Synthesis Example of 4-16

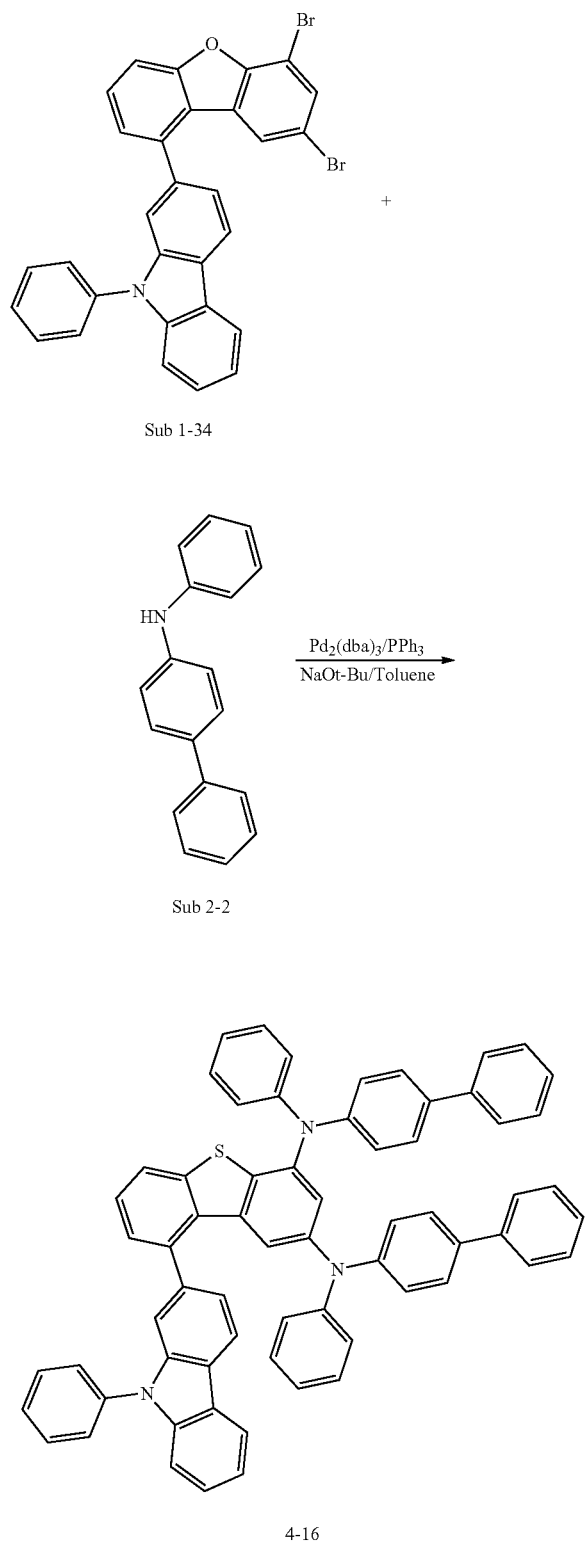

Sub 2-2 (23.2 g, 94.6 mmol) and Sub 1-34 (29.5 g, 52.0 mmol) were reacted using the synthesis method of 1-1 to give 32.2 g of the product (yield: 69%).

Synthesis Example of 4-19

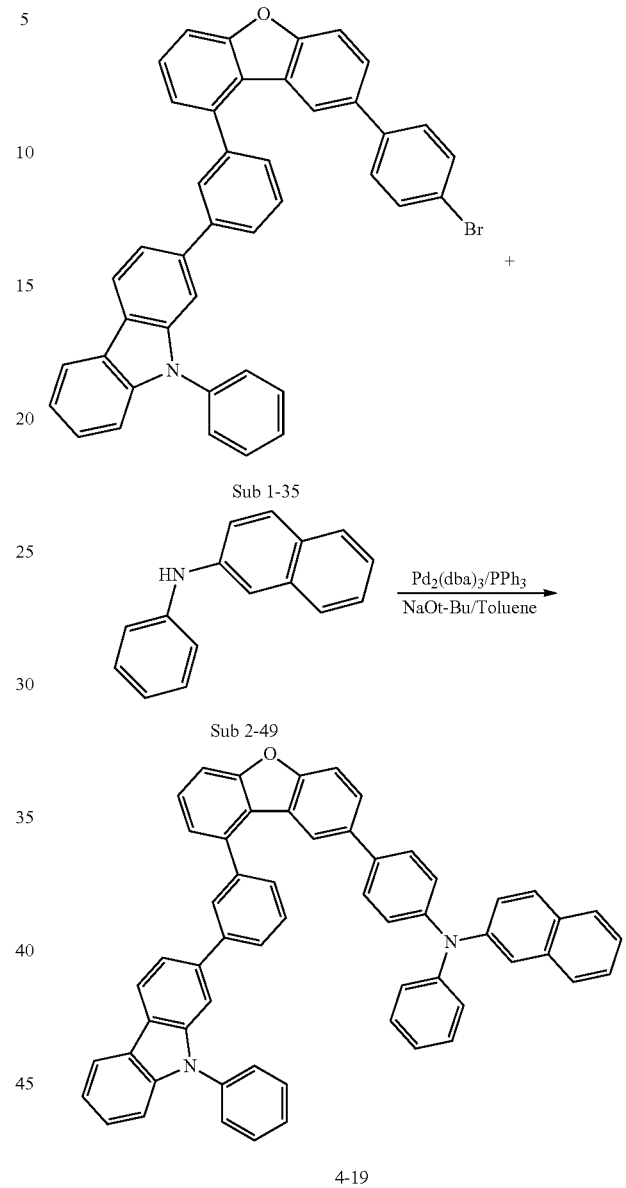

Sub 2-49 (10.4 g, 47.3 mmol) and Sub 1-35 (33.3 g, 52.0 mmol) were reacted using the synthesis method of 1-1 to give 28.4 g of the product (yield: 70%).

TABLE 3

| compound | FD-MS |
| --- | --- |
| 1-1 | m/z = 592.20($C_{42}H_{28}N_2S$ = 592.75) |
| 1-2 | m/z = 642.21($C_{46}H_{30}N_2S$ = 642.81) |
| 1-3 | m/z = 626.24($C_{46}H_{30}N_2O$ = 626.74) |
| 1-4 | m/z = 652.25($C_{48}H_{32}N_2O$ = 652.78) |
| 1-5 | m/z = 593.19($C_{41}H_{27}N_3S$ = 593.74) |
| 1-6 | m/z = 682.21($C_{48}H_{30}N_2OS$ = 682.8) |
| 1-7 | m/z = 716.25($C_{52}H_{32}N_2O_2$ = 716.82) |
| 1-8 | m/z = 692.23($C_{50}H_{32}N_2S$ = 692.87) |
| 1-9 | m/z = 652.25($C_{48}H_{32}N_2O$ = 652.78) |
| 1-10 | m/z = 752.28($C_{56}H_{36}N_2O$ = 752.90) |

TABLE 3-continued

| compound | FD-MS |
|---|---|
| 1-11 | m/z = 818.28($C_{60}H_{38}N_2S$ = 819.02) |
| 1-12 | m/z = 820.29($C_{60}H_{40}N_2S$ = 821.04) |
| 1-13 | m/z = 896.35($C_{65}H_{44}N_4O$ = 897.07) |
| 1-14 | m/z = 876.24($C_{60}H_{36}N_4S_2$ = 877.08) |
| 1-15 | m/z = 909.32($C_{66}H_{43}N_3S$ = 910.13) |
| 1-16 | m/z = 803.29($C_{59}H_{37}N_3O$ = 803.94) |
| 1-17 | m/z = 759.27($C_{54}H_{37}N_3S$ = 759.96) |
| 1-18 | m/z = 859.30($C_{62}H_{41}N_3S$ = 860.07) |
| 1-19 | m/z = 895.33($C_{64}H_{41}N_5O$ = 896.04) |
| 1-20 | m/z = 895.36($C_{66}H_{45}N_3O$ = 896.08) |
| 1-21 | m/z = 835.30($C_{60}H_{41}N_3S$ = 836.05) |
| 1-22 | m/z = 843.32($C_{62}H_{41}N_3O$ = 844.01) |
| 1-23 | m/z = 794.30($C_{57}H_{38}N_4O$ = 794.94) |
| 1-24 | m/z = 911.33($C_{66}H_{45}N_3S$ = 912.15) |
| 1-25 | m/z = 668.23($C_{48}H_{32}N_2S$ = 668.85) |
| 1-26 | m/z = 718.24($C_{52}H_{34}N_2S$ = 718.90) |
| 1-27 | m/z = 778.30($C_{58}H_{38}N_2O$ = 778.94) |
| 1-28 | m/z = 880.35($C_{66}H_{44}N_2O$ = 881.07) |
| 2-1 | m/z = 592.20($C_{42}H_{28}N_2S$ = 592.75) |
| 2-2 | m/z = 642.21($C_{46}H_{30}N_2S$ = 642.81) |
| 2-3 | m/z = 626.24($C_{46}H_{30}N_2O$ = 626.74) |
| 2-4 | m/z = 652.25($C_{48}H_{32}N_2O$ = 652.78) |
| 2-5 | m/z = 593.19($C_{41}H_{27}N_3S$ = 593.74) |
| 2-6 | m/z = 682.21($C_{48}H_{30}N_2OS$ = 682.8) |
| 2-7 | m/z = 716.25($C_{52}H_{33}N_2O_2$ = 716.82) |
| 2-8 | m/z = 692.23($C_{50}H_{32}N_2S$ = 692.87) |
| 2-9 | m/z = 652.25($C_{48}H_{32}N_2O$ = 652.78) |
| 2-10 | m/z = 752.28($C_{56}H_{36}N_2O$ = 752.90) |
| 2-11 | m/z = 818.28($C_{60}H_{38}N_2S$ = 819.02) |
| 2-12 | m/z = 820.29($C_{60}H_{40}N_2S$ = 821.04) |
| 2-13 | m/z = 896.35($C_{65}H_{44}N_4O$ = 897.07) |
| 2-14 | m/z = 876.24($C_{60}H_{36}N_4S_2$ = 877.08) |
| 2-15 | m/z = 909.32($C_{66}H_{43}N_3S$ = 910.13) |
| 2-16 | m/z = 803.29($C_{59}H_{37}N_3O$ = 803.94) |
| 2-17 | m/z = 759.27($C_{54}H_{37}N_3S$ = 759.96) |
| 2-18 | m/z = 859.30($C_{62}H_{41}N_3S$ = 860.07) |
| 2-19 | m/z = 895.0($C_{64}H_{41}N_5O$ = 896.04) |
| 2-20 | m/z = 895.36($C_{66}H_{45}N_3O$ = 896.08) |
| 2-21 | m/z = 835.30($C_{60}H_{41}N_3S$ = 836.05) |
| 2-22 | m/z = 843.32($C_{62}H_{41}N_3O$ = 844.01) |
| 2-23 | m/z = 794.30($C_{57}H_{38}N_4O$ = 794.94) |
| 2-24 | m/z = 911.33($C_{66}H_{45}N_3S$ = 912.15) |
| 2-25 | m/z = 668.23($C_{48}H_{32}N_2S$ = 668.85) |
| 2-26 | m/z = 718.24($C_{52}H_{34}N_2S$ = 718.90) |
| 2-27 | m/z = 778.30($C_{58}H_{38}N_2O$ = 778.94) |
| 2-28 | m/z = 880.35($C_{66}H_{44}N_2O$ = 881.07) |
| 3-1 | m/z = 592.20($C_{42}H_{28}N_2S$ = 592.75) |
| 3-2 | m/z = 642.21($C_{46}H_{30}N_2S$ = 642.81) |
| 3-3 | m/z = 626.24($C_{46}H_{30}N_2O$ = 626.74) |
| 3-4 | m/z = 652.25($C_{48}H_{32}N_2O$ = 652.78) |
| 3-5 | m/z = 593.19($C_{41}H_{27}N_3S$ = 593.74) |
| 3-6 | m/z = 682.21($C_{48}H_{30}N_2OS$ = 682.8) |
| 3-7 | m/z = 716.25($C_{52}H_{33}N_2O_2$ = 716.82) |
| 3-8 | m/z = 668.23($C_{48}H_{32}N_2S$ = 668.85) |
| 3-9 | m/z = 652.25($C_{48}H_{32}N_2O$ = 652.78) |
| 3-10 | m/z = 752.28($C_{56}H_{36}N_2O$ = 752.90) |
| 3-11 | m/z = 818.28($C_{60}H_{38}N_2S$ = 819.02) |
| 3-12 | m/z = 820.29($C_{60}H_{40}N_2S$ = 821.04) |
| 3-13 | m/z = 896.35($C_{65}H_{44}N_4O$ = 897.07) |
| 3-14 | m/z = 876.24($C_{60}H_{36}N_4S_2$ = 877.08) |
| 3-15 | m/z = 909.32($C_{66}H_{43}N_3S$ = 910.13) |
| 3-16 | m/z = 803.29($C_{59}H_{37}N_3O$ = 803.94) |
| 3-17 | m/z = 759.27($C_{54}H_{37}N_3S$ = 759.96) |
| 3-18 | m/z = 859.30($C_{62}H_{41}N_3S$ = 860.07) |
| 3-19 | m/z = 895.33($C_{64}H_{41}N_5O$ = 896.04) |
| 3-20 | m/z = 895.36($C_{66}H_{45}N_3O$ = 896.08) |
| 3-21 | m/z = 835.30($C_{60}H_{41}N_3S$ = 836.05) |
| 3-22 | m/z = 843.32($C_{62}H_{41}N_3O$ = 844.01) |
| 3-23 | m/z = 794.30($C_{57}H_{38}N_4O$ = 794.94) |
| 3-24 | m/z = 911.33($C_{66}H_{45}N_3S$ = 912.15) |
| 3-25 | m/z = 668.23($C_{48}H_{32}N_2S$ = 668.85) |
| 3-26 | m/z = 718.24($C_{52}H_{34}N_2S$ = 718.90) |
| 3-27 | m/z = 778.30($C_{58}H_{38}N_2O$ = 778.94) |
| 3-28 | m/z = 880.35($C_{66}H_{44}N_2O$ = 881.07) |
| 4-1 | m/z = 592.20($C_{42}H_{28}N_2S$ = 592.75) |
| 4-2 | m/z = 642.21($C_{46}H_{30}N_2S$ = 642.81) |
| 4-3 | m/z = 626.24($C_{46}H_{30}N_2O$ = 626.74) |
| 4-4 | m/z = 652.25($C_{48}H_{32}N_2O$ = 652.78) |

TABLE 3-continued

| compound | FD-MS |
|---|---|
| 4-5 | m/z = 593.19($C_{41}H_{27}N_3S$ = 593.74) |
| 4-6 | m/z = 682.21($C_{48}H_{30}N_2OS$ = 682.8) |
| 4-7 | m/z = 716.25($C_{52}H_{32}N_2O_2$ = 716.82) |
| 4-8 | m/z = 692.23($C_{50}H_{32}N_2S$ = 692.87) |
| 4-9 | m/z = 652.25($C_{48}H_{32}N_2O$ = 652.78) |
| 4-10 | m/z = 752.28($C_{56}H_{36}N_2O$ = 752.90) |
| 4-11 | m/z = 818.28($C_{60}H_{38}N_2S$ = 819.02) |
| 4-12 | m/z = 820.29($C_{60}H_{40}N_2S$ = 821.04) |
| 4-13 | m/z = 759.27($C_{54}H_{37}N_3S$ = 759.96) |
| 4-14 | m/z = 859.30($C_{62}H_{41}N_3S$ = 860.07) |
| 4-15 | m/z = 895.33($C_{64}H_{41}N_5O$ = 896.04) |
| 4-16 | m/z = 895.36($C_{66}H_{45}N_3O$ = 896.08) |
| 4-17 | m/z = 668.23($C_{48}H_{32}N_2S$ = 668.85) |
| 4-18 | m/z = 718.24($C_{52}H_{34}N_2S$ = 718.90) |
| 4-19 | m/z = 778.30($C_{58}H_{38}N_2O$ = 778.94) |
| 4-20 | m/z = 880.35($C_{66}H_{44}N_2O$ = 881.07) |

Synthesis Example 2

The final product 2 represented by Formula (13) of the present invention can be synthesized by reacting Sub 3 or Sub 4 with Sub 5 as illustrated in the following Reaction Scheme 4.

<Reaction Scheme 4>

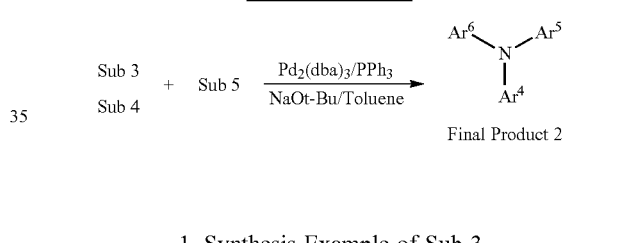

Final Product 2

1. Synthesis Example of Sub 3

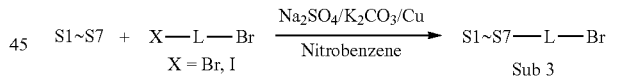

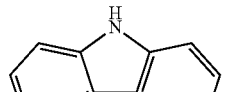

S1

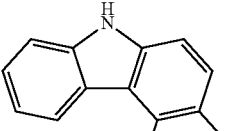

S2

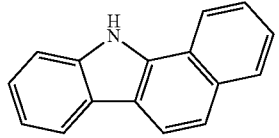

S3

-continued

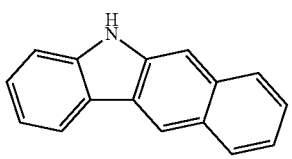

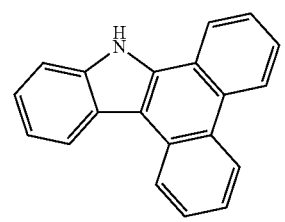

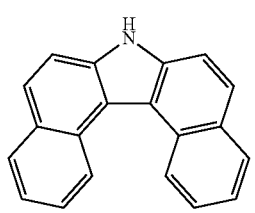

L is $L^3$ or $L^5$ defined in Formulas (2-a), (2-b) and (2-c).

1) Synthesis Example of Sub 3-1-1 (L=Biphenyl)

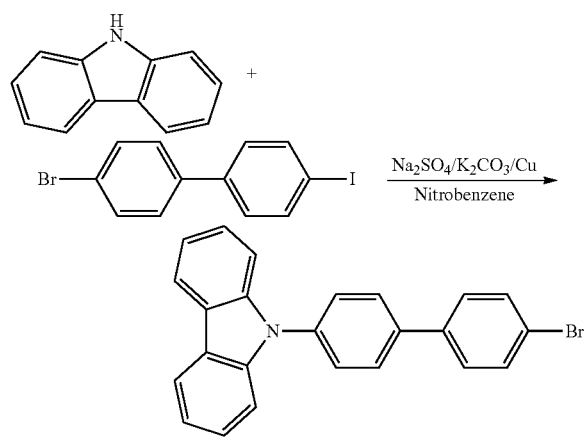

Sub 3-1-1

Starting material 9H-carbazole (50.16 g, 300 mmol) and 4-bromo-4'-iodo-1,1'-biphenyl (129.2 g, 360 mmol), Na$_2$SO$_4$ (42.6 g, 300 mmol), K$_2$CO$_3$ (41.4 g, 300 mmol), Cu (5.72 g, 90 mmol), nitrobenzene were reacted using the above synthesis method to give 80.05 g of the product. (yield: 67%).

2) Synthesis Example of Sub 3-1-2 (L=9,9-dimethyl-9H-fluorene)

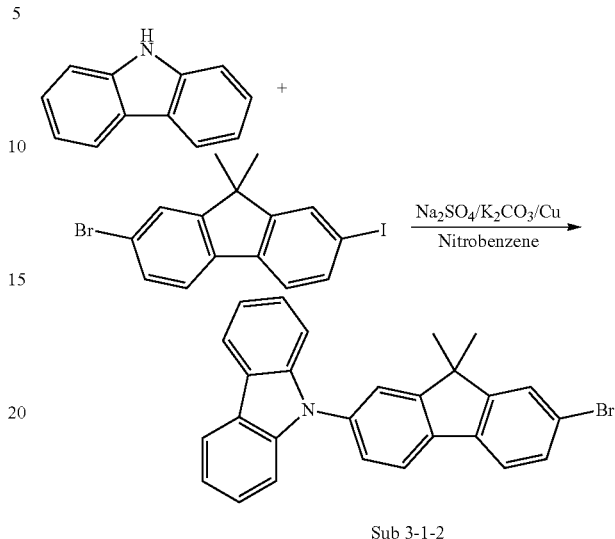

Sub 3-1-2

Starting material 9H-carbazole (50.16 g, 300 mmol) and 2-bromo-7-iodo-9,9-dimethyl-9H-fluorene (143.7 g, 360 mmol), Na$_2$SO$_4$ (42.6 g, 300 mmol), K$_2$CO$_3$ (41.4 g, 300 mmol), Cu (5.72 g, 90 mmol), nitrobenzene were reacted using the above synthesis method to give 88.11 g of the product. (yield: 67%).

3) Synthesis Example of Sub 3-1-3 (L=9,9-dimethyl-9H-fluorene)

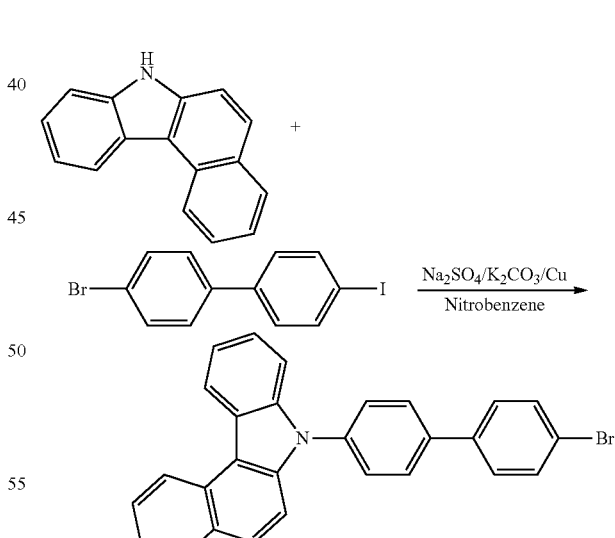

Sub 3-1-3

Starting material 7H-benzo[c]carbazole (65.18 g, 300 mmol) and 4-bromo-4'-iodo-1,1'-biphenyl (129.2 g, 360 mmol), Na$_2$SO$_4$ (42.6 g, 300 mmol), K$_2$CO$_3$ (41.4 g, 300 mmol), Cu (5.72 g, 90 mmol), nitrobenzene were reacted using the above synthesis method to give 92.8 g of the product. (yield: 69%).

4) Synthesis Example of Sub 3-1-4
(L=9,9-dimethyl-9H-fluorene)

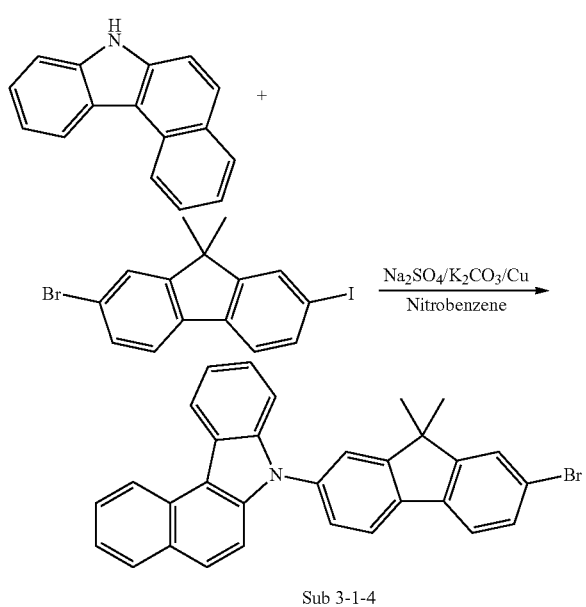

Sub 3-1-4

Starting material 7H-benzo[c]carbazole (65.18 g, 300 mmol) and 2-bromo-7-iodo-9,9-dimethyl-9H-fluorene (143.7 g, 360 mmol), Na$_2$SO$_4$ (42.6 g, 300 mmol), K$_2$CO$_3$ (41.4 g, 300 mmol), Cu (5.72 g, 90 mmol), nitrobenzene were reacted using the above synthesis method to give 95.24 g of the product. (yield: 65%).

5) Synthesis Example of Sub 3-1-5 (L=Biphenyl)

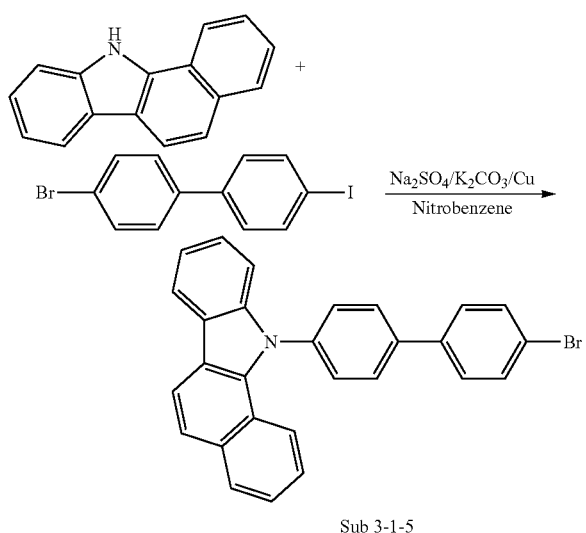

Sub 3-1-5

Starting material 11H-benzo[a]carbazole (65.18 g, 300 mmol) and 4-bromo-4'-iodo-1,1'-biphenyl (129.2 g, 360 mmol), Na$_2$SO$_4$ (42.6 g, 300 mmol), K$_2$CO$_3$ (41.4 g, 300 mmol), Cu (5.72 g, 90 mmol), nitrobenzene were reacted using the above synthesis method to give 80.05 g of the product. (yield: 62%).

6) Synthesis Example of Sub 3-1-6
(L=9,9-dimethyl-9H-fluorene)

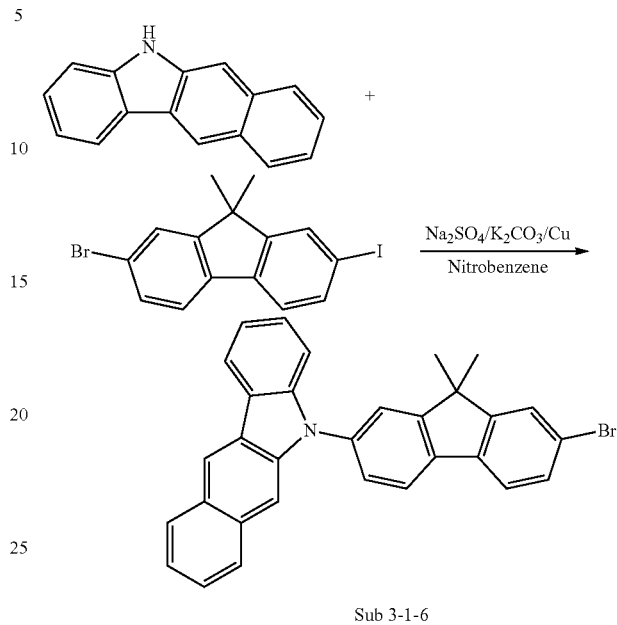

Sub 3-1-6

Starting material 5H-benzo[b]carbazole (65.18 g, 300 mmol) and 2-bromo-7-iodo-9,9-dimethyl-9H-fluorene (143.7 g, 360 mmol), Na$_2$SO$_4$ (42.6 g, 300 mmol), K$_2$CO$_3$ (41.4 g, 300 mmol), Cu (5.72 g, 90 mmol), nitrobenzene were reacted using the above synthesis method to give 93.78 g of the product. (yield: 64%).

7) Synthesis Example of Sub 3-1-7 (L=Biphenyl)

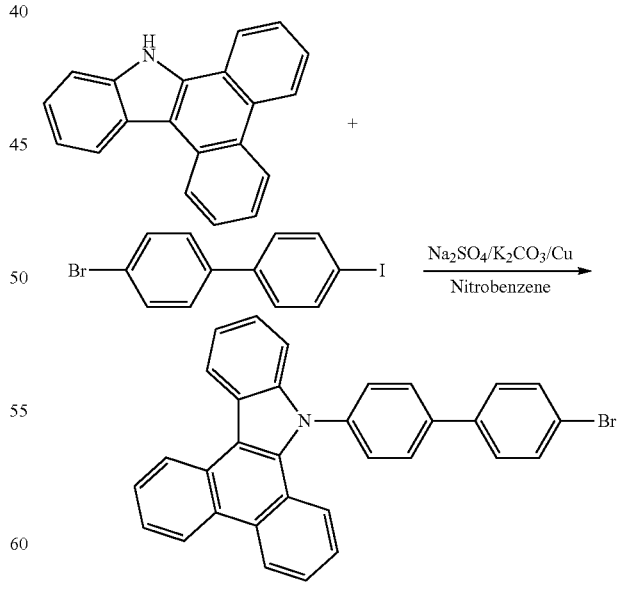

Sub 3-1-7

Starting material 9H-dibenzo[a,c]carbazole (80.2 g, 300 mmol) and 4-bromo-4'-iodo-1,1'-biphenyl (129.2 g, 360 mmol), Na$_2$SO$_4$ (42.6 g, 300 mmol), K$_2$CO$_3$ (41.4 g, 300 mmol), Cu (5.72 g, 90 mmol), nitrobenzene were reacted using the above synthesis method to give 98.7 g of the product. (yield: 66%).

8) Synthesis Example of Sub 3-1-8 (L=Biphenyl)

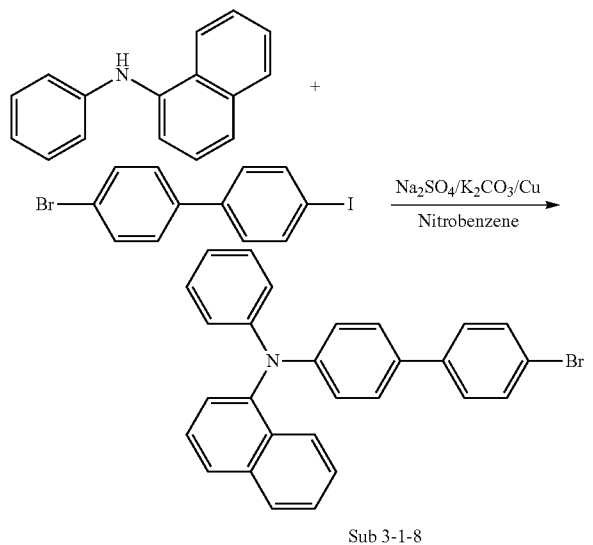

Sub 3-1-8

Starting material N-phenylnaphthalen-1-amine (65.8 g, 300 mmol) and 4-bromo-4'-iodo-1,1'-biphenyl (129.2 g, 360 mmol), Na$_2$SO$_4$ (42.6 g, 300 mmol), K$_2$CO$_3$ (41.4 g, 300 mmol), Cu (5.72 g, 90 mmol), nitrobenzene were reacted using the above synthesis method to give 89.2 g of the product. (yield: 66%).

9) Synthesis Example of Sub 3-1-9 (L=9,9-dimethyl-9H-fluorene)

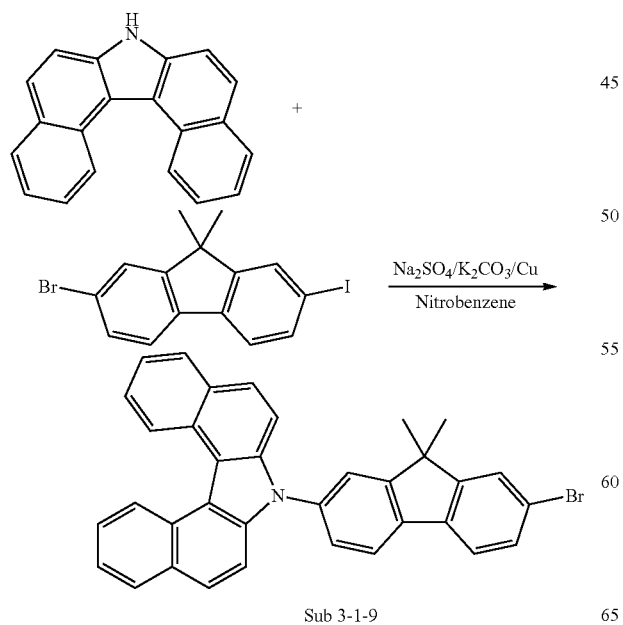

Sub 3-1-9

Starting material 7H-dibenzo[c,g]carbazole (80.2 g, 300 mmol) and 2-bromo-7-iodo-9,9-dimethyl-9H-fluorene (143.7 g, 360 mmol), Na$_2$SO$_4$ (42.6 g, 300 mmol), K$_2$CO$_3$ (41.4 g, 300 mmol), Cu (5.72 g, 90 mmol), nitrobenzene were reacted using the above synthesis method to give 98.5 g of the product. (yield: 61%).

2. Synthesis Example of Sub 4

Sub 4 of Reaction Scheme 4 can be synthesized by the reaction path of Reaction Scheme 5 below.

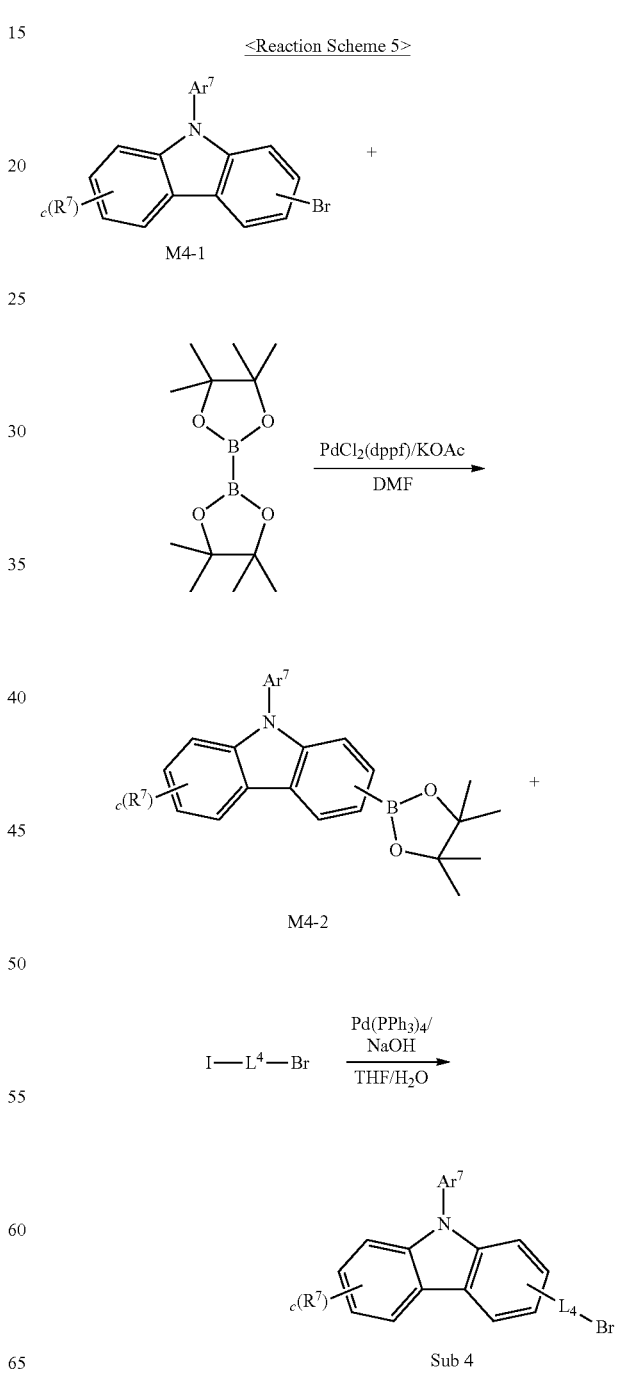

1) Synthesis Example of M4-2-1

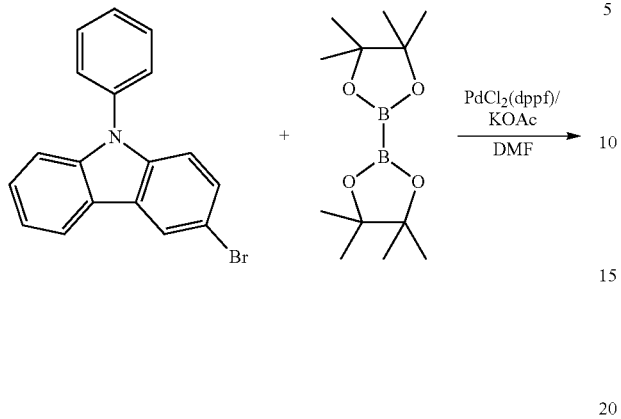

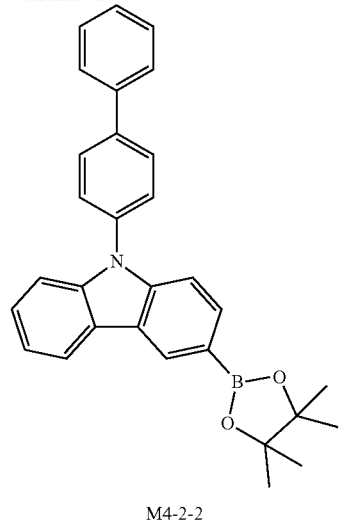

3-bromo-9-phenyl-9H-carbazole (45.1 g, 140 mmol) was dissolved in DMF 980 ml and Bispinacolborate (39.1 g, 154 mmol), $PdCl_2$(dppf) catalyst (3.43 g, 4.2 mmol), KOAc (41.3 g, 420 mmol) were added in order and stirred for 24 hours and then after synthesizing the borate compound, the obtained compound was separated over a silicagel column and recrystallization to give 35.2 g of the borate compound (yield: 68%).

2) Synthesis Example of M4-2-2

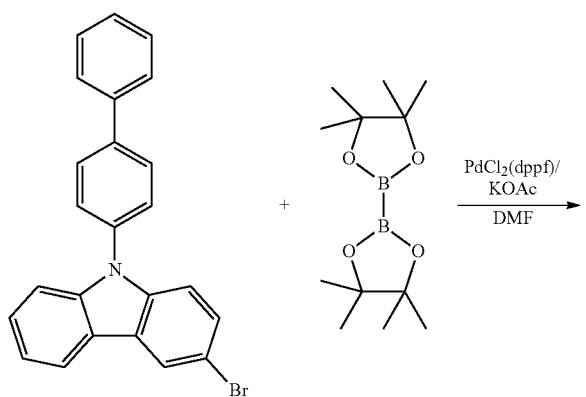

40 g (64%) was obtained through the same experimental procedure as M4-2-1.

3) Synthesis Example of Sub 4-1-1

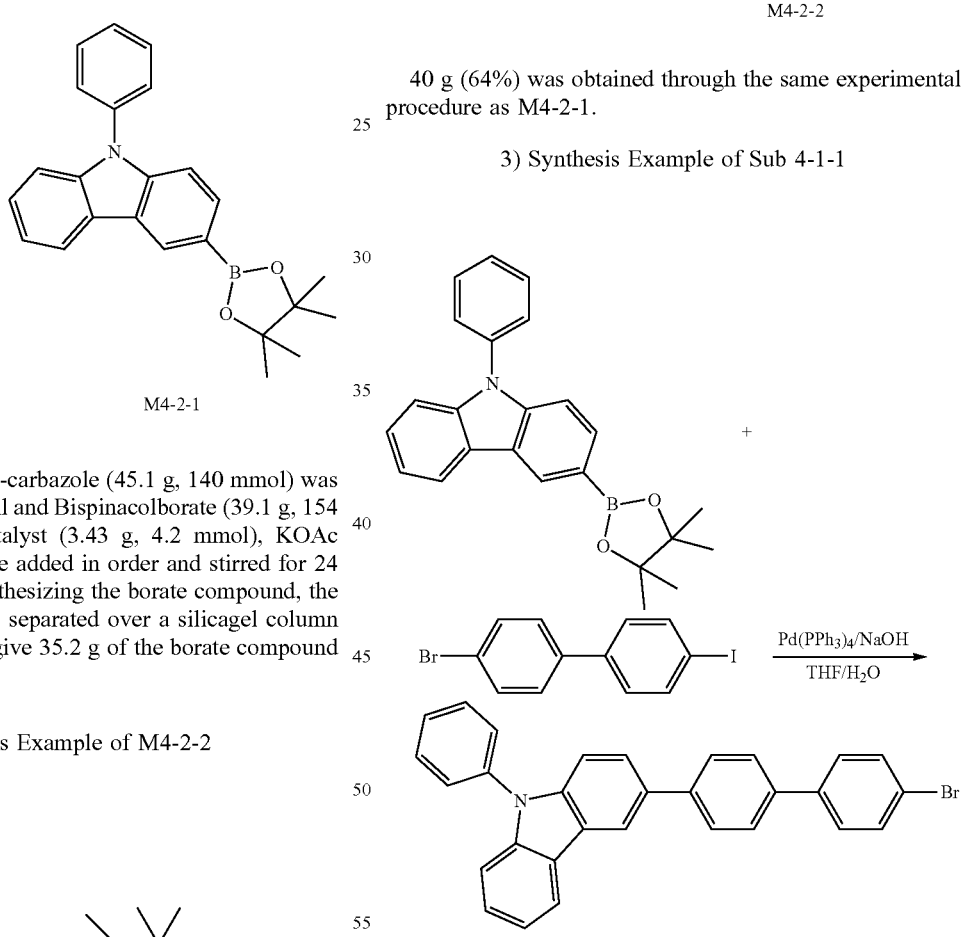

M4-2-1 (29.5 g, 80 mmol) was dissolved in THF 360 mL and 4-bromo-4'-iodo-1,1'-biphenyl (30.16 g, 84 mmol), $Pd(PPh_3)_4$ (2.8 g, 2.4 mmol), NaOH (9.6 g, 240 mmol), and water (180 mL) were added and refluxed with stirring. When the reaction was completed, the reaction mixture was extracted with ether and water. The organic layer was dried over $MgSO_4$ and concentrated. The resulting compound was separated by silicagel column chromatography and recrystallized to obtain 26.56 g (yield: 70%) of the product.

4) Synthesis Example of Sub 4-1-2

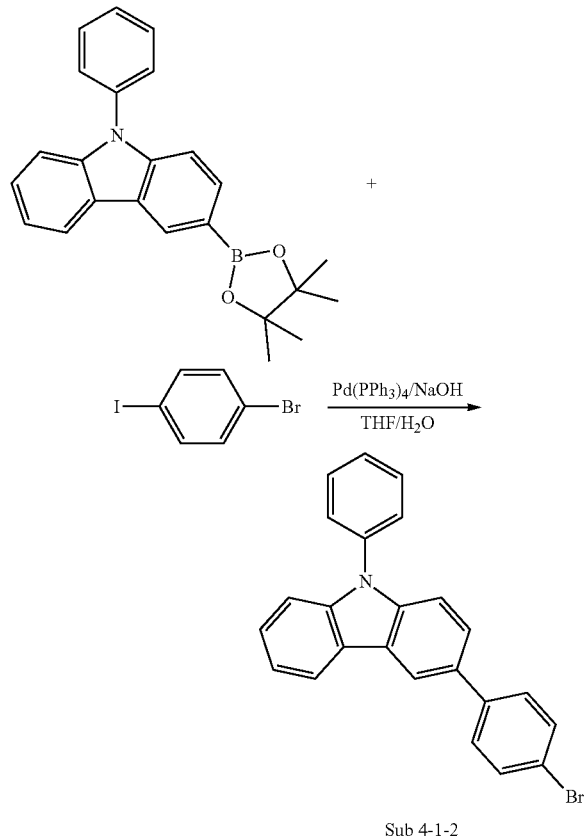

Sub 4-1-2

M4-2-1 (29.5 g, 80 mmol) was dissolved in THF 360 mL, and 1-bromo-4-iodobenzene (23.8 g, 84 mmol), Pd(PPh$_3$)$_4$ (2.8 g, 2.4 mmol), NaOH (9.6 g, 240 mmol), and water (180 mL) were added and refluxed with stirring. When the reaction was completed, the reaction mixture was extracted with ether and water. The organic layer was dried over MgSO$_4$ and concentrated. The resulting compound was separated by silicagel column chromatography and recrystallized to obtain 22.9 g (yield: 72%) of the product.

5) Synthesis Example of Sub 4-1-3

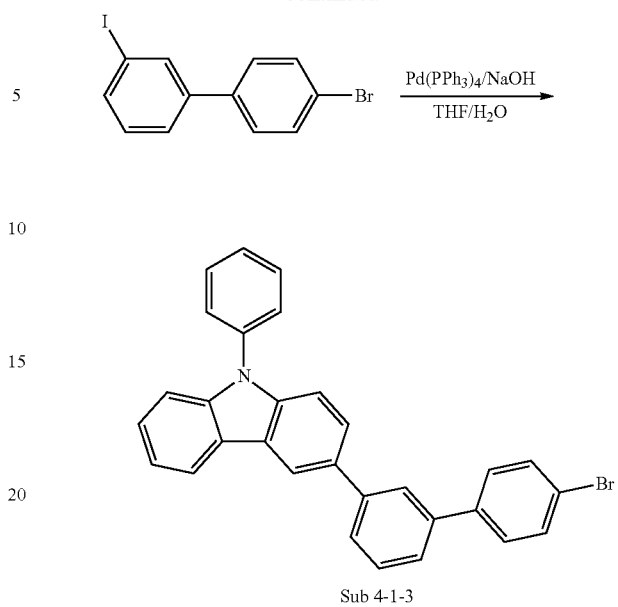

Sub 4-1-3

M4-2-1 (29.5 g, 80 mmol) was dissolved in THF 360 mL, and 4'-bromo-3-iodo-1,1'-biphenyl (30.16 g, 84 mmol), Pd(PPh$_3$)$_4$ (2.8 g, 2.4 mmol), NaOH (9.6 g, 240 mmol), and water (180 mL) were added and refluxed with stirring. When the reaction was completed, the reaction mixture was extracted with ether and water. The organic layer was dried over MgSO$_4$ and concentrated. The resulting compound was separated by silicagel column chromatography and recrystallized to obtain 24.7 g (yield: 65%) of the product.

6) Synthesis Example of Sub 4-1-4

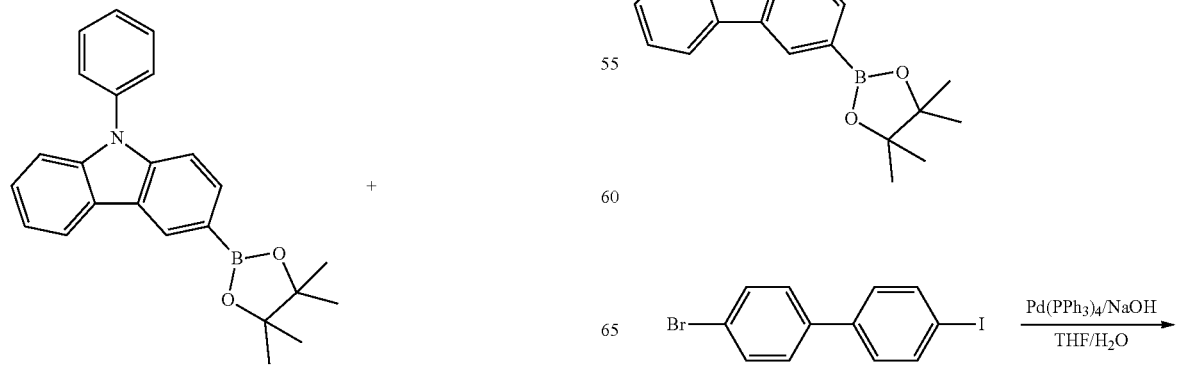

123

-continued

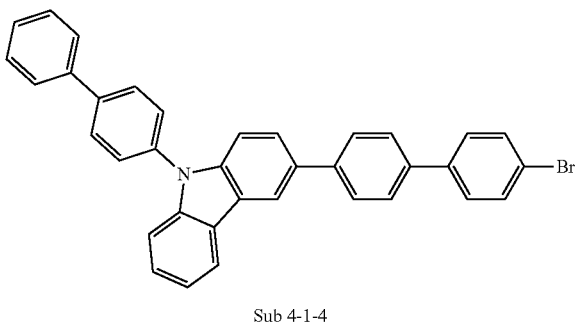

Sub 4-1-4

M4-2-2 (35.63 g, 80 mmol) was dissolved in THF 360 mL, 4-bromo-4'-iodo-1,1'-biphenyl (30.16 g, 84 mmol), Pd(PPh$_3$)$_4$ (2.8 g, 2.4 mmol), NaOH (9.6 g, 240 mmol), and water (180 mL) were added and refluxed with stirring. When the reaction was completed, the reaction mixture was extracted with ether and water. The organic layer was dried over MgSO$_4$ and concentrated. The resulting compound was separated by silicagel column chromatography and recrystallized to obtain 29.51 g (yield: 67%) of the product.

3. Synthesis Example of Sub 5

Sub 5 of Reaction Scheme 4 is the same as the synthesis example of Sub 2 of Reaction Scheme 3 below.

Synthesis of Final Product of Formula (2)

Synthesis Example of 13-17

124

-continued

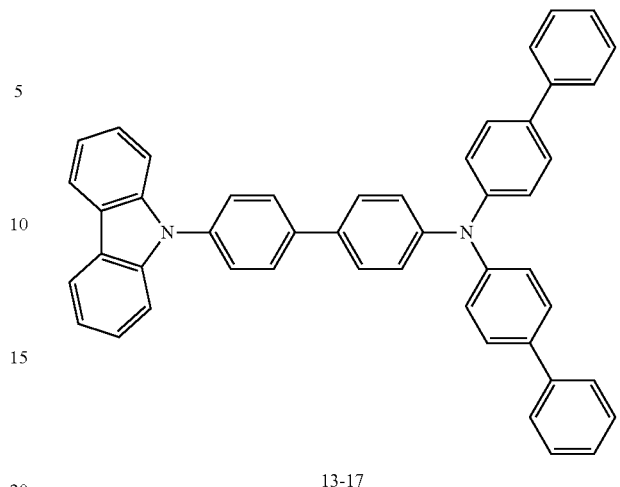

13-17

9-(4'-bromo-[1,1'-biphenyl]-4-yl)-9H-carbazole (9.6 g, 24 mmol) was dissolved in toluene, and di([1,1'-biphenyl]-4-yl)amine (6.4 g, 20 mmol), Pd$_2$(dba)$_3$ (0.05 eq.), PPh$_3$ (0.1 eq.), NaOt-Bu (3 eq.) were added and refluxed with stirring at 100° C. for 24 hours. When the reaction was completed, the reaction mixture was extracted with ether and water. The organic layer was dried over MgSO$_4$ and concentrated. The resulting compound was separated by silicagel column chromatography and recrystallized to obtain 12.9 g (yield: 84%) of the product.

Synthesis Example of 13-32

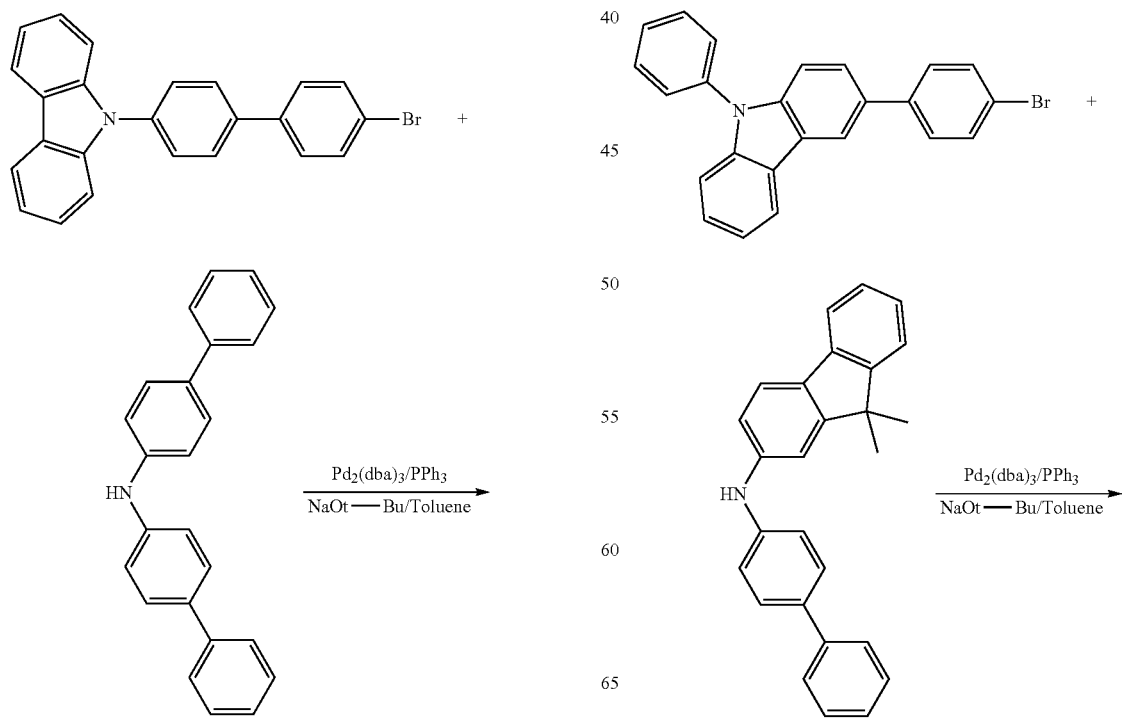

-continued

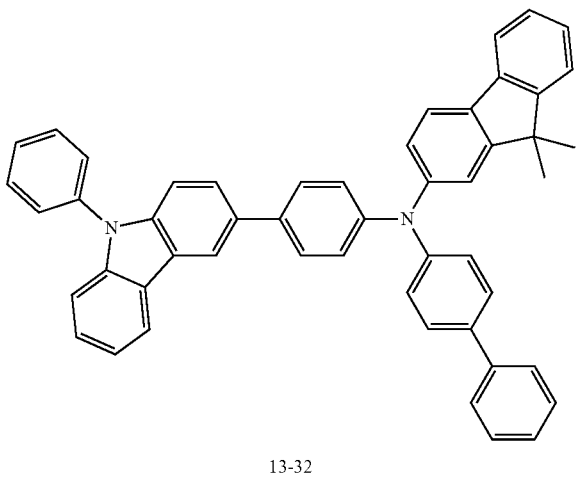

13-32

3-(4-bromophenyl)-9-phenyl-9H-carbazole (9.6 g, 24 mmol) was dissolved in toluene, and N-([1,1'-biphenyl]-4-yl)-9,9-dimethyl-9H-fluoren-2-amine (7.2 g, 20 mmol), Pd₂(dba)₃ (0.05 eq.), PPh₃ (0.1 eq.), NaOt-Bu (3 eq.) were added and refluxed with stirring at 100° C. for 24 hours. When the reaction was completed, the reaction mixture was extracted with ether and water. The organic layer was dried over MgSO₄ and concentrated. The resulting compound was separated by silicagel column chromatography and recrystallized to obtain 13.8 g (yield: 85%) of the product.

Synthesis Example of 13-61

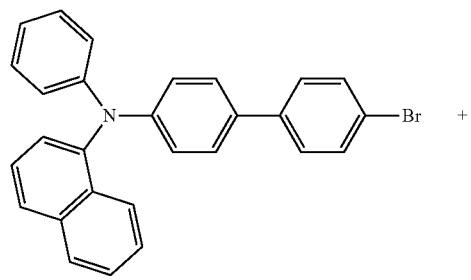

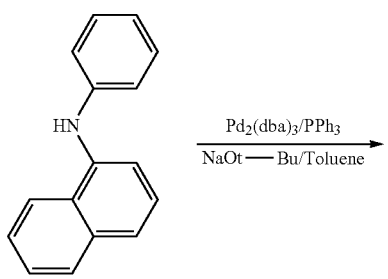

-continued

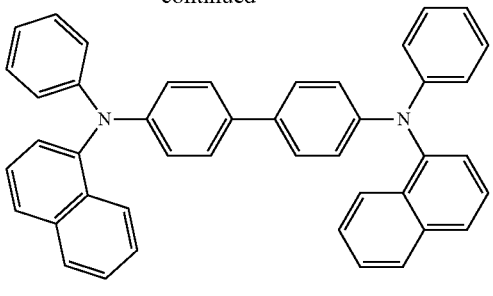

13-61

N-(4'-bromo-[1,1'-biphenyl]-4-yl)-N-phenylnaphthalen-1-amine (10.8 g, 24 mmol) was dissolved in toluene and, N-phenylnaphthalen-1-amine (4.4 g, 20 mmol), Pd₂(dba)₃ (0.05 eq.), PPh₃ (0.1 eq.), NaOt-Bu (3 eq.) were added and refluxed with stirring at 100° C. for 24 hours. When the reaction was completed, the reaction mixture was extracted with ether and water. The organic layer was dried over MgSO₄ and concentrated. The resulting compound was separated by silicagel column chromatography and recrystallized to obtain 11.4 g (yield: 81%) of the product.

Some of the products obtained above were confirmed by Mass Data as follows.

TABLE 4

| compound | FD-MS |
|---|---|
| 13-17 | m/z = 638.27 ($C_{48}H_{34}N_2$ = 638.80) |
| 13-20 | m/z = 678.30 ($C_{51}H_{38}N_2$ = 678.86) |
| 13-21 | m/z = 802.33 ($C_{61}H_{42}N_2$ = 803.00) |
| 13-22 | m/z = 800.32 ($C_{61}H_{40}N_2$ = 800.98) |
| 13-32 | m/z = 678.30 ($C_{51}H_{38}N_2$ = 678.86) |
| 13-33 | m/z = 802.33 ($C_{61}H_{42}N_2$ = 803.00) |
| 13-34 | m/z = 800.32 ($C_{61}H_{40}N_2$ = 800.98) |
| 13-43 | m/z = 714.30 ($C_{54}H_{38}N_2$ = 714.89) |
| 13-44 | m/z = 754.33 ($C_{57}H_{42}N_2$ = 754.96) |
| 13-45 | m/z = 878.37 ($C_{67}H_{46}N_2$ = 879.10) |
| 13-46 | m/z = 876.35 ($C_{67}H_{44}N_2$ = 877.08) |
| 13-47 | m/z = 744.26 ($C_{54}H_{36}N_2S$ = 744.94) |
| 13-52 | m/z = 826.33 ($C_{63}H_{42}N_2$ = 827.02) |
| 13-53 | m/z = 824.32 ($C_{63}H_{40}N_2$ = 825.01) |
| 13-54 | m/z = 688.29 ($C_{52}H_{36}N_2$ = 688.86) |
| 13-55 | m/z = 728.32 ($C_{55}H_{40}N_2$ = 728.92) |
| 13-57 | m/z = 778.33 ($C_{59}H_{42}N_2$ = 778.98) |
| 13-58 | m/z = 902.37 ($C_{69}H_{46}N_2$ = 903.12) |
| 13-59 | m/z = 900.35 ($C_{69}H_{44}N_2$ = 901.10) |
| 13-60 | m/z = 538.24 ($C_{40}H_{30}N_2$ = 538.68) |
| 13-61 | m/z = 588.26 ($C_{44}H_{32}N_2$ = 588.74) |
| 13-62 | m/z = 588.26 ($C_{44}H_{32}N_2$ = 588.74) |
| 13-63 | m/z = 614.27 ($C_{46}H_{34}N_2$ = 614.78) |

Manufacture and Evaluation of Organic Electric Element

Example 1) Manufacture and Testing of a Green Organic Light Emitting Diode

First, on an ITO layer (anode) formed on a glass substrate, $N^1$-(naphthalen-2-yl)-$N^4$,$N^4$-bis(4-(naphthalen-2-yl(phenyl)amino)phenyl)-$N^1$-phenyl benzene-1,4-diamine (hereinafter will be abbreviated as 2-TNATA) was vacuum-deposited to form a hole injection layer with a thickness of 60 nm. Subsequently, $N^1$-(naphthalen-2-yl)-$N^4$,$N^4$-bis(4-(naphthalen-2-yl(phenyl)amino)phenyl)-$N^1$-phenyl benzene-1,4-diamine (hereinafter will be abbreviated as 2-TNATA) as a hole transport compound was vapor-deposited on the film to a thickness of 60 nm to form a hole transport layer. Subsequently, the inventive compounds and examples were vacuum-deposited as an emitting-auxiliary layer material to a thickness of 20 nm to form an emitting-auxiliary layer. After forming the emitting-auxiliary layer, CBP [4,4'-N,N'-dicarbazole-biphenyl] as a host was used in the upper of an emitting auxiliary layer, and Ir(ppy)3 [tris(2-phenylpyridine)-iridium] as a dopant was vacuum deposited to form an emitting layer with a thickness of 30 nm by doping with a weight ratio of 95:5. (1,1'-bisphenyl)-4-olato)bis(2-methyl-8-quinolinolato)aluminum (hereinafter will be abbreviated as BAlq) was vacuum-deposited to a thickness of 10 nm as a hole blocking layer, and tris(8-quinolinol)aluminum (hereinafter will be abbreviated as Alq3) was deposited to a thickness of 40 nm as an electron transport layer. After that, an alkali metal halide, LiF was vacuum deposited as an electron injection layer to a thickness of 0.2 nm, and Al was deposited to a thickness of 150 nm to form a cathode to manufacture an OLED.

To the OLEDs which were manufactured by examples and comparative examples, a forward bias direct current voltage was applied, and electroluminescent (EL) properties were measured using PR-650 of Photoresearch Co., and T95 life was measured using a life measuring apparatus manufactured by McScience Inc. with a reference luminance of 5000 cd/m². In the following table, the manufacture of a device and the results of evaluation are shown.

Comparative 1

An organic electroluminescent device was manufactured in the same manner as in Example 1, except that the emitting-auxiliary layer was not used.

Comparative 2

An organic electroluminescent device was manufactured in the same manner as in Example 1, except that the emitting-auxiliary layer was formed using the Comparative Example 1 instead of the compound of the present invention.

Comparative compound 1

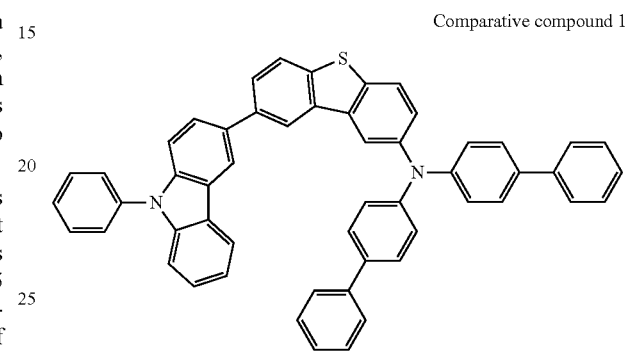

TABLE 5

| | compound | Voltage | Current Density | Brightness (cd/m2) | Efficiency | Lifetime T(95) | CIE (x, y) |
|---|---|---|---|---|---|---|---|
| comparative example(1) | — | 6.0 | 21.7 | 5000.0 | 23.0 | 61.8 | (0.31, 0.61) |
| comparative example(2) | comparative compound 1 | 6.2 | 14.3 | 5000.0 | 35.0 | 94..5 | (0.31, 0.60) |
| example(1) | Compound (1-4) | 5.7 | 11.7 | 5000.0 | 42.8 | 110.2 | (0.31, 0.60) |
| example(2) | Compound (1-6) | 5.8 | 11.6 | 5000.0 | 43.2 | 113.3 | (0.32, 0.61) |
| example(3) | Compound (1-7) | 5.8 | 11.5 | 5000.0 | 43.7 | 113.8 | (0.31, 0.61) |
| example(4) | Compound (1-9) | 5.7 | 11.2 | 5000.0 | 44.5 | 119.5 | (0.33, 0.60) |
| example(5) | Compound (1-10) | 5.7 | 11.5 | 5000.0 | 43.4 | 110.9 | (0.31, 0.60) |
| example(6) | Compound (1-11) | 5.7 | 11.4 | 5000.0 | 44.0 | 111.3 | (0.32, 0.61) |
| example(7) | Compound (1-12) | 5.8 | 11.3 | 5000.0 | 44.2 | 113.3 | (0.32, 0.61) |
| example(8) | Compound (1-15) | 5.8 | 11.1 | 5000.0 | 44.9 | 113.2 | (0.33, 0.60) |
| example(9) | Compound (1-17) | 5.5 | 11.2 | 5000.0 | 44.6 | 114.6 | (0.30, 0.61) |
| example(10) | Compound (1-18) | 5.6 | 11.4 | 5000.0 | 43.7 | 119.5 | (0.31, 0.61) |
| example(11) | Compound (1-20) | 5.5 | 11.3 | 5000.0 | 44.3 | 113.8 | (0.30, 0.60) |
| example(12) | Compound (1-21) | 5.5 | 11.5 | 5000.0 | 43.6 | 115.3 | (0.33, 0.61) |
| example(13) | Compound (1-22) | 5.5 | 11.3 | 5000.0 | 44.1 | 115.8 | (0.32, 0.61) |
| example(14) | Compound (1-24) | 5.6 | 11.6 | 5000.0 | 43.2 | 115.0 | (0.33, 0.60) |
| example(15) | Compound (2-4) | 5.7 | 12.1 | 5000.0 | 41.3 | 112.7 | (0.30, 0.61) |
| example(16) | Compound (2-6) | 5.8 | 12.8 | 5000.0 | 39.1 | 110.8 | (0.31, 0.61) |
| example(17) | Compound (2-7) | 5.7 | 12.6 | 5000.0 | 39.8 | 110.7 | (0.31, 0.61) |
| example(18) | Compound (2-9) | 5.7 | 12.2 | 5000.0 | 40.9 | 117.6 | (0.33, 0.61) |
| example(19) | Compound (2-10) | 5.7 | 12.2 | 5000.0 | 41.1 | 112.2 | (0.32, 0.60) |
| example(20) | Compound (2-11) | 5.7 | 12.1 | 5000.0 | 41.2 | 111.5 | (0.32, 0.61) |
| example(21) | Compound (2-12) | 5.7 | 12.2 | 5000.0 | 41.1 | 115.1 | (0.33, 0.61) |
| example(22) | Compound (2-15) | 5.7 | 12.4 | 5000.0 | 40.4 | 116.8 | (0.30, 0.60) |
| example(23) | Compound (2-17) | 5.6 | 12.1 | 5000.0 | 41.2 | 113.0 | (0.30, 0.61) |
| example(24) | Compound (2-18) | 5.5 | 12.3 | 5000.0 | 40.6 | 112.1 | (0.32, 0.61) |
| example(25) | Compound (2-20) | 5.6 | 12.5 | 5000.0 | 40.1 | 114.9 | (0.30, 0.61) |
| example(26) | Compound (2-21) | 5.5 | 12.2 | 5000.0 | 40.8 | 114.3 | (0.31, 0.60) |
| example(27) | Compound (2-22) | 5.5 | 12.2 | 5000.0 | 40.9 | 111.2 | (0.31, 0.60) |
| example(28) | Compound (2-24) | 5.5 | 12.4 | 5000.0 | 40.4 | 116.5 | (0.32, 0.61) |
| example(29) | Compound (3-4) | 5.8 | 11.1 | 5000.0 | 45.1 | 119.3 | (0.31, 0.61) |
| example(30) | Compound (3-6) | 5.8 | 10.7 | 5000.0 | 46.7 | 115.5 | (0.33, 0.60) |
| example(31) | Compound (3-7) | 5.8 | 11.0 | 5000.0 | 45.4 | 116.9 | (0.31, 0.60) |
| example(32) | Compound (3-8) | 5.4 | 10.2 | 5000.0 | 49.1 | 123.8 | (0.32, 0.60) |
| example(33) | Compound (3-10) | 5.8 | 11.4 | 5000.0 | 43.7 | 110.8 | (0.32, 0.61) |
| example(34) | Compound (3-11) | 5.7 | 11.2 | 5000.0 | 44.6 | 110.5 | (0.33, 0.60) |
| example(35) | Compound (3-12) | 5.8 | 11.2 | 5000.0 | 44.8 | 110.2 | (0.30, 0.61) |
| example(36) | Compound (3-15) | 5.7 | 11.0 | 5000.0 | 45.4 | 117.1 | (0.31, 0.61) |

TABLE 5-continued

| compound | | Voltage | Current Density | Brightness (cd/m2) | Efficiency | Lifetime T(95) | CIE (x, y) |
|---|---|---|---|---|---|---|---|
| example(37) | Compound (3-17) | 5.6 | 10.8 | 5000.0 | 46.5 | 116.3 | (0.31, 0.60) |
| example(38) | Compound (3-18) | 5.6 | 10.7 | 5000.0 | 46.7 | 118.9 | (0.33, 0.61) |
| example(39) | Compound (3-20) | 5.5 | 10.7 | 5000.0 | 46.7 | 111.7 | (0.32, 0.61) |
| example(40) | Compound (3-21) | 5.5 | 11.0 | 5000.0 | 45.4 | 117.8 | (0.33, 0.60) |
| example(41) | Compound (3-22) | 5.5 | 11.1 | 5000.0 | 45.2 | 112.0 | (0.30, 0.61) |
| example(42) | Compound (3-24) | 5.6 | 10.7 | 5000.0 | 46.8 | 115.4 | (0.31, 0.61) |
| example(43) | Compound (4-4) | 5.8 | 12.5 | 5000.0 | 39.9 | 116.9 | (0.31, 0.60) |
| example(44) | Compound (4-6) | 5.7 | 12.8 | 5000.0 | 39.1 | 110.5 | (0.33, 0.61) |
| example(45) | Compound (4-7) | 5.8 | 13.0 | 5000.0 | 38.5 | 116.6 | (0.32, 0.60) |
| example(46) | Compound (4-9) | 5.8 | 13.0 | 5000.0 | 38.4 | 111.8 | (0.32, 0.60) |
| example(47) | Compound (4-10) | 5.8 | 12.7 | 5000.0 | 39.5 | 115.3 | (0.33, 0.60) |
| example(48) | Compound (4-11) | 5.8 | 12.9 | 5000.0 | 38.9 | 110.6 | (0.30, 0.60) |
| example(49) | Compound (4-12) | 5.7 | 13.1 | 5000.0 | 38.3 | 114.1 | (0.30, 0.61) |
| example(50) | Compound (4-15) | 5.5 | 12.7 | 5000.0 | 39.4 | 115.8 | (0.32, 0.60) |
| example(51) | Compound (4-17) | 5.6 | 13.0 | 5000.0 | 38.5 | 116.7 | (0.31, 0.61) |
| example(52) | Compound (4-18) | 5.6 | 13.1 | 5000.0 | 38.2 | 119.5 | (0.31, 0.60) |
| example(53) | Compound (4-20) | 5.5 | 12.7 | 5000.0 | 39.3 | 111.4 | (0.31, 0.60) |

As it is apparent from the results of Table 5, when a green organic electroluminescent device is manufactured using the material for an organic electric element of the present invention as an emitting-auxiliary layer material, the driving voltage and life span can be remarkably improved as compared with the comparative examples not using the emitting-auxiliary layer or using the comparative compound 1.

The results of Comparative Example 1 using the comparative compound as the emitting auxiliary layer and Examples 1 to 53 using the compound of the present invention were superior to Comparative Example 1 not using the emitting auxiliary layer, and the compound of the present invention substituted at position 2 of Carbazole, showed the best results than Comparative compound 1 which is similar to the compound of the invention but substituted at the 3-position of Carbazole. This indicates that the HOMO value is increased and the hole injection and mobility are faster when the 2-Carbazole is substituted than when the 3-Carbazole is substituted. Therefore, as the hole injection and mobility abilities are improved, the deterioration is reduced at the ITO and HTL interfaces, and the lifetime of the device is improved, and as more holes move to the luminescent layer, the charge balance in the luminescent layer of holes and electrons is increased, so that light emission is well performed inside the emitting layer rather than at the interface of the hole transporting layer, thereby maximizing the driving voltage, efficiency and lifetime. As shown in FIG. 2, it can be confirmed that the electronic cloud degree of LUMO of 3-Carbazole and 2-Carbazole is different. That is, the LUMO electron cloud degree of 3-Carbazole is concentrated in Dibenzohiophen, but 2-Carbazole shows electron cloud formation to the inside of Carbazole.

Therefore, as described above, it can be confirmed that the physical properties of the compound are changed depending on the types and positions of the substituent, even though they are the same core, and this can act as a main factor for improving the device performance, and different results are obtained. That is, the substitution of Carbazole with the position 2 suggests that the physical properties of the compound and the result of the device are significantly different.

Example 2) Manufacture and Testing of a Red Organic Light Emitting Diode

First, on an ITO layer (anode) formed on a glass substrate, $N^1$-(naphthalen-2-yl)-$N^4$,$N^4$-bis(4-(naphthalen-2-yl(phenyl)amino)phenyl)-$N^1$-phenyl benzene-1,4-diamine (hereinafter will be abbreviated as 2-TNATA) was vacuum-deposited to form a hole injection layer with a thickness of 60 nm.

Subsequently, the inventive compound represented by Formula (13) as a hole transport compound was vapor-deposited on the film to a thickness of 60 nm to form a hole transport layer. Subsequently, the inventive compound represented by Formula (1) was vacuum-deposited as an emitting-auxiliary layer material to a thickness of 20 nm to form an emitting-auxiliary layer. After forming the emitting-auxiliary layer, CBP [4,4'-N, N'-dicarbazole-biphenyl] as a host was used in the upper of the emitting auxiliary layer, and (piq)$_2$Ir(acac) [bis-(1-phenylisoquinolyl)iridium(III) acetylacetonate] as a dopant was vacuum deposited to form an emitting layer with a thickness of 30 nm on the emitting auxiliary layer by doping with a weight ratio of 95:5. (1,1'-bisphenyl)-4-olato)bis(2-methyl-8-quinolinolato)aluminum (hereinafter will be abbreviated as BAlq) was vacuum-deposited to a thickness of 10 nm as a hole blocking layer, and tris(8-quinolinol)aluminum (hereinafter will be abbreviated as Alq3) was deposited to a thickness of 40 nm as an electron transport layer. After that, an alkali metal halide, LiF was vacuum deposited as an electron injection layer to a thickness of 0.2 nm, and Al was deposited to a thickness of 150 nm to form a cathode to manufacture an OLED.

To the OLEDs which were manufactured by examples and comparative examples, a forward bias direct current voltage was applied, and electroluminescent (EL) properties were measured using PR-650 of Photoresearch Co., and T95 life was measured using a life measuring apparatus manufactured by McScience Inc. with a reference luminance of 2500 cd/m$^2$. In the following table, the manufacture of a device and the results of evaluation are shown.

Comparative 3, 4, 5

An organic electroluminescent device was fabricated in the same manner as in Example 2 except that Comparative Compound 1 was used as the emitting-auxiliary layer.

TABLE 7

| | Hole transport compound | Emitting auxiliary compound | Voltage | Current Density | Brightness (cd/m2) | Efficiency | Lifetime T(95) |
|---|---|---|---|---|---|---|---|
| comparative compound(3) | compound(13-17) | Comparative compound 1 | 5.7 | 27.2 | 2500.0 | 9.2 | 85.3 |
| comparative compound(4) | compound(13-32) | Comparative compound 2 | 5.2 | 23.1 | 2500.0 | 10.8 | 87.7 |
| comparative compound(5) | compound(13-61) | Comparative compound 3 | 5.4 | 25.5 | 2500.0 | 9.8 | 82.9 |
| example(54) | compound(13-17) | compound(1-1) | 5.3 | 24.2 | 2500.0 | 10.3 | 95.5 |
| example(55) | compound(13-17) | compound(1-6) | 5.4 | 24.6 | 2500.0 | 10.2 | 99.5 |
| example(56) | compound(13-17) | compound(1-9) | 5.3 | 25.7 | 2500.0 | 9.7 | 95.1 |
| example(57) | compound(13-17) | compound(1-15) | 5.4 | 23.5 | 2500.0 | 10.6 | 96.2 |
| example(58) | compound(13-17) | compound(2-1) | 5.3 | 23.5 | 2500.0 | 10.6 | 98.5 |
| example(59) | compound(13-17) | compound(2-6) | 5.4 | 23.9 | 2500.0 | 10.5 | 96.8 |
| example(60) | compound(13-17) | compound(2-9) | 5.4 | 22.9 | 2500.0 | 10.9 | 98.1 |
| example(61) | compound(13-17) | compound(2-15) | 5.3 | 23.4 | 2500.0 | 10.7 | 99.7 |
| example(62) | compound(13-17) | compound(3-1) | 5.3 | 25.0 | 2500.0 | 10.0 | 99.2 |
| example(63) | compound(13-17) | compound(3-6) | 5.4 | 25.0 | 2500.0 | 10.0 | 96.3 |
| example(64) | compound(13-17) | compound(3-9) | 5.5 | 25.4 | 2500.0 | 9.9 | 97.5 |
| example(65) | compound(13-17) | compound(3-15) | 5.5 | 23.1 | 2500.0 | 10.8 | 95.4 |
| example(66) | compound(13-17) | compound(4-1) | 5.4 | 23.1 | 2500.0 | 10.8 | 95.0 |
| example(67) | compound(13-17) | compound(4-6) | 5.3 | 22.7 | 2500.0 | 11.0 | 95.1 |
| example(68) | compound(13-17) | compound(4-9) | 5.5 | 25.0 | 2500.0 | 10.0 | 99.5 |
| example(69) | compound(13-32) | compound(1-1) | 4.9 | 17.2 | 2500.0 | 14.6 | 118.3 |
| example(70) | compound(13-32) | compound(1-6) | 4.9 | 17.1 | 2500.0 | 14.6 | 101.3 |
| example(71) | compound(13-32) | compound(1-9) | 5.0 | 19.1 | 2500.0 | 13.1 | 106.5 |
| example(72) | compound(13-32) | compound(1-15) | 4.9 | 18.4 | 2500.0 | 13.6 | 111.1 |
| example(73) | compound(13-32) | compound(2-1) | 5.0 | 18.8 | 2500.0 | 13.3 | 109.3 |
| example(74) | compound(13-32) | compound(2-6) | 4.9 | 18.6 | 2500.0 | 13.4 | 101.9 |
| example(75) | compound(13-32) | compound(2-9) | 4.8 | 19.2 | 2500.0 | 13.0 | 115.9 |
| example(76) | compound(13-32) | compound(2-15) | 4.9 | 17.1 | 2500.0 | 14.6 | 107.4 |
| example(77) | compound(13-32) | compound(3-1) | 4.9 | 16.9 | 2500.0 | 14.8 | 100.4 |
| example(78) | compound(13-32) | compound(3-6) | 4.9 | 16.7 | 2500.0 | 15.0 | 105.6 |
| example(79) | compound(13-32) | compound(3-9) | 4.9 | 16.9 | 2500.0 | 14.8 | 118.3 |
| example(80) | compound(13-32) | compound(3-15) | 4.8 | 18.9 | 2500.0 | 13.2 | 111.9 |
| example(81) | compound(13-32) | compound(4-1) | 4.8 | 18.8 | 2500.0 | 13.3 | 107.3 |
| example(82) | compound(13-32) | compound(4-6) | 4.8 | 17.8 | 2500.0 | 14.1 | 115.6 |
| example(83) | compound(13-32) | compound(4-9) | 5.0 | 18.1 | 2500.0 | 13.8 | 105.7 |
| example(84) | compound(13-61) | compound(1-1) | 5.1 | 20.6 | 2500.0 | 12.1 | 108.6 |
| example(85) | compound(13-61) | compound(1-6) | 5.1 | 24.5 | 2500.0 | 10.2 | 108.7 |
| example(86) | compound(13-61) | compound(1-9) | 4.9 | 23.3 | 2500.0 | 10.7 | 104.7 |
| example(87) | compound(13-61) | compound(1-15) | 5.0 | 20.0 | 2500.0 | 12.5 | 104.7 |
| example(88) | compound(13-61) | compound(2-1) | 4.9 | 22.1 | 2500.0 | 11.3 | 105.1 |
| example(89) | compound(13-61) | compound(2-6) | 5.2 | 23.4 | 2500.0 | 10.7 | 102.8 |
| example(90) | compound(13-61) | compound(2-9) | 5.1 | 23.9 | 2500.0 | 10.4 | 108.5 |
| example(91) | compound(13-61) | compound(2-15) | 4.9 | 24.0 | 2500.0 | 10.4 | 105.0 |
| example(92) | compound(13-61) | compound(3-1) | 5.2 | 23.2 | 2500.0 | 10.8 | 109.5 |
| example(93) | compound(13-61) | compound(3-6) | 5.1 | 21.2 | 2500.0 | 11.8 | 104.1 |
| example(94) | compound(13-61) | compound(3-9) | 5.0 | 19.8 | 2500.0 | 12.6 | 103.5 |
| example(95) | compound(13-61) | compound(3-15) | 5.0 | 22.8 | 2500.0 | 11.0 | 101.1 |
| example(96) | compound(13-61) | compound(4-1) | 5.0 | 21.1 | 2500.0 | 11.8 | 101.1 |
| example(97) | compound(13-61) | compound(4-6) | 4.9 | 23.4 | 2500.0 | 10.7 | 103.7 |
| example(98) | compound(13-61) | compound(4-9) | 4.9 | 20.4 | 2500.0 | 12.3 | 100.9 |

As can be seen from the results of Table 7, when the compound represented by the Formula (13) was used as a hole transport layer and the compound represented by the Formula (1) was used as an emitting auxiliary layer, the driving voltage and lifetime, particularly the luminous efficiency, of the organic electroluminescent device are remarkably improved as compared with the comparative example using the comparative compound 1 as the emitting auxiliary layer, although other conditions are the same. This is because when the physical and chemical properties of the inventive compound represented by Formula 1 described in Table 5 together with the compound represented by Formula 13 are constituted together with the compound, the combination has electrochemical synergistic action to improve the performance of the entire device.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas comprised within the scope equivalent to the claims belong to the present invention.

What is claimed is:

1. An organic electric element comprising a first electrode, a second electrode, and organic material layers formed between the first and the second electrodes,
wherein the organic material layers comprise a hole injection layer, a hole transport layer, an emitting auxiliary layer, and an emitting layer,
the emitting auxiliary layer is adjacent to the emitting layer, and the emitting auxiliary layer includes a compound of Formula (1):

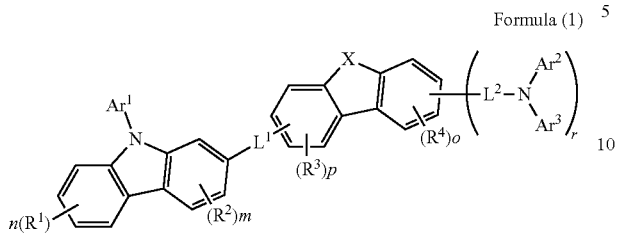

Formula (1)

wherein:

1) $Ar^1$ is selected from the group consisting of a $C_6$-$C_{25}$ aryl group; a fluorenyl group; a $C_2$-$C_{25}$ heterocyclic group including at least one hetero atom of O, N, S, Si or P;

2) $Ar^2$ and $Ar^3$ are each a $C_6$-$C_{25}$ aryl group except a fluorenyl group;

3) X is O or S,

4) $L^1$ is single bond or phenyl, and $L^2$ is a single bond;

5) n is an integer of 0 to 4, and m, p and o are an integer of 0 to 3,

6) When m, n, o or p are 1 or more, $R^1$, $R^2$, $R^3$, and $R^4$ are each independently selected from a hydrogen; a deuterium; a halogen; the group consisting of a $C_6$-$C_{24}$ aryl group; a fluorenylene group; a $C_2$-$C_{25}$ heterocyclic group including at least one hetero atom of O, N, S, Si or P; a fused ring group of a $C_3$-$C_{60}$ aliphatic ring and a $C_6$-$C_{24}$ aromatic ring; a $C_1$-$C_{50}$ alkyl group; a $C_2$-$C_{20}$ alkenyl group, or an adjacent plurality of $R^1$ or a plurality of $R^2$ or a plurality of $R^3$ or a plurality of $R^4$ may be bonded to each other to form an aromatic or a heteroaromatic ring;

7) r is an integer of 1 or 2, and when r is 2, two $L^2$s may be the same or different, and two $Ar^2$s may be the same or different, and two $Ar^3$s may be the same or different, 8) the linking position of the ring containing X in Formula (1) is represented by any one of Formulas [A-1] to [A-12] where r is 1 and any one of Formulas [A-13] to [A-20] where r is 2:

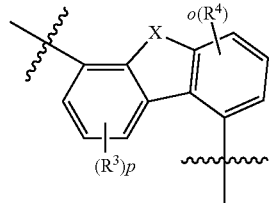

[A-1]

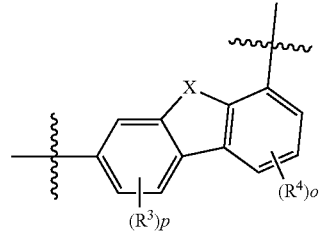

[A-2]

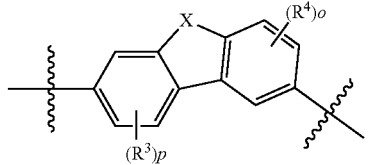

[A-3]

[A-4]

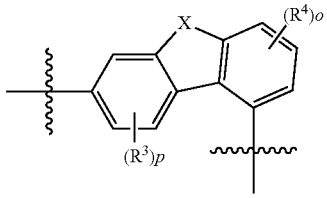

[A-5]

[A-6]

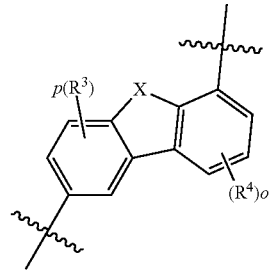

[A-7]

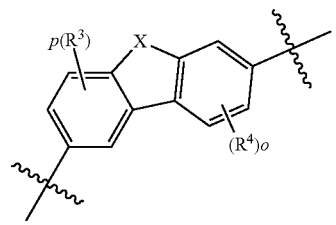

[A-8]

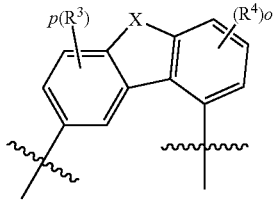

[A-9]

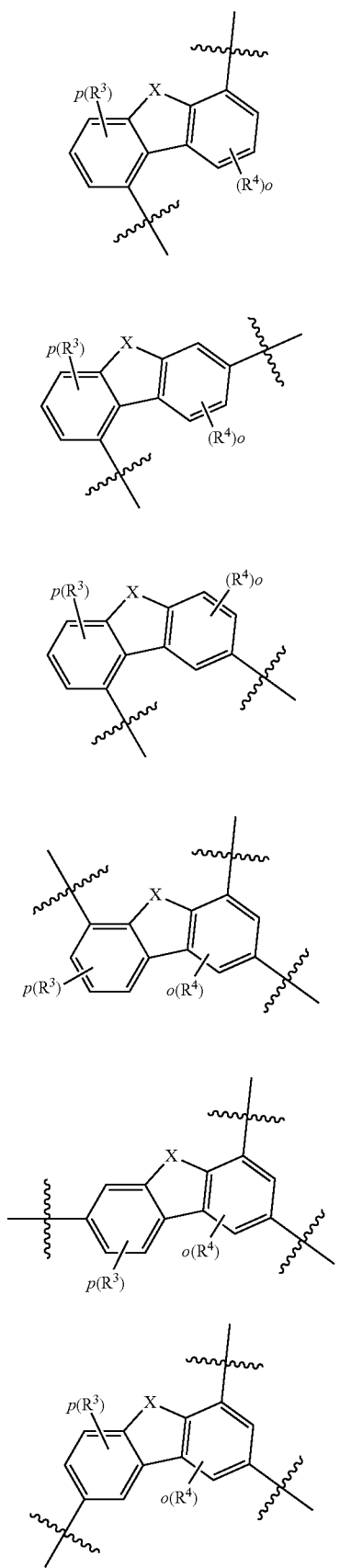

[A-10]

[A-11]

[A-12]

[A-13]

[A-14]

[A-15]

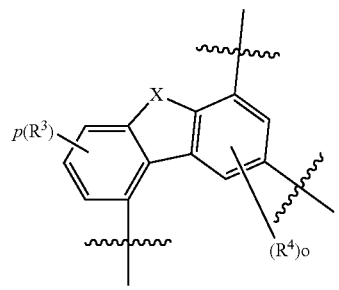

[A-16]

[A-17]

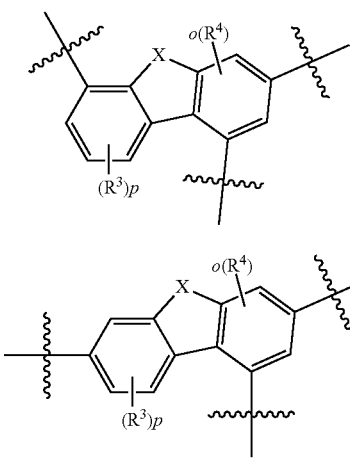

[A-18]

[A-19]

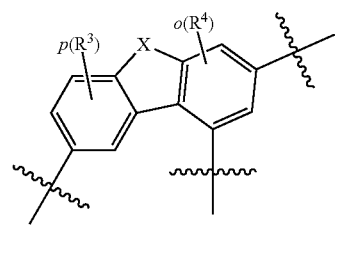

[A-20]

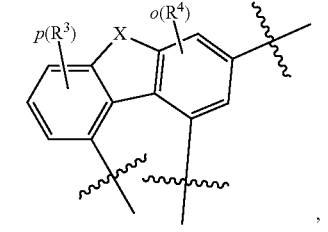

wherein, the aryl group, fluorenyl group, arylene group, heterocyclic group, alkyl group, alkenyl group may be substituted with one or more substituents selected from the group consisting of deuterium; halogen; $C_1$-$C_{20}$ alkyl group; $C_2$-$C_{20}$ alkenyl group; $C_6$-$C_{20}$ aryl group; $C_6$-$C_{20}$ aryl group substituted with deuterium; $C_2$-$C_{20}$ heterocyclic group; $C_3$-$C_{20}$ cycloalkyl group; and also, these substituents may combine each other and form a saturated or unsaturated ring, wherein the term 'ring' means a $C_6$-$C_{24}$ aromatic ring or a $C_2$-$C_{25}$ heterocyclic ring or a fused ring formed by the combination of thereof and comprises a saturated or unsaturated ring.

2. The organic electric element according to claim 1, wherein the compound represented by Formula (1) is represented by Formulas (2) or (3):

Formula (2)

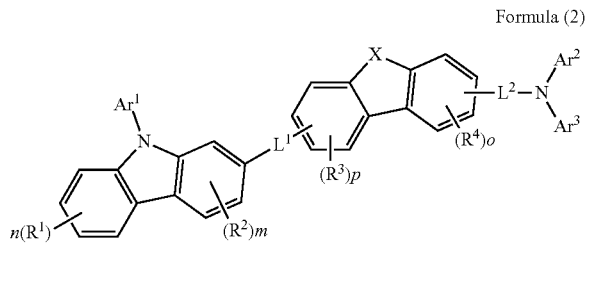

Formula (3)

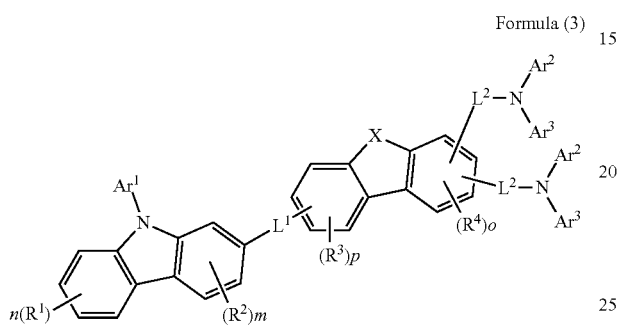

wherein R¹, R², R³, R⁴, m, n, o, p, L¹, L², Ar¹, Ar², and Ar³ are the same as defined in claim 1.

3. The organic electric element according to claim 1, wherein the compound represented by Formula (1) is represented by any of the following Formulas (4) to (7):

Formula (4)

Formula (5)

Formula (6)

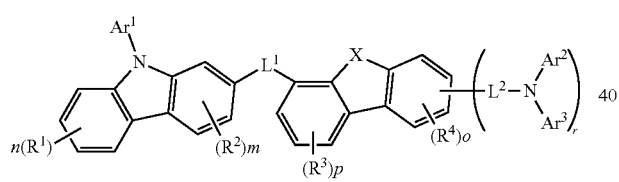

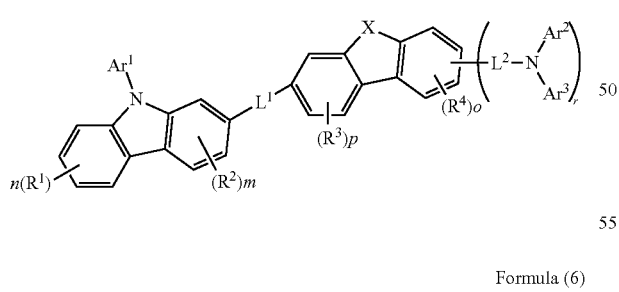

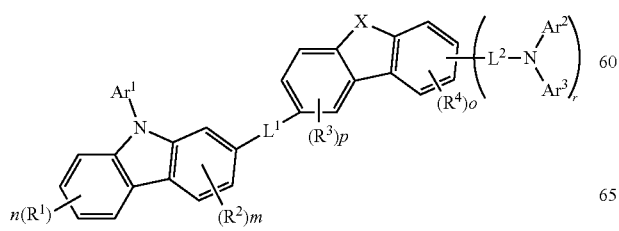

Formula (7)

wherein R¹, R², R³, R⁴, m, n, o, p, L¹, L², Ar¹, Ar², Ar³ and r are the same as defined in claim 1.

4. The organic electric element according to claim 1, wherein the compound represented by Formula (1) is represented by any of the following Formulas (8) to (11):

Formula (8)

Formula (9)

Formula (11)

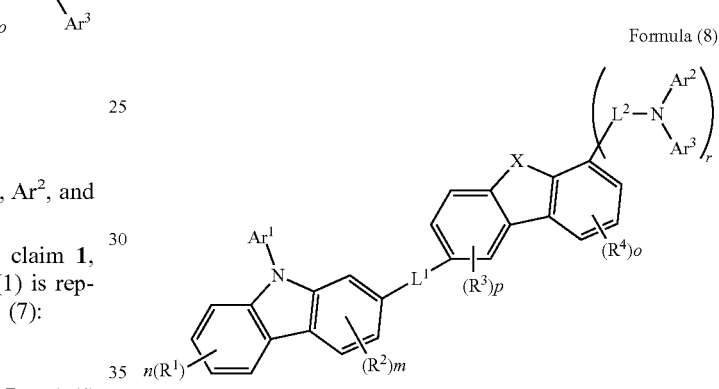

wherein R¹, R², R³, R⁴, m, n, o, p, L¹, L², Ar¹, Ar², Ar³ and r are the same as defined in claim 1, and r is 1.

5. An organic electric element comprising a first electrode, a second electrode, and organic material layers formed between the first and the second electrodes,
wherein the organic material layers comprise a hole injection layer, a hole transport layer, an emitting auxiliary layer, and an emitting layer, the emitting auxiliary layer is adjacent to the emitting layer, and
the emitting auxiliary layer includes a compound selected from the group consisting of the following compounds 1-1 to 1-25, 2-1 to 2-25, 3-1 to 3-25, and 4-1 to 4-17:
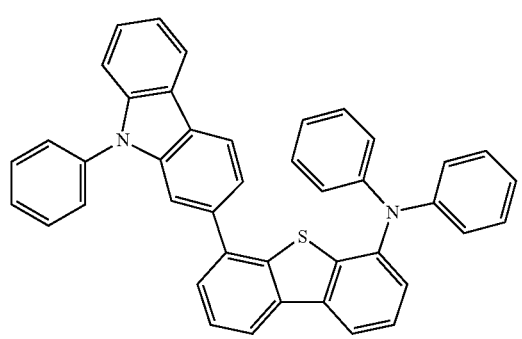
1-1
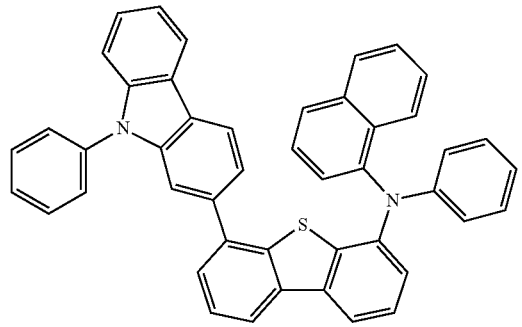
1-2
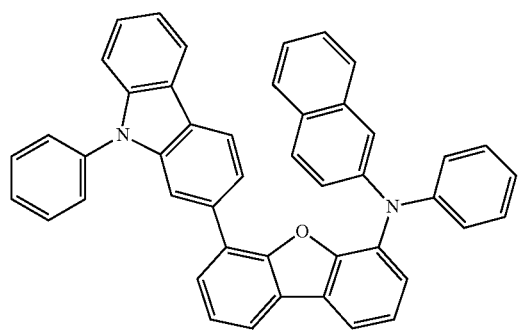
1-3
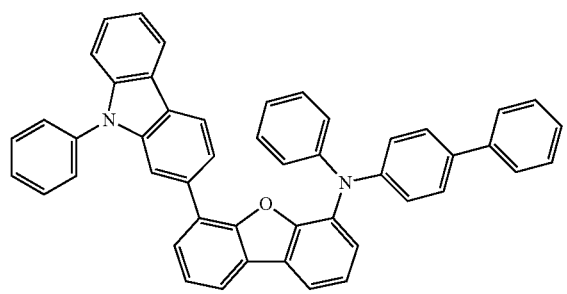
1-4
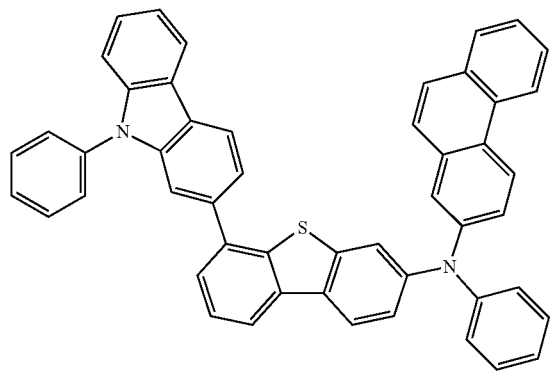
1-8
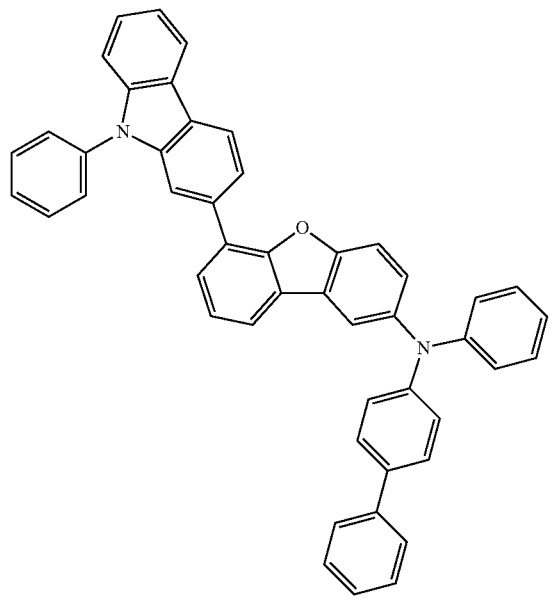
1-9

1-10
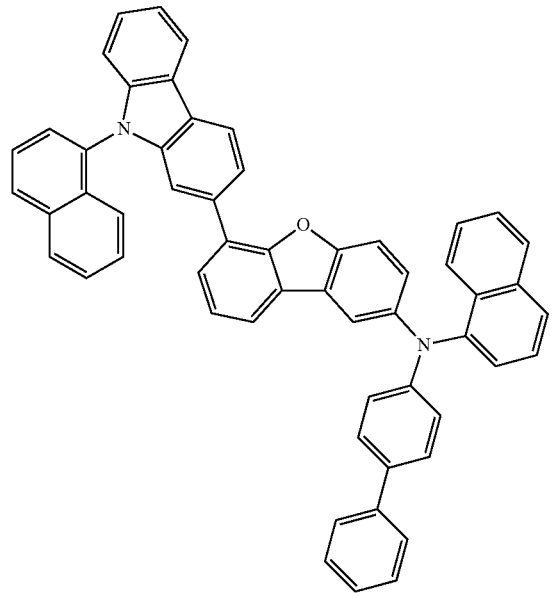
1-11
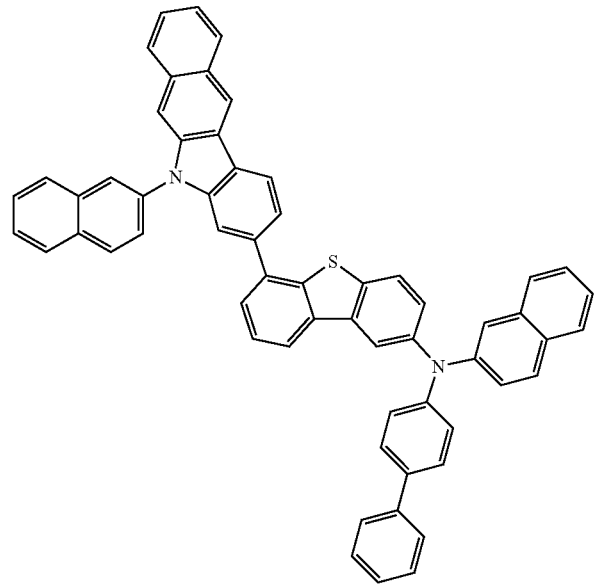
1-12
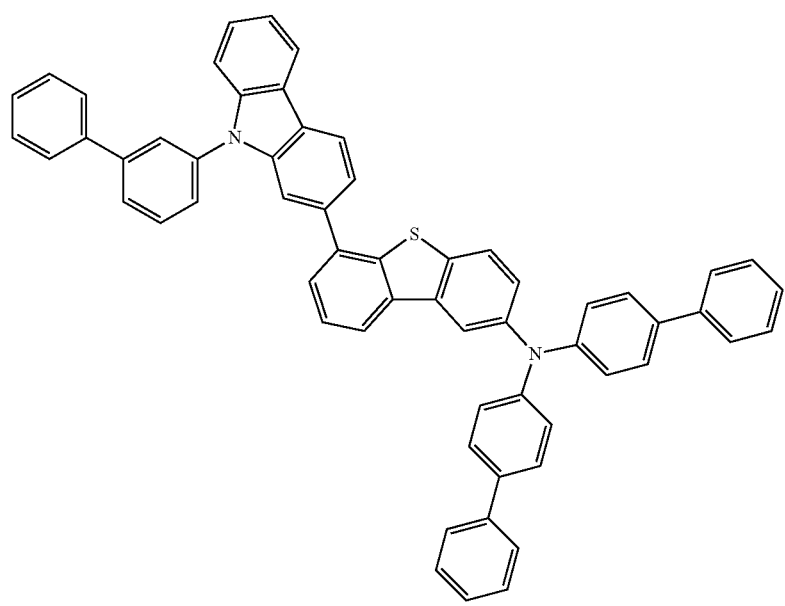

-continued
1-16
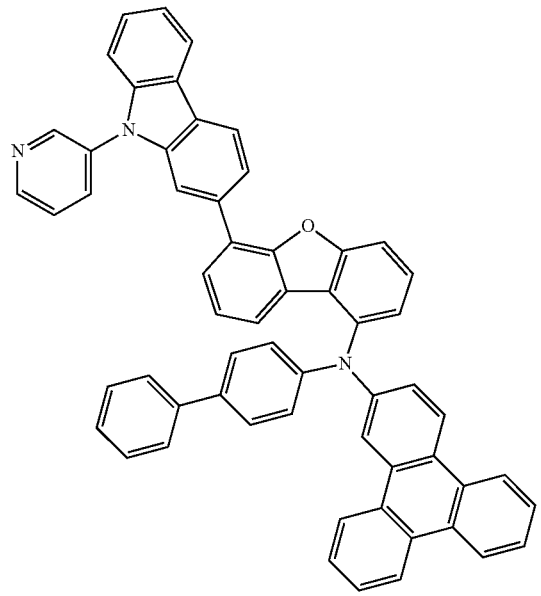
1-17
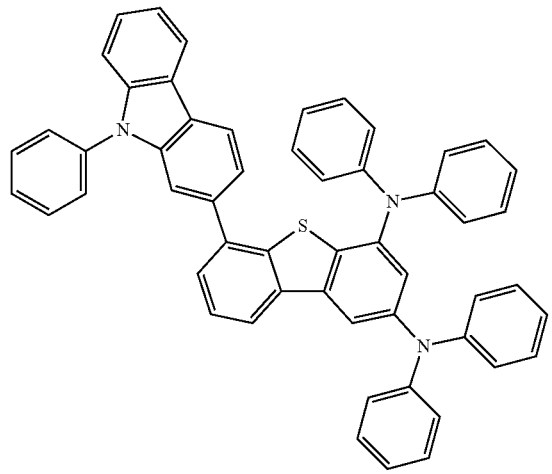
1-18
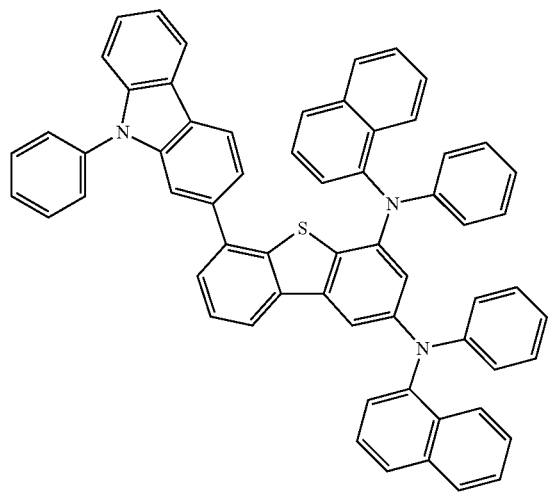
1-20
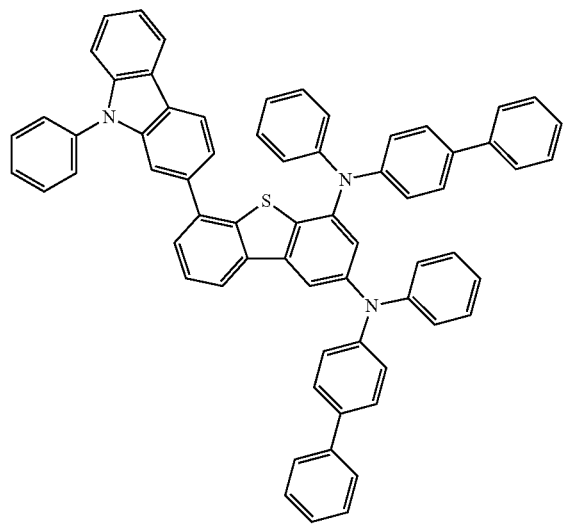
1-21
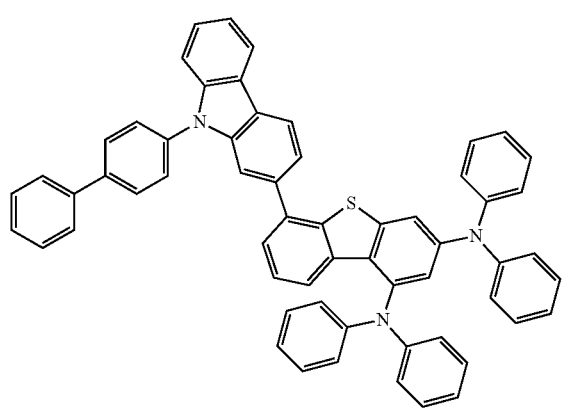
1-22
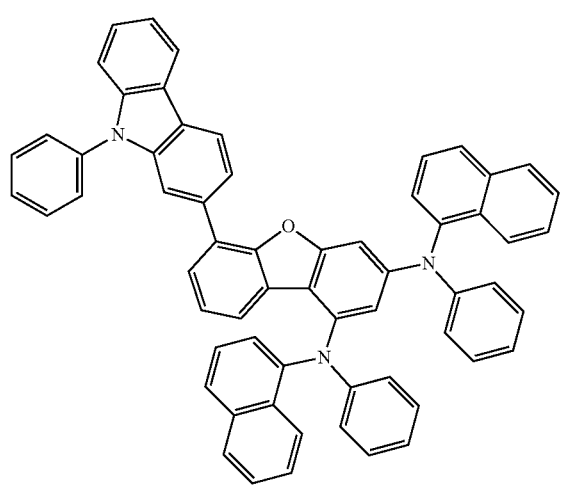

-continued
1-23
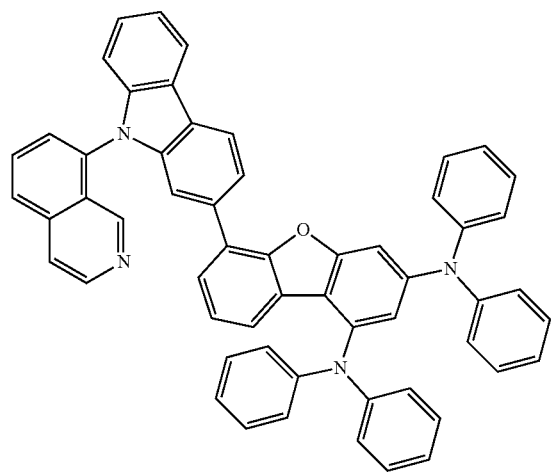
1-24
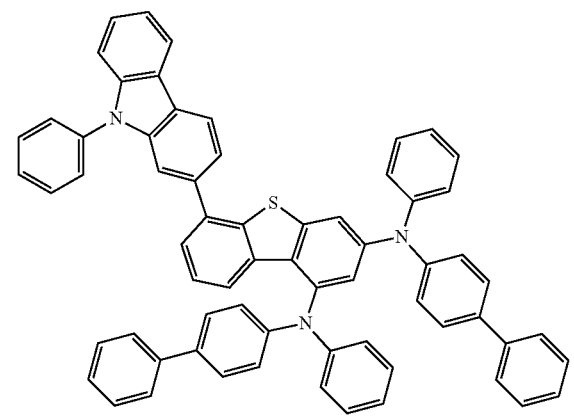
1-25
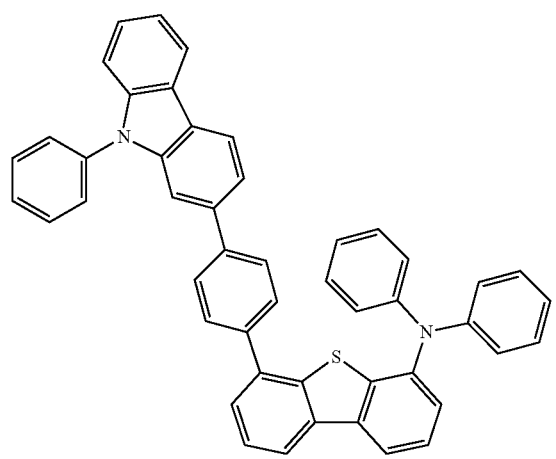
2-1
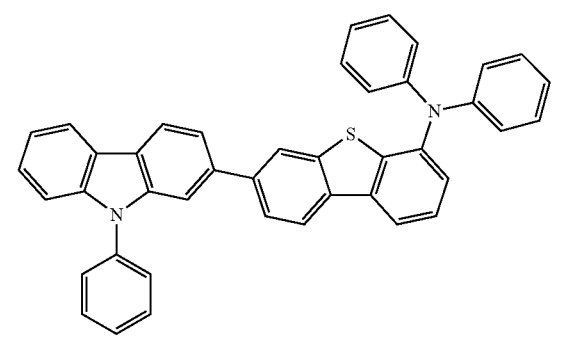
2-2
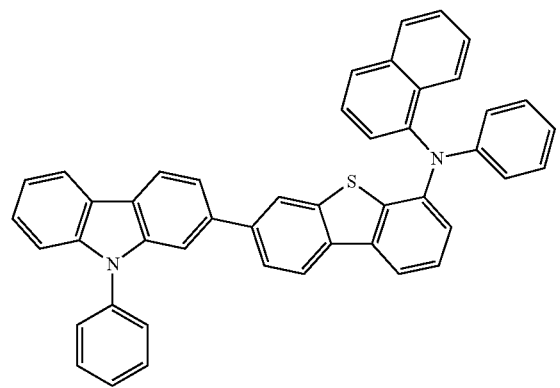
2-3
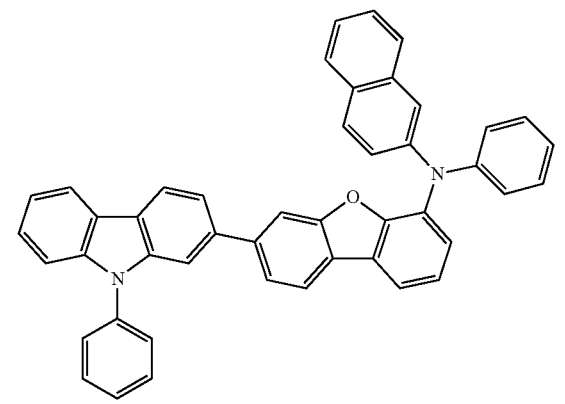

-continued
2-4
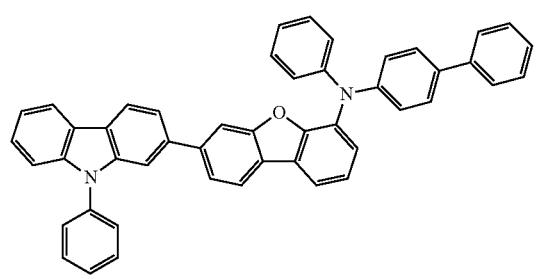
2-8
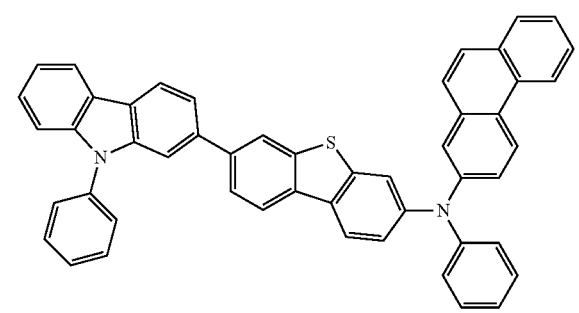
2-9
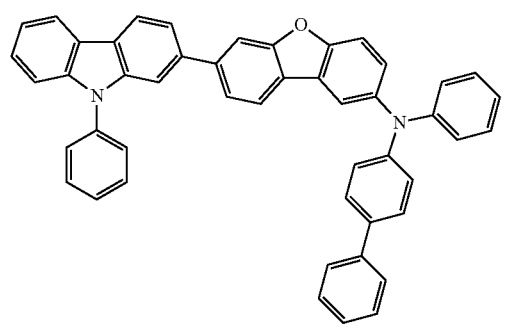
2-10
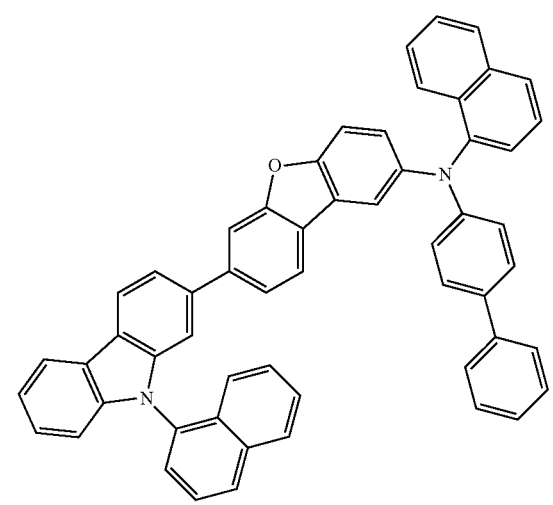
2-11
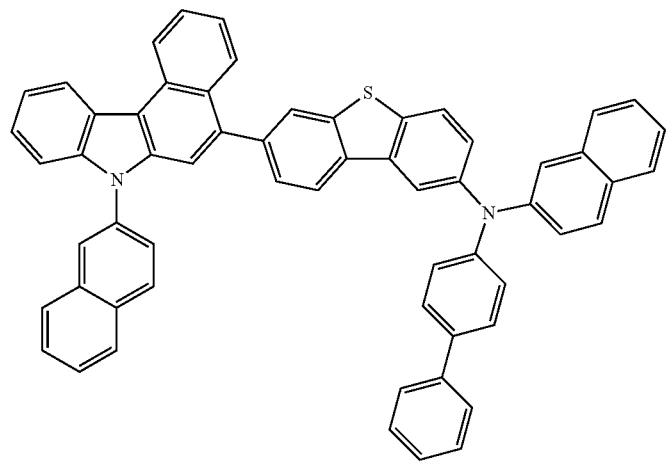

-continued
2-12
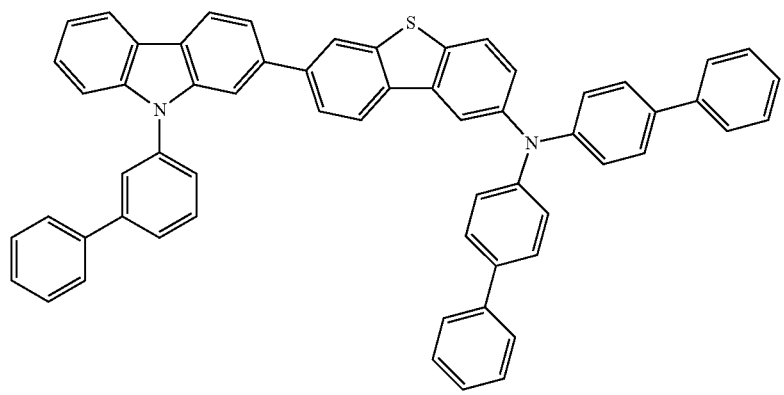
2-16
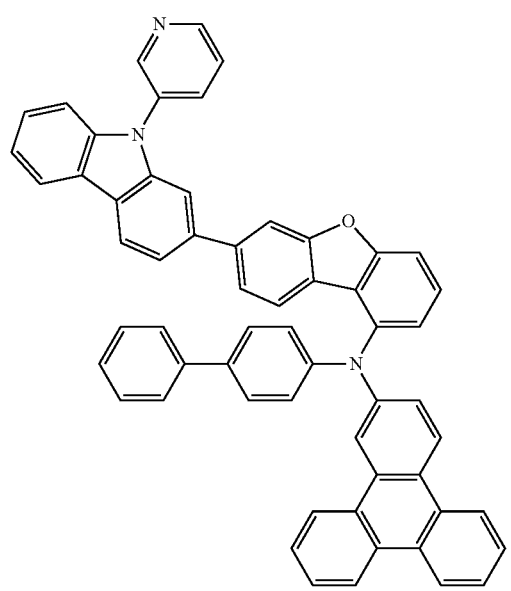
2-17
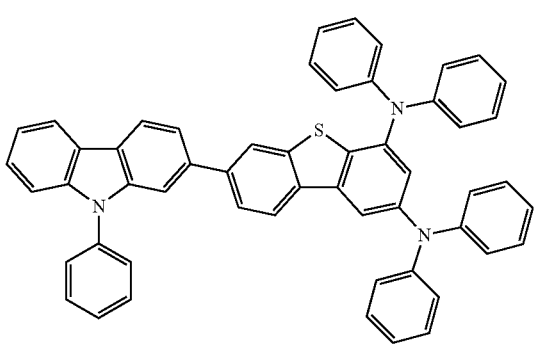
2-18
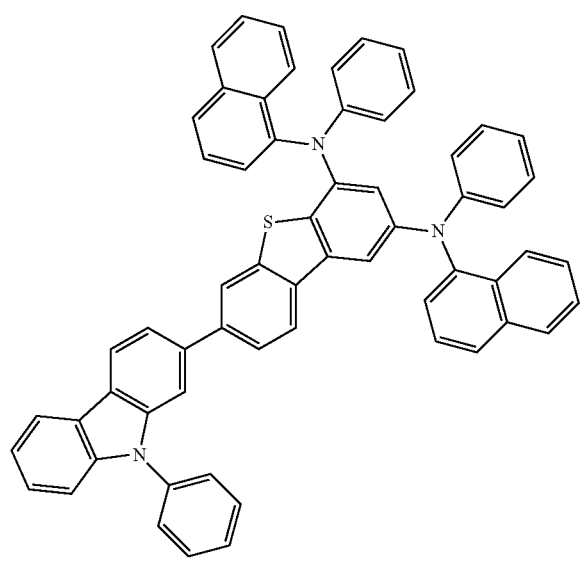
2-20
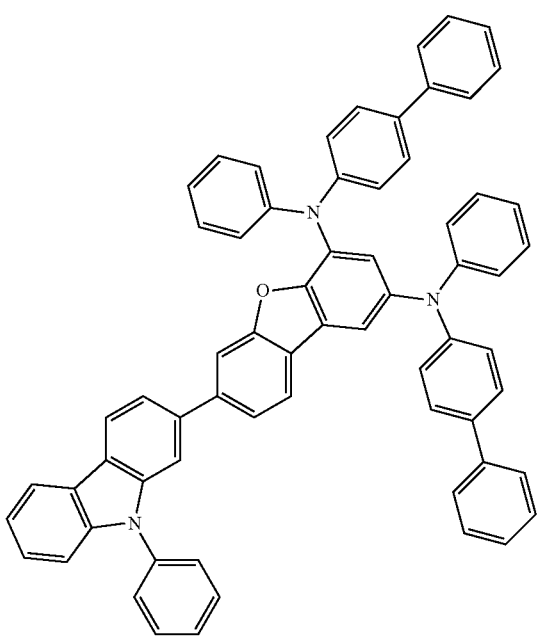

-continued
2-21
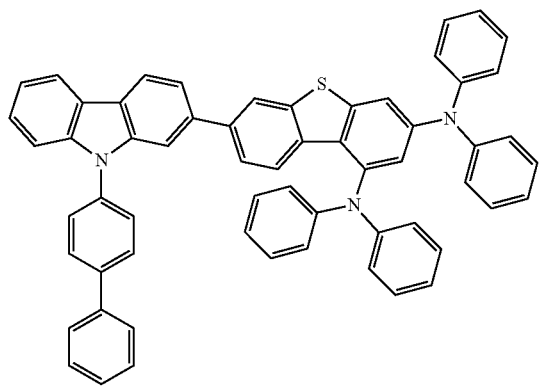
2-22
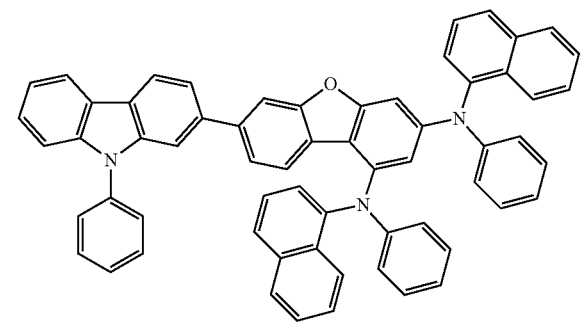
2-23
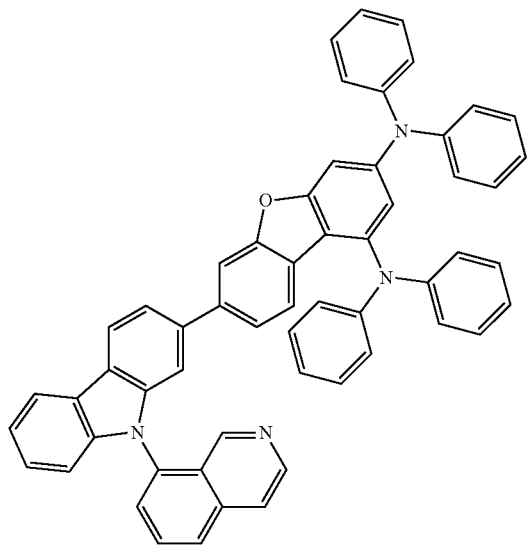
2-24
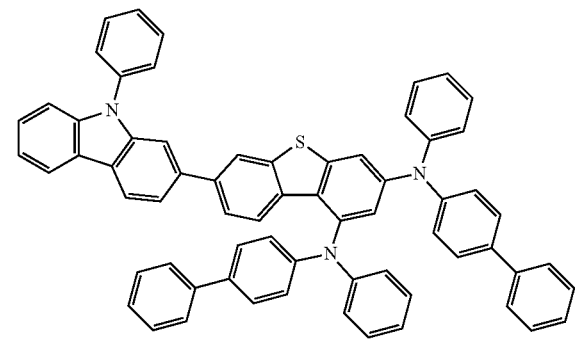
2-25
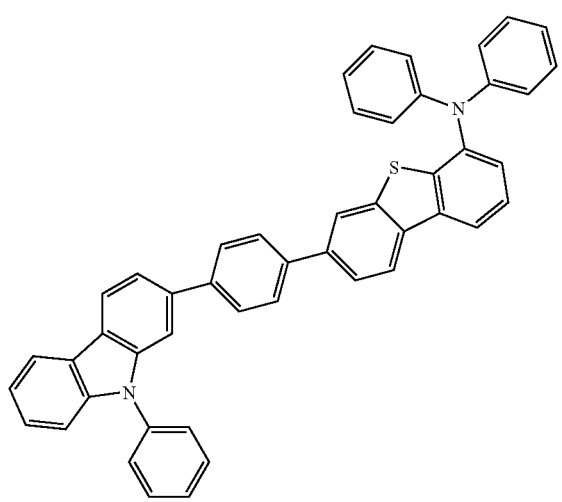
3-1
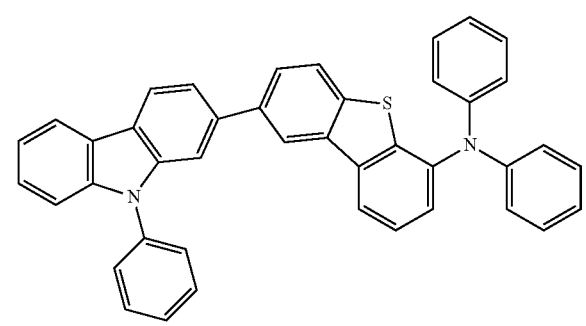

-continued
3-2
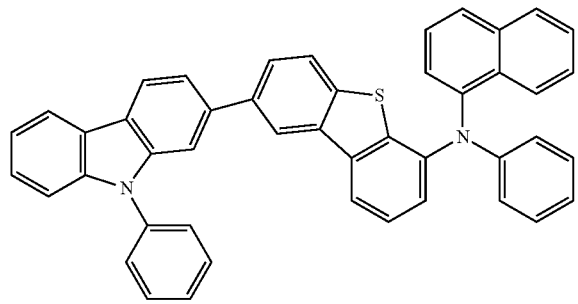
3-3
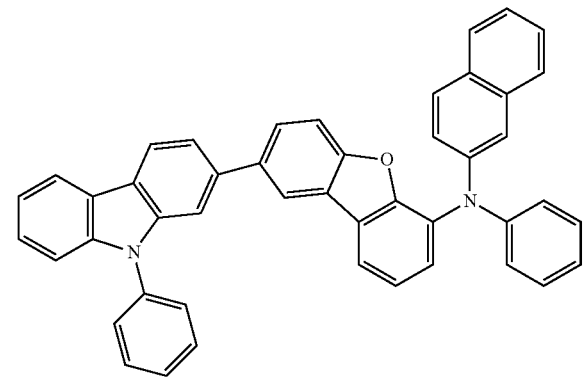
3-4
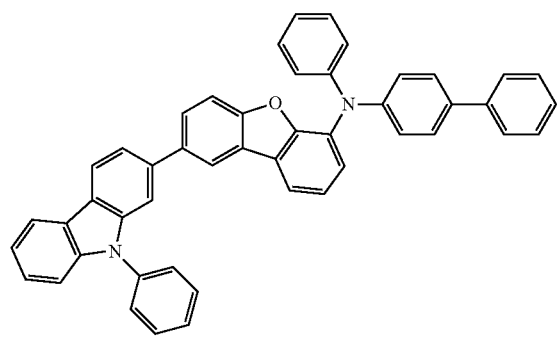
3-8
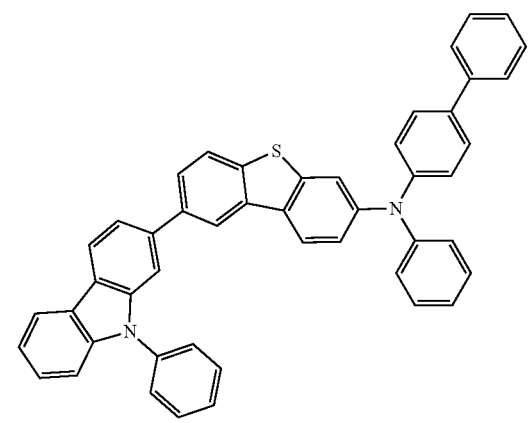
3-9
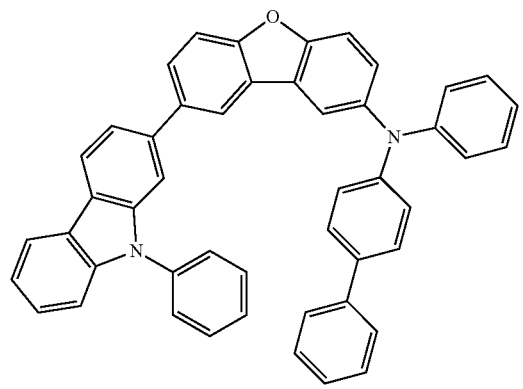
3-10
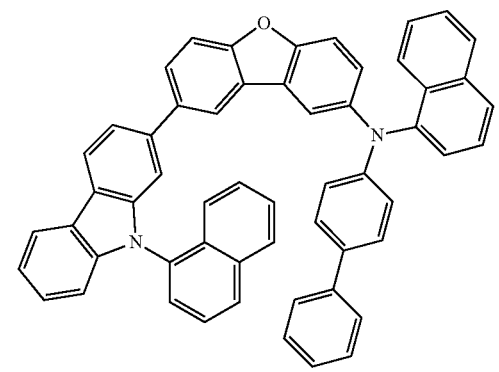
3-11
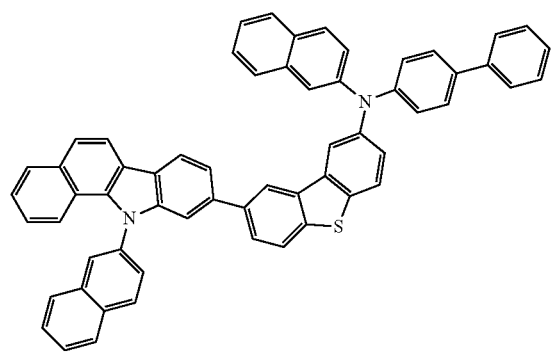
3-12
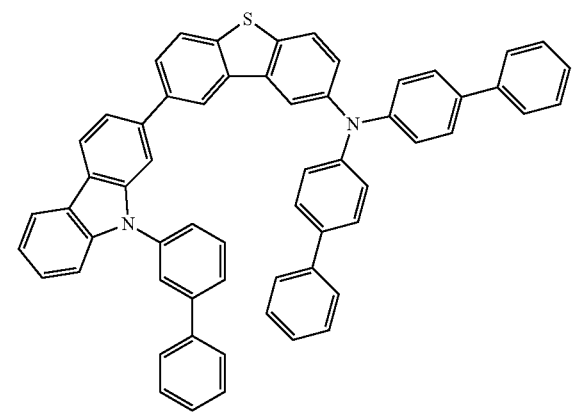

-continued
3-16
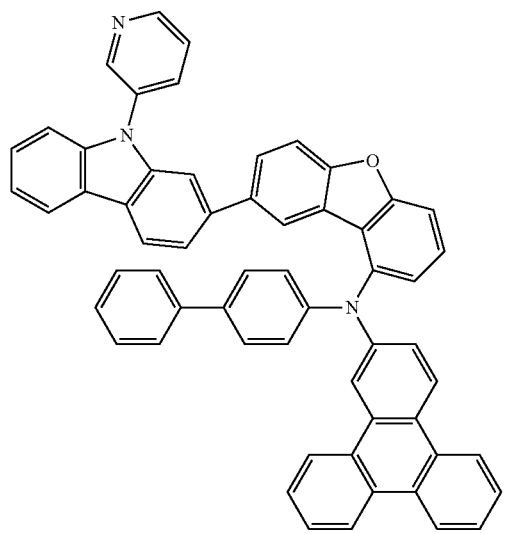
3-17
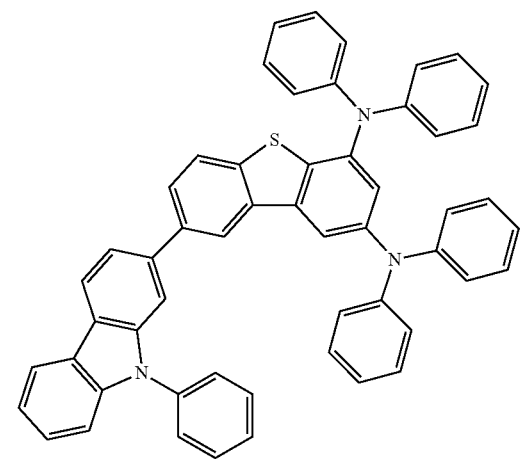
3-18
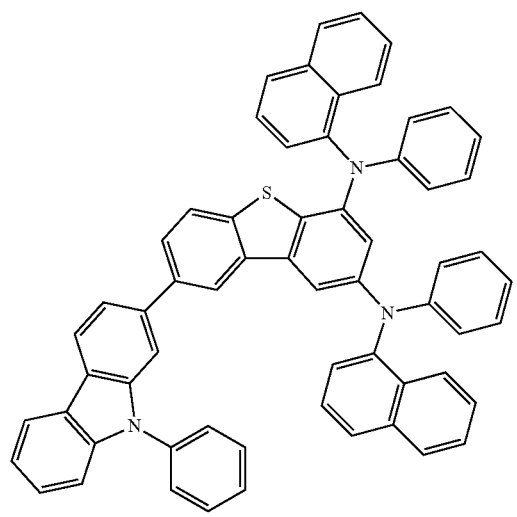
3-20
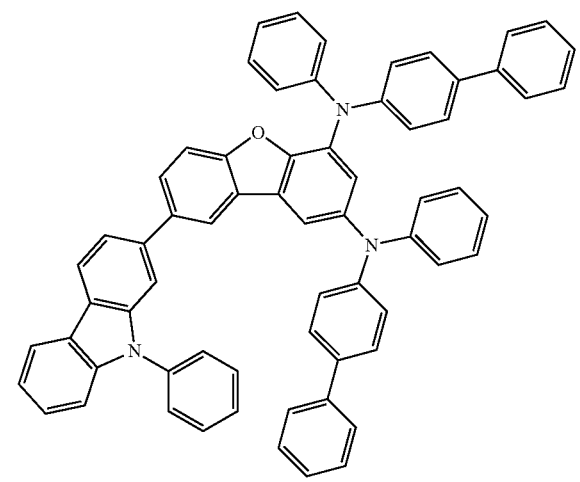
3-21
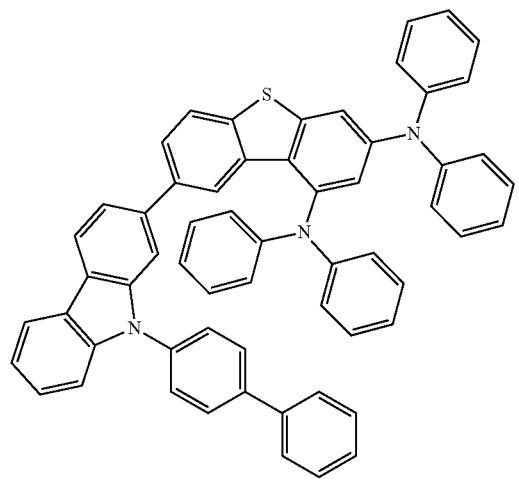
3-22
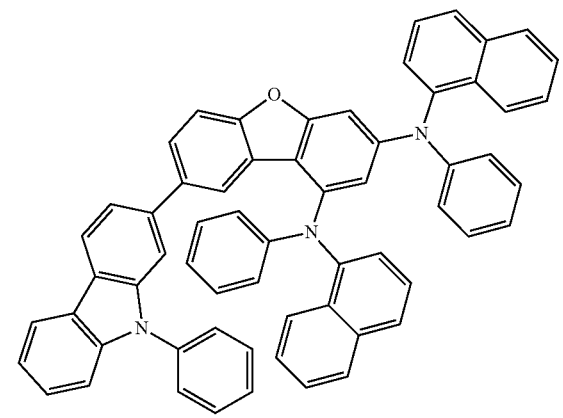

-continued
3-23
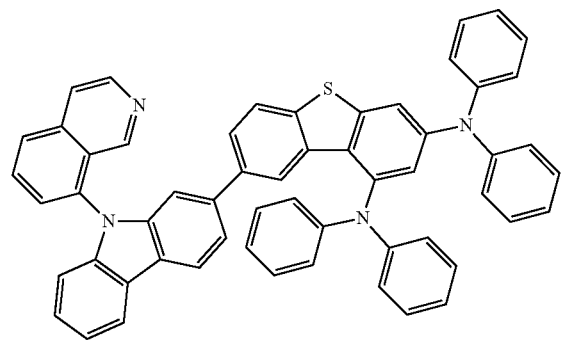
3-24
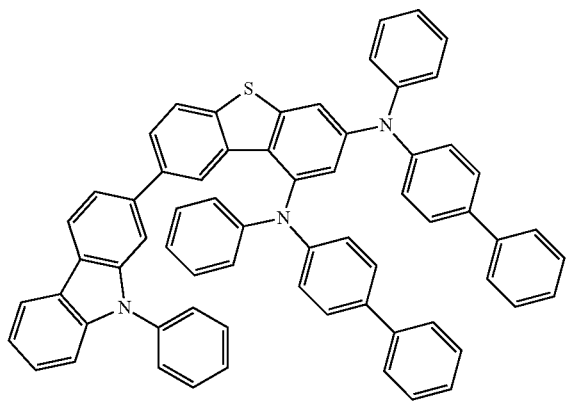
3-25
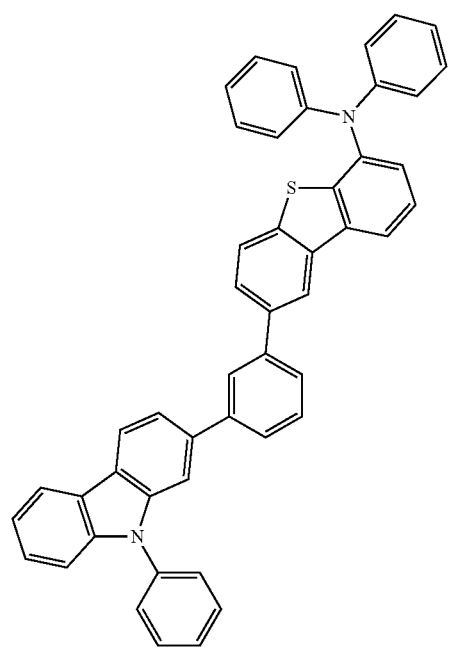
4-1
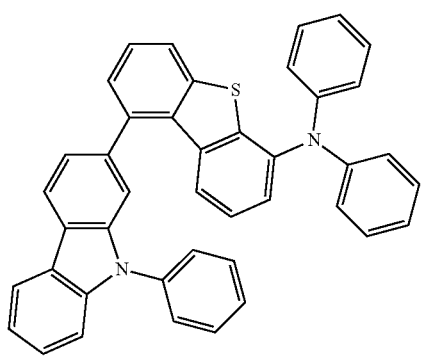
4-2
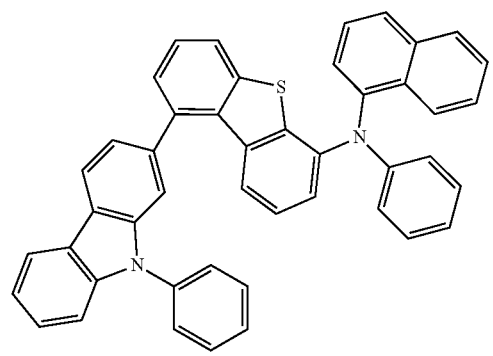
4-3
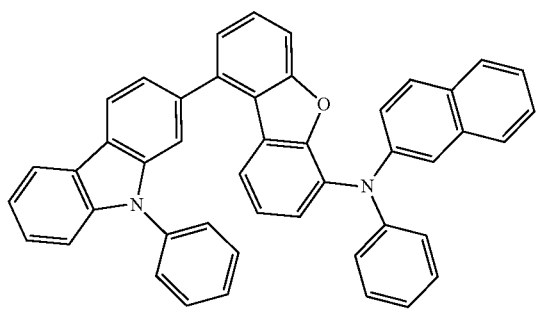

-continued
4-4
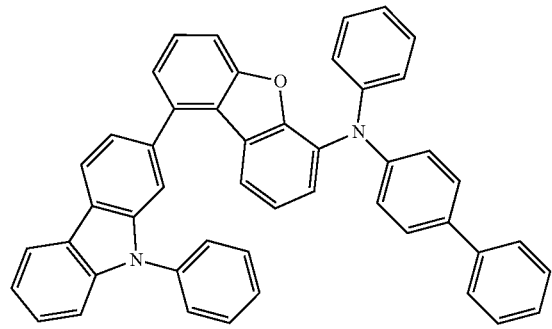
4-8
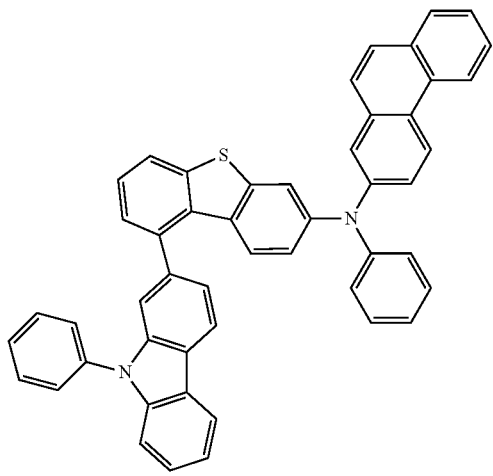
4-9
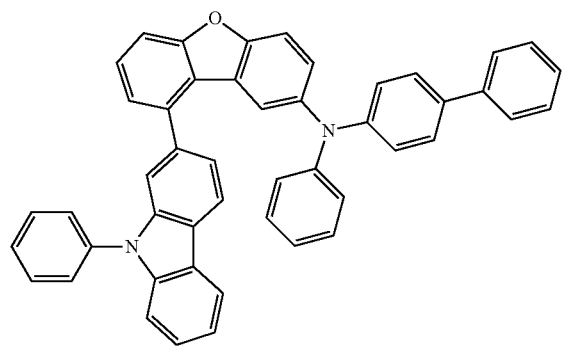
4-10
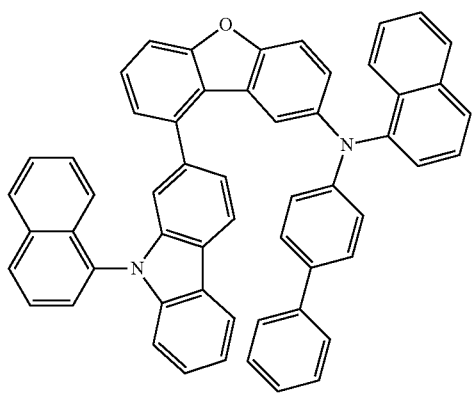
4-11
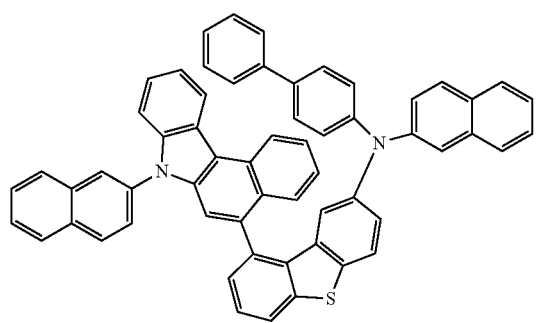
4-12
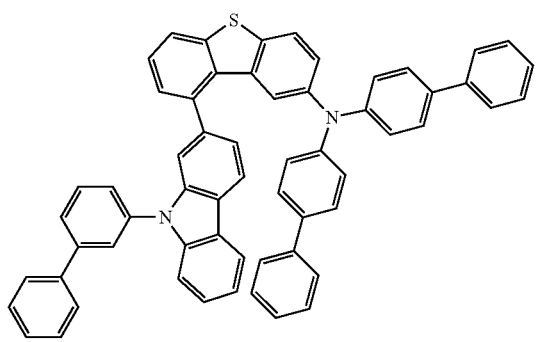

4-13
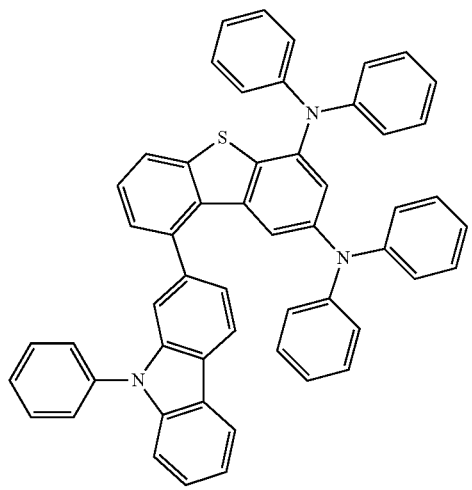

4-14
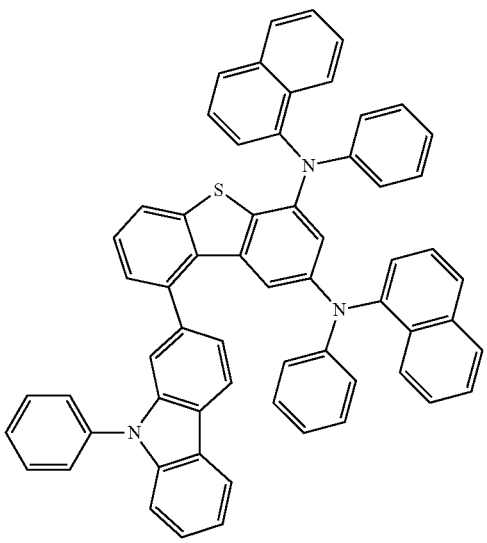

4-16
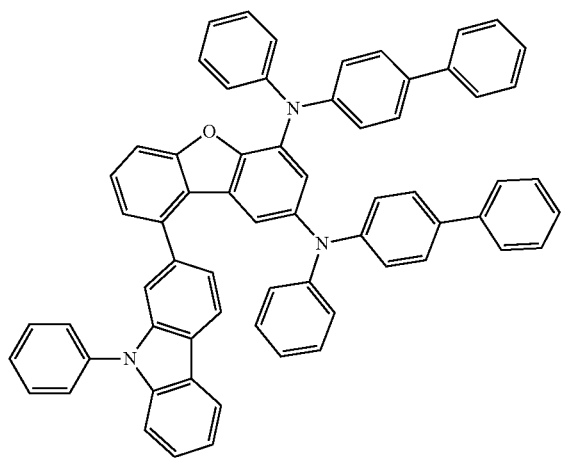

4-17
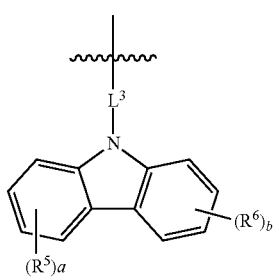

6. The organic electric element according to claim 1, wherein the emitting auxiliary layer comprises the compound as a single compound or a mixture of 2 or more of the compounds having different structures.

7. The organic electric element according to claim 1, wherein the emitting auxiliary layer comprises the compound, and the hole transport layer comprises a compound represented by Formula (13):

Formula (13)
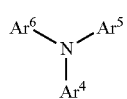

wherein:
1) $Ar^4$ and $Ar^5$ are each independently selected from the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$); or $Ar^4$ and $Ar^5$ may be bonded to each other to form a ring, 2) $Ar^6$ is any one of the following Formulas (2-a), (2-b) and (2-c):

Formula (2-a)

-continued

Formula (2-b)

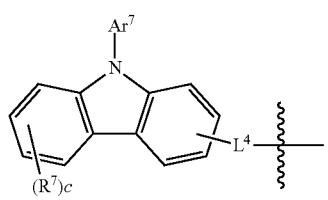

Formula (2-c)

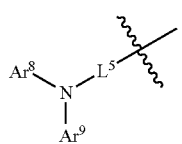

3) A, b, and c are each an integer of 0 to 4, and $R^5$, $R^6$ and $R^7$ are the same or different and are each independently selected from the group consisting of a deuterium; a halogen; a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxyl group; a $C_6$-$C_{30}$ aryloxy group; and -L'-N($R_a$)($R_b$); or in case a, b and c each are 2 or more, and $R^5$, $R^6$ and $R^7$ are each in plural and are the same or different, or a plurality of $R^5$ or a plurality of $R^6$ or a plurality of $R^7$ may be bonded to each other to form a ring, 4) $L^3$ and $L^5$ are each independently selected from the group consisting of a $C_6$-$C_{60}$ aryl group; a fluorenylene group; a fused ring group of a $C_3$-$C_{60}$ aliphatic ring and a $C_6$-$C_{60}$ aromatic ring; and a $C_2$-$C_{60}$ heterocyclic group including at least one hetero atom of O, N, S, Si or P;

5) $L^4$ is selected from a single bond of $C_6$-$C_{60}$; an arylene group; a fluorenylene group; a fused ring group of a $C_3$-$C_{60}$ aliphatic ring and a $C_6$-$C_{60}$ aromatic ring; and a $C_2$-$C_{60}$ heterocyclic group including at least one hetero atom of O, N, S, Si or P;

6) L' is selected from the group consisting of a single bond; a $C_6$-$C_{60}$ arylene group; a fluorenylene group; a fused ring group of a $C_3$-$C_{60}$ aliphatic ring and a $C_6$-$C_{60}$ aromatic ring; and a $C_2$-$C_{60}$ heterocyclic, and the $R_a$ and $R_b$ may be independently selected from the group consisting of a $C_6$-$C_{60}$ aryl group; a fluorenyl group; a fused ring group of a $C_3$-$C_{60}$ aliphatic ring and a $C_6$-$C_{60}$ aromatic ring; and a $C_2$-$C_{60}$ heterocyclic group containing at least one hetero atom of O, N, S, Si, or P;

7) $Ar^7$, $Ar^8$ and $Ar^9$ are each independently selected from the group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; wherein, the aryl group, the fluorenyl group, the arylene group, the heterocyclic group, the fused ring group, the alkyl group, the alkenyl group, the alkoxy group and the aryloxy group may be each substituted with one or more substituents selected from a group consisting of a deuterium; halogen; a silane group substituted or unsubstituted with a $C_1$-$C_{20}$ alkyl group or a $C_6$-$C_{60}$ aryl group; a siloxane group; a boron group; a germanium group; a cyano; a nitro group; -L'-N($R_a$)($R_b$); a $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group and $C_8$-$C_{20}$ arylalkenyl group, and also, these substituents may be bonded to each other to form a ring, wherein the term 'ring' means a $C_3$-$C_{60}$ aliphatic ring or a $C_6$-$C_{60}$ aromatic ring or a $C_2$-$C_{60}$ heterocyclic ring or a fused ring formed by the combination of them, and includes a saturated or unsaturated ring.

8. The organic electric element according to claim 7, wherein the compound represented by Formula (13) is any one of the following Formulas (13-1) to (13-71):

13-1

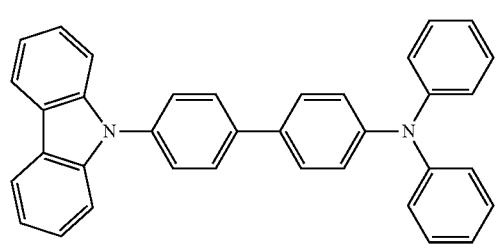

13-2

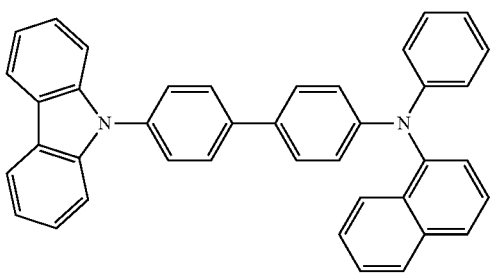

13-3

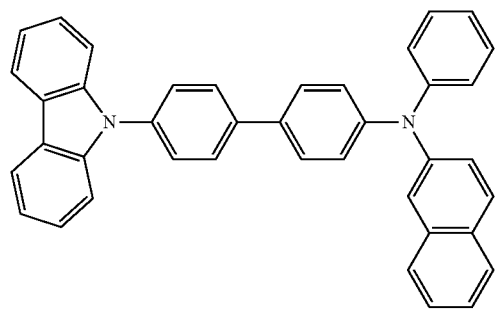

13-4

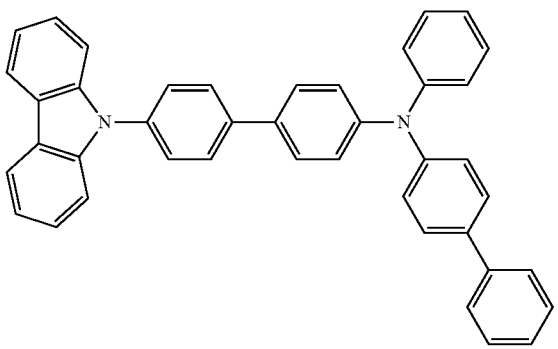

-continued
13-5
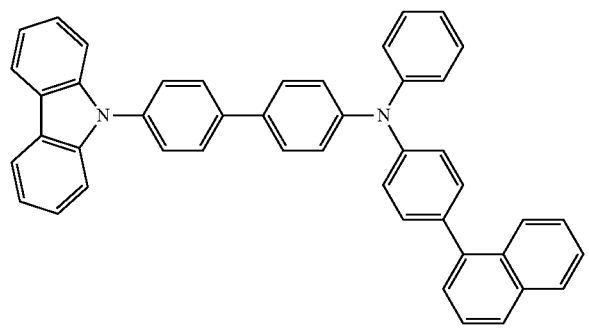
13-6
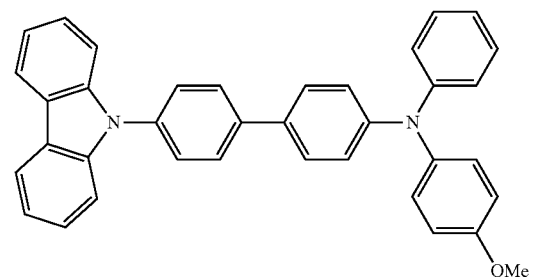
13-7
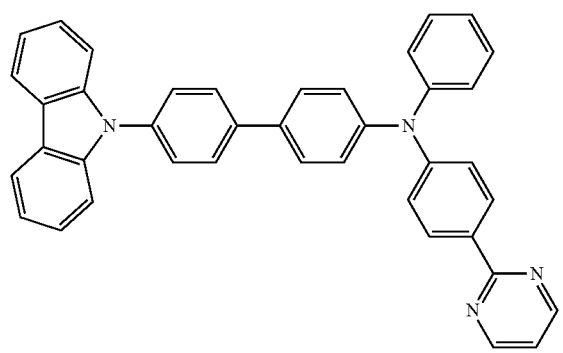
13-8
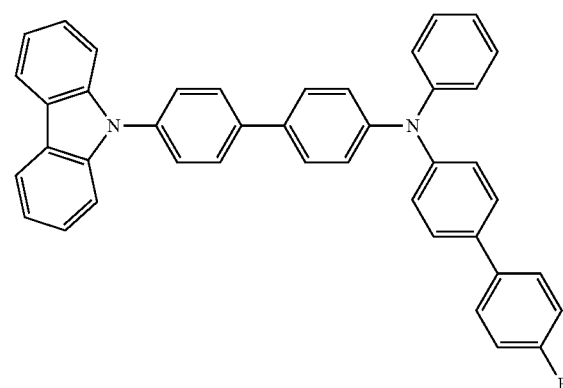
13-9
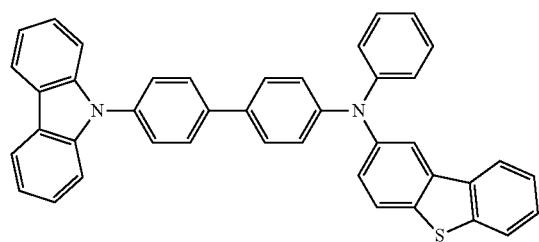
13-10
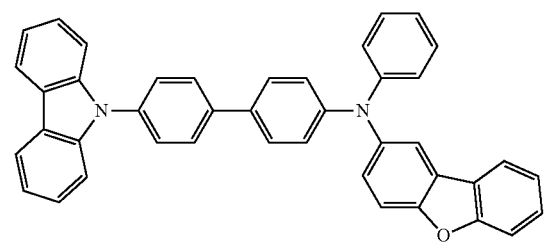
13-11
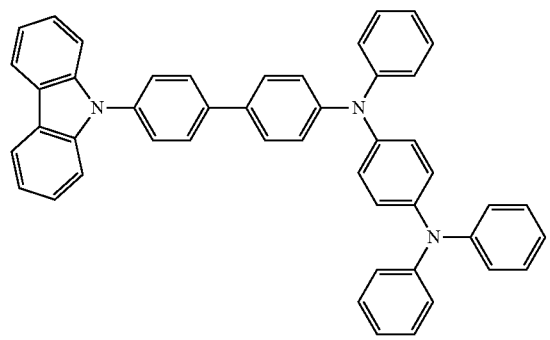
13-12
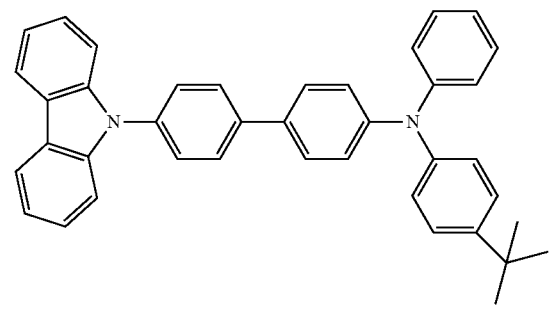

-continued
13-13
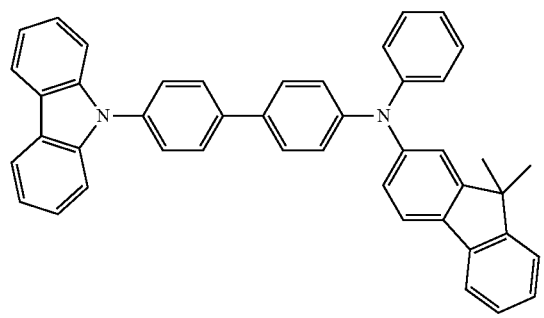
13-14
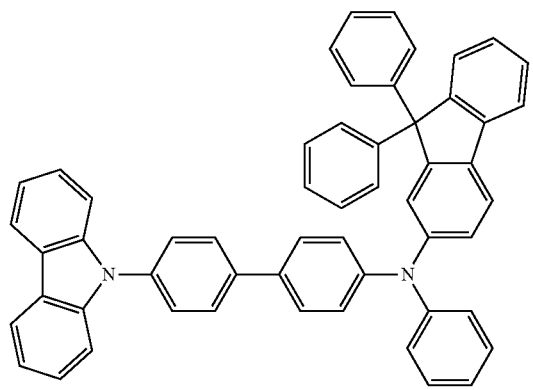
13-15
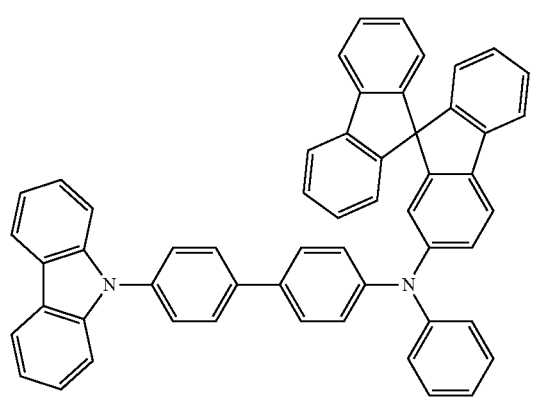
13-16
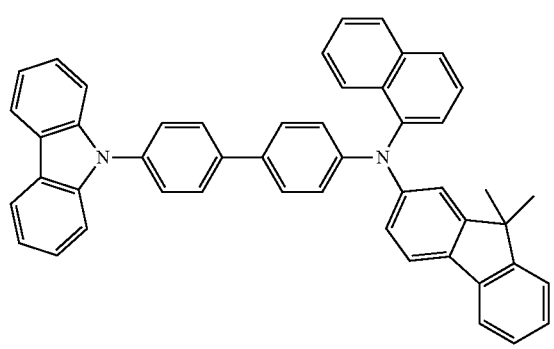
13-17
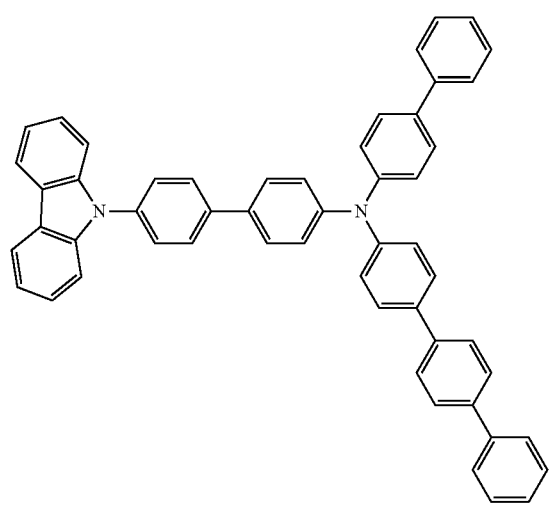
13-18
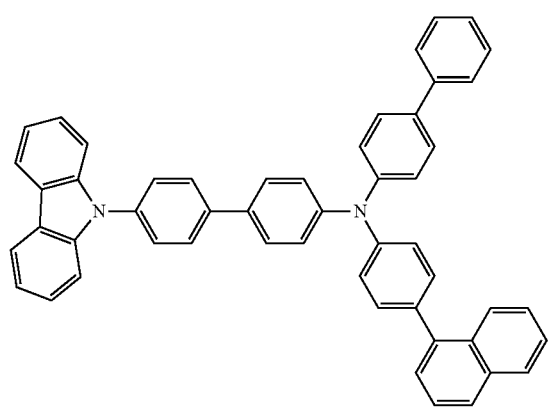

-continued
13-19
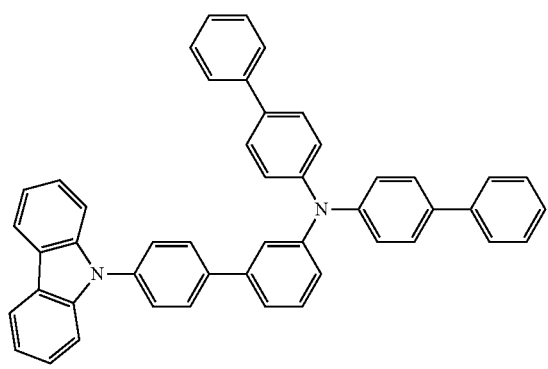
13-20
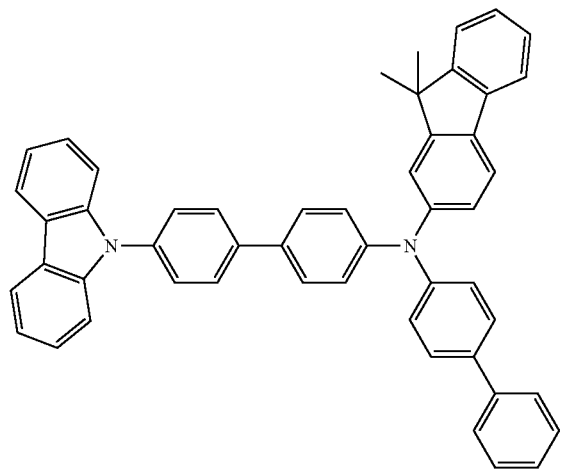
13-21
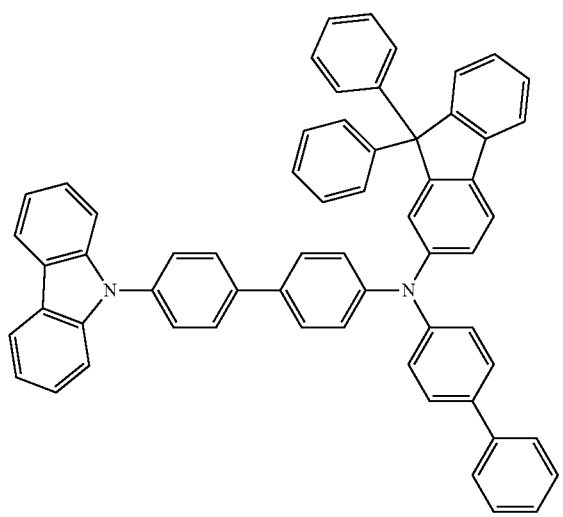
13-22
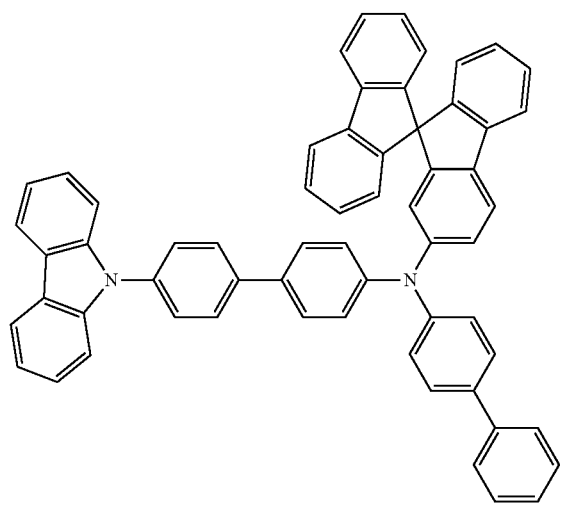
13-23
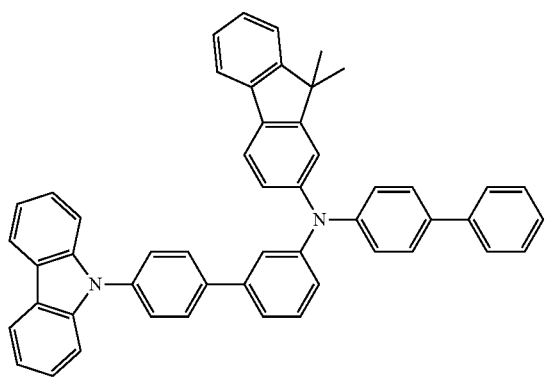
13-24
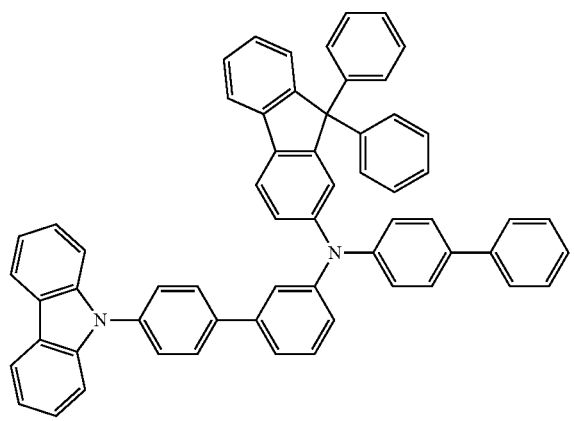

13-25 13-26
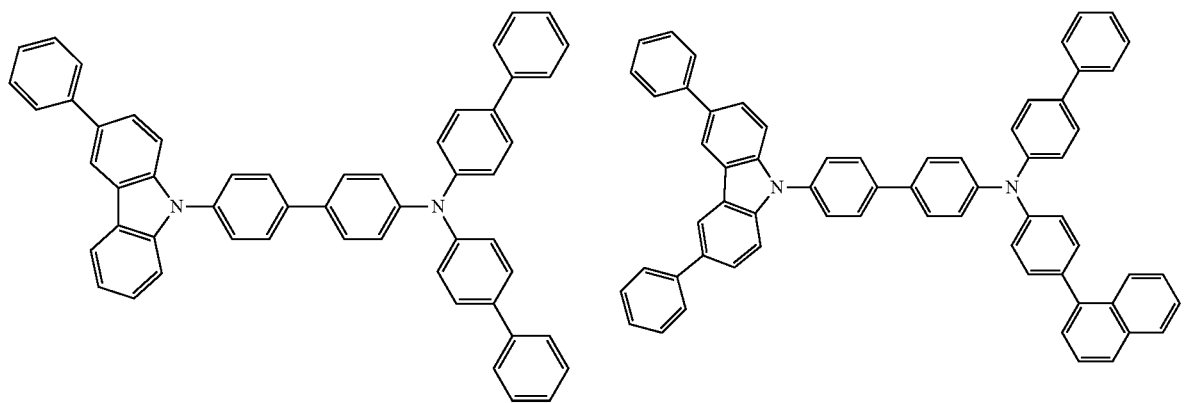
13-27
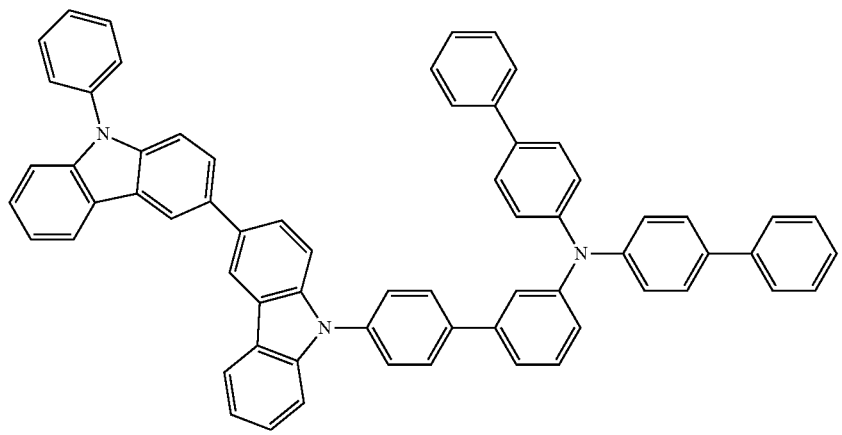
13-28 13-29
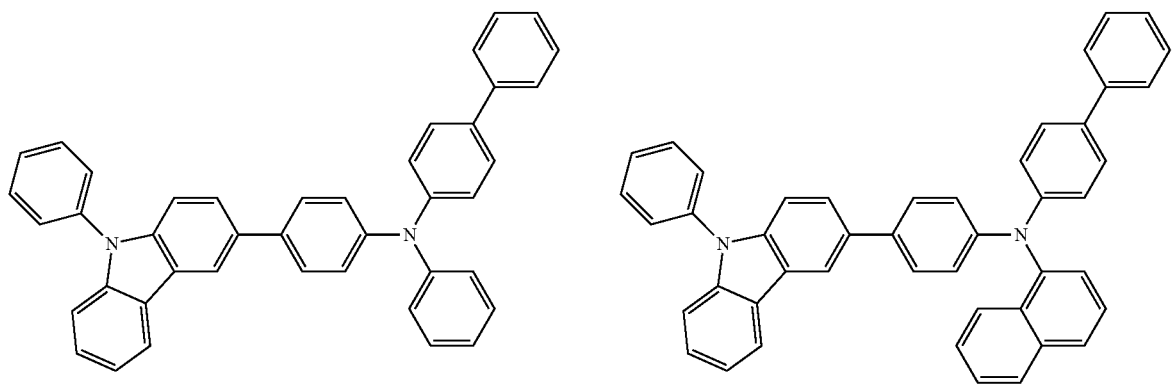

-continued
13-30
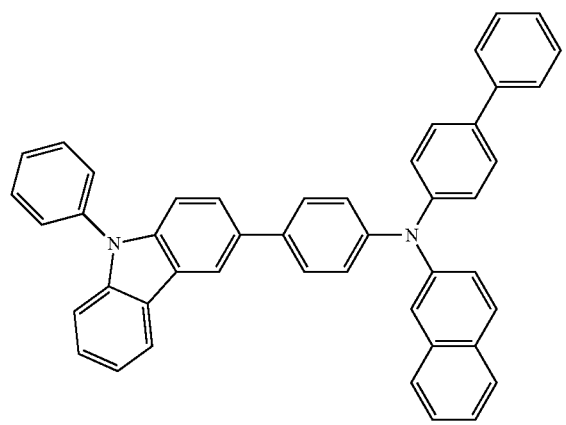
13-31
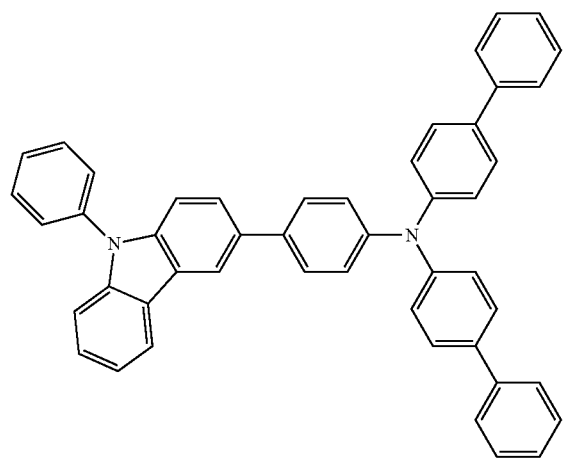
13-32
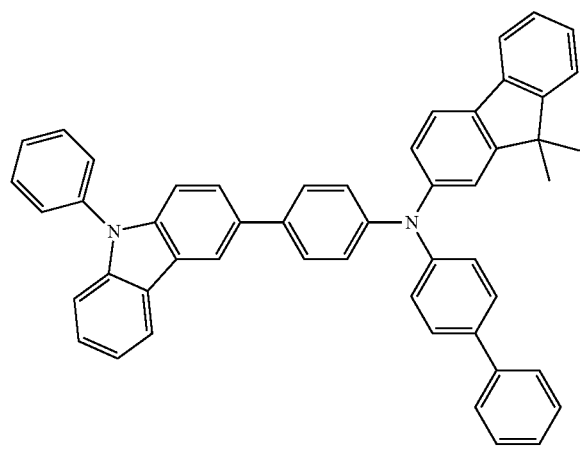
13-33
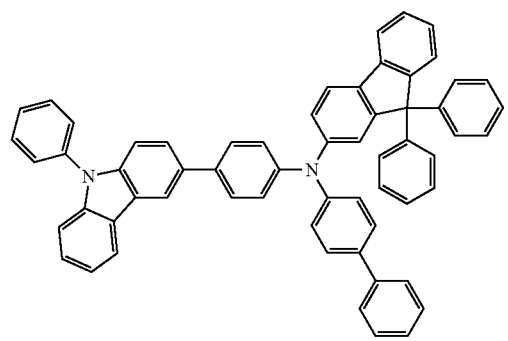
13-34
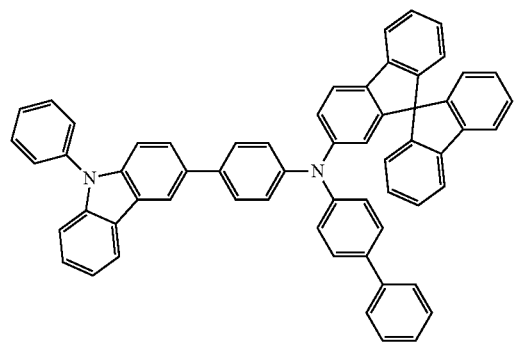
13-35
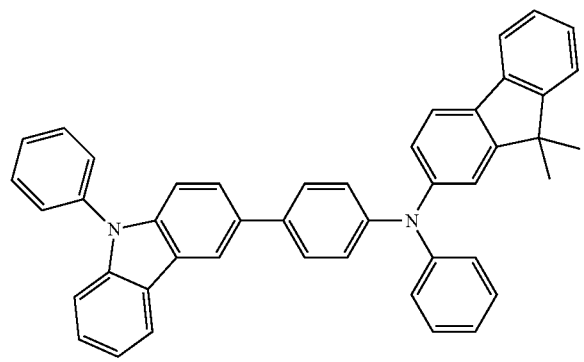

-continued
13-36
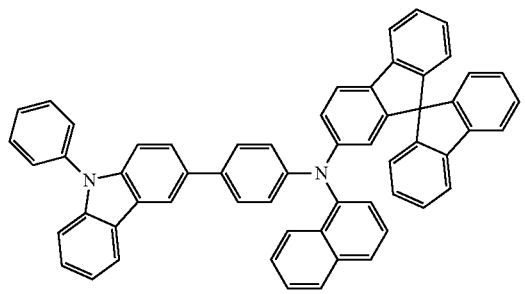
13-37
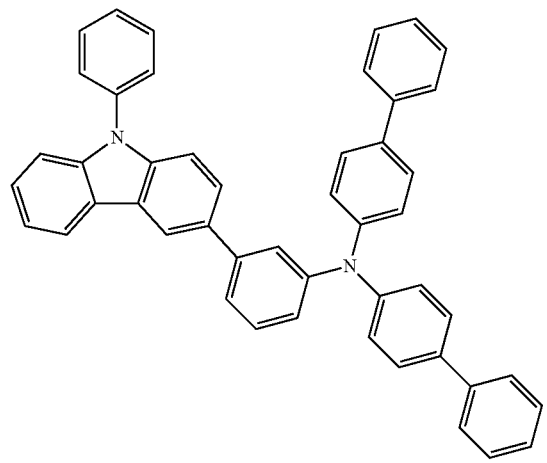
13-38
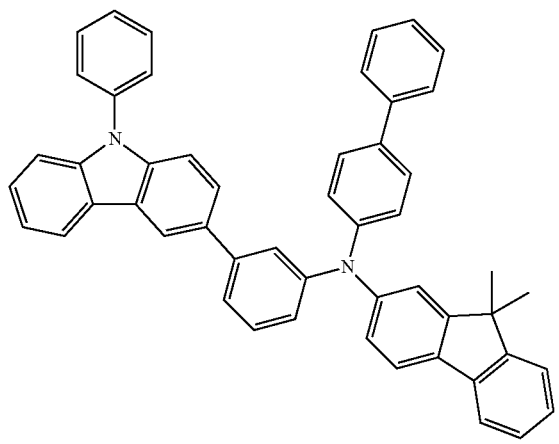
13-39
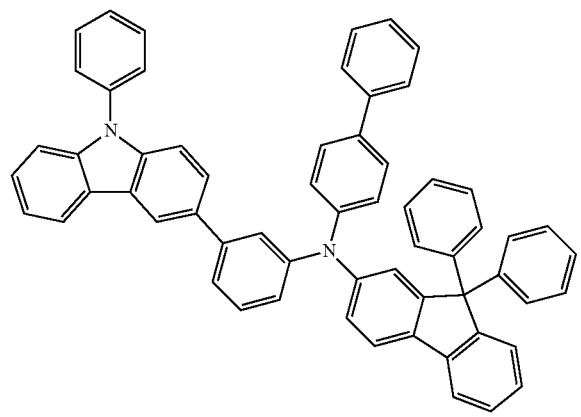
13-40
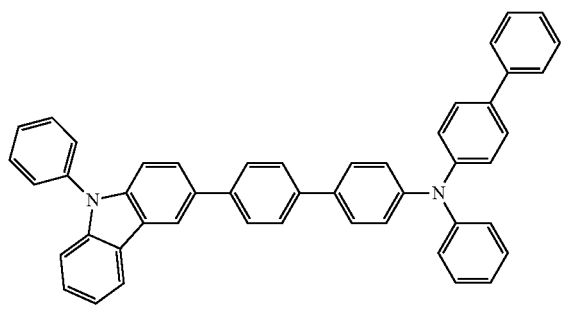
13-41
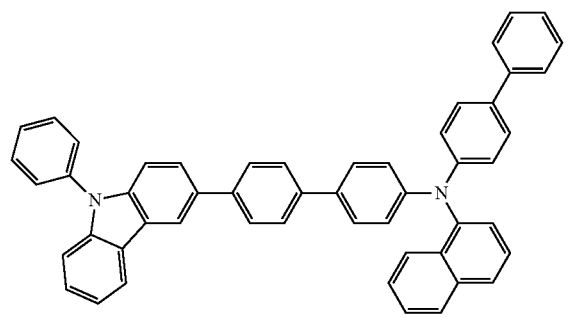

-continued
13-42
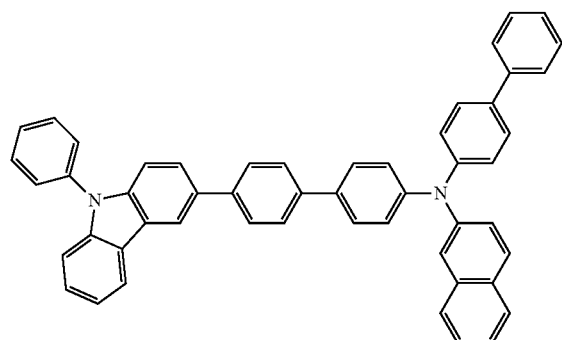
13-43
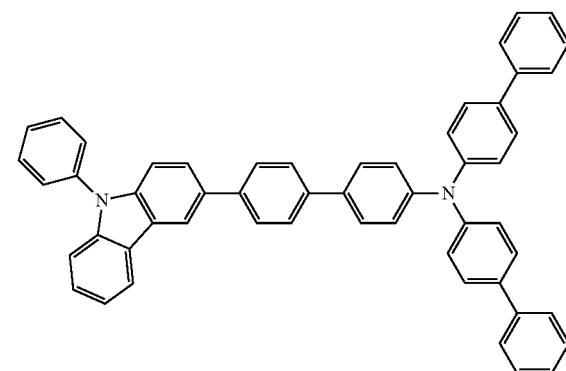
13-44
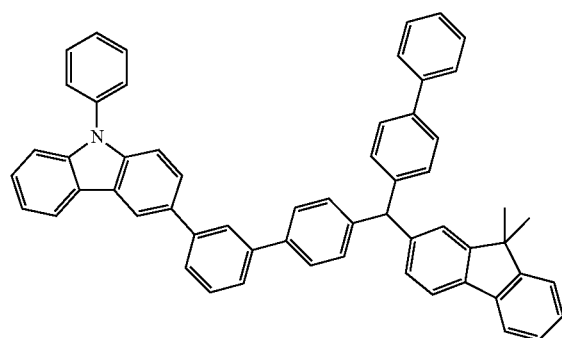
13-45
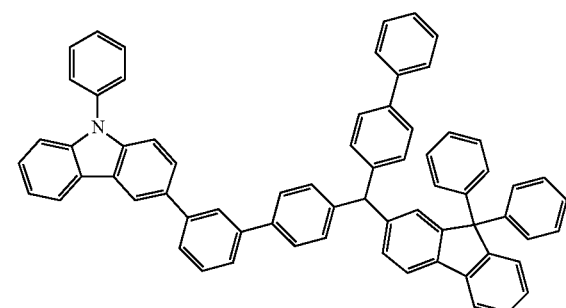
13-46
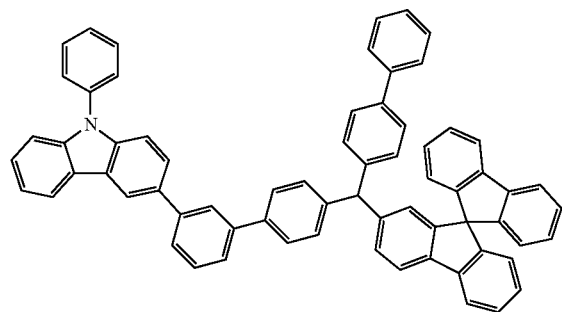
13-47
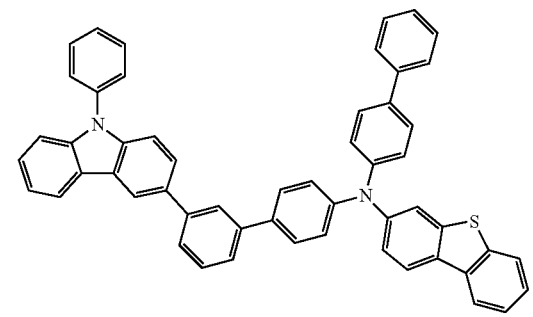
13-48
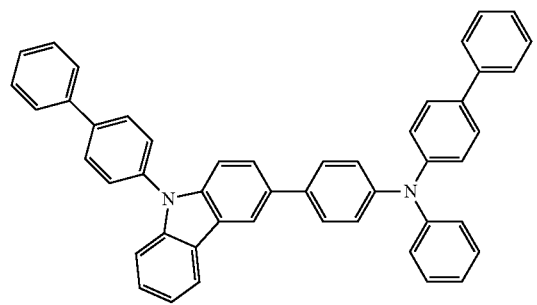
13-49
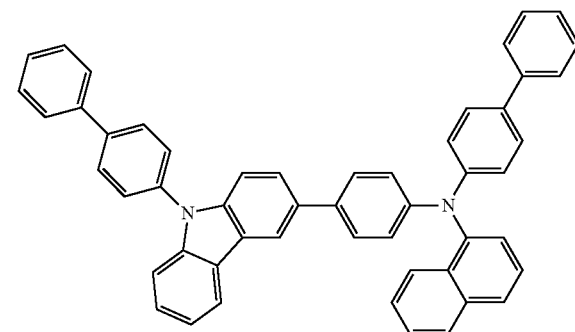

-continued
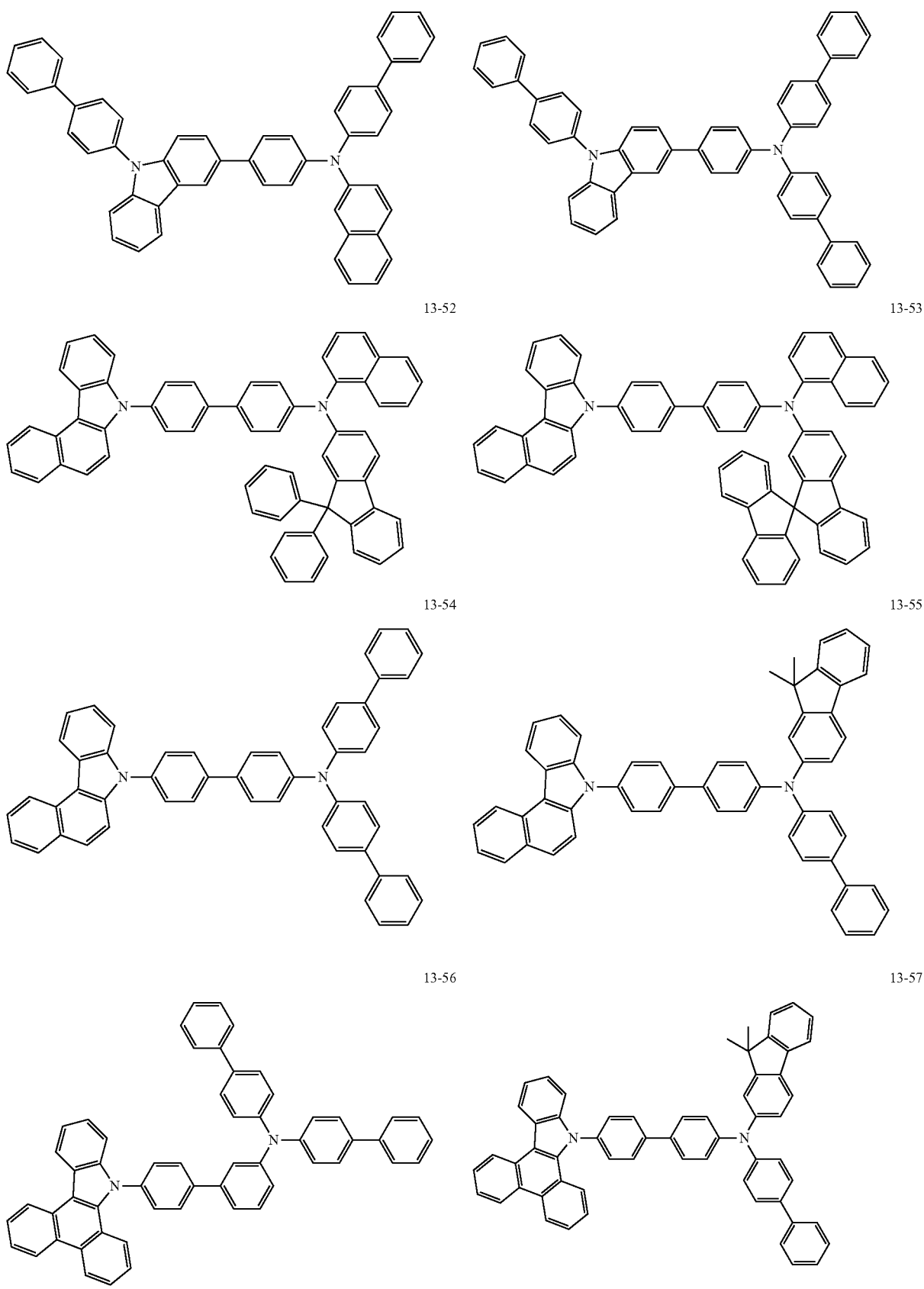

-continued
13-58
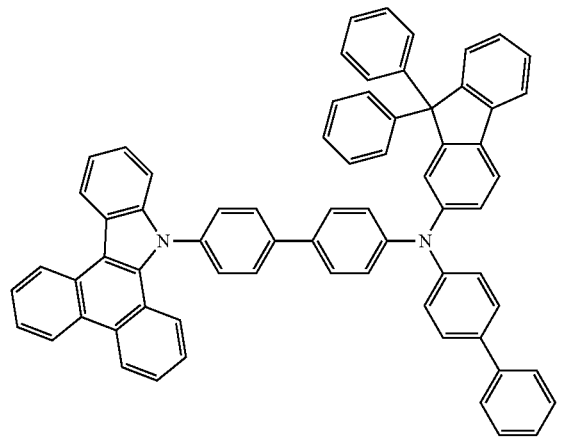
13-59
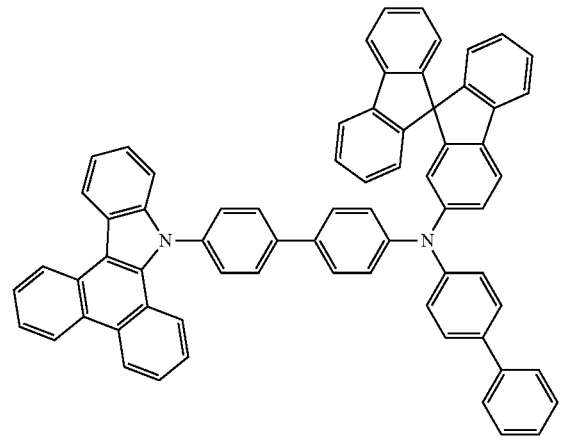
13-60
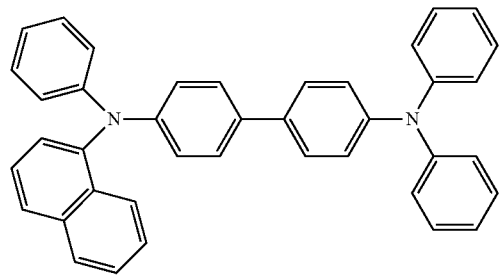
13-61
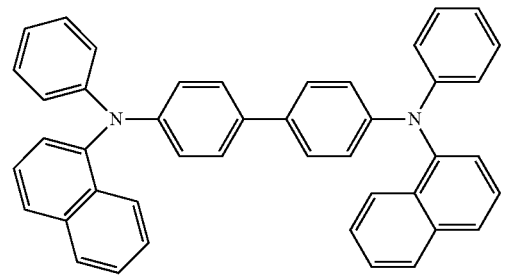
13-62
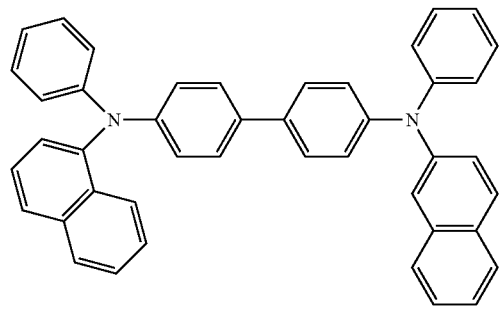
13-63
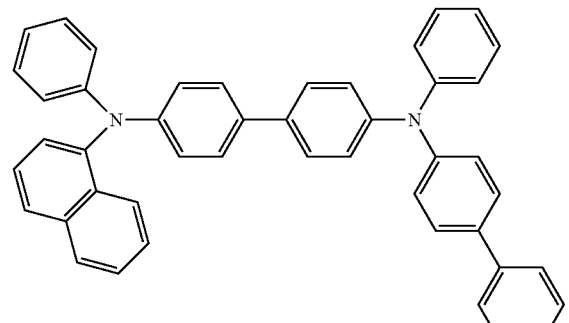
13-64
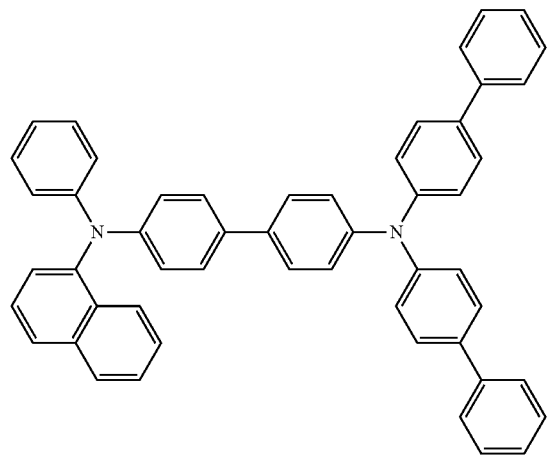
13-65
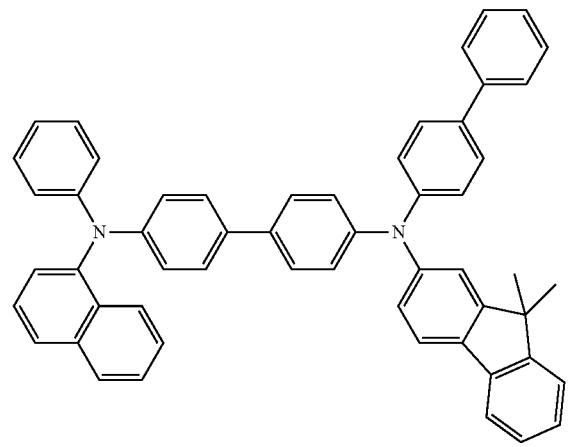

13-66

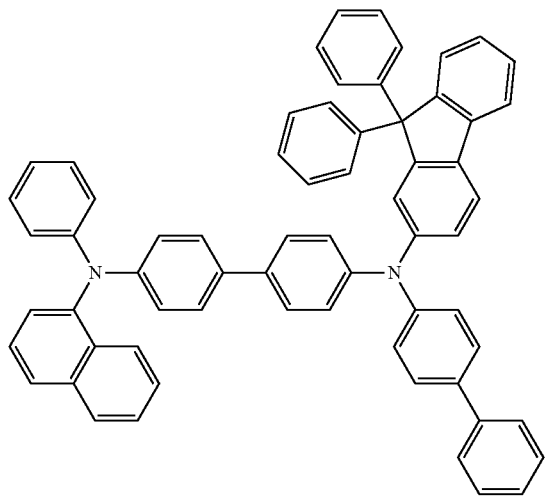

13-67

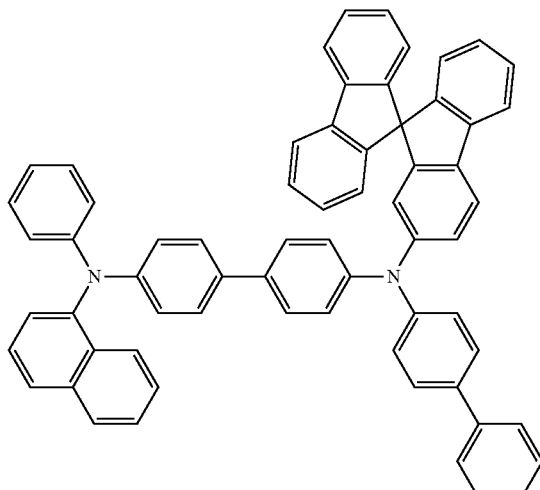

13-68

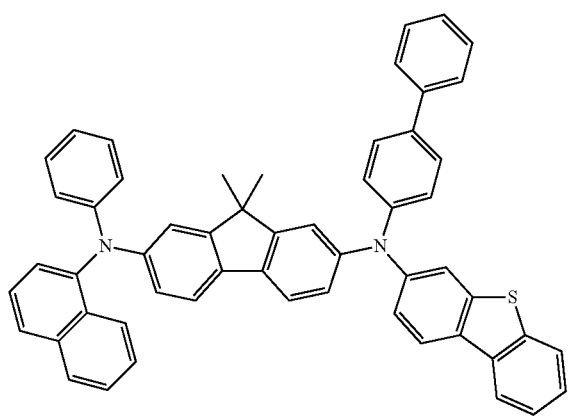

13-69

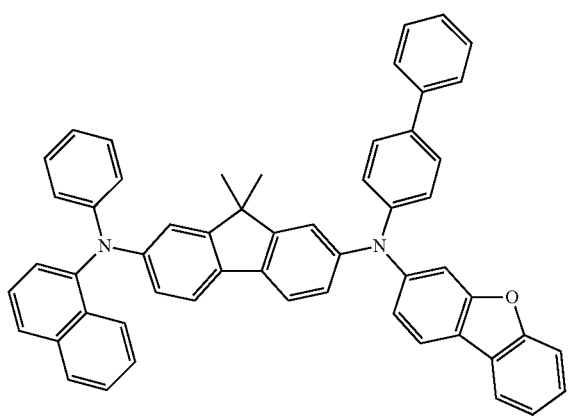

13-70

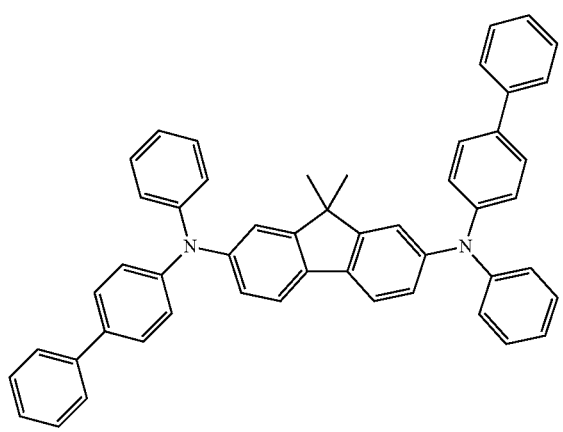

13-71

9. The organic electric element according to claim 1, wherein the organic electric element comprises a light efficiency enhancing layer formed on the side(s) of the first electrode and/or the second electrode not contacting to the organic material layer.

10. The organic electric element according to claim 1, wherein the organic electric element is formed by a spin coating process, a nozzle printing process, an inkjet printing process, a slot coating process, a dip coating process, or a roll-to-roll process.

11. An electronic device comprising a display device including the organic electric element according to claim 1; and a control unit for driving the display device.

12. The electronic device according to claim 11, wherein the organic electric element is an OLED, an organic solar cell, an organic photo conductor, an organic transistor, or an element for monochromic or white illumination.

* * * * *